United States Patent
Kiem et al.

(10) Patent No.: US 12,398,402 B2
(45) Date of Patent: Aug. 26, 2025

(54) REDUCING CD33 EXPRESSION TO SELECTIVELY PROTECT THERAPEUTIC CELLS

(71) Applicant: Fred Hutchinson Cancer Center, Seattle, WA (US)

(72) Inventors: Hans-Peter Kiem, Seattle, WA (US); Olivier Humbert, Seattle, WA (US); Roland B. Walter, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 1035 days.

(21) Appl. No.: 17/276,105

(22) PCT Filed: Sep. 12, 2019

(86) PCT No.: PCT/US2019/050859
§ 371 (c)(1),
(2) Date: Mar. 12, 2021

(87) PCT Pub. No.: WO2020/056170
PCT Pub. Date: Mar. 19, 2020

(65) Prior Publication Data
US 2022/0098613 A1 Mar. 31, 2022

Related U.S. Application Data

(60) Provisional application No. 62/730,164, filed on Sep. 12, 2018.

(51) Int. Cl.
| | | |
|---|---|---|
| C12N 15/13 | (2006.01) | |
| A61K 31/7088 | (2006.01) | |
| A61K 35/28 | (2015.01) | |
| A61K 39/395 | (2006.01) | |
| A61K 47/68 | (2017.01) | |
| A61P 37/04 | (2006.01) | |
| C07K 16/28 | (2006.01) | |
| C12N 15/113 | (2010.01) | |
| C12N 15/86 | (2006.01) | |

(52) U.S. Cl.
CPC .......... *C12N 15/86* (2013.01); *A61K 31/7088* (2013.01); *A61K 35/28* (2013.01); *A61K 39/3955* (2013.01); *A61K 47/6849* (2017.08); *A61P 37/04* (2018.01); *C07K 16/2803* (2013.01); *C12N 15/1138* (2013.01); *C07K 2317/31* (2013.01); *C07K 2317/565* (2013.01); *C07K 2319/02* (2013.01); *C07K 2319/03* (2013.01); *C07K 2319/30* (2013.01); *C07K 2319/33* (2013.01); *C12N 2310/122* (2013.01); *C12N 2310/14* (2013.01); *C12N 2310/531* (2013.01); *C12N 2320/31* (2013.01); *C12N 2740/15043* (2013.01)

(58) Field of Classification Search
CPC ................ C12N 15/86; C12N 15/1138; C12N 2310/122; C12N 2310/14; C12N 2310/531; C12N 2320/31; A61K 31/7088; A61K 35/28; A61K 39/3955; A61K 47/6849; A61P 37/04; C07K 16/2803; C07K 2317/31; C07K 2317/565; C07K 2319/02; C07K 2319/03; C07K 2319/30; C07K 2319/33
See application file for complete search history.

(56) References Cited

U.S. PATENT DOCUMENTS

| | | | |
|---|---|---|---|
| 5,773,001 A | 6/1998 | Hamann et al. | |
| 5,929,212 A | 7/1999 | Jolliffe et al. | |
| 7,557,198 B2 | 7/2009 | Davis et al. | |
| 8,759,494 B2 | 6/2014 | Bachmann et al. | |
| 9,359,442 B2 | 6/2016 | Hoffee et al. | |
| 9,415,104 B2 | 8/2016 | Farag | |
| 2002/0051780 A1 | 5/2002 | Lindhofer et al. | |
| 2008/0145362 A1 | 6/2008 | Kipriyanov et al. | |
| 2013/0309223 A1 | 11/2013 | Sutherland et al. | |
| 2017/0145094 A1 | 5/2017 | Galetto | |

FOREIGN PATENT DOCUMENTS

| | | |
|---|---|---|
| WO | WO2000018806 A1 | 4/2000 |
| WO | WO2002083738 A1 | 10/2002 |
| WO | WO2005003172 A2 | 1/2005 |
| WO | WO2009007124 A1 | 1/2009 |
| WO | WO2010028796 A1 | 3/2010 |
| WO | WO2012177639 A2 | 12/2012 |
| WO | WO2015003149 A2 | 1/2015 |

(Continued)

OTHER PUBLICATIONS

Lajaunias et al., Constitutive repressor activity of CD33 on human monocytes requires sialic acid recognition and phosphoinositide 3-kinase-mediated intracellular signaling, 2005, European Journal of Immunology, vol. 35, pp. 243-251 (Year: 2005).*

Tomar et al., Use of adeno-associated viral vector for delivery of small interfering RNA, 2003, Oncogene, vol. 22, pp. 5712-5715 (Year: 2003).*

European Search Report mailed Jan. 30, 2024 for European Application No. 23181499.7, a foreign counterpart to U.S. Appl. No. 17/276,105, 17 pages.

(Continued)

*Primary Examiner* — J. E. Angell
(74) *Attorney, Agent, or Firm* — Rachal C. Winger; Tanya M. Harding; Lee & Hayes PC

(57) ABSTRACT

Systems and methods to selectively protect therapeutic cells by reducing CD33 expression in the therapeutic cells and targeting non-therapeutic cells with an anti-CD33 therapy. The selective protection results in the enrichment of the therapeutic cells while simultaneously targeting any diseased, malignant and/or non-therapeutic CD33 expressing cells within a subject.

16 Claims, 51 Drawing Sheets

Specification includes a Sequence Listing.

(56) References Cited

FOREIGN PATENT DOCUMENTS

| WO | WO2015036583 A2 | 3/2015 |
| WO | WO2015150526 A2 | 10/2015 |
| WO | WO2016014576 A1 | 1/2016 |
| WO | WO2016105450 A2 | 6/2016 |
| WO | WO2016116626 A1 | 7/2016 |
| WO | WO2018152371 A1 | 8/2018 |
| WO | WO2018218207 A1 | 11/2018 |

OTHER PUBLICATIONS

Caron, et al., "Biological and immunological features of humanized M195 (anti-CD33) monoclonal antibodies," Cancer Res., vol. 52, No. 24, 1992, pp. 6761-6767.

Carthew, R.W., "Gene silencing by double-stranded RNA," Curr. Opin. Cell. Biol., vol. 13, No. 2, 2001, pp. 244-248.

Godwin, et al., "Targeting the membrane-proximal C2-set domain of CD33 for improved CD33-directed immunotherapy," Leukemia, vol. 35, No. 9, 2021, 2496-2507.

Haworth, et al., "In Vivo Murine-Matured Human CD3 + Cells as a Preclinical Model for T Cell-Based Immunotherapies," Mol. Ther. Methods. Clin. Dev., vol. 6, 2017, pp. 17-30.

Hoet, et al., "Generation of high-affinity human antibodies by combining donor-derived and synthetic complementarity-determining-region diversity," Nat. Biotechnol., vol. 23, No. 3, 2005, pp. 344-348.

Humbert, et al., "Engineering resistance to CD33-targeted immunotherapy in normal hematopoiesis by CRISPR/Cas9-deletion of CD33 exon 2," Leukemia, vol. 33, No. 3, 2019, pp. 762-808.

Kim, et al., "Genetic Inactivation of CD33 in Hematopoietic Stem Cells to Enable CAR T Cell Immunotherapy for Acute Myeloid Leukemia," Cell, vol. 173, 2018, pp. 1439-1453.

Laszlo, et al., "Expression and functional characterization of CD33 transcript variants in human acute myeloid leukemia," Oncotarget, vol. 7, No. 28, 2016, pp. 43281-43294.

Chen, et al, "Induction of myelodysplasia by myeloid-derived suppressor cells", The Journal of Clinical Investigation, vol. 123, No. 11, 2013, pp. 4595-4611.

Kim, et al, "Genetic Inactivation of CD33 in Hematopoietic Stem Cells to Enable CAR T Cell Immunotherapy for Acute Myeloid Leukemia", Cell, vol. 173, No. 6, 2018, pp. 1439-1453.

Ajaunias, et al, "Constitutive repressor activity of CD33 on human monocytes requires sialic acid recognition and phosphoinositide 3-kinase-mediated intracellular signaling", European Journal of Immunology, vol. 35, No. 1, 2004, pp. 243-251.

Rao, D, et al, "siRNA vs. shRNA: Similarities and differences", Advanced Drug Delivery Reviews, vol. 61, No. 9, 2009, pp. 746-759.

Walter, Roland B., "Investigational CD33-targeted therapeutics for acute myeloid leukemia", Expert Opinion on Investigational Drugs, vol. 27, No. 4, 2018, pp. 339-348 (Abstract Only; 2 pages).

Yang, et al, "The progress and current status of immunotherapy in acute myeloid leukemia", Annals of Hematology, vol. 96, No. 12, 2017, pp. 1965-1982.

Extended European Search Report mailed Nov. 29, 2022 for European Patent Application No. 19859495.4, 15 pages.

Partial European Search Report mailed Aug. 26, 2022 for European Patent Application No. 19859495.4, 17 pages.

PCT Search Report and Written Opinion for Application No. PCT/US2019/050859, mailed on Dec. 4, 2019, 8 pages.

* cited by examiner

FIG. 1B

Full-length CD33
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGGGSGCKPCICTVPEVSSVFIFPPKPKDVLTITLTPKVTCVVVDISKDDPEVQFSWFVDDVEVH
TAQTQPREEQFNSTFRSVSELPIMHQDWLNGKEFKCRVNSAAFPAPIEKTISKTKGRPKAPQV
YTIPPPKEQMAKDKVSLTCMITDFFPEDITVEWQWNGQPAENYKNTQPIMNTNGSYFVYSKLN
VQKSNWEAGNTFTCSVLHEGLHNHHTEKSLSHSPGK (SEQ ID NO: 4)

CD33$^{\Delta E2}$
MPLLLLLPLLWADLTHRPKILIPGTLEPGHSKNLTCSVSWACEQGTPPIFSWLSAAPTSLGPRTT
HSSVLIITPRPQDHGTNLTCQVKFAGAGVTTERTIQLNVTYVPQNPTTGIFPGDGSGKQETRAG
GGSGCKPCICTVPEVSSVFIFPPKPKDVLTITLTPKVTCVVVDISKDDPEVQFSWFVDDVEVHTA
QTQPREEQFNSTFRSVSELPIMHQDWLNGKEFKCRVNSAAFPAPIEKTIS (SEQ ID NO: 5)

FIG. 2

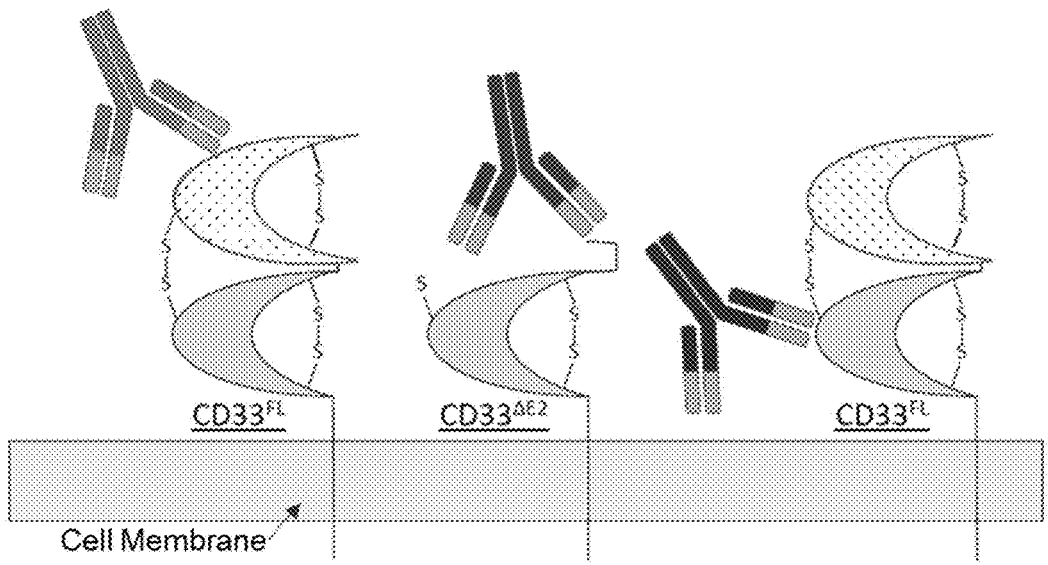

FIG. 3

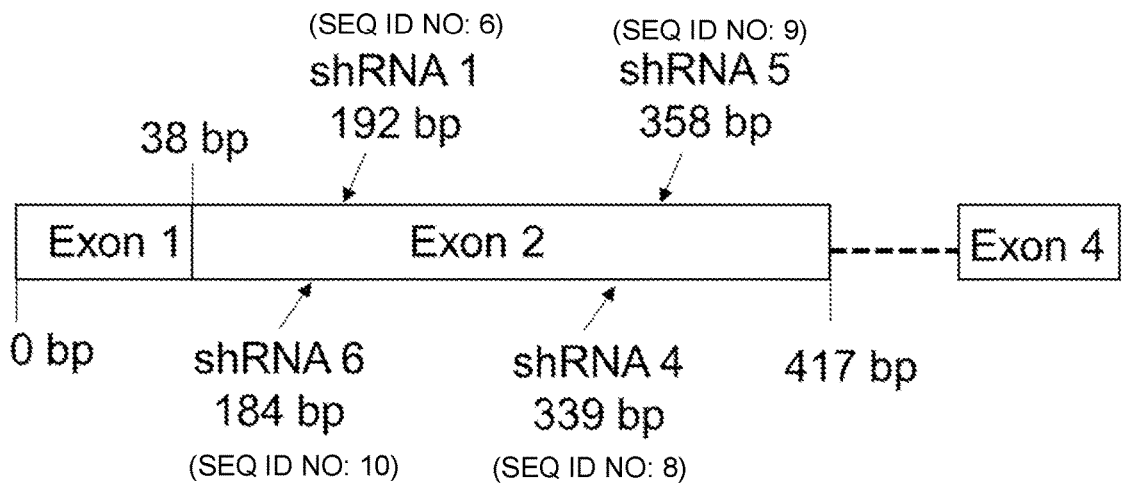

shRNA sequences targeting CD33 (5'-3' coding strand)

shRNA1: TGCCATTATATCCAGGGACTTTCAAGAGAAGTCCCTGGATATAATGGCTTTTTTC (SEQ ID NO: 6)

shRNA3: TGGATGAGGAGCTGCATTATTTCAGAATAATGCAGCTCCTCATCCTTTTTTC (SEQ ID NO: 7)

shRNA4: TGTTCATACTTCTTTCGGATTTCAAGAGAATCCGAAAGAAGTATGAACTTTTTTC (SEQ ID NO: 8)

shRNA5: TGGAGAGAGGAAGTACCAAATTCAAGAGATTTGGTACTTCCTCTCTCCTTTTTTC (SEQ ID NO: 9)

shRNA6: TGGGAAGGAGCCATTATATCTTCAAGAGAGATATAATGGCTCCTTCCCTTTTTTC (SEQ ID NO: 10)

siRNA sequences targeting CD33

GCCATTATATCCAGGGACT (SEQ ID NO: 11)
GGATGAGGAGCTGCATTAT (SEQ ID NO: 12)
GTTCATACTTCTTTCGGAT (SEQ ID NO: 13)
GGAGAGAGGAAGTACCAAA (SEQ ID NO: 14)
GGGAAGGAGCCATTATATC (SEQ ID NO: 15)

FIG. 4 cont'd
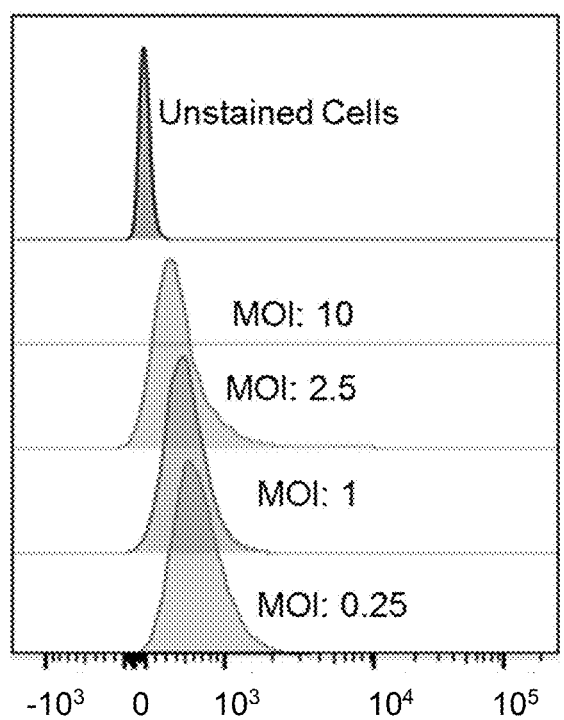
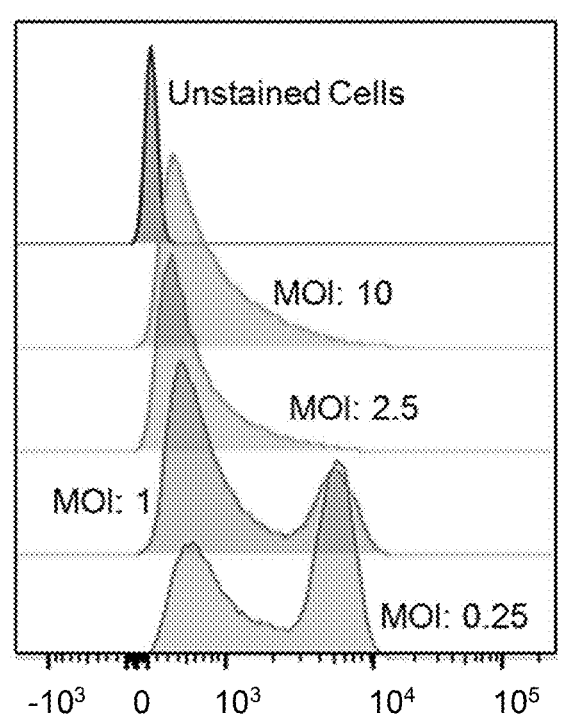

FIG. 4 cont'd
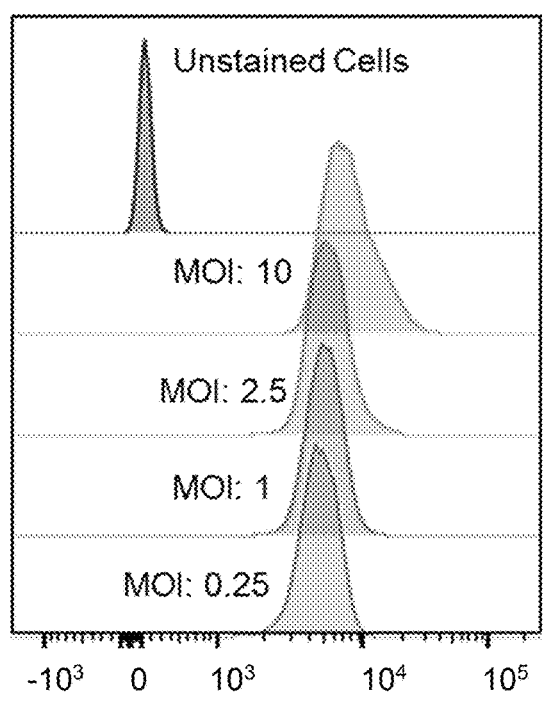
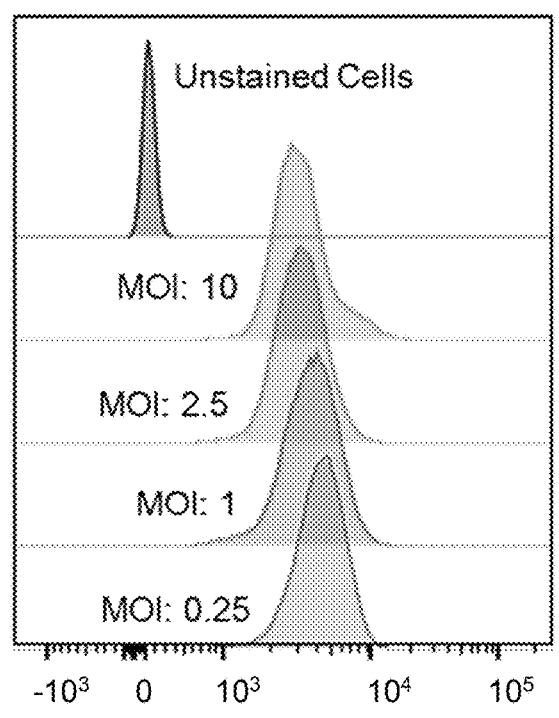

FIG. 9A
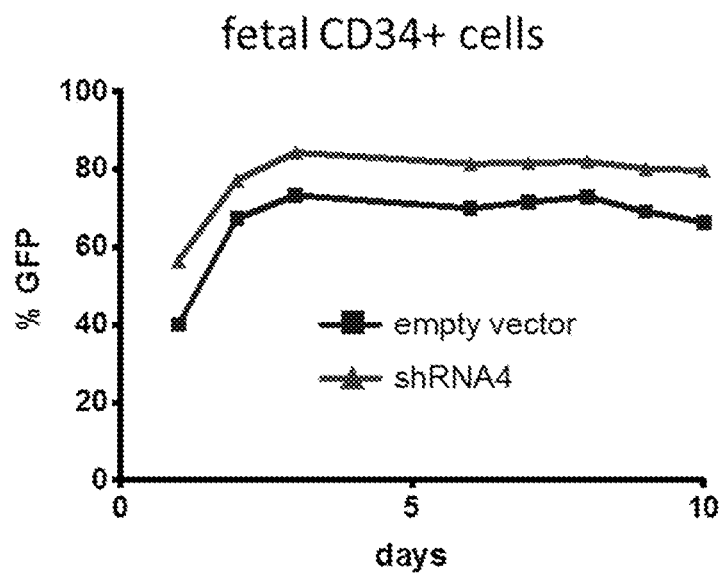
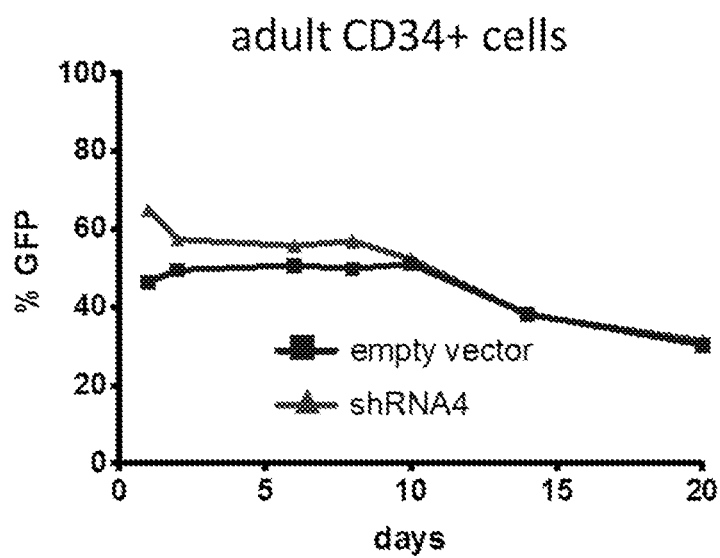

FIG. 9B
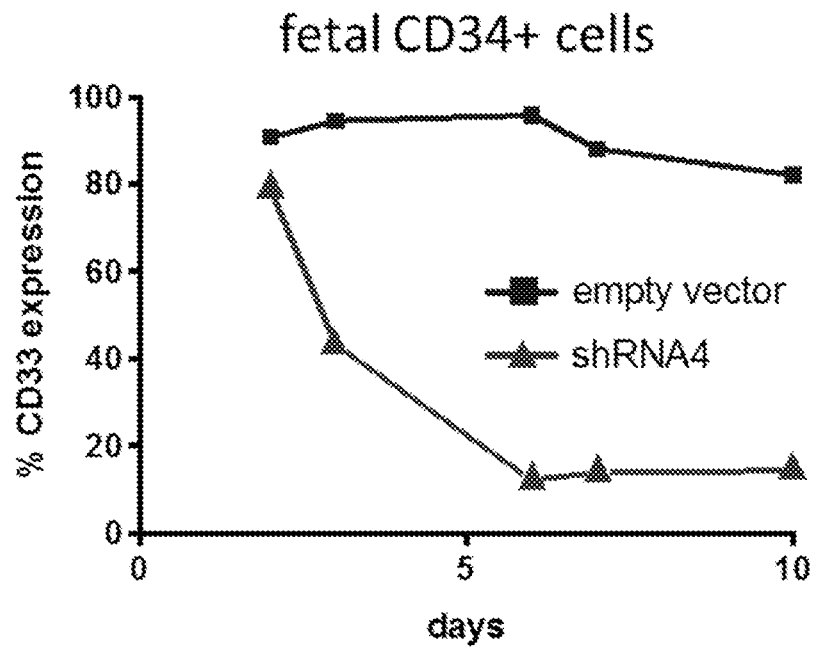
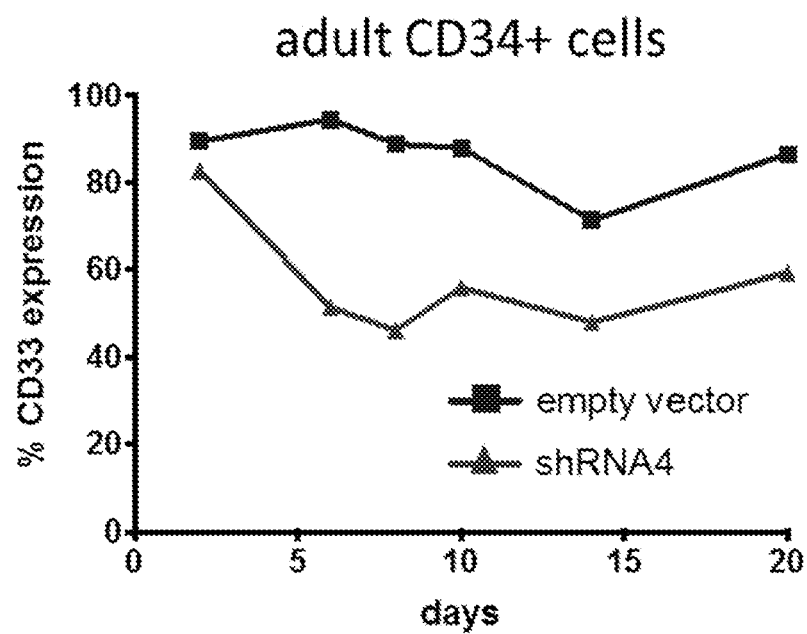

FIG. 9C
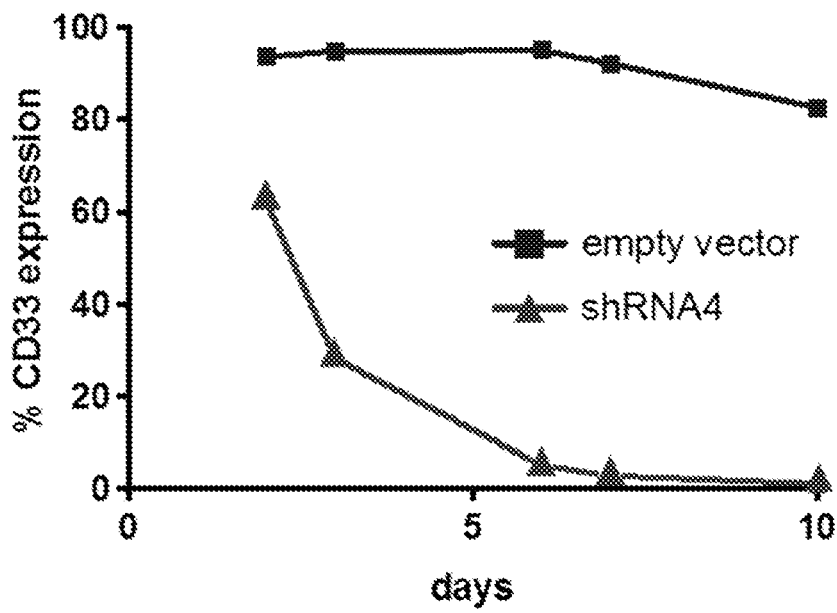
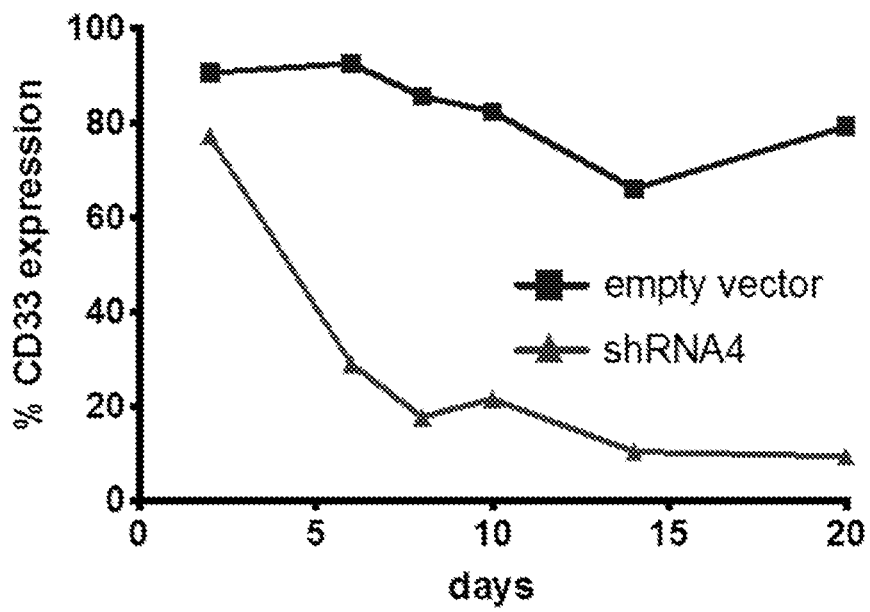

FIG. 10
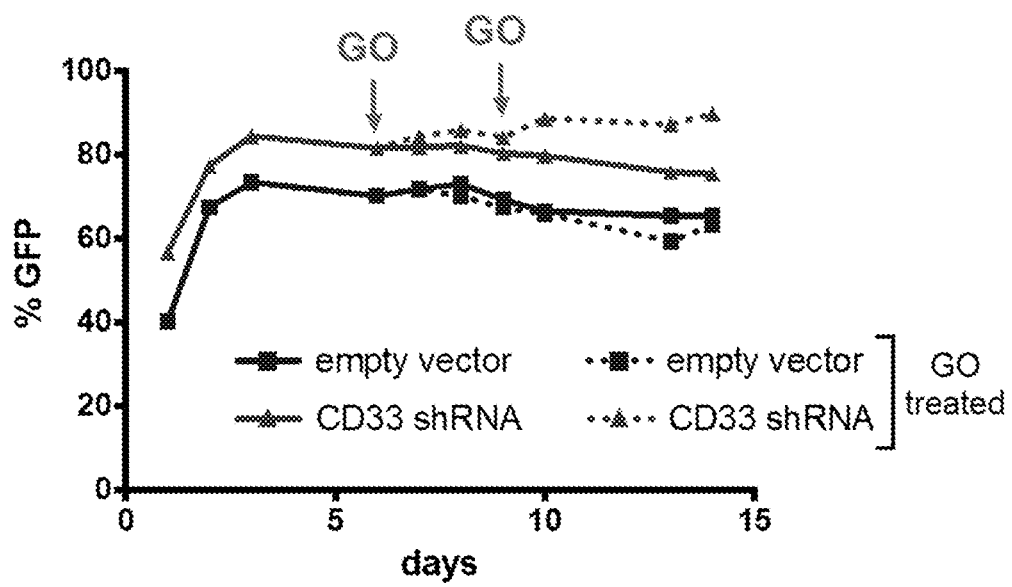
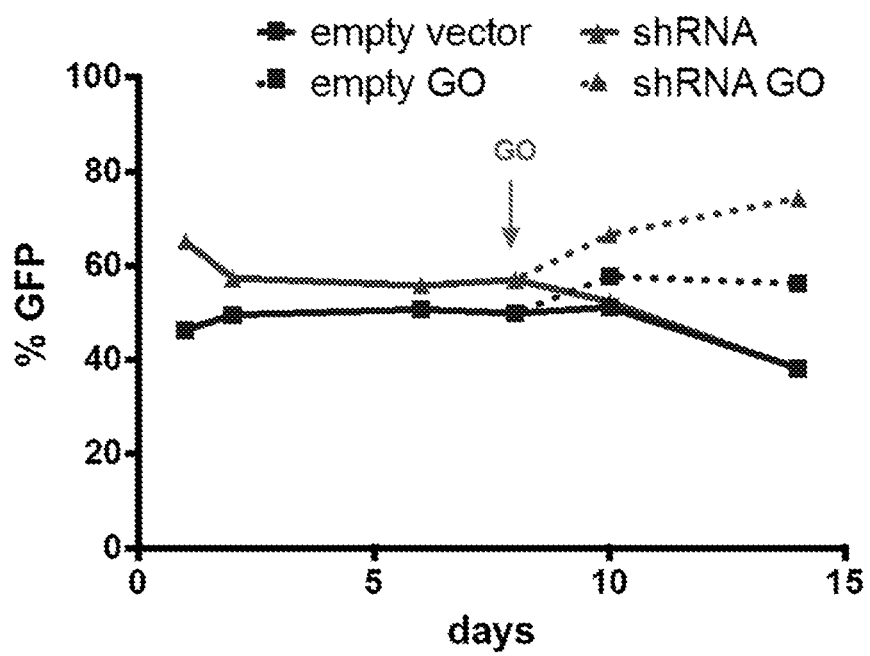

| Group | Condition | Cell Dose | # of Mice | # of mice treated with Mylotarg |
|---|---|---|---|---|
| Group 1 | pLL 'empty' vector | 0.5x10⁶ | 6 | 2 |
| Group 2 | shRNA vector | 0.5x10⁶ | 6 | 2 |

FIG. 17
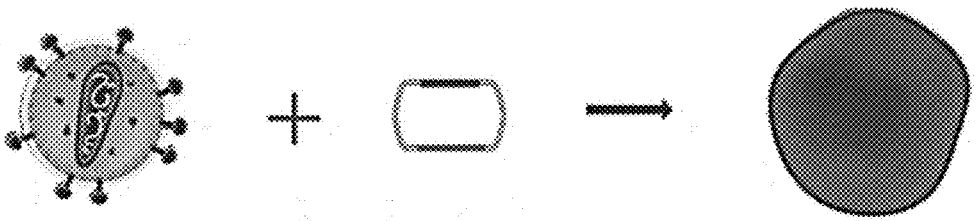
Transduce Patient's HSPCs Cells with Vector containing (1) corrected FANCA Gene and (2) CD33 Knockdown shRNA
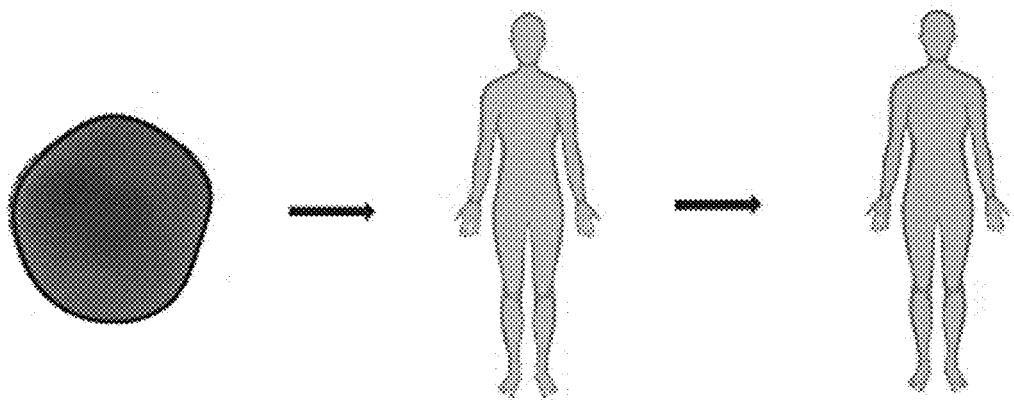
Transplant modified HSPCs into patient
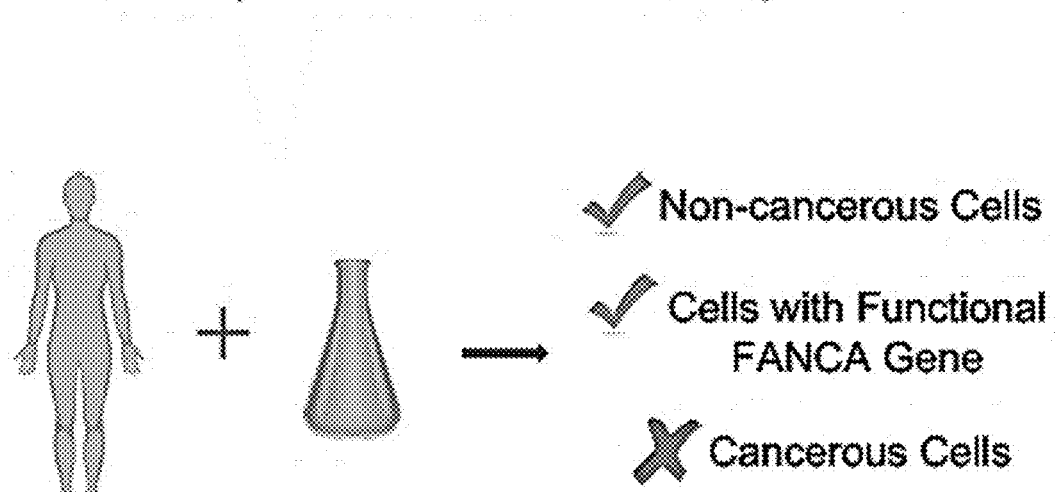
Administer Mylotarg
✓ Non-cancerous Cells
✓ Cells with Functional FANCA Gene
✗ Cancerous Cells
✗ Cells with mutated FANCA Gene

FIG. 18

Plasmid used to clone/test shRNA=pLL37
GTCGACGGATCGGGAGATCTCCCGATCCCCTATGGTGCACTCTCAGTACAATCTGCTCTG
ATGCCGCATAGTTAAGCCAGTATCTGCTCCCTGCTTGTGTGTTGGAGGTCGCTGAGTAGTG
CGCGAGCAAAATTTAAGCTACAACAAGGCAAGGCTTGACCGACAATTGCATGAAGAATCTG
CTTAGGGTTAGGCGTTTTGCGCTGCTTCGCGATGTACGGGCCAGATATACGCGTTGACATT
GATTATTGACTAGTTATTAATAGTAATCAATTACGGGGTCATTAGTTCATAGCCCATATATGG
AGTTCCGCGTTACATAACTTACGGTAAATGGCCCGCCTGGCTGACCGCCCAACGACCCCC
GCCCATTGACGTCAATAATGACGTATGTTCCCATAGTAACGCCAATAGGGACTTTCCATTG
ACGTCAATGGGTGGAGTATTTACGGTAAACTGCCCACTTGGCAGTACATCAAGTGTATCAT
ATGCCAAGTACGCCCCCTATTGACGTCAATGACGGTAAATGGCCCGCCTGGCATTATGCC
CAGTACATGACCTTATGGGACTTTCCTACTTGGCAGTACATCTACGTATTAGTCATCGCTAT
TACCATGGTGATGCGGTTTTGGCAGTACATCAATGGGCGTGGATAGCGGTTTGACTCACG
GGGATTTCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTAGGCGT
GTACGGTGGGAGGTCTATATAAGCAGCGCGTTTTGCCTGTACTGGGTCTCTCTGGTTAGAC
CAGATCTGAGCCTGGGAGCTCTCTGGCTAACTAGGGAACCCACTGCTTAAGCCTCAATAAA
GCTTGCCTTGAGTGCTTCAAGTAGTGTGTGCCCGTCTGTTGTGTGACTCTGGTAACTAGAG
ATCCCTCAGACCCTTTTAGTCAGTGTGGAAAATCTCTAGCAGTGGCGCCCGAACAGGGACT
TGAAAGCGAAAGGGAAACCAGAGGAGCTCTCTCGACGCAGGACTCGGCTTGCTGAAGCG
CGCACGGCAAGAGGCGAGGGGCGGCGACTGGTGAGTACGCCAAAAATTTTGACTAGCGG
AGGCTAGAAGGAGAGAGATGGGTGCGAGAGCGTCAGTATTAAGCGGGGGAGAATTAGAT
CGCGATGGGAAAAAATTCGGTTAAGGCCAGGGGGAAAGAAAAAATATAAATTAAAACATAT
AGTATGGGCAAGCAGGGAGCTAGAACGATTCGCAGTTAATCCTGGCCTGTTAGAAACATCA
GAAGGCTGTAGACAAATACTGGGACAGCTACAACCATCCCTTCAGACAGGATCAGAAGAA
CTTAGATCATTATATAATACAGTAGCAACCCTCTATTGTGTGCATCAAAGGATAGAGATAAA
AGACACCAAGGAAGCTTTAGACAAGATAGAGGAAGAGCAAAACAAAAGTAAGACCACCGC
ACAGCAAGCGGCCGGCCGCGCTGATCTTCAGACCTGGAGGAGGAGATATGAGGGACAAT
TGGAGAAGTGAATTATATAAATATAAAGTAGTAAAAATTGAACCATTAGGAGTAGCACCCAC
CAAGGCAAAGAGAAGAGTGGTGCAGAGAGAAAAAAGAGCAGTGGGAATAGGAGCTTTGTT
CCTTGGGTTCTTGGGAGCAGCAGGAAGCACTATGGGCGCAGCGTCAATGACGCTGACGG
TACAGGCCAGACAATTATTGTCTGGTATAGTGCAGCAGCAGAACAATTTGCTGAGGGCTAT
TGAGGCGCAACAGCATCTGTTGCAACTCACAGTCTGGGGCATCAAGCAGCTCCAGGCAAG
AATCCTGGCTGTGGAAAGATACCTAAAGGATCAACAGCTCCTGGGGATTTGGGGTTGCTCT
GGAAAACTCATTTGCACCACTGCTGTGCCTTGGAATGCTAGTTGGAGTAATAAATCTCTGG
AACAGATTTGGAATCACACGACCTGGATGGAGTGGGACAGAGAAATTAACAATTACACAAG
CTTAATACACTCCTTAATTGAAGAATCGCAAAACCAGCAAGAAAAGAATGAACAAGAATTAT
TGGAATTAGATAAATGGGCAAGTTTGTGGAATTGGTTTAACATAACAAATTGGCTGTGGTAT
ATAAAATTATTCATAATGATAGTAGGAGGCTTGGTAGGTTTAAGAATAGTTTTTGCTGTACTT
TCTATAGTGAATAGAGTTAGGCAGGGATATTCACCATTATCGTTTCAGACCCACCTCCCAAC
CCCGAGGGGACCCGACAGGCCCGAAGGAATAGAAGAAGAAGGTGGAGAGAGAGACAGAG
ACAGATCCATTCGATTAGTGAACGGATCGGCACTGCGTGCGCCAATTCTGCAGACAAATG
GCAGTATTCATCCACAATTTTAAAAGAAAGGGGGGATTGGGGGGTACAGTGCAGGGGAA
AGAATAGTAGACATAATAGCAACAGACATACAAACTAAAGAATTACAAAAACAAATTACAAA
AATTCAAAATTTTCGGGTTTATTACAGGGACAGCAGAGATCCAGTTTGGTTAGTACCGGGC
CCGCTCTAGAGATCCGACGCCGCCATCTCTAGGCCCGCGCCGGCCCCCTCGCACAGACT
TGTGGGAGAAGCTCGGCTACTCCCCTGCCCCGGTTAATTTGCATATAATATTTCCTAGTAA
CTATAGAGGCTTAATGTGCGATAAAAGACAGATAATCTGTTCTTTTTAATACTAGCTACATTT
TACATGATAGGCTTGGATTTCTATAAGAGATACAAATACTAAATTATTATTTTAAAAAACAGC
ACAAAAGGAAACTCACCCTAACTGTAAAGTAATTGTGTGTTTTGAGACTATAAATATCCCTT

FIG. 18 cont'd

```
GGAGAAAAGCCTTGTTAACGCGCGGTGACCCTCGAGGTCGACGGTATCGATAAGCTCGCT
TCACGAGATTCCAGCAGGTCGAGGGACCTAATAACTTCGTATAGCATACATTATACGAAGT
TATATTAAGGGGTTCCAAGCTTAAGCGGCCGCGTGGATAACCGTATTACCGCCATGCATTAG
TTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGT
CAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTACG
CCCCCTATTGACGTCAATGACGGTAAATGGCCCGCCTGGCATTATGCCCAGTACATGACCT
TATGGGACTTTCCTACTTGGCAGTACATCTACGTATTAGTCATCGCTATTACCATGGTGATG
CGGTTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGGGAGG
TCTATATAAGCAGAGCTGGTTTAGTGAACCGTCAGATCCGCTAGCGCTACCGGTCGCCAC
CATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCACC
TACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATG
AAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACAC
CCTGGTGAACCGCATCGAGCTGAAGGGCATCGACTTCAAGGAGGACGGCAACATCCTGG
GGCACAAGCTGGAGTACAACTACAACAGCCACAACGTCTATATCATGGCCGACAAGCAGA
AGAACGGCATCAAGGTGAACTTCAAGATCCGCCACAACATCGAGGACGGCAGCGTGCAGC
TCGCCGACCACTACCAGCAGAACACCCCCATCGGCGACGGCCCCGTGCTGCTGCCCGAC
AACCACTACCTGAGCACCCAGTCCGCCCTGAGCAAAGACCCCAACGAGAAGCGCGATCAC
ATGGTCCTGCTGGAGTTCGTGACCGCCGCCGGGATCACTCTCGGCATGGACGAGCTGTAC
AAGTAGGAATTCGTCGAGGGACCTAATAACTTCGTATAGCATACATTATACGAAGTTATACA
TGTTTAAGGGTTCCGGTTCCACTAGGTACAATTCGATATCAAGCTTATCGATAATCAACCTC
TGGATTACAAAATTTGTGAAAGATTGACTGGTATTCTTAACTATGTTGCTCCTTTTACGCTAT
GTGGATACGCTGCTTTAATGCCTTTGTATCATGCTATTGCTTCCCGTATGGCTTTCATTTTC
TCCTCCTTGTATAAATCCTGGTTGCTGTCTCTTTATGAGGAGTTGTGGCCCGTTGTCAGGC
AACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATT
CCGTGGTGTTGTCGGGGAAATCATCGTCCTTTCCTTGGCTGCTCGCCTGTGTTGCCACCT
GGATTCTGCGCGGGACGTCCTTCTGCTACGTCCCTTCGGCCCTCAATCCAGCGGACCTTC
CTTCCCGCGGCCTGCTGCCGGCTCTGCGGCCTCTTCCGCGTCTTCGCCTTCGCCCTCAGA
CGAGTCGGATCTCCCTTTGGGCCGCCTCCCCGCATCGATACCGTCGACCTCGATCGAGAC
CTAGAAAACATGGAGCAATCACAAGTAGCAATACAGCAGCTACCAATGCTGATTGTGCCT
GGCTAGAAGCACAAGAGGAGGAGGAGGTGGGTTTTCCAGTCACACCTCAGGTACCTTTAA
GACCAATGACTTACAAGGCAGCTGTAGATCTTAGCCACTTTTTAAAAGAAAAGGGGGGACT
GGAAGGGCTAATTCACTCCCAACGAAGACAAGATATCCTTGATCTGTGGATCTACCACACA
CAAGGCTACTTCCCTGATTGGCAGAACTACACACCAGGGCCAGGGATCAGATATCCACTG
ACCTTTGGATGGTGCTACAAGCTAGTACCAGTTGAGCAAGAGAAGGTAGAAGAAGCCAAT
GAAGGAGAGAACACCCGCTTGTTACACCCTGTGAGCCTGCATGGGATGGATGACCCGGAG
AGAGAAGTATTAGAGTGGAGGTTTGACAGCCGCCTAGCATTTCATCACATGGCCCGAGAG
CTGCATCCGGACTGTACTGGGTCTCTCTGGTTAGACCAGATCTGAGCCTGGGAGCTCTCT
GGCTAACTAGGGAACCCACTGCTTAAGCCTCAATAAAGCTTGCCTTGAGTGCTTCAAGTAG
TGTGTGCCCGTCTGTTGTGTGACTCTGGTAACTAGAGATCCCTCAGACCCTTTTAGTCAGT
GTGGAAAATCTCTAGCAGCATGTGAGCAAAAGGCCAGCAAAAGGCCAGGAACCGTAAAAA
```

FIG. 18 cont'd

GGCCGCGTTGCTGGCGTTTTTCCATAGGCTCCGCCCCCCTGACGAGCATCACAAAAATCG
ACGCTCAAGTCAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCGTTCAGCCCGACCG
CTGCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCTGCGCT
CTGCTGAAGCCAGTTACCTTCGGAAAAGAGTTGGTAGCTCTTGATCCGGCAAACAAACCA
CCGCTGGTAGCGGTGGTTTTTTTGTTTGCAAGCAGCAGATTACGCGCAGAAAAAAGGATC
TCAAGAAGATCCTTTGATCTTTTCTACGGGGTCTGACGCTCAGTGGAACGAAAACTCACGT
TAAGGGATTTTGGTCATGAGATTATCAAAAGGATCTTCACCTAGATCCTTTTAAATTAAAAA
TGAAGTTTTAAATCAATCTAAAGTATATATGAGTAAACTTGGTCTGACAGTTACCAATGCTTA
ATCAGTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTTCCCAAC
GATCAAGGCGAGTTACATGATCCCCATGTTGTGCAAAAAGCGGTTAGCTCCTTCGGTCC
TCCGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACG
GGATAATACCGCGCCACATAGCAGAACTTTAAAAGTGCTCATCATTGGAAAACGTTCTTCG
GGGCGAAAACTCTCAAGGATCTTACCGCTGTTGAGATCCAGTTCGATGTAACCCACTCGTG
CACCCAACTGATCTTCAGCATCTTTTACTTTCACCAGCGTTTCTGGGTGAGCAAAAACAGG
AAGGCAAAATGCCGCAAAAAAGGGAATAAGGGCGACACGGAAATGTTGAATACTCATACTC
TTCCTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTGCCAC
CTGAC (SEQ ID NO: 16)

FIG. 19

Fanconi destination plasmid in which the active shRNAs can be cloned
CAGGTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAAAAG
GAAGAGTATGAGTATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATC
CGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCG
GAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACAC
GACGGGGAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATTGATTTAAA
ACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCT
TCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAAC
GCGGCCTTTTTACGGTTCCTGGCCTTTTGCTGGCCTTTTGCTCACATGTTCTTTCCTGCGTT
ATCCCCTGATTCTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCGCCCAATACG
CAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGC
ACCCCAGGCTTTACACTTTATGCTTCCGGCTCGTATGTTGTGTGGAATTGTGAGCGGATAA
CAATTTCACACAGGAAACAGCTATGACCATGATTACGCCAAGCGCGCAATTAACCCTCACT
AAAGGGAACAAAAGCTGGAGCTGCAAGCTTAATGTAGTCTTATGCAATACTCTTGTAGTCTT
GCAACATGGTAACGATGAGTTAGCAACATGCCTTACAAGGAGAGAAAAGCACCGTGCAT
GCCGATTGGTGGAAGTAAGGTGGTACGATCGTGCCTTATTAGGAAGGCAACAGACGGGTC
TGACATGGATTGGACGAACCACTGAATTGCCGCATTGCAGAGATATTGTATTTAAGTGCCT
AGCTCGATACAATAAACGGGTCTCTCTGGTTAGACCAGATCTGAGCCTGGGAGCTCTCTG
GCTAACTAGGGAACCCACTGCTTAAGCCTCAATAAAGCTTGCCTTGAGTGCTTCAAGTAGT
GTGTGCCCGTCTGTTGTGTGACTCTGGTAACTAGAGATCCCTCAGACCCTTTTAGTCAGTG
TGGAAAATCTCTAGCAGTGGCGCCCGAACAGGGACCTGAAAGCGAAAGGGAAACCAGAG
CTCTCTCGACGCAGGACTCGGCTTGCTGAAGCGCGCACGGCAAGAGGCGAGGGGCGGC
GACTGGTGAGTACGCCAAAAATTTTGACTAGCGGAGGCTAGAAGGAGAGAGATGGGTGCG
AGAGCGTCAGTATTAAGCGGGGGAGAATTAGATCGCGATGGGAAAAAATTCGGTTAAGGC
CAGGGGGAAAGAAAAAATATAAATTAAAACATATAGTATGGGCAAGCAGGGAGCTAGAACG

FIG. 19 cont'd

ATTCGCAGTTAATCCTGGCCTGTTAGAAACATCAGAAGGCTGTAGACAAATACTGGGACAG
CTACAACCATCCCTTCAGACAGGATCAGAAGAACTTAGATCATTATATAATACAGTAGCAAC
CCTCTATTGTGTGCATCAAAGGATAGAGATAAAAGACACCAAGGAAGCTTTAGACAAGATA
GAGGAAGAGCAAAACAAAAGTAAGACCACCGCACAGCAAGCGGCCGCTGATCTTCAGACC
TGGAGGAGGAGATATGAGGGACAATTGGAGAAGTGAATTATATAAATATAAAGTAGTAAAA
ATTGAACCATTAGGAGTAGCACCCACCAAGGCAAAGAGAAGAGTGGTGCAGAGAGAAAAA
AGAGCAGTGGGAATAGGAGCTTTGTTCCTTGGGTTCTTGGGAGCAGCAGGAAGCACTATG
GGCGCAGCCTCAATGACGCTGACGGTACAGGCCAGACAATTATTGTCTGGTATAGTGCAG
CAGCAGAACAATTTGCTGAGGGCTATTGAGGCGCAACAGCATCTGTTGCAACTCACAGTCT
GGGGCATCAAGCAGCTCCAGGCAAGAATCCTGGCTGTGGAAAGATACCTAAAGGATCAAC
AGCTCCTGGGGATTTGGGGTTGCTCTGGAAAACTCATTTGCACCACTGCTGTGCCTTGGAA
TGCTAGTTGGAGTAATAAATCTCTGGAACAGATTGGAATCACACGACCTGGATGGAGTGGG
ACAGAGAAATTAACAATTACACAAGCTTAATACACTCCTTAATTGAAGAATCGCAAAACCAG
CAAGAAAAGAATGAACAAGAATTATTGGAATTAGATAAATGGGCAAGTTTGTGGAATTGGTT
TAACATAACAAATTGGCTGTGGTATATAAAATTATTCATAATGATAGTAGGAGGCTTGGTAG
GTTTAAGAATAGTTTTTGCTGTACTTTCTATAGTGAATAGAGTTAGGCAGGGATATTCACCA
TTATCGTTTCAGACCCACCTCCCAACCCCGAGGGGACCCGACAGGCCCGAAGGAATAGAA
GAAGAAGGTGGAGAGAGAGACAGAGACAGATCCATTCGATTAGTGAACGGATCTCGACGG
TATCGGTTAACTTTTAAAAGAAAAGGGGGGATTGGGGGGTACAGTGCAGGGGAAAGAATA
GTAGACATAATAGCAACAGACATACAAACTAAAGAATTACAAAAACAAATTACAAAAATTCAA
AATTTTCCGATCACGAGACTAGCCTCGAGAAGCTTGATATCGAATTCCCACGGGGTTGGGG
TTGCGCCTTTTCCAAGGCAGCCCTGGGTTTGCGCAGGGACGCGGCTGCTCTGGGCGTGG
TTCCGGGAAACGCAGCGGCGCCGACCCTGGGTCTCGCACATTCTTCACGTCCGTTCGCAG
CGTCACCCGGATCTTCGCCGCTACCCTTGTGGGCCCCCGGCGACGCTTCCTGCTCCGC
CCCTAAGTCGGGAAGGTTCCTTGCGGTTCGCGGCGTGCCGGACGTGACAAACGGAAGCC
GCACGTCTCACTAGTACCCTCGCAGACGGACAGCGCCAGGGAGCAATGGCAGCGCGCCG
ACCGCGATGGGCTGTGGCCAATAGCGGCTGCTCAGCGGGGCGCGCCGAGAGCAGCGGC
CGGGAAGGGGCGGTGCGGGAGGCGGGGTGTGGGCGGTAGTGTGGGCCCTGTTCCTGC
CCGCGCGGTGTTCCGCATTCTGCAAGCCTCCGGAGCGCACGTCGGCAGTCGGCTCCCTC
GTTGACCGAATCACCGACCTCTCTCCCCAGGGGGATCCACCGGTCCGCCAAGGCCATGTC
CGACTCGTGGGTCCCGAACTCCGCCTCGGGCCAGGACCCAGGGGGCCGCCGGAGGGCC
TGGGCCGAGCTGCTGGCGGGAAGGGTCAAGAGGGAAAAATATAATCCTGAAAGGGCACA
GAAATTAAAGGAATCAGCTGTGCGCCTCCTGCGAAGCCATCAGGACCTGAATGCCCTTTTG
CTTGAGGTAGAAGGTCCACTGTGTAAAAAATTGTCTCTCAGCAAAGTGATTGACTGTGACA
GTTCTGAGGCCTATGCTAATCATTCTAGTTCATTTATAGGCTCTGCTTTGCAGGATCAAGCC
TCAAGGCTGGGGGTTCCCGTGGGTATTCTCTCAGCCGGGATGGTTGCCTCTAGCGTGGGA
CAGATCTGCACGGCTCCAGCGGAGACCAGTCACCCTGTGCTGCTGACTGTGGAGCAGAG
AAAGAAGCTGTCTTCCCTGTTAGAGTTTGCTCAGTATTTATTGGCACACAGTATGTTCTCCC
GTCTTTCCTTCTGTCAAGAATTATGGAAAATACAGAGTTCTTTGTTGCTTGAAGCGGTGTGG
CATCTTCACGTACAAGGCATTGTGAGCCTGCAAGAGCTGCTGGAAAGCCATCCCGACATG
CATGCTGTGGGATCGTGGCTCTTCAGGAATCTGTGCTGCCTTTGTAACAGATGGAAGCAT
CCTGCCAGCATGCTGACGTCGCCAGGGCCATGCTTTCTGATTTTGTTCAAATGTTTGTTTT
GAGGGGATTTCAGAAAAACTCAGATCTGAGAAGAACTGTGGAGCCTGAAAAAATGCCGCA
GGTCACGGTTGATGTACTGCAGAGAATGCTGATTTTTGCACTTGACGCTTTGGCTGCTGGA
GTACAGGAGGAGTCCTCCACTCACAAGATCGTGAGGTGCTGGTTCGGAGTGTTCAGTGGA
CACACGCTTGGCAGTGTAATTTCCACAGATCCTCTGAAGAGGTTCTTCAGTCATACCCTGA
CTCAGATACTCACTCACAGCCCTGTGCTGAAAGCATCTGATGCTGTTCAGATGCAGAGAGA
GTGGAGCTTTGCGCGGACACACCCTCTGCTCACCTCACTGTACCGCAGGCTCTTTGTGAT
GCTGAGTGCAGAGGAGTTGGTTGGCCATTTGCAAGAAGTTCTGGAAACGCAGGAGGTTCA

FIG. 19 cont'd

```
CTGGCAGAGAGTGCTCTCCTTTGTGTCTGCCCTGGTTGTCTGCTTTCCAGAAGCGCAGCA
GCTGCTTGAAGACTGGGTGGCGCGTTTGATGGCCCAGGCATTCGAGAGCTGCCAGCTGG
ACAGCATGGTCACTGCGTTCCTGGTTGTGCGCCAGGCAGCACTGGAGGGCCCCTCTGCG
TTCCTGTCATATGCAGACTGGTTCAAGGCCTCCTTTGGGAGCACACGAGGCTACCATGGCT
GCAGCAAGAAGGCCCTGGTCTTCCTGTTTACGTTCTTGTCAGAACTCGTGCCTTTTGAGTC
TCCCCGGTACCTGCAGGTGCACATTCTCCACCCACCCCTGGTTCCCAGCAAGTACCGCTC
CCTCCTCACAGACTACATCTCATTGGCCAAGACACGGCTGGCCGACCTCAAGGTTTCTATA
GAAAACATGGGACTCTACGAGGATTTGTCATCAGCTGGGGACATTACTGAGCCCCACAGC
CAAGCTCTTCAGGATGTTGAAAAGGCCATCATGGTGTTTGAGCATACGGGGAACATCCCAG
TCACCGTCATGGAGGCCAGCATATTCAGGAGGCCTTACTACGTGTCCCACTTCCTCCCCG
CCCTGCTCACACCTCGAGTGCTCCCCAAAGTCCCTGACTCCCGTGTGGCGTTTATAGAGT
CTCTGAAGAGAGCAGATAAAATCCCCCCATCTCTGTACTCCACCTACTGCCAGGCCTGCTC
TGCTGCTGAAGAGAAGCCAGAAGATGCAGCCCTGGGAGTGAGGGCAGAACCCAACTCTG
CTGAGGAGCCCCTGGGACAGCTCACAGCTGCACTGGGAGAGCTGAGAGCCTCCATGACA
GACCCCAGCCAGCGTGATGTTATATCGGCACAGGTGGCAGTGATTTCTGAAAGACTGAGG
GCTGTCCTGGGCCACAATGAGGATGACAGCAGCGTTGAGATATCAAAGATTCAGCTCAGC
ATCAACACGCCGAGACTGGAGCCACGGGAACACATTGCTGTGGACCTCCTGCTGACGTCT
TTCTGTCAGAACCTGATGGCTGCCTCCAGTGTCGCTCCCCGGAGAGGCAGGGTCCCTGG
GCTGCCCTCTTCGTGAGGACCATGTGTGGACGTGTGCTCCCTGCAGTGCTCACCCGGCTC
TGCCAGCTGCTCCGTCACCAGGGCCCGAGCCTGAGTGCCCCACATGTGCTGGGGTTGGC
TGCCCTGGCCGTGCACCTGGGTGAGTCCAGGTCTGCGCTCCCAGAGGTGGATGTGGGTC
CTCCTGCACCTGGTGCTGGCCTTCCTGTCCCTGCGCTCTTTGACAGCCTCCTGACCTGTA
GGACGAGGGATTCCTTGTTCTTCTGCCTGAAATTTTGTACAGCAGCAATTTCTTACTCTCTC
TGCAAGTTTTCTTCCCAGTCACGAGATACTTTGTGCAGCTGCTTATCTCCAGGCCTTATTAA
AAAGTTTCAGTTCCTCATGTTCAGATTGTTCTCAGAGGCCCGACAGCCTCTTTCTGAGGAG
GACGTAGCCAGCCTTTCCTGGAGACCCTTGCACCTTCCTTCTGCAGACTGGCAGAGAGCT
GCCCTCTCTCTGGACACACAGAACCTTCCGAGAGGTGTTGAAAGAGGAAGATGTTCACT
TAACTTACCAAGACTGGTTACACCTGGAGCTGGAAATTCAACCTGAAGCTGATGCTCTTTC
AGATACTGAACGGCAGGACTTCCACCAGTGGGCGATCCATGAGCACTTTCTCCCTGAGTC
CTCGGCTTCAGGGGGCTGTGACGGAGACCTGCAGGCTGCGTGTACCATTCTTGTCAACGC
ACTGATGGATTTCCACCAAAGCTCAAGGAGTTATGACCACTCAGAAAATTCTGATTTGGTCT
TTGGTGGCCGCACAGGAAATGAGGATATTATTTCCAGATTGCAGGAGATGGTAGCTGACCT
GGAGCTGCAGCAAGACCTCATAGTGCCTCTCGGCCACACCCCTTCCCAGGAGCACTTCCT
CTTTGAGATTTTCCGCAGACGGCTCCAGGCTCTGACAAGCGGGTGGAGCGTGGCTGCCAG
CCTTCAGAGACAGAGGGAGCTGCTAATGTACAAACGGATCCTCCTCCGCCTGCCTTCGTC
TGTCCTCTGCGGCAGCAGCTTCCAGGCAGAACAGCCCATCACTGCCAGATGCGAGCAGTT
CTTCCACTTGGTCAACTCTGAGATGAGAAACTTCTGCTCCCACGGAGGTGCCCTGACACAG
GACATCACTGCCCACTTCTTCAGGGGCCTCCTGAACGCCTGTCTGCGGAGCAGAGACCCC
TCCCTGATGGTCGACTTCATACTGGCCAAGTGCCAGACGAAATGCCCCTTAATTTTGACCT
CTGCTCTGGTGTGGTGGCCGAGCCTGGAGCCTGTGCTGCTCTGCCGGTGGAGGAGACAC
TGCCAGAGCCCGCTGCCCCGGGAACTGCAGAAGCTACAAGAAGGCCGGCAGTTTGCCAG
CGATTTCCTCTCCCCTGAGGCTGCCTCCCCAGCACCCAACCCGGACTGGCTCTCAGCTGC
TGCACTGCACTTTGCGATTCAACAAGTCAGGGAAGAAAACATCAGGAAGCAGCTAAAGAAG
CTGGACTGCGAGAGAGGGAGCTATTGGTTTTCCTTTTCTTCTTCTCCTTGATGGGCCTGC
TGTCGTCACATCTGACCTCAAATAGCACCACAGACCTGCCAAAGGCTTTCCACGTTTGTGC
AGCAATCCTCGAGTGTTTAGAGAAGAGGAAGATATCCTGGCTGGCACTCTTTCAGTTGACA
GAGAGTGACCTCAGGCTGGGGCGGCTCCTCCTCCGTGTGGCCCCGGATCAGCACACCAG
GCTGCTGCCTTTCGCTTTTTACAGTCTTCTCTCCTACTTCCATGAAGACGCGGCCATCAGG
GAAGAGGCCTTCCTGCATGTTGCTGTGGACATGTACTTGAAGCTGGTCCAGCTCTTCGTG
```

FIG. 19 cont'd

GCTGGGGATACAAGCACAGTTTCACCTCCAGCTGGCAGGAGCCTGGAGCTCAAGGGTCA
GGGCAACCCCGTGGAACTGATAACAAAAGCTCGTCTTTTTCTGCTGCAGTTAATACCTCGG
TGCCCGAAAAAGAGCTTCTCACACGTGGCAGAGCTGCTGGCTGATCGTGGGGACTGCGAC
CCAGAGGTGAGCGCCGCCCTCCAGAGCAGACAGCAGGCTGCCCCTGACGCTGACCTGTC
CCAGGAGCCTCATCTCTTCTGACGGGACCTGCGTTTAAACGAATTCGAGCATCTTACCGCC
ATTTATTCCCATATTTGTTCTGTTTTTCTTGATTTGGGTATACATTTAAATGTTAATAAAACAA
AATGGTGGGGCAATCATTTACATTTTTAGGGATATGTAATTACTAGTTCAGGTGTATTGCCA
CAAGACAAACATGTTAAGAAACTTTCCCGTTATTTACGCTCTGTTCCTGTTAATCAACCTCT
GGATTACAAAATTTGTGAAAGATTGACTGATATTCTTAACTATGTTGCTCCTTTTACGCTGTG
TGGATATGCTGCTTTATAGCCTCTGTATCTAGCTATTGCTTCCCGTACGGCTTTCGTTTTCT
CCTCCTTGTATAAATCCTGGTTGCTGTCTCTTTTAGAGGAGTTGTGGCCCGTTGTCCGTCA
ACGTGGCGTGGTGTGCTCTGTGTTTGCTGACGCAACCCCCACTGGCTGGGGCATTGCCAC
CACCTGTCAACTCCTTTCTGGGACTTTCGCTTTCCCCCTCCCGATCGCCACGGCAGAACTC
ATCGCCGCCTGCCTTGCCCGCTGCTGGACAGGGGCTAGGTTGCTGGGCACTGATAATTCC
GTGGTGTTGTCCGAAGTCGACCTCGAGGGGGGGCCCGGTACCTTTAAGACCAATGACTTA
CAAGGCAGCTGTAGATCTTAGCCACTTTTTAAAAGAAAAGGGGGGACTGGAAGGGCTAATT
CACTCCCAACGAAGACAAGATCTGCTTTTTGCTTGTACTGGGTCTCTCTGGTTAGACCAGA
TCTGAGCCTGGGAGCTCTCTGGCTAACTAGGGAACCCACTGCTTAAGCCTCAATAAAGCTT
GCCTTGAGTGCTTCAAGTAGTGTGTGCCCGTCTGTTGTGTGACTCTGGTAACTAGAGATCC
CTCAGACCCTTTTAGTCAGTGTGGAAAATCTCTAGCAGTAGTAGTTCATGTCATCTTATTAT
TCAGTATTTATAACTTGCAAAGAAATGAATATCAGAGAGTGAGAGGAACTTGTTTATTGCAG
CTTATAATGGTTACAAATAAAGCAATAGCATCACAAATTTCACAAATAAAGCATTTTTTCAC
TGCATTCTAGTTGTGGTTTGTCCAAACTCATCAATGTATCTTATCATGTCTGGCTCTAGCTAT
CCCGCCCCTAACTCCGCCCAGTTCCGCCCATTCTCCGCCCCATGGCTGACTAATTTTTTTT
ATTTATGCAGAGGCCGAGGCCGCCTCGGCCTCTGAGCTATTCCAGAAGTAGTGAGGAGGC
TTTTTTGGAGGCCTAGGCTTTTGCGTCGAGACGTACCCAATTCGCCCTATAGTGAGTCGTA
TTACGCGCGCTCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGCGCGACGCGC
CCTGTAGCGGCGCATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGT
TCCAAACTGGAACAACACTCAACCCTATCTCGGTCTATTCTTTTGATTTATAAGGGATTTTG
CCGATTTCGGCCTATTGGTTAAAAAATGAGCTGATTTAACAAAAATTTAACGCGAATTTTAA
CAAAATATTAACGTTTACAATTTCC (SEQ ID NO: 17)

FIG. 20

Destination Plasmid
CAGGTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAAAAG
GAAGAGTATGAGTATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCG
GAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACAC
GACGGGGAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATTGATTTAAA
ACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCT
TCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAAC
GCGGCCTTTTTACGGTTCCTGGCCTTTTGCTGGCCTTTTGCTCACATGTTCTTTCCTGCGTT
ATCCCCTGATTCTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCGCCCAATACG
CAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGC
ACCCCAGGCTTTACACTTTATGCTTCCGGCTCGTATGTTGTGTGGAATTGTGAGCGGATAA
CAATTTCACACAGGAAACAGCTATGACCATGATTACGCCAAGCGCGCAATTAACCCTCACT
AAAGGGAACAAAAGCTGGAGCTGCAAGCTTAATGTAGTCTTATGCAATACTCTTGTAGTCTT
GCAACATGGTAACGATGAGTTAGCAACATGCCTTACAAGGAGAGAAAAAGCACCGTGCAT
GCCGATTGGTGGAAGTAAGGTGGTACGATCGTGCCTTATTAGGAAGGCAACAGACGGGTC
TGACATGGATTGGACGAACCACTGAATTGCCGCATTGCAGAGATATTGTATTTAAGTGCCT
AGCTCGATACAATAAACGGGTCTCTCTGGTTAGACCAGATCTGAGCCTGGGAGCTCTCTG
GCTAACTAGGGAACCCACTGCTTAAGCCTCAATAAAGCTTGCCTTGAGTGCTTCAAGTAGT
GTGTGCCCGTCTGTTGTGTGACTCTGGTAACTAGAGATCCCTCAGACCCTTTTAGTCAGTG
TGGAAAATCTCTAGCAGTGGCGCCCGAACAGGGACCTGAAAGCGAAAGGGAAACCAGAG
CTCTCTCGACGCAGGACTCGGCTTGCTGAAGCGCGCACGGCAAGAGGCGAGGGGCGGC
GACTGGTGAGTACGCCAAAAATTTTGACTAGCGGAGGCTAGAAGGAGAGAGATGGGTGCG
AGAGCGTCAGTATTAAGCGGGGGAGAATTAGATCGCGATGGGAAAAAATTCGGTTAAGGC
CAGGGGGAAAGAAAAAATATAAATTAAAACATATAGTATGGGCAAGCAGGGAGCTAGAACG
ATTCGCAGTTAATCCTGGCCTGTTAGAAACATCAGAAGGCTGTAGACAAATACTGGGACAG

FIG. 20 cont'd

CTACAACCATCCCTTCAGACAGGATCAGAAGAACTTAGATCATTATATAATACAGTAGCAAC
CCTCTATTGTGTGCATCAAAGGATAGAGATAAAAGACACCAAGGAAGCTTTAGACAAGATA
GAGGAAGAGCAAAACAAAAGTAAGACCACCGCACAGCAAGCGGCCGCTGATCTTCAGACC
TGGAGGAGGAGATATGAGGGACAATTGGAGAAGTGAATTATATAAATATAAAGTAGTAAAA
ATTGAACCATTAGGAGTAGCACCCACCAAGGCAAAGAGAAGAGTGGTGCAGAGAGAAAAA
AGAGCAGTGGGAATAGGAGCTTTGTTCCTTGGGTTCTTGGGAGCAGCAGGAAGCACTATG
GGCGCAGCCTCAATGACGCTGACGGTACAGGCCAGACAATTATTGTCTGGTATAGTGCAG
CAGCAGAACAATTTGCTGAGGGCTATTGAGGCGCAACAGCATCTGTTGCAACTCACAGTCT
GGGGCATCAAGCAGCTCCAGGCAAGAATCCTGGCTGTGGAAAGATACCTAAAGGATCAAC
AGCTCCTGGGGATTTGGGGTTGCTCTGGAAAACTCATTTGCACCACTGCTGTGCCTTGGAA
TGCTAGTTGGAGTAATAAATCTCTGGAACAGATTGGAATCACACGACCTGGATGGAGTGGG
ACAGAGAAATTAACAATTACACAAGCTTAATACACTCCTTAATTGAAGAATCGCAAAACCAG
CAAGAAAAGAATGAACAAGAATTATTGGAATTAGATAAATGGGCAAGTTTGTGGAATTGGTT
TAACATAACAAATTGGCTGTGGTATATAAAATTATTCATAATGATAGTAGGAGGCTTGGTAG
GTTTAAGAATAGTTTTTGCTGTACTTTCTATAGTGAATAGAGTTAGGCAGGGATATTCACCA
TTATCGTTTCAGACCCACCTCCCAACCCCGAGGGGACCCGACAGGCCCGAAGGAATAGAA
GAAGAAGGTGGAGAGAGAGACAGAGACAGATCCATTCGATTAGTGAACGGATCTCGACGG
TATCGGTTAACTTTTAAAAGAAAAGGGGGGATTGGGGGGTACAGTGCAGGGGAAAGAATA
GTAGACATAATAGCAACAGACATACAAACTAAAGAATTACAAAAACAAATTACAAAAATTCAA
AATTTTCCGATCACGAGACTAGCCTCGAGAAGCTTGATATCGAATTCCCACGGGGTTGGGG
TTGCGCCTTTTCCAAGGCAGCCCTGGGTTTGCGCAGGGACGCGGCTGCTCTGGGCGTGG
TTCCGGGAAACGCAGCGGCGCCGACCCTGGGTCTCGCACATTCTTCACGTCCGTTCGCAG
CGTCACCCGGATCTTCGCCGCTACCCTTGTGGGCCCCCGGCGACGCTTCCTGCTCCGC
CCCTAAGTCGGGAAGGTTCCTTGCGGTTCGCGGCGTGCCGGACGTGACAAACGGAAGCC
GCACGTCTCACTAGTACCCTCGCAGACGGACAGCGCCAGGGAGCAATGGCAGCGCGCCG
ACCGCGATGGGCTGTGGCCAATAGCGGCTGCTCAGCGGGGCGCGCCGAGAGCAGCGGC
CGGGAAGGGGCGGTGCGGGAGGCGGGGTGTGGGCGGTAGTGTGGGCCCTGTTCCTGC
CCGCGCGGTGTTCCGCATTCTGCAAGCCTCCGGAGCGCACGTCGGCAGTCGGCTCCCTC
GTTGACCGAATCACCGACCTCTCTCCCCAGGGGGATCCACCGGTCCGCCAAGGCC (SEQ
ID NO: 18) [insert therapeutic gene here]
CGGGACCTGCGTTTAAACGAATTCGAGCATCTTACCGCCATTTATTCCCATATTTGTTCTGT
TTTTCTTGATTTGGGTATACATTTAAATGTTAATAAAACAAAATGGTGGGGCAATCATTTACA
TTTTTAGGGATATGTAATTACTAGTTCAGGTGTATTGCCACAAGACAAACATGTTAAGAAAC
TTTCCCGTTATTTACGCTCTGTTCCTGTTAATCAACCTCTGGATTACAAAATTTGTGAAAGAT
TGACTGATATTCTTAACTATGTTGCTCCTTTTACGCTGTGTGGATATGCTGCTTTATAGCCT
CTGTATCTAGCTATTGCTTCCCGTACGGCTTTCGTTTTCTCCTCCTTGTATAAATCCTGGTT
GCTGTCTCTTTTAGAGGAGTTGTGGCCCGTTGTCCGTCAACGTGGCGTGGTGTGCTCTGT
GTTTGCTGACGCAACCCCCACTGGCTGGGGCATTGCCACCACCTGTCAACTCCTTTCTGG
GACTTTCGCTTTCCCCCTCCCGATCGCCACGGCAGAACTCATCGCCGCCTGCCTTGCCCG
CTGCTGGACAGGGGCTAGGTTGCTGGGCACTGATAATTCCGTGGTGTTGTCCGAAGTCGA
CCTCGAGGGGGGGCCCGGTACCTTTAAGACCAATGACTTACAAGGCAGCTGTAGATCTTA
GCCACTTTTTAAAAGAAAAGGGGGGACTGGAAGGGCTAATTCACTCCCAACGAAGACAAG
ATCTGCTTTTTGCTTGTACTGGGTCTCTCTGGTTAGACCAGATCTGAGCCTGGGAGCTCTC
TGGCTAACTAGGGAACCCACTGCTTAAGCCTCAATAAAGCTTGCCTTGAGTGCTTCAAGTA
GTGTGTGCCCGTCTGTTGTGTGACTCTGGTAACTAGAGATCCCTCAGACCCTTTTAGTCAG
TGTGGAAAATCTCTAGCAGTAGTAGTTCATGTCATCTTATTATTCAGTATTTATAACTTGCAA
AGAAATGAATATCAGAGAGTGAGAGGAACTTGTTTATTGCAGCTTATAATGGTTACAAATAA
AGCAATAGCATCACAAATTTCACAAATAAAGCATTTTTTTCACTGCATTCTAGTTGTGGTTTG
TCCAAACTCATCAATGTATCTTATCATGTCTGGCTCTAGCTATCCCGCCCCTAACTCCGCCC

FIG. 20 cont'd

AGTTCCGCCCATTCTCCGCCCCATGGCTGACTAATTTTTTTATTTATGCAGAGGCCGAGG
CCGCCTCGGCCTCTGAGCTATTCCAGAAGTAGTGAGGAGGCTTTTTGGAGGCCTAGGCT
TTTGCGTCGAGACGTACCCAATTCGCCCTATAGTGAGTCGTATTACGCGCGCTCACTGGCC
GTCGTTTTACAACGTCGTGACTGGGAAAACCCTGGCGTTACCCAACTTAATCGCCTTGCAG
CACATCCCCCTTTCGCCAGCTGGCGTAATAGCGAAGAGGCCCGCACCGATCGCCCTTCCC
AACAGTTGCGCAGCCTGAATGGCGAATGGCGCGACGCGCCCTGTAGCGGCGCATTAAGC
GCGGCGGGTGTGGTGGTTACGCGCAGCGTGACCGCTACACTTGCCAGCGCCCTAGCGCC
CGCTCCTTTCGCTTTCTTCCCTTCCTTTCTCGCCACGTTCGCCGGCTTTCCCCGTCAAGCT
CTAAATCGGGGGCTCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTTTCGCCC
TTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGTTTACAATTT
CC (SEQ ID NO: 19)

>Homo sapiens FancA cds
ATGTCCGACTCGTGGGTCCCGAACTCCGCCTCGGGCCAGGACCCAGGGGGCCGCCGGA
GGGCCTGGGCCGAGCTGCTGGCGGGAAGGGTCAAGAGGGAAAAATATAATCCTGAAAGG
GCACAGAAATTAAAGGAATCAGCTGTGCGCCTCCTGCGAAGCCATCAGGACCTGAATGCC
CTTTTGCTTGAGGTAGAAGGTCCACTGTGTAAAAATTGTCTCTCAGCAAAGTGATTGACTG
TGACAGTTCTGAGGCCTATGCTAATCATTCTAGTTCATTTATAGGCTCTGCTTTGCAGGATC
AAGCCTCAAGGCTGGGGGTTCCCGTGGGTATTCTCTCAGCCGGGATGGTTGCCTCTAGCG
TGGGACAGATCTGCACGGCTCCAGCGGAGACCAGTCACCCTGTGCTGCTGACTGTGGAG
CAGAGAAAGAAGCTGTCTTCCCTGTTAGAGTTTGCTCAGTATTTATTGGCACACAGTATGTT
CTCCCGTCTTTCCTTCTGTCAAGAATTATGGAAAATACAGAGTTCTTTGTTGCTTGAAGCGG
TGTGGCATCTTCACGTACAAGGCATTGTGAGCCTGCAAGAGCTGCTGGAAAGCCATCCCG
ACATGCATGCTGTGGGATCGTGGCTCTTCAGGAATCTGTGCTGCCTTTGTGAACAGATGGA
AGCATCCTGCCAGCATGCTGACGTCGCCAGGGCCATGCTTTCTGATTTTGTTCAAATGTTT
GTTTTGAGGGGATTTCAGAAAAACTCAGATCTGAGAAGAACTGTGGAGCCTGAAAAAATGC
CGCAGGTCACGGTTGATGTACTGCAGAGAATGCTGATTTTTGCACTTGACGCTTTGGCTGC
TGGAGTACAGGAGGAGTCCTCCACTCACAAGATCGTGAGGTGCTGGTTCGGAGTGTTCAG
TGGACACACGCTTGGCAGTGTAATTTCCACAGATCCTCTGAAGAGGTTCTTCAGTCATACC
CTGACTCAGATACTCACTCACAGCCCTGTGCTGAAAGCATCTGATGCTGTTCAGATGCAGA
GAGAGTGGAGCTTTGCGCGGACACACCCTCTGCTCACCTCACTGTACCGCAGGCTCTTTG
TGATGCTGAGTGCAGAGGAGTTGGTTGGCCATTTGCAAGAAGTTCTGGAAACGCAGGAGG
TTCACTGGCAGAGAGTGCTCTCCTTTGTGTCTGCCCTGGTTGTCTGCTTTCCAGAAGCGCA
GCAGCTGCTTGAAGACTGGGTGGCGCGTTTGATGGCCCAGGCATTCGAGAGCTGCCAGC
TGGACAGCATGGTCACTGCGTTCCTGGTTGTGCGCCAGGCAGCACTGGAGGGCCCCTCT
GCGTTCCTGTCATATGCAGACTGGTTCAAGGCCTCCTTTGGGAGCACACGAGGCTACCAT
GGCTGCAGCAAGAAGGCCCTGGTCTTCCTGTTTACGTTCTTGTCAGAACTCGTGCCTTTG
AGTCTCCCCGGTACCTGCAGGTGCACATTCTCCACCCACCCCTGGTTCCCAGCAAGTACC
GCTCCCTCCTCACAGACTACATCTCATTGGCCAAGACACGGCTGGCCGACCTCAAGGTTT
CTATAGAAAACATGGGACTCTACGAGGATTTGTCATCAGCTGGGGACATTACTGAGCCCCA
CAGCCAAGCTCTTCAGGATGTTGAAAAGGCCATCATGGTGTTTGAGCATACGGGGAACATC
CCAGTCACCGTCATGGAGGCCAGCATATTCAGGAGGCCTTACTACGTGTCCCACTTCCTC
CCCGCCCTGCTCACACCTCGAGTGCTCCCCAAAGTCCCTGACTCCCGTGTGGCGTTTATA
GAGTCTCTGAAGAGAGCAGATAAAATCCCCCATCTCTGTACTCCACCTACTGCCAGGCCT
GCTCTGCTGCTGAAGAGAAGCCAGAAGATGCAGCCCTGGGAGTGAGGGCAGAACCCAAC
TCTGCTGAGGAGCCCCTGGGACAGCTCACAGCTGCACTGGGAGAGCTGAGAGCCTCCAT

FIG. 20 cont'd

```
GACAGACCCCAGCCAGCGTGATGTTATATCGGCACAGGTGGCAGTGATTTCTGAAAGACT
GAGGGCTGTCCTGGGCCACAATGAGGATGACAGCAGCGTTGAGATATCAAAGATTCAGCT
CAGCATCAACACGCCGAGACTGGAGCCACGGGAACACATTGCTGTGGACCTCCTGCTGAC
GTCTTTCTGTCAGAACCTGATGGCTGCCTCCAGTGTCGCTCCCCGGAGAGGCAGGGTCC
CTGGGCTGCCCTCTTCGTGAGGACCATGTGTGGACGTGTGCTCCCTGCAGTGCTCACCCG
GCTCTGCCAGCTGCTCCGTCACCAGGGCCCGAGCCTGAGTGCCCCACATGTGCTGGGGT
TGGCTGCCCTGGCCGTGCACCTGGGTGAGTCCAGGTCTGCGCTCCCAGAGGTGGATGTG
GGTCCTCCTGCACCTGGTGCTGGCCTTCCTGTCCCTGCGCTCTTTGACAGCCTCCTGACC
TGTAGGACGAGGGATTCCTTGTTCTTCTGCCTGAAATTTTGTACAGCAGCAATTTCTTACTC
TCTCTGCAAGTTTTCTTCCCAGTCACGAGATACTTTGTGCAGCTGCTTATCTCCAGGCCTTA
TTAAAAAGTTTCAGTTCCTCATGTTCAGATTGTTCTCAGAGGCCCGACAGCCTCTTTCTGAG
GAGGACGTAGCCAGCCTTTCCTGGAGACCCTTGCACCTTCCTTCTGCAGACTGGCAGAGA
GCTGCCCTCTCTCTGGACACACAGAACCTTCCGAGAGGTGTTGAAAGAGGAAGATGTT
CACTTAACTTACCAAGACTGGTTACACCTGGAGCTGGAAATTCAACCTGAAGCTGATGCTC
TTTCAGATACTGAACGGCAGGACTTCCACCAGTGGGCGATCCATGAGCACTTTCTCCCTGA
GTCCTCGGCTTCAGGGGGCTGTGACGGAGACCTGCAGGCTGCGTGTACCATTCTTGTCAA
CGCACTGATGGATTTCCACCAAAGCTCAAGGAGTTATGACCACTCAGAAAATTCTGATTTG
GTCTTTGGTGGCCGCACAGGAAATGAGGATATTATTTCCAGATTGCAGGAGATGGTAGCTG
ACCTGGAGCTGCAGCAAGACCTCATAGTGCCTCTCGGCCACACCCCTTCCCAGGAGCACT
TCCTCTTTGAGATTTTCCGCAGACGGCTCCAGGCTCTGACAAGCGGGTGGAGCGTGGCTG
CCAGCCTTCAGAGACAGAGGGAGCTGCTAATGTACAAACGGATCCTCCTCCGCCTGCCTT
CGTCTGTCCTCTGCGGCAGCAGCTTCCAGGCAGAACAGCCCATCACTGCCAGATGCGAGC
AGTTCTTCCACTTGGTCAACTCTGAGATGAGAAACTTCTGCTCCCACGGAGGTGCCCTGAC
ACAGGACATCACTGCCCACTTCTTCAGGGGCCTCCTGAACGCCTGTCTGCGGAGCAGAGA
CCCCTCCCTGATGGTCGACTTCATACTGGCCAAGTGCCAGACGAAATGCCCCTTAATTTTG
ACCTCTGCTCTGGTGTGGTGGCCGAGCCTGGAGCCTGTGCTGCTCTGCCGGTGGAGGAG
ACACTGCCAGAGCCCGCTGCCCCGGGAACTGCAGAAGCTACAAGAAGGCCGGCAGTTTG
CCAGCGATTTCCTCTCCCCTGAGGCTGCCTCCCCAGCACCCAACCCGGACTGGCTCTCAG
CTGCTGCACTGCACTTTGCGATTCAACAAGTCAGGGAAGAAAACATCAGGAAGCAGCTAAA
GAAGCTGGACTGCGAGAGAGGAGCTATTGGTTTTCCTTTTCTTCTTCTCCTTGATGGGC
CTGCTGTCGTCACATCTGACCTCAAATAGCACCACAGACCTGCCAAAGGCTTTCCACGTTT
GTGCAGCAATCCTCGAGTGTTTAGAGAAGAGGAAGATATCCTGGCTGGCACTCTTTCAGTT
GACAGAGAGTGACCTCAGGCTGGGGCGGCTCCTCCTCCGTGTGGCCCCGGATCAGCACA
CCAGGCTGCTGCCTTTCGCTTTTACAGTCTTCTCTCCTACTTCCATGAAGACGCGGCCAT
CAGGGAAGAGGCCTTCCTGCATGTTGCTGTGGACATGTACTTGAAGCTGGTCCAGCTCTT
CGTGGCTGGGGATACAAGCACAGTTTCACCTCCAGCTGGCAGGAGCCTGGAGCTCAAGG
GTCAGGGCAACCCCGTGGAACTGATAACAAAAGCTCGTCTTTTCTGCTGCAGTTAATACC
TCGGTGCCCGAAAAAGAGCTTCTCACACGTGGCAGAGCTGCTGGCTGATCGTGGGGACTG
CGACCCAGAGGTGAGCGCCGCCCTCCAGAGCAGACAGCAGGCTGCCCCTGACGCTGACC
TGTCCCAGGAGCCTCATCTCTTCTGA  (SEQ ID NO: 117)
```

>Homo sapiens FANCC cds (nucleotides 263-1939 of NCBI Reference Sequence NM_000136.2)
```
ATGGCTCAAGATTCAGTAGATCTTTCTTGTGATTATCAGTTTTGGATGCAGAAGCTTTCTGT
ATGGGATCAGGCTTCCACTTTGGAAACCCAGCAAGACACCTGTCTTCACGTGGCTCAGTTC
CAGGAGTTCCTAAGGAAGATGTATGAAGCCTTGAAAGAGATGGATTCTAATACAGTCATTG
AAAGATTCCCCACAATTGGTCAACTGTTGGCAAAAGCTTGTTGGAATCCTTTTATTTTAGCA
TATGATGAAAGCCAAAAAATTCTAATATGGTGCTTATGTTGTCTAATTAACAAAGAACCACA
GAATTCTGGACAATCAAAACTTAACTCCTGGATACAGGGTGTATTATCTCATATACTTTCAG
```

FIG. 20 cont'd

CACTCAGATTTGATAAAGAAGTTGCTCTTTTCACTCAAGGTCTTGGGTATGCACCTATAGAT
TACTATCCTGGTTTGCTTAAAAATATGGTTTTATCATTAGCGTCTGAACTCAGAGAGAATCAT
CTTAATGGATTTAACACTCAAAGGCGAATGGCTCCCGAGCGAGTGGCGTCCCTGTCACGA
GTTTGTGTCCCACTTATTACCCTGACAGATGTTGACCCCTGGTGGAGGCTCTCCTCATCT
GTCATGGACGTGAACCTCAGGAAATCCTCCAGCCAGAGTTCTTTGAGGCTGTAAACGAGG
CCATTTTGCTGAAGAAGATTTCTCTCCCCATGTCAGCTGTAGTCTGCCTCTGGCTTCGGCA
CCTTCCCAGCCTTGAAAAGCAATGCTGCATCTTTTTGAAAAGCTAATCTCCAGTGAGAGAA
ATTGTCTGAGAAGGATCGAATGCTTTATAAAGATTCATCGCTGCCTCAAGCAGCCTGCCA
CCCTGCCATATTCCGGGTTGTTGATGAGATGTTCAGGTGTGCACTCCTGGAAACCGATGG
GGCCCTGGAAATCATAGCCACTATTCAGGTGTTTACGCAGTGCTTTGTAGAAGCTCTGGAG
AAAGCAAGCAAGCAGCTGCGGTTTGCACTCAAGACCTACTTCCTTACACTTCTCCATCTCT
TGCCATGGTGCTGCTGCAAGACCCTCAAGATATCCCTCGGGGACACTGGCTCCAGACACT
GAAGCATATTTCTGAACTGCTCAGAGAAGCAGTTGAAGACCAGACTCATGGGTCCTGCGG
AGGTCCCTTTGAGAGCTGGTTCCTGTTCATTCACTTCGGAGGATGGGCTGAGATGGTGGC
AGAGCAATTACTGATGTCGGCAGCCGAACCCCCACGGCCCTGCTGTGGCTCTTGGCCTT
CTACTACGGCCCCCGTGATGGGAGGCAGCAGAGAGCACAGACTATGGTCCAGGTGAAGG
CCGTGCTGGGCCACCTCCTGGCAATGTCCAGAAGCAGCAGCCTCTCAGCCCAGGACCTG
CAGACGGTAGCAGGACAGGGCACAGACACAGACCTCAGAGCTCCTGCACAACAGCTGATC
AGGCACCTTCTCCTCAACTTCCTGCTCTGGGCTCCTGGAGGCCACACGATCGCCTGGGAT
GTCATCACCCTGATGGCTCACACTGCTGAGATAACTCACGAGATCATTGGCTTTCTTGACC
AGACCTTGTACAGATGGAATCGTCTTGGCATTGAAAGCCCTAGATCAGAAAAACTGGCCCG
AGAGCTCCTTAAAGAGCTGCGAACTCAAGTCTAG (SEQ ID NO: 118)

>Homo sapiens FANCE cds (nucleotides 186-1796 of NCBI Reference Sequence NM_021922.2)
ATGGCGACACCGGACGCGGGGCTCCCTGGGGCTGAGGGCGTGGAGCCGGCGCCCTGGG
CGCAGCTGGAGGCCCCGCCCGCCTCCTGCTGCAGGCGCTGCAGGCGGGGCCTGAGGG
GGCGCGGCGCGGCCTGGGGGTGCTCCGGGCGCTGGGCAGCCGCGGCTGGGAGCCCTT
CGACTGGGGTCGCTTGCTCGAGGCCCTGTGCCGGGAGGAGCCGGTCGTGCAGGGGCCT
GACGGCCGTCTGGAGCTGAAACCACTGTTGCTGCGATTGCCCCGGATATGCCAGAGGAAC
CTGATGTCCCTGCTGATGGCCGTTCGGCCATCGCTGCCGGAAAGTGGGCTCCTCTCTGTG
CTGCAGATTGCCCAGCAGGACCTAGCCCTGACCCAGATGCCTGGCTCCGTGCCCTGGG
GGAATTGCTGCGAAGGGATTTGGGGGTGGGGACCTCCATGGAGGGAGCTTCTCCACTGT
CTGAAAGATGCCAGAGACAGCTCCAAAGTCTATGTAGGGGGCTGGGCCTGGGGGGCAGG
AGGTTGAAATCCCCCAGGCTCCAGACCCTGAAGAAGAGGAGAACAGGGACTCCCAGCA
GCCTGGGAAACGCAGAAAGGACTCAGAGGAAGAGGCTGCCAGTCCTGAGGGGAAGAGGG
TCCCCAAAAGATTACGGTGTTGGGAAGAGGAAGAAGATCATGAGAAGGAGAGACCCGAAC
ATAAGTCACTGGAATCCCTGGCAGATGGAGGAAGTGCATCTCCTATTAAGGACCAGCCTGT
CATGGCAGTTAAGACTGGCGAGGACGGTTCGAATCTGGATGATGCTAAAGGTCTGGCTGA
GAGTTTGGAGTTGCCCAAAGCTATCCAGGACCAGCTTCCCAGGCTGCAGCAGCTGCTGAA
GACCTTGGAGGAGGGGTTAGAGGGATTGGAGGATGCCCCCCAGTTGAGCTACAGCTTCT
TCACGAATGTAGTCCCAGCCAGATGGACTTGCTGTGTGCCCAGCTGCAGCTCCCTCAGCT
CTCAGACCTCGGTCTCCTGCGGCTCTGCACCTGGCTGCTGGCCCTTTCACCTGATCTCAG
CCTCAGCAATGCTACTGTGCTGACCAGAAGCCTCTTCTTGGACGGATCCTCTCCTTGACT
TCCTCAGCCTCCCGCCTGCTTACAACTGCCCTGACCTCCTTCTGTGCCAAATATACATACC
CTGTCTGCAGCGCCCTCCTTGACCCTGTGCTCCAGGCCCCAGGCACAGGTCCTGCTCAAA
CAGAGTTACTGTGTTGCCTTGTGAAGATGGAGTCCCTGGAGCCAGATGCACAGGTTCTAAT
GCTGGGACAGATCTTGGAGCTGCCCTGGAAGGAGGAAACTTTCTTGGTGTTGCAGTCACT
CCTAGAGCGGCAGGTGGAGATGACCCCTGAGAAGTTCAGTGTCTTAATGGAGAAGCTCTG

FIG. 20 cont'd

TAAAAAGGGGCTGGCAGCCACCACCTCCATGGCCTATGCCAAGCTCATGCTGACAGTGAT
GACCAAGTATCAGGCTAACATCACTGAGACCCAGAGGCTGGGCCTGGCTATGGCCCTAGA
ACCTAACACCACCTTCCTGAGGAAGTCCCTGAAGGCCGCCTTGAAACATTTGGGCCCCTG
A (SEQ ID NO: 119)

>Homo sapiens FANCF cds (nucleotides 32-1156 of NCBI Reference Sequence
NM_022725.3)
ATGGAATCCCTTCTGCAGCACCTGGATCGCTTTTCCGAGCTTCTGGCGGTCTCAAGCACTA
CCTACGTCAGCACCTGGGACCCCGCCACCGTGCGCCGGGCCTTGCAGTGGGCGCGCTAC
CTGCGCCACATCCATCGGCGCTTTGGTCGGCATGGCCCCATTCGCACGGCTCTGGAGCG
GCGGCTGCACAACCAGTGGAGGCAAGAGGGCGGCTTTGGGCGGGGTCCAGTTCCGGGAT
TAGCGAACTTCCAGGCCCTCGGTCACTGTGACGTCCTGCTCTCTGCGCCTGCTGGAGA
ACCGGGCCCTCGGGGATGCAGCTCGTTACCACCTGGTGCAGCAACTCTTTCCCGGCCCG
GGCGTCCGGGACGCCGATGAGGAGACACTCCAAGAGAGCCTGGCCCGCCTTGCCCGCC
GGCGGTCTGCGGTGCACATGCTGCGCTTCAATGGCTATAGAGAGAACCCAAATCTCCAGG
AGGACTCTCTGATGAAGACCCAGGCGGAGCTGCTGCTGGAGCGTCTGCAGGAGGTGGGG
AAGGCCGAAGCGGAGCGTCCCGCCAGGTTTCTCAGCAGCCTGTGGGAGCGCTTGCCTCA
GAACAACTTCCTGAAGGTGATAGCGGTGGCGCTGTTGCAGCCGCCTTTGTCTCGTCGGCC
CCAAGAAGAGTTGGAACCCGGCATCCACAAATCACCTGGAGAGGGGAGCCAAGTGCTAGT
CCACTGGCTTCTGGGGAATTCGGAAGTCTTTGCTGCCTTTTGTCGCGCCCTCCCAGCCGG
GCTTTTGACTTTAGTGACTAGCCGCCACCCAGCGCTGTCTCCTGTCTATCTGGGTCTGCTA
ACAGACTGGGGTCAACGTTTGCACTATGACCTTCAGAAAGGCATTTGGGTTGGAACTGAGT
CCCAAGATGTGCCCTGGGAGGAGTTGCACAATAGGTTTCAAAGCCTCTGTCAGGCCCCTC
CACCTCTGAAAGATAAAGTTCTAACTGCCCTGGAGACCTGTAAAGCGCAGGATGGAGATTT
TGAAGTACCTGGTCTTAGCATCTGGACAGACCTCTTATTAGCTCTTCGTAGTGGTGCATTTA
GGAAAAGACAAGTTTTGGGTCTCAGCGCAGGCCTCAGTTCTGTATAG (SEQ ID NO: 120)

>Homo sapiens FANCG cds (nucleotides 493-2361 of NCBI Reference Sequence
NM_004629.1)
ATGTCCCGCCAGACCACCTCTGTGGGCTCCAGCTGCCTGGACCTGTGGAGGGAAAAGAAT
GACCGGCTCGTTCGACAGGCCAAGGTGGCTCAGAACTCCGGTCTGACTCTGAGGCGACA
GCAGTTGGCTCAGGATGCACTGGAAGGGCTCAGAGGGCTCCTCCATAGTCTGCAAGGGCT
CCCTGCAGCTGTTCCTGTTCTTCCCTTGGAGCTGACTGTCACCTGCAACTTCATTATCCTG
AGGGCAAGCTTGGCCCAGGGTTTCACAGAGGATCAGGCCCAGGATATCCAGCGGAGCCT
AGAGAGAGTGCTGGAGACACAGGAGCAGCAGGGGCCCAGGTTGGAACAGGGGCTCAGG
GAGCTGTGGACTCTGTCCTTCGTGCTTCCTGCCTTCTGCCGGAGCTGCTGTCTGCCCTG
CACCGCCTGGTTGGCCTGCAGGCTGCCCTCTGGTTGAGTGCTGACCGTCTTGGGGACCT
GGCCTTGTTACTAGAGACCCTGAATGGCAGCCAGAGTGGAGCCTCTAAGGATCTGCTGTT
ACTTCTGAAAACTTGGAGTCCCCAGCTGAGGAATTAGATGCTCCATTGACCCTGCAGGAT
GCCCAGGGATTGAAGGATGTCCTCCTGACAGCATTTGCCTACCGCCAAGGTCTCCAGGAG
CTGATCACAGGGAACCCAGACAAGGCACTAAGCAGCCTTCATGAAGCGGCCTCAGGCCTG
TGTCCACGGCCTGTGTTGGTCCAGGTGTACACAGCACTGGGGTCCTGTCACCGTAAGATG
GGAAATCCACAGAGAGCACTGTTGTACTTGGTTGCAGCCCTGAAAGAGGGATCAGCCTGG
GGTCCTCCACTTCTGGAGGCCTCTAGGCTCTATCAGCAACTGGGGGACACAACAGCAGAG
CTGGAGAGTCTGGAGCTGCTAGTTGAGGCCTTGAATGTCCCATGCAGTTCCAAAGCCCCG
CAGTTTCTCATTGAGGTAGAATTACTACTGCCACCACCTGACCTAGCCTCACCCCTTCATTG
TGGCACTCAGAGCCAGACCAAGCACATACTAGCAAGCAGGTGCCTACAGACGGGGAGGG
CAGGAGACGCTGCAGAGCATTACTTGGACCTGCTGGCCCTGTTGCTGGATAGCTCGGAGC
CAAGGTTCTCCCCACCCCCCTCCCCTCCAGGGCCCTGTATGCCTGAGGTGTTTTTGGAGG

FIG. 20 cont'd

CAGCGGTAGCACTGATCCAGGCAGGCAGAGCCCAAGATGCCTTGACTCTATGTGAGGAGT
TGCTCAGCCGCACATCATCTCTGCTACCCAAGATGTCCCGGCTGTGGGAAGATGCCAGAA
AAGGAACCAAGGAACTGCCATACTGCCCACTCTGGGTCTCTGCCACCCACCTGCTTCAGG
GCCAGGCCTGGGTTCAACTGGGTGCCCAAAAAGTGGCAATTAGTGAATTTAGCAGGTGCC
TCGAGCTGCTCTTCCGGGCCACACCTGAGGAAAAAGAACAAGGGGCAGCTTTCAACTGTG
AGCAGGGATGTAAGTCAGATGCGGCACTGCAGCAGCTTCGGGCAGCCGCCCTAATTAGTC
GTGGACTGGAATGGGTAGCCAGCGGCCAGGATACCAAAGCCTTACAGGACTTCCTCCTCA
GTGTGCAGATGTGCCCAGGTAATCGAGACACTTACTTTCACCTGCTTCAGACTCTGAAGAG
GCTAGATCGGAGGGATGAGGCCACTGCACTCTGGTGGAGGCTGGAGGCCCAAACTAAGG
GGTCACATGAAGATGCTCTGTGGTCTCTCCCCCTGTACCTAGAAAGCTATTTGAGCTGGAT
CCGTCCTCTGATCGTGACGCCTTCCTTGAAGAATTTCGGACATCTCTGCCAAAGTCTTGT
GACCTGTAG (SEQ ID NO: 121)

>FancA protein
MSDSWVPNSASGQDPGGRRRAWAELLAGRVKREKYNPERAQKLKESAVRLLRSHQDLNALL
LEVEGPLCKKLSLSKVIDCDSSEAYANHSSSFIGSALQDQASRLGVPVGILSAGMVASSVGQIC
TAPAETSHPVLLTVEQRKKLSSLLEFAQYLLAHSMFSRLSFCQELWKIQSSLLLEAVWHLVQG
IVSLQELLESHPDMHAVGSWLFRNLCCLCEQMEASCQHADVARAMLSDFVQMFVLRGFQKNS
DLRRTVEPEKMPQVTVDVLQRMLIFALDALAAGVQEESSTHKIVRCWFGVFSGHTLGSVISTDP
LKRFFSHTLTQILTHSPVLKASDAVQMQREWSFARTHPLLTSLYRRLFVMLSAEELVGHLQEVL
ETQEVHWQRVLSFVSALVVCFPEAQQLLEDWVARLMAQAFESCQLDSMVTAFLVVRQAALEG
PSAFLSYADWFKASFGSTRGYHGCSKKALVFLFTFLSELVPFESPRYLQVHILHPPLVPSKYRS
LLTDYISLAKTRLADLKVSIENMGLYEDLSSAGDITEPHSQALQDVEKAIMVFEHTGNIPVTVMEA
SIFRRPYYVSHFLPALLTPRVLPKVPDSRVAFIESLKRADKIPPSLYSTYCQACSAAEEKPEDAAL
GVRAEPNSAEEPLGQLTAALGELRASMTDPSQRDVISAQVAVISERLAVLGHNEDDSSVEISK
IQLSINTPRLEPREHIAVDLLLTSFCQNLMAASSVAPPERQGPWAALFVRTMCGRVLPAVLTRL
CQLLRHQGPSLSAPHVLGLAALAVHLGESRSALPEVDVGPPAPGAGLPVPALFDSLLTCRTRD
SLFFCLKFCTAAISYSLCKFSSQSRDTLCSCLSPGLIKKFQFLMFRLFSEARQPLSEEDVASLSW
RPLHLPSADWQRAALSLWTHRTFREVLKEEDVHLTYQDWLHLELEIQPEADALSDTERQDFHQ
WAIHEHFLPESSASGGCDGDLQAACTILVNALMDFHQSSRSYDHSENSDLVFGGRTGNEDIIS
RLQEMVADLELQQDLIVPLGHTPSQEHFLFEIFRRRLQALTSGWSVAASLQRQRELLMYKRILL
RLPSSVLCGSSFQAEQPITARCEQFFHLVNSEMRNFCSHGGALTQDITAHFFRGLLNACLRSR
DPSLMVDFILAKCQTKCPLILTSALVWWPSLEPVLLCRWRRHCQSPLPRELQKLQEGRQFASD
FLSPEAASPAPNPDWLSAAALHFAIQQVREENIRKQLKKLDCEREELLVFLFFFSLMGLLSSHLT
SNSTTDLPKAFHVCAAILECLEKRKISWLALFQLTESDLRLGRLLLRVAPDQHTRLLPFAFYSLLS
YFHEDAAIREEAFLHVAVDMYLKLVQLFVAGDTSTVSPPAGRSLELKGQGNPVELITKARLFLLQ
LIPRCPKKSFSHVAELLADRGDCDPEVSAALQSRQQAAPDADLSQEPHLF (SEQ ID NO: 122)

>Homo sapiens FANCC (UniProt Accession Q00597)
MAQDSVDLSCDYQFWMQKLSVWDQASTLETQQDTCLHVAQFQEFLRKMYEALKEMDSNTVI
ERFPTIGQLLAKACWNPFILAYDESQKILIWCLCCLINKEPQNSGQSKLNSWIQGVLSHILSALRF
DKEVALFTQGLGYAPIDYYPGLLKNMVLSLASELRENHLNGFNTQRRMAPERVASLSRVCVPLI
TLTDVDPLVEALLICHGREPQEILQPEFFEAVNEAILLKKISLPMSAVVCLWLRHLPSLEKAMLHL
FEKLISSERNCLRRIECFIKDSSLPQAACHPAIFRVVDEMFRCALLETDGALEIIATIQVFTQCFVE
ALEKASKQLRFALKTYFPYTSPSLAMVLLQDPQDIPRGHWLQTLKHISELLREAVEDQTHGSCG
GPFESWFLFIHFGGWAEMVAEQLLMSAAEPPTALLWLLAFYYGPRDGRQQRAQTMVQVKAVL
GHLLAMSRSSSLSAQDLQTVAGQGTDTDLRAPAQQLIRHLLNFLLWAPGGHTIAWDVITLMAH
TAEITHEIIGFLDQTLYRWNRLGIESPRSEKLARELLKELRTQV (SEQ ID NO: 123)

FIG. 20 cont'd

>Homo sapiens FANCE (UniProt Accession Q9HB96)
MATPDAGLPGAEGVEPAPWAQLEAPARLLLQALQAGPEGARRGLGVLRALGSRGWEPFDWG
RLLEALCREEPVVQGPDGRLELKPLLLRLPRICQRNLMSLLMAVRPSLPESGLLSVLQIAQQDL
APDPDAWLRALGELLRRDLGVGTSMEGASPLSERCQRQLQSLCRGLGLGGRRLKSPQAPDP
EEEENRDSQQPGKRRKDSEEEAASPEGKRVPKRLRCWEEEEDHEKERPEHKSLESLADGGS
ASPIKDQPVMAVKTGEDGSNLDDAKGLAESLELPKAIQDQLPRLQQLLKTLEEGLEGLEDAPPV
ELQLLHECSPSQMDLLCAQLQLPQLSDLGLLRLCTWLLALSPDLSLSNATVLTRSLFLGRILSLT
SSASRLLTTALTSFCAKYTYPVCSALLDPVLQAPGTGPAQTELLCCLVKMESLEPDAQVLMLGQ
ILELPWKEETFLVLQSLLERQVEMTPEKFSVLMEKLCKKGLAATTSMAYAKLMLTVMTKYQANI
TETQRLGLAMALEPNTTFLRKSLKAALKHLGP (SEQ ID NO: 124)

>Homo sapiens FANCF (UniProt Accession Q9NPI8)
MESLLQHLDRFSELLAVSSTTYVSTWDPATVRRALQWARYLRHIHRRFGRHGPIRTALERRLH
NQWRQEGGFGRGPVPGLANFQALGHCDVLLSLRLLENRALGDAARYHLVQQLFPGPGVRDA
DEETLQESLARLARRRSAVHMLRFNGYRENPNLQEDSLMKTQAELLLERLQEVGKAEAERPA
RFLSSLWERLPQNNFLKVIAVALLQPPLSRRPQEELEPGIHKSPGEGSQVLVHWLLGNSEVFAA
FCRALPAGLLTLVTSRHPALSPVYLGLLTDWGQRLHYDLQKGIWVGTESQDVPWEELHNRFQ
SLCQAPPPLKDKVLTALETCKAQDGDFEVPGLSIWTDLLLALRSGAFRKRQVLGLSAGLSSV
(SEQ ID NO: 125)

>Homo sapiens FANCG (UniProt Accession O15287)
MSRQTTSVGSSCLDLWREKNDRLVRQAKVAQNSGLTLRRQQLAQDALEGLRGLLHSLQGLPA
AVPVLPLELTVTCNFIILRASLAQGFTEDQAQDIQRSLERVLETQEQQGPRLEQGLRELWDSVL
RASCLLPELLSALHRLVGLQAALWLSADRLGDLALLLETLNGSQSGASKDLLLLLKTWSPPAEE
LDAPLTLQDAQGLKDVLLTAFAYRQGLQELITGNPDKALSSLHEAASGLCPRPVLVQVYTALGS
CHRKMGNPQRALLYLVAALKEGSAWGPPLLEASRLYQQLGDTTAELESLELLVEALNVPCSSK
APQFLIEVELLLPPPDLASPLHCGTQSQTKHILASRCLQTGRAGDAAEHYLDLLALLLDSSEPRF
SPPPSPPGPCMPEVFLEAAVALIQAGRAQDALTLCEELLSRTSSLLPKMSRLWEDARKGTKEL
PYCPLWVSATHLLQGQAWVQLGAQKVAISEFSRCLELLFRATPEEKEQGAAFNCEQGCKSDA
ALQQLRAAALISRGLEWVASGQDTKALQDFLLSVQMCPGNRDTYFHLLQTLKRLDRRDEATAL
WWRLEAQTKGSHEDALWSLPLYLESYLSWIRPSDRDAFLEEFRTSLPKSCDL (SEQ ID NO: 126)

>codon optimized Human gammaC DNA
ATGCTGAAACCAAGCCTGCCCTTTACAAGCCTGCTGTTCCTGCAGCTGCCACTGCTGGGG
GTCGGACTGAATACTACAATCCTGACACCAAACGGAAATGAGGACACCACAGCCGATTTCT
TTCTGACTACCATGCCCACTGACAGTCTGTCAGTGAGCACCCTGCCACTGCCCGAGGTCC
AGTGCTTCGTGTTTAACGTCGAATATATGAACTGTACCTGGAATAGCTCCTCTGAACCTCAG
CCAACAAATCTGACTCTGCACTACTGGTATAAGAACTCTGACAATGATAAGGTGCAGAAAT
GCTCACATTATCTGTTCAGCGAGGAAATCACCTCCGGCTGTCAGCTGCAGAAGAAAGAGAT
TCACCTGTACCAGACATTTGTGGTCCAGCTGCAGGATCCCCGGGAACCTCGGAGACAGGC
CACTCAGATGCTGAAGCTGCAGAACCTGGTCATCCCATGGGCTCCCGAGAATCTGACCCT
GCATAAACTGTCCGAGTCTCAGCTGGAACTGAACTGGAACAATAGGTTCCTGAATCACTGC
CTGGAGCATCTGGTGCAGTACCGCACAGACTGGGATCACTCTTGGACTGAACAGAGTGTG
GACTATCGACATAAGTTTAGTCTGCCTTCAGTGGATGGGCAGAAAGGTACACATTCAGGG
TCCGCTCTCGGTTCAACCCACTGTGCGGAAGCGCCCAGCACTGGAGCGAGTGGTCCCAC
CCCATCCATTGGGGGTCTAACACCAGCAAGGAGAATCCTTTCCTGTTTGCCCTGGAAGCTG
TGGTCATTTCAGTGGGAAGCATGGGCCTGATCATTAGCCTGCTGTGCGTGTACTTCTGGCT
GGAGCGGACCATGCCTAGAATCCCAACACTGAAGAACCTGGAGGACCTGGTGACAGAATA

FIG. 20 cont'd

TCACGGCAATTTTTCCGCTTGGTCTGGGGTCAGTAAAGGACTGGCAGAGAGCCTGCAGCC
CGATTACTCCGAGCGGCTGTGCCTGGTGTCCGAAATTCCCCCTAAAGGCGGGGCACTGG
GAGAAGGCCCTGGGGCCTCCCCCTGCAACCAGCACTCACCCTATTGGGCACCACCCTGTT
ACACCCTGAAACCCGAAACTTAA (SEQ ID NO: 127)

>native Human gammaC DNA
ATGTTGAAGCCATCATTACCATTCACATCCCTCTTATTCCTGCAGCTGCCCCTGCTGGGAG
TGGGGCTGAACACGACAATTCTGACGCCCAATGGGAATGAAGACACCACAGCTGATTTCTT
CCTGACCACTATGCCCACTGACTCCCTCAGCGTTTCCACTCTGCCCCTCCCAGAGGTTCAG
TGTTTTGTGTTCAATGTCGAGTACATGAATTGCACTTGGAACAGCAGCTCTGAGCCCCAGC
CTACCAACCTCACTCTGCATTATTGGTACAAGAACTCGGATAATGATAAAGTCCAGAAGTG
CAGCCACTATCTATTCTCTGAAGAAATCACTTCTGGCTGTCAGTTGCAAAAAAAGGAGATCC
ACCTCTACCAAACATTTGTTGTTCAGCTCCAGGACCCACGGGAACCCAGGAGACAGGCCA
CACAGATGCTAAAACTGCAGAATCTGGTGATCCCCTGGGCTCCAGAGAACCTAACACTTCA
CAAACTGAGTGAATCCCAGCTAGAACTGAACTGGAACAACAGATTCTTGAACCACTGTTTG
GAGCACTTGGTGCAGTACCGGACTGACTGGGACCACAGCTGGACTGAACAATCAGTGGAT
TATAGACATAAGTTCTCCTTGCCTAGTGTGGATGGGCAGAAACGCTACACGTTTCGTGTTC
GGAGCCGCTTTAACCCACTCTGTGGAAGTGCTCAGCATTGGAGTGAATGGAGCCACCCAA
TCCACTGGGGGAGCAATACTTCAAAAGAGAATCCTTTCCTGTTTGCATTGGAAGCCGTGGT
TATCTCTGTTGGCTCCATGGGATTGATTATCAGCCTTCTCTGTGTGTATTTCTGGCTGGAAC
GGACGATGCCCCGAATTCCCACCCTGAAGAACCTAGAGGATCTTGTTACTGAATACCACG
GGAACTTTTCGGCCTGGAGTGGTGTGTCTAAGGGACTGGCTGAGAGTCTGCAGCCAGACT
ACAGTGAACGACTCTGCCTCGTCAGTGAGATTCCCCAAAAGGAGGGGCCCTTGGGGAG
GGGCCTGGGGCCTCCCCATGCAACCAGCATAGCCCCTACTGGGCCCCCCCATGTTACAC
CCTAAAGCCTGAAACCTGA (SEQ ID NO: 128)

>native canine gammaC DNA
ATGTTGAAGCCACCATTGCCACTCAGATCCCTCTTATTCCTGCAGCTGTCTCTGCTGGGGG
TGGGGCTGAACTCCACGGTCCCCATGCCCAATGGGAATGAAGACATCACACCTGATTTCTT
CCTGACCGCTACACCCTCCGAGACCCTCAGTGTTTCCTCCCTGCCCCTCCCAGAGGTCCA
GTGTTTTGTGTTCAATGTTGAGTACATGAATTGCACTTGGAACAGCAGCTCTGAGCCCCGG
CCCACCAACCTGACCCTGCACTACTGGTATAAGAACTCCAATGATGATAAAGTCCAGGAGT
GTGGCCACTACCTATTCTCTAGAGAGGTCACTGCTGGCTGTTGGTTGCAGAAGGAGGAGA
TCCATCTCTACGAAACATTTGTTGTCCAGCTCCGGGACCCACGGGAACCCAGGAGGCAGT
CCACACAGAAGCTAAAACTGCAAAATCTGGTGATCCCCTGGGCTCCGGAGAACCTAACCC
TTCACAACCTGAGCGAATCCCAGCTAGAACTGAGCTGGAGCAACAGACACTTGGACCACT
GTTTGGAGCATGTTGTGCAGTACCGGAGTGACTGGGACCGCAGCTGGACTGAACAGTCAG
TGGACCACCGAAATAGCTTCTCTCTGCCTAGCGTGGATGGGCAGAAGTTCTACACGTTCC
GTGTCCGAAGCCGCTATAACCCACTCTGTGGAAGCGCTCAGCGTTGGAGTGAATGGAGCC
ACCCTATCCACTGGGGGAGCAATACCTCCAAGGAGAATCCTTTGTTTGCATCGGAAGCTGT
GCTTATCCCCCTTGGCTCCATGGGATTGATTATTAGCCTTATCTGTGTGTACTACTGGCTG
GAACGGTCGATCCCCCGAATTCCTACCCTCAAGAACCTGGAGGATCTGGTTACTGAATATC
ACGGGAATTTTTCGGCCTGGAGTGGAGTGTCTAAGGGACTGGCGGAGAGTCTGCAGCCA
GACTACAGTGAATGGCTCTGCCACGTCAGTGAGATTCCCCAAAAGGAGGGGCTCCAGGG
GAGGGTCCTGGGGGCTCCCCCTGCAGCCAGCATAGCCCCTACTGGGCTCCCCCATGTTAT
ACCCTGAAACCTGAAACTGGAGCCCTGA (SEQ ID NO: 129)

FIG. 20 cont'd

>human gammaC AA
MLKPSLPFTSLLFLQLPLLGVGLNTTILTPNGNEDTTADFFLTTMPTDSLSVSTLPLPEVQCFVFN
VEYMNCTWNSSSEPQPTNLTLHYWYKNSDNDKVQKCSHYLFSEEITSGCQLQKKEIHLYQTFV
VQLQDPREPRRQATQMLKLQNLVIPWAPENLTLHKLSESQLELNWNNRFLNHCLEHLVQYRTD
WDHSWTEQSVDYRHKFSLPSVDGQKRYTFRVRSRFNPLCGSAQHWSEWSHPIHWGSNTSK
ENPFLFALEAVVISVGSMGLIISLLCVYFWLERTMPRIPTLKNLEDLVTEYHGNFSAWSGVSKGL
AESLQPDYSERLCLVSEIPPKGGALGEGPGASPCNQHSPYWAPPCYTLKPET (SEQ ID NO: 130)

>native canine gammaC AA (91% conserved with human)
MLKPPLPLRSLLFLQLSLLGVGLNSTVPMPNGNEDITPDFFLTATPSETLSVSSLPLPEVQCFVF
NVEYMNCTWNSSSEPRPTNLTLHYWYKNSNDDKVQECGHYLFSREVTAGCWLQKEEIHLYET
FVVQLRDPREPRRQSTQKLKLQNLVIPWAPENLTLHNLSESQLELSWSNRHLDHCLEHVVQYR
SDWDRSWTEQSVDHRNSFSLPSVDGQKFYTFRVRSRYNPLCGSAQRWSEWSHPIHWGSNT
SKENPLFASEAVLIPLGSMGLIISLICVYYWLERSIPRIPTLKNLEDLVTEYHGNFSAWSGVSKGL
AESLQPDYSEWLCHVSEIPPKGGAPGEGPGGSPCSQHSPYWAPPCYTLKPETGALIP (SEQ ID NO: 131)

>Homo sapiens JAK3 cds (nucleotides 101-3475 of NCBI Reference Sequence: NM_000215.3)
ATGGCACCTCCAAGTGAAGAGACGCCCCTGATCCCTCAGCGTTCATGCAGCCTCTTGTCC
ACGGAGGCTGGTGCCCTGCATGTGCTGCTGCCCGCTCGGGGCCCCGGGCCCCCCAGC
GCCTATCTTTCTCCTTTGGGGACCACTTGGCTGAGGACCTGTGCGTGCAGGCTGCCAAGG
CCAGCGGCATCCTGCCTGTGTACCACTCCCTCTTTGCTCTGGCCACGGAGGACCTGTCCT
GCTGGTTCCCCCCGAGCCACATCTTCTCCGTGGAGGATGCCAGCACCCAAGTCCTGCTGT
ACAGGATTCGCTTTTACTTCCCCAATTGGTTTGGGCTGGAGAAGTGCCACCGCTTCGGGCT
ACGCAAGGATTTGGCCAGTGCTATCCTTGACCTGCCAGTCCTGGAGCACCTCTTTGCCCA
GCACCGCAGTGACCTGGTGAGTGGGCGCCTCCCCGTGGGCCTCAGTCTCAAGGAGCAGG
GTGAGTGTCTCAGCCTGGCCGTGTTGGACCTGGCCCGGATGGCGCGAGAGCAGGCCCAG
CGGCCGGGAGAGCTGCTGAAGACTGTCAGCTACAAGGCCTGCCTACCCCAAGCCTGCG
CGACCTGATCCAGGGCCTGAGCTTCGTGACGCGGAGGCGTATTCGGAGGACGGTGCGCA
GAGCCCTGCGCCGCGTGGCCGCCTGCCAGGCAGACCGGCACTCGCTCATGGCCAAGTAC
ATCATGGACCTGGAGCGGCTGGATCCAGCCGGGGCCGCCGAGACCTTCCACGTGGGCCT
CCCTGGGGCCCTTGGTGGCCACGACGGGCTGGGGCTGCTCCGCGTGGCTGGTGACGGC
GGCATCGCCTGGACCCAGGGAGAACAGGAGGTCCTCCAGCCCTTCTGCGACTTTCCAGAA
ATCGTAGACATTAGCATCAAGCAGGCCCCGCGCGTTGGCCCGGCCGGAGAGCACCGCCT
GGTCACTGTTACCAGGACAGACAACCAGATTTTAGAGGCCGAGTTCCCAGGGCTGCCCGA
GGCTCTGTCGTTCGTGGCGCTCGTGGACGGCTACTTCCGGCTGACCACGGACTCCCAGC
ACTTCTTCTGCAAGGAGGTGGCACCGCCGAGGCTGCTGGAGGAAGTGGCCGAGCAGTGC
CACGGCCCCATCACTCTGGACTTTGCCATCAACAAGCTCAAGACTGGGGGCTCACGTCCT
GGCTCCTATGTTCTCCGCCGCAGCCCCAGGACTTTGACAGCTTCCTCCTCACTGTCTGTG
TCCAGAACCCCCTTGGTCCTGATTATAAGGGCTGCCTCATCCGGCGCAGCCCCACAGGAA
CCTTCCTTCTGGTTGGCCTCAGCCGACCCCACAGCAGTCTTCGAGAGCTCCTGGCAACCT
GCTGGGATGGGGGCTGCACGTAGATGGGGTGGCAGTGACCCTCACTTCCTGCTGTATC
CCCAGACCCAAAGAAAAGTCCAACCTGATCGTGGTCCAGAGAGGTCACAGCCCACCCACA
TCATCCTTGGTTCAGCCCCAATCCCAATACCAGCTGAGTCAGATGACATTTCACAAGATCC
CTGCTGACAGCCTGGAGTGGCATGAGAACCTGGGCCATGGGTCCTTCACCAAGATTTACC
GGGGCTGTCGCCATGAGGTGGTGGATGGGGAGGCCCGAAAGACAGAGGTGCTGCTGAAG
GTCATGGATGCCAAGCACAAGAACTGCATGGAGTCATTCCTGGAAGCAGCGAGCTTGATG

FIG. 20 cont'd

AGCCAAGTGTCGTACCGGCATCTCGTGCTGCTCCACGGCGTGTGCATGGCTGGAGACAG
CACCATGGTGCAGGAATTTGTACACCTGGGGGCCATAGACATGTATCTGCGAAAACGTGG
CCACCTGGTGCCAGCCAGCTGGAAGCTGCAGGTGGTCAAACAGCTGGCCTACGCCCTCA
ACTATCTGGAGGACAAAGGCCTGCCCCATGGCAATGTCTCTGCCCGGAAGGTGCTCCTGG
CTCGGGAGGGGGCTGATGGGAGCCCGCCCTTCATCAAGCTGAGTGACCCTGGGGTCAGC
CCCGCTGTGTTAAGCCTGGAGATGCTCACCGACAGGATCCCCTGGGTGGCCCCGAGTG
TCTCCGGGAGGCGCAGACACTTAGCTTGGAAGCTGACAAGTGGGGCTTCGGCGCCACGG
TCTGGGAAGTGTTTAGTGGCGTCACCATGCCCATCAGTGCCCTGGATCCTGCTAAGAAACT
CCAATTTTATGAGGACCGGCAGCAGCTGCCGGCCCCAAGTGGACAGAGCTGGCCCTGC
TGATTCAACAGTGCATGGCCTATGAGCCGGTCCAGAGGCCCTCCTTCCGAGCCGTCATTC
GTGACCTCAATAGCCTCATCTCTTCAGACTATGAGCTCCTCTCAGACCCCACACCTGGTGC
CCTGGCACCTCGTGATGGGCTGTGGAATGGTGCCCAGCTCTATGCCTGCCAAGACCCCAC
GATCTTCGAGGAGAGACACCTCAAGTACATCTCACAGCTGGGCAAGGGCAACTTTGGCAG
CGTGGAGCTGTGCCGCTATGACCCGCTAGGCGACAATACAGGTGCCCTGGTGGCCGTGA
AACAGCTGCAGCACAGCGGGCCAGACCAGCAGAGGGACTTTCAGCGGGAGATTCAGATC
CTCAAAGCACTGCACAGTGATTTCATTGTCAAGTATCGTGGTGTCAGCTATGGCCCGGGCC
GCCAGAGCCTGCGGCTGGTCATGGAGTACCTGCCCAGCGGCTGCTTGCGCGACTTCCTG
CAGCGGCACCGCGCGCGCCTCGATGCCAGCCGCCTCCTTCTCTATTCCTCGCAGATCTGC
AAGGGCATGGAGTACCTGGGCTCCCGCCGCTGCGTGCACCGCGACCTGGCCGCCCGAAA
CATCCTCGTGGAGAGCGAGGCACACGTCAAGATCGCTGACTTCGGCCTAGCTAAGCTGCT
GCCGCTTGACAAAGACTACTACGTGGTCCGCGAGCCAGGCCAGAGCCCCATTTTCTGGTA
TGCCCCCGAATCCCTCTCGGACAACATCTTCTCTCGCCAGTCAGACGTCTGGAGCTTCGG
GGTCGTCCTGTACGAGCTCTTCACCTACTGCGACAAAAGCTGCAGCCCTCGGCCGAGTT
CCTGCGGATGATGGGATGTGAGCGGGATGTCCCCGCCCTCTGCCGCCTCTTGGAACTGCT
GGAGGAGGGCCAGAGGCTGCCGGCGCCTCCTGCCTGCCCTGCTGAGGTTCACGAGCTCA
TGAAGCTGTGCTGGGCCCCTAGCCCACAGGACCGGCCATCATTCAGCGCCCTGGGCCCC
CAGCTGGACATGCTGTGGAGCGGAAGCCGGGGGTGTGAGACTCATGCCTTCACTGCTCA
CCCAGAGGGCAAACACCACTCCCTGTCCTTTTCATAG (SEQ ID NO: 132)

>Homo sapiens PNP cds (nucleotides 147-1016 of NCBI Reference Sequence:
NM_000270.3)
ATGGAGAACGGATACACCTATGAAGATTATAAGAACACTGCAGAATGGCTTCTGTCTCACA
CTAAGCACCGACCTCAAGTTGCAATAATCTGTGGTTCTGGATTAGGAGGTCTGACTGATAA
ATTAACTCAGGCCCAGATCTTTGACTACGGTGAAATCCCCAACTTTCCCCGAAGTACAGTG
CCAGGTCATGCTGGCCGACTGGTGTTTGGGTTCCTGAATGGCAGGGCCTGTGTGATGATG
CAGGGCAGGTTCCACATGTATGAAGGGTACCCACTCTGGAAGGTGACATTCCCAGTGAGG
GTTTTCCACCTTCTGGGTGTGGACACCCTGGTAGTCACCAATGCAGCAGGAGGGCTGAAC
CCCAAGTTTGAGGTTGGAGATATCATGCTGATCCGTGACCATATCAACCTACCTGGTTTCA
GTGGTCAGAACCCTCTCAGAGGGCCCAATGATGAAAGGTTTGGAGATCGTTTCCCTGCCA
TGTCTGATGCCTACGACCGGACTATGAGGCAGAGGGCTCTCAGTACCTGGAAACAAATGG
GGGAGCAACGTGAGCTACAGGAAGGCACCTATGTGATGGTGGCAGGCCCCAGCTTTGAG
ACTGTGGCAGAATGTCGTGTGCTGCAGAAGCTGGGAGCAGACGCTGTTGGCATGAGTACA
GTACCAGAAGTTATCGTTGCACGGCACTGTGGACTTCGAGTCTTTGGCTTCTCACTCATCA
CTAACAAGGTCATCATGGATTATGAAAGCCTGGAGAAGGCCAACCATGAAGAAGTCTTAGC
AGCTGGCAAACAAGCTGCACAGAAATTGGAACAGTTTGTCTCCATTCTTATGGCCAGCATT
CCACTCCCTGACAAAGCCAGTTGA (SEQ ID NO: 133)

FIG. 20 cont'd

>Homo sapiens ADA cds (nucleotides 152-1243 of NCBI Reference Sequence: NM_000022.3)
ATGGCCCAGACGCCCGCCTTCGACAAGCCCAAAGTAGAACTGCATGTCCACCTAGACGGA
TCCATCAAGCCTGAAACCATCTTATACTATGGCAGGAGGAGAGGGATCGCCCTCCCAGCT
AACACAGCAGAGGGGCTGCTGAACGTCATTGGCATGGACAAGCCGCTCACCCTTCCAGAC
TTCCTGGCCAAGTTTGACTACTACATGCCTGCTATCGCGGGCTGCCGGGAGGCTATCAAA
AGGATCGCCTATGAGTTTGTAGAGATGAAGGCCAAAGAGGGCGTGGTGTATGTGGAGGTG
CGGTACAGTCCGCACCTGCTGGCCAACTCCAAAGTGGAGCCAATCCCCTGGAACCAGGCT
GAAGGGGACCTCACCCCAGACGAGGTGGTGGCCCTAGTGGGCCAGGGCCTGCAGGAGG
GGGAGCGAGACTTCGGGGTCAAGGCCCGGTCCATCCTGTGCTGCATGCGCCACCAGCCC
AACTGGTCCCCAAGGTGGTGGAGCTGTGTAAGAAGTACCAGCAGCAGACCGTGGTAGCC
ATTGACCTGGCTGGAGATGAGACCATCCCAGGAAGCAGCCTCTTGCCTGGACATGTCCAG
GCCTACCAGGAGGCTGTGAAGAGCGGCATTCACCGTACTGTCCACGCCGGGGAGGTGGG
CTCGGCCGAAGTAGTAAAAGAGGCTGTGGACATACTCAAGACAGAGCGGCTGGGACACG
GCTACCACACCCTGGAAGACCAGGCCCTTTATAACAGGCTGCGGCAGGAAAACATGCACT
TCGAGATCTGCCCCTGGTCCAGCTACCTCACTGGTGCCTGGAAGCCGGACACGGAGCATG
CAGTCATTCGGCTCAAAAATGACCAGGCTAACTACTCGCTCAACACAGATGACCCGCTCAT
CTTCAAGTCCACCCTGGACACTGATTACCAGATGACCAAACGGGACATGGGCTTTACTGAA
GAGGAGTTTAAAAGGCTGAACATCAATGCGGCCAATCTAGTTTCCTCCCAGAAGATGAAA
AGAGGGAGCTTCTCGACCTGCTCTATAAAGCCTATGGGATGCCACCTTCAGCCTCTGCAG
GGCAGAACCTCTGA (SEQ ID NO: 134)

>Homo sapiens RAG1 cds (nucleotides 125-3256 of NCBI Reference Sequence: NM_000448.2)
ATGGCAGCCTCTTTCCCACCCACCTTGGGACTCAGTTCTGCCCCAGATGAAATTCAGCACC
CACATATTAAATTTTCAGAATGGAAATTTAAGCTGTTCCGGGTGAGATCCTTTGAAAAGACA
CCTGAAGAAGCTCAAAAGGAAAAGAAGGATTCCTTTGAGGGGAAACCCTCTCTGGAGCAAT
CTCCAGCAGTCCTGGACAAGGCTGATGGTCAGAAGCCAGTCCCAACTCAGCCATTGTTAA
AAGCCCACCCTAAGTTTTCAAAGAAATTTCACGACAACGAGAAAGCAAGAGGCAAAGCGAT
CCATCAAGCCAACCTTCGACATCTCTGCCGCATCTGTGGGAATTCTTTTAGAGCTGATGAG
CACAACAGGAGATATCCAGTCCATGGTCCTGTGGATGGTAAAACCCTAGGCCTTTTACGAA
AGAAGGAAAAGAGAGCTACTTCCTGGCCGGACCTCATTGCCAAGGTTTTCCGGATCGATG
TGAAGGCAGATGTTGACTCGATCCACCCCACTGAGTTCTGCCATAACTGCTGGAGCATCAT
GCACAGGAAGTTTAGCAGTGCCCCATGTGAGGTTTACTTCCCGAGGAACGTGACCATGGA
GTGGCACCCCCACACACCATCCTGTGACATCTGCAACACTGCCCGTCGGGGACTCAAGAG
GAAGAGTCTTCAGCCAAACTTGCAGCTCAGCAAAAAACTCAAAACTGTGCTTGACCAAGCA
AGACAAGCCCGTCAGCGCAAGAGAAGAGCTCAGGCAAGGATCAGCAGCAAGGATGTCAT
GAAGAAGATCGCCAACTGCAGTAAGATACATCTTAGTACCAAGCTCCTTGCAGTGGACTTC
CCAGAGCACTTTGTGAAATCCATCTCCTGCCAGATCTGTGAACACATTCTGGCTGACCCTG
TGGAGACCAACTGTAAGCATGTCTTTTGCCGGGTCTGCATTCTCAGATGCCTCAAAGTCAT
GGGCAGCTATTGTCCCTCTTGCCGATATCCATGCTTCCCTACTGACCTGGAGAGTCCAGTG
AAGTCCTTTCTGAGCGTCTTGAATTCCCTGATGGTGAAATGTCCAGCAAAAGAGTGCAATG
AGGAGGTCAGTTTGGAAAAATATAATCACCACATCTCAAGTCACAAGGAATCAAAAGAGATT
TTTGTGCACATTAATAAAGGGGGCCGGCCCCGCCAACATCTTCTGTCGCTGACTCGGAGA
GCTCAGAAGCACCGGCTGAGGGAGCTCAAGCTGCAAGTCAAAGCCTTTGCTGACAAAGAA
GAAGGTGGAGATGTGAAGTCCGTGTGCATGACCTTGTTCCTGCTGGCTCTGAGGGCGAGG
AATGAGCACAGGCAAGCTGATGAGCTGGAGGCCATCATGCAGGGAAAGGGCTCTGGCCT
GCAGCCAGCTGTTTGCTTGGCCATCCGTGTCAACACCTTCCTCAGCTGCAGTCAGTACCAC
AAGATGTACAGGACTGTGAAAGCCATCACAGGGAGACAGATTTTTCAGCCTTTGCATGCCC

FIG. 20 cont'd

TTCGGAATGCTGAGAAGGTACTTCTGCCAGGCTACCACCACTTTGAGTGGCAGCCACCTCT
GAAGAATGTGTCTTCCAGCACTGATGTTGGCATTATTGATGGGCTGTCTGGACTATCATCC
TCTGTGGATGATTACCCAGTGGACACCATTGCAAAGAGGTTCCGCTATGATTCAGCTTTGG
TGTCTGCTTTGATGGACATGGAAGAAGACATCTTGGAAGGCATGAGATCCCAAGACCTTGA
TGATTACCTGAATGGCCCCTTCACTGTGGTGGTGAAGGAGTCTTGTGATGGAATGGGAGA
CGTGAGTGAGAAGCATGGGAGTGGGCCTGTAGTTCCAGAAAAGGCAGTCCGTTTTTCATT
CACAATCATGAAATTACTATTGCCCACAGCTCTCAGAATGTGAAAGTATTTGAAGAAGCCA
AACCTAACTCTGAACTGTGTTGCAAGCCATTGTGCCTTATGCTGGCAGATGAGTCTGACCA
CGAGACGCTGACTGCCATCCTGAGTCCTCTCATTGCTGAGAGGGAGGCCATGAAGAGCAG
TGAATTAATGCTTGAGCTGGGAGGCATTCTCCGGACTTTCAAGTTCATCTTCAGGGGCACC
GGCTATGATGAAAAACTTGTGCGGGAAGTGGAAGGCCTCGAGGCTTCTGGCTCAGTCTAC
ATTTGTACTCTTTGTGATGCCACCCGTCTGGAAGCCTCTCAAAATCTTGTCTTCCACTCTAT
AACCAGAAGCCATGCTGAGAACCTGGAACGTTATGAGGTCTGGCGTTCCAACCCTTACCAT
GAGTCTGTGGAAGAACTGCGGGATCGGGTGAAGGGGTCTCAGCTAAACCTTTCATTGAG
ACAGTCCCTTCCATAGATGCACTCCACTGTGACATTGGCAATGCAGCTGAGTTCTACAAGA
TCTTCCAGCTAGAGATAGGGGAAGTGTATAAGAATCCCAATGCTTCCAAAGAGGAAAGGAA
AAGGTGGCAGGCCACACTGGACAAGCATCTCCGGAAGAAGATGAACCTCAAACCAATCAT
GAGGATGAATGGCAACTTTGCCAGGAAGCTCATGACCAAAGAGACTGTGGATGCAGTTTG
TGAGTTAATTCCTTCCGAGGAGAGGCACGAGGCTCTGAGGGAGCTGATGGATCTTTACCT
GAAGATGAAACCAGTATGGCGATCATCATGCCCTGCTAAAGAGTGCCCAGAATCCCTCTGC
CAGTACAGTTTCAATTCACAGCGTTTTGCTGAGCTCCTTTCTACGAAGTTCAAGTATAGGTA
TGAGGGAAAAATCACCAATTATTTTCACAAAACCCTGGCCCATGTTCCTGAAATTATTGAGA
GGGATGGCTCCATTGGGGCATGGGCAAGTGAGGGAAATGAGTCTGGTAACAAACTGTTTA
GGCGCTTCCGGAAAATGAATGCCAGGCAGTCCAAATGCTATGAGATGGAAGATGTCCTGA
AACACCACTGGTTGTACACCTCCAAATACCTCCAGAAGTTTATGAATGCTCATAATGCATTA
AAAACCTCTGGGTTTACCATGAACCCTCAGGCAAGCTTAGGGGACCCATTAGGCATAGAG
GACTCTCTGGAAAGCCAAGATTCAATGGAATTTTAA (SEQ ID NO: 135)

>Homo sapiens RAG2 cds (nucleotides 206-1789 of NCBI Reference Sequence:
NM_000536.3)
ATGTCTCTGCAGATGGTAACAGTCAGTAATAACATAGCCTTAATTCAGCCAGGCTTCTCACT
GATGAATTTTGATGGACAAGTTTTCTTCTTTGGACAAAAAGGCTGGCCCAAAAGATCCTGC
CCCACTGGAGTTTTCCATCTGGATGTAAAGCATAACCATGTCAAACTGAAGCCTACAATTTT
CTCTAAGGATTCCTGCTACCTCCCTCCTCTTCGCTACCCAGCCACTTGCACATTCAAAGGC
AGCTTGGAGTCTGAAAAGCATCAATACATCATCCATGGAGGGAAAACACCAAACAATGAGG
TTTCAGATAAGATTTATGTCATGTCTATTGTTTGCAAGAACAACAAAAAGGTTACTTTTCGCT
GCACAGAGAAAGACTTGGTAGGAGATGTTCCTGAAGCCAGATATGGTCATTCCATTAATGT
GGTGTACAGCCGAGGGAAAAGTATGGGTGTTCTCTTTGGAGGACGCTCATACATGCCTTCT
ACCCACAGAACCACAGAAAAATGGAATAGTGTAGCTGACTGCCTGCCCTGTGTTTTCCTGG
TGGATTTTGAATTTGGGTGTGCTACATCATACATTCTTCCAGAACTTCAGGATGGGCTATCT
TTTCATGTCTCTATTGCCAAAAATGACACCATCTATATTTTAGGAGGACATTCACTTGCCAAT
AATATCCGGCCTGCCAACCTGTACAGAATAAGGGTTGATCTTCCCTGGGTAGCCCAGCT
GTGAATTGCACAGTCTTGCCAGGAGGAATCTCTGTCTCCAGTGCAATCCTGACTCAAACTA
ACAATGATGAATTTGTTATTGTTGGTGGCTATCAGCTTGAAAATCAAAAAGAATGATCTGC
AACATCATCTCTTTAGAGGACAACAAGATAGAAATTCGTGAGATGGAGACCCCAGATTGGA
CCCCAGACATTAAGCACAGCAAGATATGGTTTGGAAGCAACATGGGAAATGGAACTGTTTT
TCTTGGCATACCAGGAGACAATAAACAAGTTGTTTCAGAAGGATTCTATTTCTATATGTTGA
AATGTGCTGAAGATGATACTAATGAAGAGCAGACAACATTCACAAACAGTCAAACATCAACA
GAAGATCCAGGGGATTCCACTCCCTTTGAAGACTCTGAAGAATTTTGTTTCAGTGCAGAAG

FIG. 20 cont'd

CAAATAGTTTTGATGGTGATGATGAATTTGACACCTATAATGAAGATGATGAAGAAGATGAG
TCTGAGACAGGCTACTGGATTACATGCTGCCCTACTTGTGATGTGGATATCAACACTTGGG
TACCATTCTATTCAACTGAGCTCAACAAACCCGCCATGATCTACTGCTCTCATGGGGATGG
GCACTGGGTCCATGCTCAGTGCATGGATCTGGCAGAACGCACACTCATCCATCTGTCAGC
AGGAAGCAACAAGTATTACTGCAATGAGCATGTGGAGATAGCAAGAGCTCTACACACTCCC
CAAAGAGTCCTACCCTTAAAAAAGCCTCCAATGAAATCCCTCCGTAAAAAAGGTTCTGGAA
AAATCTTGACTCCTGCCAAGAAATCCTTTCTTAGAAGGTTGTTTGATTAG (SEQ ID NO: 136)

>Homo sapiens JAK3 isoform 2 (UniProt Accession P52333-1)
MAPPSEETPLIPQRSCSLLSTEAGALHVLLPARGPGPPQRLSFSFGDHLAEDLCVQAAKASGIL
PVYHSLFALATEDLSCWFPPSHIFSVEDASTQVLLYRIRFYFPNWFGLEKCHRFGLRKDLASAIL
DLPVLEHLFAQHRSDLVSGRLPVGLSLKEQGECLSLAVLDLARMAREQAQRPGELLKTVSYKA
CLPPSLRDLIQGLSFVTRRRIRRTVRRALRRVAACQADRHSLMAKYIMDLERLDPAGAAETFHV
GLPGALGGHDGLGLLRVAGDGGIAWTQGEQEVLQPFCDFPEIVDISIKQAPRVGPAGEHRLVT
VTRTDNQILEAEFPGLPEALSFVALVDGYFRLTTDSQHFFCKEVAPPRLLEEVAEQCHGPITLDF
AINKLKTGGSRPGSYVLRRSPQDFDSFLLTVCVQNPLGPDYKGCLIRRSPTGTFLLVGLSRPHS
SLRELLATCWDGGLHVDGVAVTLTSCCIPRPKEKSNLIVVQRGHSPPTSSLVQPQSQYQLSQM
TFHKIPADSLEWHENLGHGSFTKIYRGCRHEVVDGEARKTEVLLKVMDAKHKNCMESFLEAAS
LMSQVSYRHLVLLHGVCMAGDSTMVQEFVHLGAIDMYLRKRGHLVPASWKLQVVKQLAYALN
YLEDKGLPHGNVSARKVLLAREGADGSPPFIKLSDPGVSPAVLSLEMLTDRIPWVAPECLREAQ
TLSLEADKWGFGATVWEVFSGVTMPISALDPAKKLQFYEDRQQLPAPKWTELALLIQQCMAYE
PVQRPSFRAVIRDLNSLISSDYELLSDPTPGALAPRDGLWNGAQLYACQDPTIFEERHLKYISQL
GKGNFGSVELCRYDPLGDNTGALVAVKQLQHSGPDQQRDFQREIQILKALHSDFIVKYRGVSY
GPGRQSLRLVMEYLPSGCLRDFLQRHRARLDASRLLLYSSQICKGMEYLGSRRCVHRDLAAR
NILVESEAHVKIADFGLAKLLPLDKDYYVVREPGQSPIFWYAPESLSDNIFSRQSDVWSFGVVLY
ELFTYCDKSCSPSAEFLRMMGCERDVPALCRLLELLEEGQRLPAPPACPAEVHELMKLCWAP
SPQDRPSFSALGPQLDMLWSGSRGCETHAFTAHPEGKHHSLSFS (SEQ ID NO: 137)

>Homo sapiens PNP (UniProt Accession P00491)
MENGYTYEDYKNTAEWLLSHTKHRPQVAIICGSGLGGLTDKLTQAQIFDYGEIPNFPRSTVPGH
AGRLVFGFLNGRACVMMQGRFHMYEGYPLWKVTFPVRVFHLLGVDTLVVTNAAGGLNPKFEV
GDIMLIRDHINLPGFSGQNPLRGPNDERFGDRFPAMSDAYDRTMRQRALSTWKQMGEQRELQ
EGTYVMVAGPSFETVAECRVLQKLGADAVGMSTVPEVIVARHCGLRVFGFSLITNKVIMDYESL
EKANHEEVLAAGKQAAQKLEQFVSILMASIPLPDKAS (SEQ ID NO: 138)

>Homo sapiens ADA (UniProt Accession P00813)
MAQTPAFDKPKVELHVHLDGSIKPETILYYGRRRGIALPANTAEGLLNVIGMDKPLTLPDFLAKF
DYYMPAIAGCREAIKRIAYEFVEMKAKEGVVYVEVRYSPHLLANSKVEPIPWNQAEGDLTPDEV
VALVGQGLQEGERDFGVKARSILCCMRHQPNWSPKVVELCKKYQQQTVVAIDLAGDETIPGSS
LLPGHVQAYQEAVKSGIHRTVHAGEVGSAEVVKEAVDILKTERLGHGYHTLEDQALYNRLRQE
NMHFEICPWSSYLTGAWKPDTEHAVIRLKNDQANYSLNTDDPLIFKSTLDTYQMTKRDMGFT
EEEFKRLNINAAKSSFLPEDEKRELLDLLYKAYGMPPSASAGQNL (SEQ ID NO: 139)

>Homo sapiens RAG1 isoform 1 (UniProt Accession P15918-1)
MAASFPPTLGLSSAPDEIQHPHIKFSEWKFKLFRVRSFEKTPEEAQKEKKDSFEGKPSLEQSPA
VLDKADGQKPVPTQPLLKAHPKFSKKFHDNEKARGKAIHQANLRHLCRICGNSFRADEHNRRY
PVHGPVDGKTLGLLRKKEKRATSWPDLIAKVFRIDVKADVDSIHPTEFCHNCWSIMHRKFSSAP
CEVYFPRNVTMEWHPHTPSCDICNTARRGLKRKSLQPNLQLSKKLKTVLDQARQARQHKRRA
QARISSKDVMKKIANCSKIHLSTKLLAVDFPEHFVKSISCQICEHILADPVETNCKHVFCRVCILR

FIG. 20 cont'd

CLKVMGSYCPSCRYPCFPTDLESPVKSFLSVLNSLMVKCPAKECNEEVSLEKYNHHISSHKES
KEIFVHINKGGRPRQHLLSLTRRAQKHRLRELKLQVKAFADKEEGGDVKSVCMTLFLLALRARN
EHRQADELEAIMQGKGSGLQPAVCLAIRVNTFLSCSQYHKMYRTVKAITGRQIFQPLHALRNAE
KVLLPGYHHFEWQPPLKNVSSSTDVGIIDGLSGLSSSVDDYPVDTIAKRFRYDSALVSALMDME
EDILEGMRSQDLDDYLNGPFTVVVKESCDGMGDVSEKHGSGPVVPEKAVRFSFTIMKITIAHSS
QNVKVFEEAKPNSELCCKPLCMLADESDHETLTAILSPLIAEREAMKSSELMLELGGILRTFKFI
FRGTGYDEKLVREVEGLEASGSVYICTLCDATRLEASQNLVFHSITRSHAENLERYEVWRSNP
YHESVEELRDRVKGVSAKPFIETVPSIDALHCDIGNAAEFYKIFQLEIGEVYKNPNASKEERKRW
QATLDKHLRKKMNLKPIMRMNGNFARKLMTKETVDAVCELIPSEERHEALRELMDLYLKMKPV
WRSSCPAKECPESLCQYSFNSQRFAELLSTKFKYRYEGKITNYFHKTLAHVPEIIERDGSIGAW
ASEGNESGNKLFRRFRKMNARQSKCYEMEDVLKHHWLYTSKYLQKFMNAHNALKTSGFTMN
PQASLGDPLGIEDSLESQDSMEF (SEQ ID NO: 140)

>Homo sapiens RAG2 (UniProt Accession P55895)
MSLQMVTVSNNIALIQPGFSLMNFDGQVFFFGQKGWPKRSCPTGVFHLDVKHNHVKLKPTIFS
KDSCYLPPLRYPATCTFKGSLESEKHQYIIHGGKTPNNEVSDKIYVMSIVCKNNKKVTFRCTEKD
LVGDVPEARYGHSINVVYSRGKSMGVLFGGRSYMPSTHRTTEKWNSVADCLPCVFLVDFEFG
CATSYILPELQDGLSFHVSIAKNDTIYILGGHSLANNIRPANLYRIRVDLPLGSPAVNCTVLPGGIS
VSSAILTQTNNDEFVIVGGYQLENQKRMICNIISLEDNKIEIREMETPDWTPDIKHSKIWFGSNMG
NGTVFLGIPGDNKQVVSEGFYFYMLKCAEDDTNEEQTTFTNSQTSTEDPGDSTPFEDSEEFCF
SAEANSFDGDDEFDTYNEDDEEDESETGYWITCCPTCDVDINTWVPFYSTELNKPAMIYCSHG
DGHWVHAQCMDLAERTLIHLSAGSNKYYCNEHVEIARALHTPQRVLPLKKPPMKSLRKKGSGK
ILTPAKKSFLRRLFD (SEQ ID NO: 141)

>PGK promoter associated with FANCA gene
GGGGTTGGGGTTGCGCCTTTTCCAAGGCAGCCCTGGGTTTGCGCAGGGACGCGGCTGCT
CTGGGCGTGGTTCCGGGAAACGCAGCGGCGCCGACCCTGGGTCTCGCACATTCTTCACG
TCCGTTCGCAGCGTCACCCGGATCTTCGCCGCTACCCTTGTGGGCCCCCCGGCGACGCTT
CCTGCTCCGCCCCTAAGTCGGGAAGGTTCCTTGCGGTTCGCGGCGTGCCGGACGTGACA
AACGGAAGCCGCACGTCTCACTAGTACCCTCGCAGACGGACAGCGCCAGGGAGCAATGG
CAGCGCGCCGACCGCGATGGGCTGTGGCCAATAGCGGCTGCTCAGCGGGGCGCGCCGA
GAGCAGCGGCCGGGAAGGGGCGGTGCGGAGGCGGGGTGTGGGCGGTAGTGTGGGC
CCTGTTCCTGCCCGCGCGGTGTTCCGCATTCTGCAAGCCTCCGGAGCGCACGTCGGCAG
TCGGCTCCTCGTTGACCGAATCACCGACCTCTCTCCCAGGGGATCCACCGGTCCGCC
AAGGCCATGTCCGACTCGTGGGTCCCGAACTCCGCCTCGGGCCAGGACCCAGGGGGCCG
CCGGAGGGCCTGGGCCGAGCTGCTGGCGGGAAGGGTCAAGAGGGAAAAATATAATCCTG
AAAGGGCACAGAAATTAAAGGAATCAGCTGTGCGCCTCCTGCGAAGCCATCAGGACCTGA
ATGCCCTTTTGCTTGAGGTAGAAGGTCCACTGTGTAAAAAATTGTCTCTCAGCAAAGTGATT
GACTGTGACAGTTCTGAGGCCTATGCTAATCATTCTAGTTCATTTATAGGCTCTGCTTTGCA
GGATCAAGCCTCAAGGCTGGGGGTTCCCGTGGGTATTCTCTCAGCCGGGATGGTTGCCTC
TAGCGTGGGACAGATCTGCACGGCTCCAGCGGAGACCAGTCACCCTGTGCTGCTGACTGT
GGAGCAGAGAAAGAAGCTGTCTTCCCTGTTAGAGTTTGCTCAGTATTTATTGGCACACAGT
ATGTTCTCCCGTCTTTCCTTCTGTCAAGAATTATGGAAAATACAGAGTTCTTTGTTGCTTGAA
GCGGTGTGGCATCTTCACGTACAAGGCATTGTGAGCCTGCAAGAGCTGCTGGAAAGCCAT
CCCGACATGCATGCTGTGGGATCGTGGCTCTTCAGGAATCTGTGCTGCCTTTGTGAACAG
ATGGAAGCATCCTGCCAGCATGCTGACGTCGCCAGGGCCATGCTTTCTGATTTTGTTCAAA
TGTTTGTTTTGAGGGGATTTCAGAAAACTCAGATCTGAGAAGAACTGTGGAGCCTGAAAA
AATGCCGCAGGTCACGGTTGATGTACTGCAGAGAATGCTGATTTTGCACTTGACGCTTTG
GCTGCTGGAGTACAGGAGGAGTCCTCCACTCACAAGATCGTGAGGTGCTGGTTCGGAGTG

FIG. 20 cont'd

TTCAGTGGACACACGCTTGGCAGTGTAATTTCCACAGATCCTCTGAAGAGGTTCTTCAGTC
ATACCCTGACTCAGATACTCACTCACAGCCCTGTGCTGAAAGCATCTGATGCTGTTCAGAT
GCAGAGAGAGTGGAGCTTTGCGCGGACACACCCTCTGCTCACCTCACTGTACCGCAGGCT
CTTTGTGATGCTGAGTGCAGAGGAGTTGGTTGGCCATTTGCAAGAAGTTCTGGAAACGCA
GGAGGTTCACTGGCAGAGAGTGCTCTCCTTTGTGTCTGCCCTGGTTGTCTGCTTTCCAGAA
GCGCAGCAGCTGCTTGAAGACTGGGTGGCGCGTTTGATGGCCCAGGCATTCGAGAGCTG
CCAGCTGGACAGCATGGTCACTGCGTTCCTGGTTGTGCGCCAGGCAGCACTGGAGGGCC
CCTCTGCGTTCCTGTCATATGCAGACTGGTTCAAGGCCTCCTTTGGGAGCACACGAGGCT
ACCATGGCTGCAGCAAGAAGGCCCTGGTCTTCCTGTTTACGTTCTTGTCAGAACTCGTGCC
TTTTGAGTCTCCCCGGTACCTGCAGGTGCACATTCTCCACCCACCCCTGGTTCCCAGCAAG
TACCGCTCCCTCCTCACAGACTACATCTCATTGGCCAAGACACGGCTGGCCGACCTCAAG
GTTTCTATAGAAAACATGGGACTCTACGAGGATTTGTCATCAGCTGGGGACATTACTGAGC
CCCACAGCCAAGCTCTTCAGGATGTTGAAAAGGCCATCATGGTGTTTGAGCATACGGGGA
ACATCCCAGTCACCGTCATGGAGGCCAGCATATTCAGGAGGCCTTACTACGTGTCCCACTT
CCTCCCCGCCCTGCTCACACCTCGAGTGCTCCCCAAAGTCCCTGACTCCCGTGTGGCGTT
TATAGAGTCTCTGAAGAGAGCAGATAAAATCCCCCCATCTCTGTACTCCACCTACTGCCAG
GCCTGCTCTGCTGCTGAAGAGAAGCCAGAAGATGCAGCCCTGGGAGTGAGGGCAGAACC
CAACTCTGCTGAGGAGCCCCTGGGACAGCTCACAGCTGCACTGGGAGAGCTGAGAGCCT
CCATGACAGACCCCAGCCAGCGTGATGTTATATCGGCACAGGTGGCAGTGATTTCTGAAA
GACTGAGGGCTGTCCTGGGCCACAATGAGGATGACAGCAGCGTTGAGATATCAAAGATTC
AGCTCAGCATCAACACGCCGAGACTGGAGCCACGGGAACACATTGCTGTGGACCTCCTGC
TGACGTCTTTCTGTCAGAACCTGATGGCTGCCTCCAGTGTCGCTCCCCGGAGAGGCAGG
GTCCCTGGGCTGCCCTCTTCGTGAGGACCATGTGTGGACGTGTGCTCCCTGCAGTGCTCA
CCCGGCTCTGCCAGCTGCTCCGTCACCAGGGCCCGAGCCTGAGTGCCCCACATGTGCTG
GGGTTGGCTGCCCTGGCCGTGCACCTGGGTGAGTCCAGGTCTGCGCTCCCAGAGGTGGA
TGTGGGTCCTCCTGCACCTGGTGCTGGCCTTCCTGTCCCTGCGCTCTTTGACAGCCTCCT
GACCTGTAGGACGAGGGATTCCTTGTTCTTCTGCCTGAAATTTGTACAGCAGCAATTTCTT
ACTCTCTCTGCAAGTTTTCTTCCCAGTCACGAGATACTTTGTGCAGCTGCTTATCTCCAGGC
CTTATTAAAAAGTTTCAGTTCCTCATGTTCAGATTGTTCTCAGAGGCCCGACAGCCTCTTTC
TGAGGAGGACGTAGCCAGCCTTTCCTGGAGACCCTTGCACCTTCCTTCTGCAGACTGGCA
GAGAGCTGCCCTCTCTCTGGACACACAGAACCTTCCGAGAGGTGTTGAAAGAGGAAGA
TGTTCACTTAACTTACCAAGACTGGTTACACCTGGAGCTGGAAATTCAACCTGAAGCTGAT
GCTCTTTCAGATACTGAACGGCAGGACTTCCACCAGTGGGCGATCCATGAGCACTTTCTCC
CTGAGTCCTCGGCTTCAGGGGGCTGTGACGGAGACCTGCAGGCTGCGTGTACCATTCTTG
TCAACGCACTGATGGATTTCCACCAAAGCTCAAGGAGTTATGACCACTCAGAAAATTCTGA
TTTGGTCTTTGGTGGCCGCACAGGAAATGAGGATATTATTTCCAGATTGCAGGAGATGGTA
GCTGACCTGGAGCTGCAGCAAGACCTCATAGTGCCTCTCGGCCACACCCCTTCCCAGGAG
CACTTCCTCTTTGAGATTTTCCGCAGACGGCTCCAGGCTCTGACAAGCGGGTGGAGCGTG
GCTGCCAGCCTTCAGAGACAGAGGGAGCTGCTAATGTACAAACGGATCCTCCTCCGCCTG
CCTTCGTCTGTCCTCTGCGGCAGCAGCTTCCAGGCAGAACAGCCCATCACTGCCAGATGC
GAGCAGTTCTTCCACTTGGTCAACTCTGAGATGAGAAACTTCTGCTCCCACGGAGGTGCCC
TGACACAGGACATCACTGCCCACTTCTTCAGGGGCCTCCTGAACGCCTGTCTGCGGAGCA
GAGACCCCTCCCTGATGGTCGACTTCATACTGGCCAAGTGCCAGACGAAATGCCCCTTAAT
TTTGACCTCTGCTCTGGTGTGGTGGCCGAGCCTGGAGCCTGTGCTGCTCTGCCGGTGGAG
GAGACACTGCCAGAGCCCGCTGCCCGGGAACTGCAGAAGCTACAAGAAGGCCGGCAGT
TTGCCAGCGATTTCCTCTCCCCTGAGGCTGCCTCCCAGCACCCAACCCGGACTGGCTCT
CAGCTGCTGCACTGCACTTTGCGATTCAACAAGTCAGGGAAGAAAACATCAGGAAGCAGC
TAAAGAAGCTGGACTGCGAGAGAGAGGAGCTATTGGTTTTCCTTTTCTTCTTCTCCTTGATG
GGCCTGCTGTCGTCACATCTGACCTCAAATAGCACCACAGACCTGCCAAAGGCTTTCCAC

FIG. 20 cont'd

GTTTGTGCAGCAATCCTCGAGTGTTTAGAGAAGAGGAAGATATCCTGGCTGGCACTCTTTC
AGTTGACAGAGAGTGACCTCAGGCTGGGGCGGCTCCTCCTCCGTGTGGCCCCGGATCAG
CACACCAGGCTGCTGCCTTTCGCTTTTTACAGTCTTCTCTCCTACTTCCATGAAGACGCGG
CCATCAGGGAAGAGGCCTTCCTGCATGTTGCTGTGGACATGTACTTGAAGCTGGTCCAGC
TCTTCGTGGCTGGGGATACAAGCACAGTTTCACCTCCAGCTGGCAGGAGCCTGGAGCTCA
AGGGTCAGGGCAACCCCGTGGAACTGATAACAAAAGCTCGTCTTTTTCTGCTGCAGTTAAT
ACCTCGGTGCCCGAAAAAGAGCTTCTCACACGTGGCAGAGCTGCTGGCTGATCGTGGGGA
CTGCGACCCAGAGGTGAGCGCCGCCCTCCAGAGCAGACAGCAGGCTGCCCCTGACGCTG
ACCTGTCCCAGGAGCCTCATCTCTTCTGA (SEQ ID NO: 142)

>506 PGK.FancA
TCGCGCGTTCTCGAGGAGCTTGGCCCATTGCATACGTTGTATCCATATCATAATATGTACAT
TTATATTGGCTCATGTCCAACATTACCGCCATGTTGACATTGATTATTGACTAGTTATTAATA
GTAATCAATTACGGGGTCATTAGTTCATAGCCCATATATGGAGTTCCGCGTTACATAACTTA
CGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTT
ACGCTAAACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTTTTG
GCAGTACATCAATGGGCGTGGATAGCGGTTTGACTCACGGGGATTTCCAAGTCTCCACCC
CATTGACGCAAATGGGCGGTAGGCGTGTACGGTGGGAGGTCTATATAAGCAGAGCTTCTA
GATTGTACGGGAGCTCTCTCTTCACTACTCGCTGCGTCGAGAGTGTACGAGACTCTCCAG
GTTTGGTAAGAAATATTTTATATTGTTATAATGTTACTATGATCCATTAACACTCTGCTTATAG
ATTGTAAGGGTGATTGCAATGCTTTCTGCATAAAACTTTGGTTTTCTTGTTAATCAATAAACC
GACTTGATTCGAGAACCTACTCATATATTATTGTCTCTTTTATACTTTATTAAGTAAAAGGAT
TTGTATATTAGCCTTGCTAAGGGAGACATCTAGTGATATAAGTGTGAACTACACTTATCTTA
AATGATGTAACTCCTTAGGATAATCAATATACAAAATTCCATGACAATTGGCGCCCAACGTG
GGGCTCGAATATAAGTCGGGTTTATTTGTAAATTATCCCTAGGGACCTCCGAGCATAGCGG
GAGGCATATAAAAGCCAATAGACAATGGCTAGCAGGAAGTAATGTTGAAGAATATGAACTT
GATGTTGAAGCTCTGGTTGTAATTTTAAGAGATAGAAATATACCAAGAAATCCTTTACATGG
AGAAGTTATAGGTCTTCGCCTTACTGAAGGATGGTGGGGACAAATTGAGAGATTTCAGATG
GTACGTTGATTCGAATTAAGGCTATGGATTTGGCCATGGGACAAGAAATATTAGTTTATAGT
CCCATTGTATCTATGACTAAAATACAAAAACTCCACTACCAGAAAGAAAAGCTTTACCCAT
TAGATGGATAACATGGATGACTTATTTAGAAGATCCAAGAATCCAATTTCATTATGATAAAAC
CTTACCAGAACTTAAGCATATTCCAGATGTATATACATCTAGTCAGTCTCCTGTTAAACATC
CTTCTCAATATGAAGGAGTGTTTTATACTGATGGCTCGGCCATCAAAAGTCCTGATCCTACA
AAAAGCAATAATGCTGGCATGGGAATAGTACATGCCACATACAAACCTGAATATCAAGTTTT
GAATCAATGGTCAATACCACTAGGTAATCATACTGCTCAGATGGCTGAAATAGCTGCAGTT
GAATTTGCCTGTAAAAAGCTTTAAAAATACCTGGTCCTGTATTAGTTATAACTGATAGTTTC
TATGTAGCAGAAAGTGCTAATAAAGAATTACCATACTGGAAATCTAATGGGTTTGTTAATAA
TAAGAAAAAGCCTCTTAAACATATCTCCAAATGGAAATCTATTGCTGAGTGTTTATCTATGAA
ACCAGACATTACTATTCAACATGAAAAAGGCATCAGCCTACAAATACCAGTATTCATACTGA
AAGGCAATGCCCTAGCAGATAAGCTTGCCACCCAAGGAAGTTATGTGGTTAATTGTAATAC
CAAAAAACCAAACCTGGATGCAGAGTTGGATCAATTATTACAGGGTCATTATATAAAAGGAT
ATCCCAAACAATATACATATTTTTAGAAGATGGCAAAGTAAAAGTTTCCAGACCTGAAGGG
GTTAAAATTATTCCCCCTCAGTCAGACAGACAAAAAATTGTGCTTCAAGCCCACAATTTGGC
TCACACCGGACGTGAAGCCACTCTTTTAAAAATTGCCAACCTTTATTGGTGGCCAAATATGA
GAAAGGATGTGGTTAAACAACTAGGACGCTGTCAACAGTGTTTAATCACAAATGCTTCCAA
CAAAGCCTCTGGTCCTATTCTAAGACCAGATAGGCCTCAAAAACCTTTTGATAAATTCTTTA

FIG. 20 cont'd

```
TTGACTATATTGGACCTTTGCCACCTTCACAGGGATACCTATATGTATTAGTAGTTGTTGAT
GGAATGACAGGATTCACTTGGTTATACCCCACTAAGGCTCCTTCTACTAGCGCAACTGTTA
AATCTCTCAATGTACTCACTAGTATTGCAATTCCAAAGGTGATTCACTCTGATCAAGGTGCA
GCATTCACTTCTTCAACCTTTGCTGAATGGGCAAAGGAAAGAGGTATACATTTGGAATTCAG
TACTCCTTATCACCCCCAAAGTGGTAGTAAGGTGGAAAGGAAAAATAGTGATATAAAACGA
CTTTTAACTAAACTGCTAGTAGGAAGACCCACAAAGTGGTATGACCTATTGCCTGTTGTACA
ACTTGCTTTAAACAACACCTATAGCCCTGTATTAAAATATACTCCACATCAACTCTTATTTGG
TATAGATTCAAATACTCCATTTGCAAATCAAGATACACTTGACTTGACCAGAGAAGAAGAAC
TTTCTCTTTTACAGGAAATTCGTACTTCTTTATACCATCCATCCACCCCTCCAGCCTCCTCTC
GTTCCTGGTCTCCTGTTGTTGGCCAATTGGTCCAGGAGAGGGTGGCTAGGCCTGCTTCTTT
GAGACCTCGTTGGCATAAACCGTCTACTGTACTTAAGGTGTTGAATCCAAGGACTGTTGTT
ATTTTGGACCATCTTGGCAACAACAGAACTGTAAGTATAGATAATTTAAAACCTACTTCTCAT
CAGAATGGCACCACCAATGACACTGCAACAATGGATCATTTGGAAAAAAATGAATAAAGCG
CATGAGGCACTTCAAAATACAACAACTGTGACTGAACAGCAGAAGGAACAAATTATACTGG
ACATTCAAAATGAAGAAGTACAACCAACTAGGAGAGATAAATTTAGATATCTGCTTTATACTT
GTTGTGCTACTAGCTCAAGAGTATTGGCCTGGATGTTTTTAGTTTGTATATTGTTAATCATTG
TTTTGGTTTCATGCTTTGTGACTATATCCAGAATACAATGGAATAAGGATATTCAGGTATTAG
GACCTGTAATAGACTGGAATGTTACTCAAAGAGCTGTTTATCAACCCTTACAGACTAGAAG
GATTGCACGTTCCCTTAGAATGCAGCATCCTGTTCCAAAATATGTGGAGGTAAATATGACTA
GTATTCCACAAGGTGTATACTATGAACCCCATCCGGCGCGCCAGATCTGCATGCCACGGG
GTTGGGGTTGCGCCTTTTCCAAGGCAGCCCTGGGTTTGCGCAGGGACGCGGCTGCTCTG
GGCGTGGTTCCGGGAAACGCAGCGGCGCCGACCCTGGGTCTCGCACATTCTTCACGTCC
GTTCGCAGCGTCACCCGGATCTTCGCCGCTACCCTTGTGGGCCCCCGGCGACGCTTCCT
GCTCCGCCCCTAAGTCGGGAAGGTTCCTTGCGGTTCGCGGCGTGCCGGACGTGACAAAC
GGAAGCCGCACGTCTCACTAGTACCCTCGCAGACGGACAGCGCCAGGGAGCAATGGCAG
CGCGCCGACCGCGATGGGCTGTGGCCAATAGCGGCTGCTCAGCGGGGCGCGCCGAGAG
CAGCGGCCGGGAAGGGGCGGTGCGGGAGGCGGGGTGTGGGCGGTAGTGTGGGCCCT
GTTCCTGCCCGCGCGGTGTTCCGCATTCTGCAAGCCTCCGGAGCGCACGTCGGCAGTCG
GCTCCCTCGTTGACCGAATCACCGACCTCTCTCCCCAGGGGGATCCACCGGTCCGCCAAG
GCCATGTCCGACTCGTGGGTCCCGAACTCCGCCTCGGGCCAGGACCCAGGGGGCCGCC
GGAGGGCCTGGGCCGAGCTGCTGGCGGGAAGGGTCAAGAGGGAAAAATATAATCCTGAA
AGGGCACAGAAATTAAAGGAATCAGCTGTGCGCCTCCTGCGAAGCCATCAGGACCTGAAT
GCCCTTTTGCTTGAGGTAGAAGGTCCACTGTGTAAAAAATTGTCTCTCAGCAAAGTGATTG
ACTGTGACAGTTCTGAGGCCTATGCTAATCATTCTAGTTCATTTATAGGCTCTGCTTTGCAG
GATCAAGCCTCAAGGCTGGGGGTTCCCGTGGGTATTCTCTCAGCCGGGATGGTTGCCTCT
AGCGTGGGACAGATCTGCACGGCTCCAGCGGAGACCAGTCACCCTGTGCTGCTGACTGT
GGAGCAGAGAAGAAGCTGTCTTCCCTGTTAGAGTTTGCTCAGTATTTATTGGCACACAGT
ATGTTCTCCCGTCTTTCCTTCTGTCAAGAATTATGGAAAATACAGAGTTCTTTGTTGCTTGAA
GCGGTGTGGCATCTTCACGTACAAGGCATTGTGAGCCTGCAAGAGCTGCTGGAAAGCCAT
CCCGACATGCATGCTGTGGGATCGTGGCTCTTCAGGAATCTGTGCTGCCTTTGTAACAG
ATGGAAGCATCCTGCCAGCATGCTGACGTCGCCAGGGCCATGCTTTCTGATTTTGTTCAAA
TGTTTGTTTTGAGGGGATTTCAGAAAAACTCAGATCTGAGAAGAACTGTGGAGCCTGAAAA
AATGCCGCAGGTCACGGTTGATGTACTGCAGAGAATGCTGATTTTTGCACTTGACGCTTTG
GCTGCTGGAGTACAGGAGGAGTCCTCCACTCACAAGATCGTGAGGTGCTGGTTCGGAGTG
TTCAGTGGACACACGCTTGGCAGTGTAATTTCCACAGATCCTCTGAAGAGGTTCTTCAGTC
ATACCCTGACTCAGATACTCACTCACAGCCCTGTGCTGAAAGCATCTGATGCTGTTCAGAT
GCAGAGAGAGTGGAGCTTTGCGCGGACACACCCTCTGCTCACCTCACTGTACCGCAGGCT
CTTTGTGATGCTGAGTGCAGAGGAGTTGGTTGGCCATTTGCAAGAAGTTCTGGAAACGCA
GGAGGTTCACTGGCAGAGAGTGCTCTCCTTTGTGTCTGCCCTGGTTGTCTGCTTTCCAGAA
```

FIG. 20 cont'd

GCGCAGCAGCTGCTTGAAGACTGGGTGGCGCGTTTGATGGCCCAGGCATTCGAGAGCTG
CCAGCTGGACAGCATGGTCACTGCGTTCCTGGTTGTGCGCCAGGCAGCACTGGAGGGCC
CCTCTGCGTTCCTGTCATATGCAGACTGGTTCAAGGCCTCCTTTGGGAGCACACGAGGCT
ACCATGGCTGCAGCAAGAAGGCCCTGGTCTTCCTGTTTACGTTCTTGTCAGAACTCGTGCC
TTTTGAGTCTCCCCGGTACCTGCAGGTGCACATTCTCCACCCACCCCTGGTTCCCAGCAAG
TACCGCTCCCTCCTCACAGACTACATCTCATTGGCCAAGACACGGCTGGCCGACCTCAAG
GTTTCTATAGAAAACATGGGACTCTACGAGGATTTGTCATCAGCTGGGGACATTACTGAGC
CCCACAGCCAAGCTCTTCAGGATGTTGAAAAGGCCATCATGGTGTTTGAGCATACGGGGA
ACATCCCAGTCACCGTCATGGAGGCCAGCATATTCAGGAGGCCTTACTACGTGTCCCACTT
CCTCCCCGCCCTGCTCACACCTCGAGTGCTCCCCAAAGTCCCTGACTCCCGTGTGGCGTT
TATAGAGTCTCTGAAGAGAGCAGATAAAATCCCCCATCTCTGTACTCCACCTACTGCCAG
GCCTGCTCTGCTGCTGAAGAGAAGCCAGAAGATGCAGCCCTGGGAGTGAGGGCAGAACC
CAACTCTGCTGAGGAGCCCCTGGGACAGCTCACAGCTGCACTGGGAGAGCTGAGAGCCT
CCATGACAGACCCCAGCCAGCGTGATGTTATATCGGCACAGGTGGCAGTGATTTCTGAAA
GACTGAGGGCTGTCCTGGGCCACAATGAGGATGACAGCAGCGTTGAGATATCAAAGATTC
AGCTCAGCATCAACACGCCGAGACTGGAGCCACGGGAACACATTGCTGTGGACCTCCTGC
TGACGTCTTTCTGTCAGAACCTGATGGCTGCCTCCAGTGTCGCTCCCCGGAGAGGCAGG
GTCCCTGGGCTGCCCTCTTCGTGAGGACCATGTGTGGACGTGTGCTCCCTGCAGTGCTCA
CCCGGCTCTGCCAGCTGCTCCGTCACCAGGGCCCGAGCCTGAGTGCCCCACATGTGCTG
GGGTTGGCTGCCCTGGCCGTGCACCTGGGTGAGTCCAGGTCTGCGCTCCCAGAGGTGGA
TGTGGGTCCTCCTGCACCTGGTGCTGGCCTTCCTGTCCCTGCGCTCTTTGACAGCCTCCT
GACCTGTAGGACGAGGGATTCCTTGTTCTTCTGCCTGAAATTTTGTACAGCAGCAATTTCTT
ACTCTCTCTGCAAGTTTTCTTCCCAGTCACGAGATACTTTGTGCAGCTGCTTATCTCCAGGC
CTTATTAAAAAGTTTCAGTTCCTCATGTTCAGATTGTTCTCAGAGGCCCGACAGCCTCTTTC
TGAGGAGGACGTAGCCAGCCTTTCCTGGAGACCCTTGCACCTTCCTTCTGCAGACTGGCA
GAGAGCTGCCCTCTCTCTGGACACACAGAACCTTCCGAGAGGTGTTGAAAGAGGAAGA
TGTTCACTTAACTTACCAAGACTGGTTACACCTGGAGCTGGAAATTCAACCTGAAGCTGAT
GCTCTTTCAGATACTGAACGGCAGGACTTCCACCAGTGGGCGATCCATGAGCACTTTCTCC
CTGAGTCCTCGGCTTCAGGGGGCTGTGACGGAGACCTGCAGGCTGCGTGTACCATTCTTG
TCAACGCACTGATGGATTTCCACCAAAGCTCAAGGAGTTATGACCACTCAGAAAATTCTGA
TTTGGTCTTTGGTGGCCGCACAGGAAATGAGGATATTATTTCCAGATTGCAGGAGATGGTA
GCTGACCTGGAGCTGCAGCAAGACCTCATAGTGCCTCTCGGCCACACCCCTTCCCAGGAG
CACTTCCTCTTTGAGATTTTCCGCAGACGGCTCCAGGCTCTGACAAGCGGGTGGAGCGTG
GCTGCCAGCCTTCAGAGACAGAGGGAGCTGCTAATGTACAAACGGATCCTCCTCCGCCTG
CCTTCGTCTGTCCTCTGCGGCAGCAGCTTCCAGGCAGAACAGCCCATCACTGCCAGATGC
GAGCAGTTCTTCCACTTGGTCAACTCTGAGATGAGAAACTTCTGCTCCCACGGAGGTGCCC
TGACACAGGACATCACTGCCCACTTCTTCAGGGGCCTCCTGAACGCCTGTCTGCGGAGCA
GAGACCCCTCCCTGATGGTCGACTTCATACTGGCCAAGTGCCAGACGAAATGCCCCTTAAT
TTTGACCTCTGCTCTGGTGTGGTGGCCGAGCCTGGAGCCTGTGCTGCTCTGCCGGTGGAG
GAGACACTGCCAGAGCCCGCTGCCCCGGGAACTGCAGAAGCTACAAGAAGGCCGGCAGT
TTGCCAGCGATTTCCTCTCCCTGAGGCTGCCTCCCAGCACCCAACCCGGACTGGCTCT
CAGCTGCTGCACTGCACTTTGCGATTCAACAAGTCAGGGAAGAAAACATCAGGAAGCAGC
TAAAGAAGCTGGACTGCGAGAGAGGGAGCTATTGGTTTTCCTTTTCTTCTTCCTTGATG
GGCCTGCTGTCGTCACATCTGACCTCAAATAGCACCACAGACCTGCCAAAGGCTTTCCAC
GTTTGTGCAGCAATCCTCGAGTGTTTAGAGAAGAGGAAGATATCCTGGCTGGCACTCTTTC
AGTTGACAGAGAGTGACCTCAGGCTGGGGCGGCTCCTCCTCCGTGTGGCCCCGGATCAG
CACACCAGGCTGCTGCCTTTCGCTTTTACAGTCTTCTCTCCTACTTCCATGAAGACGCGG
CCATCAGGGAAGAGGCCTTCCTGCATGTTGCTGTGGACATGTACTTGAAGCTGGTCCAGC
TCTTCGTGGCTGGGGATACAAGCACAGTTTCACCTCCAGCTGGCAGGAGCCTGGAGCTCA

FIG. 20 cont'd

AGGGTCAGGGCAACCCCGTGGAACTGATAACAAAAGCTCGTCTTTTCTGCTGCAGTTAAT
ACCTCGGTGCCCGAAAAGAGCTTCTCACACGTGGCAGAGCTGCTGGCTGATCGTGGGGA
CTGCGACCCAGAGGTGAGCGCCGCCCTCCAGAGCAGACAGCAGGCTGCCCCTGACGCTG
ACCTGTCCCAGGAGCCTCATCTCTTCTGACGGGACCTGCCACTGCACACCAGCCCAGCTC
CCGTGTAAATAATTTATTACAAGCATAACATGGAGCTCTTGTTGCACTAAAAAGTGGATTAC
AAATCTCCTCGACTGCTTTAGTGGGGAAAGGAATCAATTATTTATGAACTGTCCGGCCCCG
AGTCACTCAGCGTTTGCGGGAAAATAAACCACTGGTCCCAGAGCAGAGGAAGGCTACTTG
AGCCGGACACCAAGCCCGCCTCCAGCACCAAGGGCGGGCAGCACCCTCCGACCCTCCCA
TGCGGGTGCACACGAAGGGTGAGGCTGACACAGCCACTGCGGAGTCCAGGCTGCTAGAG
GTGCTCATCCTCACTGCCGTCCTCAGGTGGGTTCGGGCTTCACCGCCTGGCCCTCTGTGG
TCACAGAGGGGCTCGGTGGCCCAGGTGGTGGTTCCGCCTCCAGGGGCAGGGCCTTGTCC
TGGGTCTGTGTCAGCGGGTGCACCATGGACATGTGTACAAGTAAAGCGGCCGCGTCGAG
GGCTGCAGGAATTCGAGCATCTTACCGCCATTTATTCCCATATTTGTTCTGTTTTCTTGATT
TGGGTATACATTTAAATGTTAATAAAACAAAATGGTGGGGCAATCATTTACATTTTTAGGGAT
ATGTAATTACTAGTTCAGGTGTATTGCCACAAGACAAACATGTTAAGAAACTTTCCCGTTAT
TTACGCTCTGTTCCTGTTAATCAACCTCTGGATTACAAAATTTGTGAAAGATTGACTGATATT
CTTAACTATGTTGCTCCTTTTACGCTGTGTGGATATGCTGCTTTATAGCCTCTGTATCTAGC
TATTGCTTCCCGTACGGCTTTCGTTTTCTCCTCCTTGTATAAATCCTGGTTGCTGTCTCTTTT
AGAGGAGTTGTGGCCCGTTGTCCGTCAACGTGGCGTGGTGTGCTCTGTGTTTGCTGACGC
AACCCCCACTGGCTGGGGCATTGCCACCACCTGTCAACTCCTTTCTGGGACTTTCGCTTTC
CCCCTCCCGATCGCCACGGCAGAACTCATCGCCGCCTGCCTTGCCCGCTGCTGGACAGG
GGCTAGGTTGCTGGGCACTGATAATTCCGTGGTGTTGTCGGGGAAGCTGACGTCCTTTCG
AATTCGATATCAAGCTTATCGATACCGTCGACGGTTACCAAGCAGCTATGGAAGCTTATGG
ACCTCAGAGAGGAAGTAACGAGGAGAGGGTGTGGTGGAATGCCACTAGAAACCAGGGAA
AACAAGGAGGAGAGTATTACAGGGAAGGAGGTGAAGAACCTCATTACCCAAATACTCCTG
CTCCTCATAGACGTACCTGGGATGAGAGACACAAGGTTCTTAAATTGTCCTCATTCGCTAC
TCCCTCTGACATCCAACGCTGGGCTACTAACTCTAGATTGTACGGGAGCTCTCTTCACTAC
TCGCTGCGTCGAGAGTGTACGAGACTCTCCAGGTTTGGTAAGAAATATTTTATATTGTTATA
ATGTTACTATGATCCATTAACACTCTGCTTATAGATTGTAAGGGTGATTGCAATGCTTTCTG
CATAAAACTTTGGTTTTCTTGTTAATCAATAAACCGACTTGATTCGAGAACCTACTCATATAT
TATTGTCTCTTTTATACTTTATTAAGTAAAAGGATTTGTATATTAGCCTTGCTAAGGGAGACA
TCTAGTGATATAAGTGTGAACTACACTTATCTTAAATGATGTAACTCCTTAGGATAATCAATA
TACAAAATTCCATGACAATTGGCGATACCCAGCTGCGCTCTTCCGCTTCCTCGCTCACTGA
CTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAA
CAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATT
ACGCGCAGAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAGGATCTTCAC
CTAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTT

FIG. 20 cont'd

CATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCTTC
ATTCAGCTCCGGTTCCCAACGATCAAGGCGAGTTACATGATCCCCATGTTGTGCAAAAAA
GCGGTTAGCTCCTTCGGTCCTCCGATCGTTGTCAGAAGTAAGTTGGCCGCAGTGTTATCAC
TCATGGTTATGGCAGCACTGCATAATTCTCTTACTGTCATGCCATCCGTAAGATGCTTTTCT
GTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGT
TCGATGTAACCCACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCGCACAT
TTCCCCGAAAAGTGCCACCTGACGTCTAAGAAACCATTATTATCATGACATTAACCTATAAA
AATAGGCGTATCACGAGGCCCTTTCGTC (SEQ ID NO: 143)

>FV Pol gene DNA
ATGAATCCCCTCCAACTGTTGCAGCCTCTGCCCGCAGAGATCAAAGGGACTAAACTGCTG
GCTCATTGGGACTCTGGAGCAACCATAACATGCATACCAGAAAGCTTCCTTGAGGACGAG
CAGCCTATCAAAAAAACATTGATTAAGACGATCCACGGGGAAAAGCAGCAGAACGTGTATT
ACGTTACCTTTAAGGTGAAGGGCCGGAAAGTCGAGGCCGAGGTCATTGCCTCTCCATACG
AATACATTCTGCTCTCACCCACCGACGTGCCATGGTTGACCCAGCAGCCTCTTCAGCTGAC
TATCCTGGTCCCTTTGCAGGAGTACCAGGAAAAGATTCTGAGCAAGACGGCGCTTCCCGA
AGATCAGAAACAGCAGCTGAAGACCCTCTTCGTGAAATACGATAATCTCTGGCAGCACTGG
GAAAACCAGGTGGGCCATCGGAAGATTCGACCCCACAATATCGCCACGGGCGACTATCCA
CCTAGGCCTCAGAAGCAGTATCCCATCAACCCAAAAGCAAAACCAAGCATCCAGATCGTCA
TCGATGATTTGCTTAAGCAAGGAGTGCTCACCCCACAAAATAGCACTATGAACACCCCAGT
GTACCCCGTGCCCAAACCGGACGGCAGATGGAGAATGGTATTGGACTATCGCGAAGTTAA
CAAAACCATACCTTTGACCGCAGCCCAGAATCAACACAGCGCCGGCATCTTGGCTACGAT
CGTGAGACAGAAGTACAAAACAACTCTCGATCTGGCCAACGGCTTTTGGGCTCACCCAATC
ACTCCAGAGAGCTACTGGCTTACCGCCTTTACATGGCAGGGGAAACAATACTGTTGGACC
CGGCTGCCTCAGGGGTTCTTGAATTCACCCGCACTGTTTACAGCTGACGTCGTTGATCTGC
TGAAAGAAATCCCCAATGTGCAGGTATACGTGGACGACATCTATCTTTCCCACGACGATCC
AAAAGAGCATGTTCAGCAGCTCGAAAAAGTTTTCCAGATCCTGCTGCAGGCTGGTTATGTC
GTCTCACTCAAGAAGTCTGAGATAGGACAAAAGACTGTGGAGTTTCTGGGATTTAACATCA
CCAAGGAAGGACGGGGATTGACTGATACGTTCAAGACTAAGCTGCTCAACATTACTCCTCC
CAAGGATCTTAAGCAGCTGCAGAGTATTCTTGGCTTGCTCAATTTTGCCCGGAATTTTATCC
CTAACTTCGCTGAGCTTGTTCAGCCCCTGTATAATCTGATAGCCTCCGCCAAGGGTAAGTA
CATCGAATGGAGCGAGGAGAATACTAAACAGTTGAACATGGTGATTGAGGCACTTAACACT
GCCTCCAACTTGGAGGAACGACTGCCAGAGCAGCGACTTGTGATTAAAGTGAACACCTCA
CCAAGTGCGGGGTACGTGCGCTACTACAACGAGACAGGCAAAAAGCCCATAATGTACCTG
AACTATGTCTTCTCAAAAGCTGAGCTCAAGTTTAGCATGCTCGAGAAGCTGCTTACTACCAT
GCACAAGGCCCTGATAAAGGCCATGGACCTTGCCATGGGGCAAGAAATCCTCGTGTACAG
CCCCATCGTTTCCATGACGAAGATCCAGAAAACACCACTGCCCGAACGAAAGGCCTTGCC
TATCAGATGGATTACTTGGATGACCTACCTTGAGGACCCCCGCATCCAGTTTCATTATGATA

FIG. 20 cont'd

AGACCCTGCCTGAACTGAAACACATCCCAGACGTGTACACCTCCAGTCAGTCCCCAGTCAA
GCACCCTTCTCAATATGAAGGAGTGTTTTATACCGATGGGAGTGCCATCAAATCCCCTGAC
CCCACAAAAAGTAACAACGCCGGTATGGGTATCGTCCACGCGACCTATAAGCCCGAGTAT
CAGGTACTGAACCAGTGGTCCATCCCGCTGGGGAATCATACCGCCCAGATGGCGGAAATT
GCCGCAGTCGAGTTTGCCTGCAAAAAGGCATTGAAAATCCCAGGGCCTGTCCTGGTCATC
ACCGACTCTTTCTACGTAGCCGAGTCAGCCAATAAGGAACTGCCCTATTGGAAAAGTAATG
GCTTCGTGAACAACAAGAAGAAGCCACTGAAACATATTAGCAAATGGAAATCTATTGCCGA
GTGTCTGTCTATGAAGCCCGACATCACTATCCAGCACGAAAAGGGCCATCAGCCCACCAA
CACTAGTATCCATACGGAGGGAAACGCTCTGGCCGATAAGCTAGCCACTCAAGGGAGTTA
CGTCGTGAACTGCAACACCAAGAAACCTAACCTTGACGCCGAATTGGACCAATTGCTGCAG
GGACATTACATAAAGGGCTACCCCAAGCAGTATACCTATTTCTGGAAGACGGCAAGGTAA
AAGTGTCCCGGCCAGAGGGCGTCAAGATCATCCCGCCACAAAGCGACAGACAGAAAATCG
TTCTGCAGGCCCACAACCTCGCTCATACTGGGCGCGAAGCTACTCTGCTCAAGATTGCCA
ATCTGTATTGGTGGCCGAATATGAGAAAAGACGTCGTAAAGCAACTGGGGCGCTGTCAGC
AGTGTTTGATCACTAACGCAAGTAACAAAGCAAGTGGGCCGATTCTTCGACCAGACCGCCC
TCAGAAACCGTTCGATAAGTTTTTTATAGATTACATTGGACCTCTGCCTCCCAGTCAAGGCT
ACCTCTACGTGCTGGTAGTGGTCGATGGCATGACGGGATTCACATGGCTGTACCCGACCA
AGGCGCCGAGTACTTCCGCGACGGTCAAGAGCCTTAACGTTCTCACCTCCATAGCTATCC
CCAAAGTTATCCACTCCGACCAGGGCGCAGCTTTCACCAGCTCTACCTTCGCGGAGTGGG
CCAAAGAGAGGGGGATTCACTTGGAATTCTCAACGCCTTACCACCCCAATCTAGCGGAAA
GGTCGAGAGAAAAATTCAGATATCAAAAGACTGTTGACCAAGCTGCTTGTTGGCCGCCCT
ACAAAGTGGTATGACCTCCTGCCTGTCGTCCAGCTGGCACTGAACAACACCTACAGCCCC
GTGCTCAAGTATACACCTCATCAGTTGCTGTTTGGTATTGATAGTAACACTCCTTTCGCAAA
TCAGGATACGTTGGATCTCACTCGCGAAGAAGAGCTCAGTTTGCTGCAGGAGATACGCAC
GAGTCTGTACCACCCTTCCACTCCTCCCACTTCTAGTAGGTCTTGGTCTCCAGTTGTGGGA
CAGCTTGTTCAGGAAAGAGTCGCCCGGCCCGCATCACTGCGGCCCCGGTGGCACAAACC
GTCTACTGTACTGAAGGTGCTCAACCCACGGACGGTGGTAATCCTTGACCATCTCGGAAAC
AACCGGACAGTGTCAATCGATAACCTCAAGCCAACCTCCCACCAAAACGGCACAACCAATG
ACACAGCCACAATGGATCATTAG (SEQ ID NO: 104)

To generate integration deficient foamy vector, either bolded A is mutated to C in underlined sequence or underlined A is mutated to C in bolded sequence >FV Pol gene AA
MNPLQLLQPLPAEIKGTKLLAHWDSGATITCIPESFLEDEQPIKKTLIKTIHGEKQQNVYYVTFKV
KGRKVEAEVIASPYEYILLSPTDVPWLTQQPLQLTILVPLQEYQEKILSKTALPEDQKQQLKTLFV
KYDNLWQHWENQVGHRKIRPHNIATGDYPPRPQKQYPINPKAKPSIQIVIDDLLKQGVLTPQNS
TMNTPVYPVKPDGRWRMVLDYREVNKTIPLTAAQNQHSAGILATIVRQKYKTTLDLANGFWA
HPITPESYWLTAFTWQGKQYCWTRLPQGFLNSPALFTADVVDLLKEIPNVQVYVDDIYLSHDDP
KEHVQQLEKVFQILLQAGYVVSLKKSEIGQKTVEFLGFNITKEGRGLTDTFKTKLLNITPPKDLKQ
LQSILGLLNFARNFIPNFAELVQPLYNLIASAKGKYIEWSEENTKQLNMVIEALNTASNLEERLPE
QRLVIKVNTSPSAGYVRYYNETGKKPIMYLNYVFSKAELKFSMLEKLLTTMHKALIKAMDLAMG
QEILVYSPIVSMTKIQKTPLPERKALPIRWITWMTYLEDPRIQFHYDKTLPELKHIPDVYTSSQSP
VKHPSQYEGVFYTDGSAIKSPDPTKSNNAGMGIVHATYKPEYQVLNQWSIPLGNHTAQMAEIA
AVEFACKKALKIPGPVLVITDSFYVAESANKELPYWKSNGFVNNKKKPLKHISKWKSIAECLSMK
PDITIQHEKGHQPTNTSIHTEGNALADKLATQGSYVVNCNTKKPNLDAELDQLLQGHYIKGYPK
QYTYFLEDGKVKVSRPEGVKIIPPQSDRQKIVLQAHNLAHTGREATLLKIANLYWWPNMRKDVV

FIG. 20 cont'd

KQLGRCQQCLITNASNKASGPILRPDRPQKPFDKFFI<u>D</u>YIGPLPPSQGYLYVLVVVDGMTGFTW
LYPTKAPSTSATVKSLNVLTSIAIPKVIHS<u>D</u>QGAAFTSSTFAEWAKERGIHLEFSTPYHPQSSGK
VERKNSDIKRLLTKLLVGRPTKWYDLLPVVQLALNNTYSPVLKYTPHQLLFGIDSNTPFANQDTL
DLTREEELSLLQEIRTSLYHPSTPPTSSRSWSPVVGQLVQERVARPASLRPRWHKPSTVLKVL
NPRTVVILDHLGNNRTVSIDNLKPTSHQNGTTNDTATMDH* (SEQ ID NO: 105)

To generate integration deficient foamy vector (IDFV), underlined D is mutated to A (separately, 2 different versions)

>PGK promoter
GGGGTTGGGGTTGCGCCTTTTCCAAGGCAGCCCTGGGTTTGCGCAGGGACGCGGCTGCT
CTGGGCGTGGTTCCGGGAAACGCAGCGGCGCCGACCCTGGGTCTCGCACATTCTTCACG
TCCGTTCGCAGCGTCACCCGGATCTTCGCCGCTACCCTTGTGGGCCCCCCGGCGACGCTT
CCTGCTCCGCCCCTAAGTCGGGAAGGTTCCTTGCGGTTCGCGGCGTGCCGGACGTGACA
AACGGAAGCCGCACGTCTCACTAGTACCCTCGCAGACGGACAGCGCCAGGGAGCAATGG
CAGCGCGCCGACCGCGATGGGCTGTGGCCAATAGCGGCTGCTCAGCGGGGCGCGCCGA
GAGCAGCGGCCGGGAAGGGGCGGTGCGGGAGGCGGGGTGTGGGGCGGTAGTGTGGGC
CCTGTTCCTGCCCGCGCGGTGTTCCGCATTCTGCAAGCCTCCGGAGCGCACGTCGGCAG
TCGGCTCCCTCGTTGACCGAATCACCGACCTCTCTCCCCAG (SEQ ID NO: 106)

LTG 1906 EF1a-VH-4 CD33-CD8 TM-41BB-CD3 zeta
MLLLVTSLLLCELPHPAFLLIPEVQLVESGGGLVQPGGSLRLSCAASGFTFSSYGMSWVRQAP
RQGLEWVANIKQDGSEKYYADSVKGRFTISRDNSKNTLYLQMNSLRAEDTATYYCAKENVDW
GQGTLVTVSSAAATTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKF
SRSADAPAYQQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR (SEQ ID NO: 144)

LTG 1905 EF1a VH-2 CD33-CD8 TM-41BB-CD3 zeta
MLLLVTSLLLCELPHPAFLLIPEVQLVESGGGLVQPGGSLRLSCAASGFTFSSYGMSWVRQAP
RKGLEWIGEINHSGSTNYNPSLKSRVTISRDNSKNTLYLQMNSLRAEDTATYYCARPLNYYYY
MDVWGKGTTVTVSSAAATTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEEGGCE
LRVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO: 145)

His Tag
HHHHHH (SEQ ID NO: 146)

Flag tag
DYKDDDDK (SEQ ID NO: 147)

Xpress tag
DLYDDDDK (SEQ ID NO: 148)

Avi tag
GLNDIFEAQKIEWHE (SEQ ID NO: 149)

FIG. 20 cont'd

Calmodulin tag
KRRWKKNFIAVSAANRFKKISSSGAL (SEQ ID NO: 150)

HA tag
YPYDVPDYA (SEQ ID NO: 151)

Myc tag
EQKLISEEDL (SEQ ID NO: 152)

Softag 1
SLAELLNAGLGGS (SEQ ID NO: 153)

Softag 3
TQDPSRVG (SEQ ID NO: 154)

V5 tag
GKPIPNPLLGLDST (SEQ ID NO: 155)

REDUCING CD33 EXPRESSION TO SELECTIVELY PROTECT THERAPEUTIC CELLS

CROSS-REFERENCE TO RELATED APPLICATIONS

This application is a U.S. National Phase Application based on International Patent Application no. PCT/US2019/050859, filed Sep. 12, 2019, which claims priority to and the benefit of the earlier filing date of U.S. Provisional Application No. 62/730,164, filed Sep. 12, 2018, each of which is incorporated by reference herein in its entirety as if fully set forth herein.

STATEMENT REGARDING FEDERALLY SPONSORED RESEARCH OR DEVELOPMENT

This invention was made with government support under HL136135 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2G51591_ST25.txt. The text file is 224 KB, was created on Feb. 25, 2021, and is being submitted electronically via EFS-Web.

FIELD OF THE DISCLOSURE

The current disclosure provides systems and methods to selectively protect therapeutic cells by reducing CD33 expression in the therapeutic cells and targeting non-therapeutic or unmodified native cells with an anti-CD33 therapy. The selective protection results in the enrichment of the therapeutic cells while simultaneously targeting any diseased, malignant and/or non-therapeutic CD33 expressing cells within a subject.

BACKGROUND OF THE DISCLOSURE

Hematopoietic stem cells (HSC) are stem cells that can give rise to all blood cell types such as the white blood cells of the immune system (e.g., virus-fighting T cells and antibody-producing B cells), platelets, and red blood cells. The therapeutic administration of HSC can be used to treat a variety of adverse conditions including immune deficiency diseases, non-malignant blood disorders, cancers, infections, and radiation exposure (e.g., cancer treatment, accidental, or attack-based).

As particular examples of conditions that can be treated with HSC, more than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders.

One example of a primary immune deficiency is Fanconi anemia (FA). FA is an inherited blood disorder that leads to bone marrow (BM) failure. It is characterized, in part, by a deficient DNA-repair mechanism. At least 20% of patients with FA develop cancers such as acute myeloid leukemias and cancers of the skin, liver, gastrointestinal tract, and gynecological system. The skin and gastrointestinal tumors are usually squamous cell carcinomas. The average age of FA patients who develop cancer is 15 years for leukemia, 16 years for liver tumors, and 23 years for other tumors.

X-linked severe combined immunodeficiency (SCID-X1) is both a cellular and humoral immune depletion caused by mutations in the common gamma chain gene ($\gamma$C), which result in the absence of T and natural killer (NK) lymphocytes and the presence of nonfunctional B lymphocytes. SCID-X1 is fatal in the first two years of life unless the immune system is reconstituted, for example, through bone marrow transplant (BMT) or cell and gene therapy.

Secondary, or acquired, immune deficiencies are not the result of inherited genetic abnormalities, but rather occur in individuals in which the immune system is compromised by factors outside the immune system. Examples include trauma, viruses, chemotherapy, toxins, and pollution. Acquired immunodeficiency syndrome (AIDS) is an example of a secondary immune deficiency disorder caused by a virus, the human immunodeficiency virus (HIV), in which a depletion of T lymphocytes renders the body unable to fight infection.

Immune deficiencies, blood cancers, and other blood-related disorders can be treated by a BMT or by administering hematopoietic cells. In some instances, the hematopoietic cells can be genetically modified to provide a functioning gene that the patient lacks. In each of these scenarios, however, it is important to remove a patient's existing hematopoietic system, so that diseased cells do not remain following treatment. Removing a patient's existing hematopoietic system is most often accomplished utilizing a process referred to as conditioning.

Traditionally, conditioning has involved the delivery of maximally tolerated doses of chemotherapeutic agents with nonoverlapping toxicities, with or without radiation. Current conditioning regimens involve total body irradiation (TBI) and/or cytotoxic drugs. These regimens are non-targeted, genotoxic, and have multiple short- and long-term adverse effects such as an increased risk of developing DNA repair disorders, interstitial pneumonitis, idiopathic pulmonary fibrosis, reduced lung pulmonary function, renal damage, sinusoidal obstruction syndrome (SOS), infertility, cataract formation, hyperthyroidism, thyroiditis, and secondary cancers. Besides morbidity, these regimens are also associated with significant mortality. Therefore, methods to reduce or eliminate the need for conditioning in these patients is desperately needed.

CD33 is a protein that is expressed on normal hematopoietic cells as they mature. Thus, therapeutic cells administered as a treatment for immune deficiencies or other blood-related disorders express or begin to express CD33. CD33, however, is also widely expressed on malignant cells in patients with myeloid neoplasms, such as acute myeloid leukemia (AML). Accordingly, CD33 represents a cellular marker for both administered therapeutic cells and unwanted non-treated, cancerous, and/or malignant cells within a patient.

Because CD33 is a target to kill diseased and/or unwanted cells, there has been great interest in developing therapeutic antibodies directed at CD33. However, because CD33 is also expressed on normal immune cells and other non-malignant cells, treatments that target it have created what are referred to as significant "on-target, but off-leukemia" or "on-target, off-tumor" effects." Such effects include suppression of the blood and immune system in the forms of severe thrombocytopenia, neutropenia, and monocytopenia in patients. For example, the CD33 antibody-drug conjugate (ADC) gemtuzumab ozogamicin (GO; MYLOTARG®, Pfizer, New York, NY) when given alone causes almost universal severe thrombocytopenia and neutropenia, and combined with conventional chemotherapy resulted in prolongation of cytopenias and increased non-relapse related mortality, in part due to fatal infections, in some clinical trials.

SUMMARY OF THE DISCLOSURE

The current disclosure provides systems and methods to protect beneficial therapeutic hematopoietic cells from anti-CD33 therapies while leaving residual diseased cells susceptible to anti-CD33 treatments. The systems and methods achieve this benefit by genetically modifying HSC to have reduced or eliminated expression of CD33, thus protecting them from anti-CD33 based therapies. In this manner, genetically modified therapeutic cells will not be harmed by concurrent or subsequent anti-CD33 therapies a patient may receive. However, pre-existing CD33-expressing cells in the patient and/or administered cells that lack the genetic modification will not be protected, resulting in positive selection for the therapeutic cells over other cells.

In particular embodiments, the HSC genetically modified to have reduced CD33 expression are also genetically modified for an additional therapeutic purpose. The genetic modification for an additional therapeutic purpose can provide a gene to treat a disorder such as an immune deficiency (e.g., Fanconi anemia, SCID, HIV), a cancer (e.g., leukemia, lymphoma, solid tumor), a blood-related disorder (e.g., sickle cell disease), a lysosomal storage disease (e.g., Pompe disease, Gaucher disease, Fabry disease, Mucopolysaccharidosis type I), or provide a therapeutic cassette that encodes a chimeric antigen receptor, engineered T-cell receptor, checkpoint inhibitor, or therapeutic antibody.

In particular embodiments, when a therapeutic gene is provided in addition to reduced CD33 expression, the systems and methods disclosed herein can provide an important advance by ensuring that only cells that have been genetically modified with the therapeutic gene also have reduced CD33 expression that results in cellular protection. In particular embodiments, this advance is achieved by linking the therapeutic gene and a CD33 blocking molecule in a single intracellular delivery vehicle. In particular embodiments, the single intracellular delivery vehicle is a viral vector.

In particular embodiments, the CD33 blocking molecule is an shRNA or siRNA CD33 blocking molecule combined with a therapeutic gene by inclusion within a common viral vector. In particular embodiments, the CD33 blocking molecule is shRNA referred to herein as shRNA4 encoded by SEQ ID NO: 8 or shRNA5 encoded by SEQ ID NO: 9. In particular embodiments, the viral vector is a lentiviral vector, a foamy viral vector, or an adenoviral vector.

In particular embodiments, the systems and methods described herein further provide systems and methods to reduce or eliminate the need for genotoxic conditioning. In particular embodiments, the systems and methods allow the targeting and removal of any remaining CD33-expressing cells following conditioning in preparation for a bone marrow transplant or administration of therapeutic cells (e.g., genetically-modified therapeutic cells). In particular embodiments, the systems and methods clear the bone marrow niche and allow for further expansion of gene-corrected cells. In particular embodiments, the systems and methods deplete residual disease-related cells. The therapeutically administered cells with reduced CD33 expression are protected from the CD33-targeting and are able to reconstitute the patient's blood and immune systems. In combination, the approach can eliminate residual non-modified CD33-expressing cells, resulting in a completely corrected hematopoiesis, and minimizing risks of future myeloid malignancy after gene therapy or allogeneic transplantation.

In particular embodiments, the genetically-modified therapeutic cells described herein are administered alone or in combination with a CD33-targeting treatment, such as an anti-CD33 antibody, an anti-CD33 immunotoxin, an anti-CD33 antibody-drug conjugate, an anti-CD33 antibody-radioisotope conjugate, an anti-CD33 bispecific antibody, an anti-CD33 bispecific immune cell activating antibody, an anti-CD33 trispecific antibody, and/or an anti-CD33 chimeric antigen receptor (CAR) or T cell receptor (TCR) modified immune cell.

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIGS. 1A, 1B. Protein sequences for CD33. (1A) Annotated sequence alignments for CD33 proteins from *Macaca fascicularis* (SEQ ID NO: 1), *Homo sapiens* (SEQ ID NO: 2), and *Mus musculus* (SEQ ID NO: 3). (1B) Protein sequences for full-length CD33 (SEQ ID NO: 4) and $CD33^{\Delta E2}$ (SEQ ID NO: 5).

FIG. 2. Schematic of antibody targeting of CD33.

FIG. 3. Schematic of the different shRNA target sites within the CD33 coding region and sequences of the shRNA (SEQ ID NOs: 6-10) as well as of the respective siRNA sequences targeting CD33 (SEQ ID NOs: 11-15).

FIGS. 9A-9C. Efficient transduction and knockdown of CD33 in human CD34+ cells using shRNA4 lentiviral vector. Cells were transduced with control (empty vector) or shRNA4 lentiviral vectors and cultured for several days post transduction. (9A) Green fluorescent protein (GFP) expression was used as a marker for transduction to determine the transduction efficiency. (9B) CD33 expression was measured by flow cytometry over time for the total cell population. (9C) CD33 expression was measured by flow cytometry over time for the GFP+ cell fraction.

FIG. 10. In vitro selection for CD33 shRNA-modified cells in human CD34+ cells following one or two rounds of GO treatment. Cells were transduced with control (empty) or shRNA 4 lentiviral vectors (shRNA), cultured for several days post transduction and treated with GO for 6 hours at the indicated times (arrow). GFP expression was measured to assess the frequency of gene modified cells.

FIG. 17. Schematic of exemplary clinical application of CD33 shRNA for gene therapy treatment.

FIG. 18. DNA sequence of lentilox 3.7 lentiviral vector (pLL37) used for cloning and delivery of CD33 shRNA (SEQ ID NO: 16).

FIG. 19. DNA sequence of FANCA lentiviral vector used for cloning CD33 shRNA (SEQ ID NO: 17).

FIG. 20. Additional supporting sequences (SEQ ID NOs: 18, 19, 117-155).

DETAILED DESCRIPTION

Figure 1A:
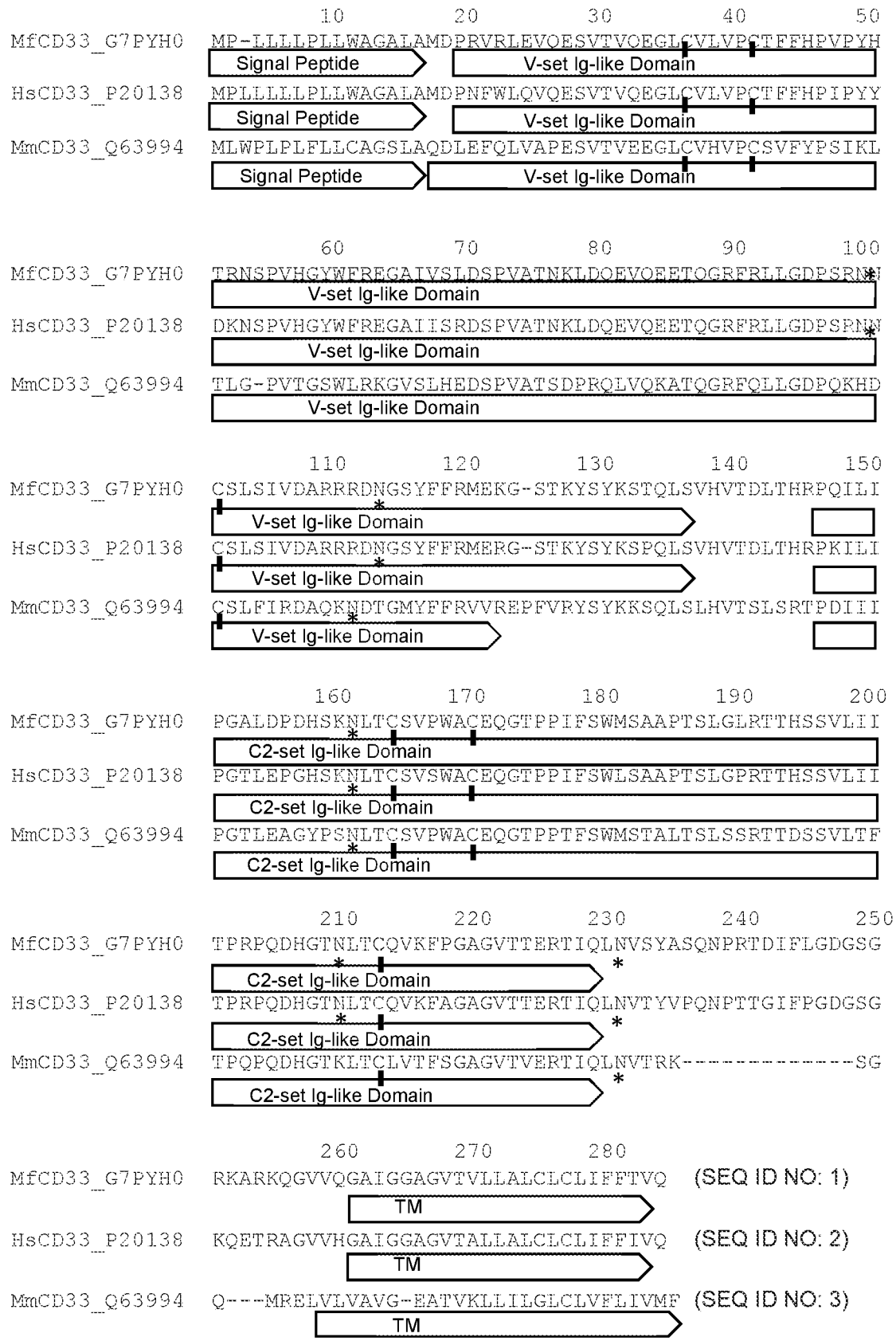

Hematopoietic stem cells (HSC) are stem cells that can give rise to all blood cell types such as the white blood cells of the immune system (e.g., virus-fighting T cells and antibody-producing B cells), platelets, and red blood cells. The therapeutic administration of HSC can be used to treat a variety of adverse conditions including immune deficiency diseases, blood disorders, malignant cancers, infections, and radiation exposure (e.g., cancer treatment, accidental, or attack-based). As examples, more than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders.

One example of a primary immune deficiency is Fanconi anemia (FA). FA is an inherited blood disorder that leads to bone marrow (BM) failure. It is characterized, in part, by a deficient DNA-repair mechanism. At least 20% of patients with FA develop cancers such as acute myeloid leukemias, and cancers of the skin, liver, gastrointestinal tract, and gynecological system. The skin and gastrointestinal tumors are usually squamous cell carcinomas. The average age of patients who develop cancer is 15 years for leukemia, 16 years for liver tumors, and 23 years for other tumors.

X-linked severe combined immunodeficiency (SCID-X1) is both a cellular and humoral immune depletion caused by mutations in the common gamma chain gene (γC), which result in the absence of T and natural killer (NK) lymphocytes and the presence of nonfunctional B lymphocytes. SCID-X1 is fatal in the first two years of life unless the immune system is reconstituted, for example, through bone marrow transplant (BMT) or gene therapy.

Secondary, or acquired, immune deficiencies are not the result of inherited genetic abnormalities, but rather occur in individuals in which the immune system is compromised by factors outside the immune system. Examples include trauma, viruses, chemotherapy, toxins, and pollution. Acquired immunodeficiency syndrome (AIDS) is an example of a secondary immune deficiency disorder caused by a virus, the human immunodeficiency virus (HIV), in which a depletion of T lymphocytes renders the body unable to fight infection.

FA, SCID, and other immune deficiencies or blood disorders as well as viral infections and cancer can be treated by a bone marrow transplant (BMT) or by administering hematopoietic cells that have been genetically modified to provide a functioning gene that the patient lacks. Therapeutic genes that can treat FA and SCID are described below. Therapeutic genes can also provide enzymes that are currently used for Enzyme replacement therapies (ERT) for lysosomal storage diseases such as Pompe disease (acid alpha-glucosidase), Gaucher disease (glucocerebrosidase), Fabry disease (alpha-galactosidase A), and Mucopolysaccharidosis type I (alpha-L-Iduronidase); blood-related cardiovascular diseases (e.g. familial apolipoprotein E deficiency and atherosclerosis (ApoE)); viral infections by expression of viral decoy receptors (e.g. for HIV-soluble CD4, or broadly neutralizing antibodies (bNAbs)) for HIV, chronic HCV, or HBV infections; and cancer (e.g. controlled expression of monoclonal antibodies (e.g. trastuzumab) or checkpoint inhibitors (e.g. aPDL1). Other additional uses are described in more detail elsewhere herein.

In these treatment scenarios, it is important to remove a patient's existing hematopoietic system to avoid leaving diseased cells behind following the treatment. This is in part because, if left, the diseased, residual cells can lead to malignancies later in life.

Currently, conditioning is used to remove a patient's existing hematopoietic system. All of the currently used conditioning regimens, however, whether myeloablative or nonmyeloablative, rely on the use of alkylating chemotherapy drugs and/or radiation such as involve total body irradiation (TBI) and/or cytotoxic drugs. Aside from any potential remaining residual cells, these conditioning regimens are also independently associated with an increased risk of developing malignancies, especially in DNA repair disorders like FA. These regimens are non-targeted, genotoxic, and have multiple short- and long-term adverse effects (La Nasa, et al., Bone Marrow Transplant. 2005; 36:971-975 and Chen, et al., Blood. 2006; 107:3764-3771) such as an increased risk of developing DNA repair disorders, interstitial pneumonitis, idiopathic pulmonary fibrosis, reduced lung pulmonary function, renal damage, sinusoidal obstruction syndrome (SOS), infertility, cataract formation, hyperthyroidism, and thyroiditis (Gyurkocza, et al., Blood. 2014; 124:344-353). Not only do these regimens result in impaired immune function, but they are associated with significant morbidity and mortality (Armitage. N Engl J Med. 1996; 330:827-837). Therefore, methods to reduce or eliminate the need for conditioning in these patients are desperately needed.

CD33 is primarily displayed on maturing and mature cells of the myeloid lineage, including multipotent myeloid precursors. CD33 is not found on pluripotent hematopoietic stem cells or non-blood cells. Consistent with its role as a myeloid differentiation antigen, CD33 is widely expressed on malignant cells in patients with myeloid neoplasms, particularly acute myeloid leukemia (AML), where it is displayed on at least a subset of the leukemia blasts in almost all cases and possibly leukemia stem cells in some. Because of this expression pattern, there has been great interest in developing therapeutic antibodies directed at CD33. While unconjugated monoclonal CD33 antibodies proved ineffective in patients with AML, several randomized trials with the CD33 antibody-drug conjugate (ADC) gemtuzumab ozogamicin (GO) have demonstrated improved survival in some AML patients. This establishes the value of antibodies in this disease and validates CD33 as the first and so far only therapeutic target for AML immunotherapy. This benefit of GO in randomized trials led to regulatory re-approval by the U.S. Food & Drug Administration (FDA) in 2017 for the treatment of newly-diagnosed as well as relapsed or refractory CD33-expressing AML. In 2018, GO was also approved by the European Medicines Agency (EMA) in Europe for the treatment of patients ≥15 years in combination with intensive chemotherapy for the treatment of newly-diagnosed de novo AML.

The expression of CD33 on maturing and mature cells of the myeloid lineage leads to significant on-target, off-leukemia effects of CD33-targeted immunotherapy, manifesting primarily as severe thrombocytopenia, neutropenia, and monocytopenia. For example, with GO monotherapy given at standard dose, grade 3/4 toxicities include invariable myelosuppression. When combined with conventional chemotherapy, GO has resulted in prolongation of cytopenias and increased non-relapse mortality, in part due to more frequent fatal infections, in some clinical trials. Some non-randomized studies similarly reported substantially increased hematologic toxicities with the use of GO together with conventional chemotherapeutics, indicating a narrow therapeutic window. Several CD33-targeting therapeutics, including newer-generation ADCs (SGN-CD33A, IMGN779), bispecific antibodies (AMG330, AMG673, AMV-564), and CAR-modified T-cells have entered clinical testing and are more potent than GO. Among these recently developed investigational agents, most advanced in development was SGN-CD33A, with clinical data from early-phase clinical trials indicating not only anti-leukemia efficacy but also the potential to cause prolonged cytopenias and life-threatening sequelae (e.g., bleeding, infection). The latter problem is, perhaps best exemplified by the premature termination of the CASCADE trial (phase 3 trial testing SGN-CD33A addition to DNA methyltransferase inhibitor) because of an increase in deaths including fatal infections with SGN-CD33A. In fact, partly because of these results, SGN-CD33A is no longer currently pursued as a clinical therapeutic. While no robust data are available yet for many of the other newer-generation anti-CD33 therapeutics, highly effective elimination of CD33-positive cells is expected to cause very prolonged cytopenias and increase risks of infection and bleeding with such potent CD33-targeted immunotherapies.

The experience with GO and SGN-CD33A suggests that clinically-relevant toxicity of CD33-targeted immunotherapy could be minimized in the presence of normal hematopoietic cells that do not display or have reduced expression of the CD33 antigen.

The current disclosure provides systems and methods to protect beneficial therapeutic hematopoietic cells from anti-CD33 therapies while leaving residual diseased cells susceptible to anti-CD33 treatments. The systems and methods achieve this benefit by genetically modifying HSC to have reduced or eliminated expression of CD33, thus protecting them from anti-CD33 based therapies. Importantly, CD33 knockout in HSC does not impair functional, multilineage hematopoiesis, and yields cells resistant to CD33-targeting immunotherapy. In this manner, genetically modified cells will not be harmed by concurrent or subsequent anti-CD33 therapies a patient may receive. Thus, the systems and methods disclosed herein can be used to improve therapies involving blood BMT, autologous cell therapies, and treatments for diseases associated with cellular expression of CD33.

In particular embodiments, the HSC genetically modified to have reduced CD33 expression are also genetically modified for an additional therapeutic purpose. The genetic modification for an additional therapeutic purpose can provide a gene to treat a disorder such as an immune deficiency (e.g., Fanconi anemia, SCID, HIV), a blood cancer (e.g., leukemia, lymphoma), a blood-related disorder (e.g., sickle cell disease), or a lysosomal storage disease (e.g., Pompe disease, Gaucher disease, Fabry disease, Mucopolysaccharidosis type I). Additional examples of conditions that can be treated with the systems and methods disclosed herein are described below.

In particular embodiments, the systems and methods reduce or eliminate the need for genotoxic conditioning. In particular embodiments, the systems and methods allow for the simultaneous targeting and removal of any remaining CD33-expressing diseased cells following conditioning in preparation for a bone marrow transplant or administration of genetically-modified therapeutic cells. In particular embodiments, the systems and methods clear the niche and allow for further expansion of gene-corrected cells. In particular embodiments, the systems and methods deplete residual disease-related cells. The therapeutically administered cells with reduced CD33 expression are selectively protected from the CD33-targeting molecules. Thus, the systems and methods provide a selective protective advantage to the genetically modified cells as they reconstitute the patient's blood and immune systems while also allowing the continued use of anti-CD33 therapies to target remaining, diseased and/or malignant CD33-expressing cells within a subject as well as any administered cells lacking the intended genetic modification. In combination, the approaches disclosed herein can eliminate CD33-expressing cells, resulting in a completely gene-corrected hematopoiesis, and minimizing risks of future myeloid malignancy after gene therapy or allogeneic transplantation.

Importantly, and as indicated, the design of the systems and methods disclosed herein provide further embodiments that not only genetically modify cells to be protected from a CD33-targeting agent but also include a therapeutic gene. In particular embodiments, the present disclosure provides for ensuring that only cells that have been genetically modified with the therapeutic gene also have reduced CD33 expression that results in cellular protection. In particular embodiments, this advance is achieved by combining the CD33 blocking molecule and a therapeutic gene in a single intracellular delivery vehicle. In particular embodiments, the single intracellular delivery vehicle is a viral vector.

In particular embodiments, the CD33 blocking molecule is an shRNA or siRNA CD33 blocking molecule. In particular embodiments, the cell is genetically modified using a common viral vector. In particular embodiments, the CD33 blocking molecule is shRNA referred to herein as shRNA4 and encoded by SEQ ID NO: 8 or shRNA5 encoded by SEQ ID NO: 9.

In particular embodiments, the viral vector is a lentiviral vector, a foamy viral vector, or an adenoviral vector and the CD33 blocking molecule is shRNA encoded by a sequence selected from SEQ ID NO: 8 or SEQ ID NO: 9 and the therapeutic gene treats FA, SCID, Pompe disease, Gaucher disease, Fabry disease, Mucopolysaccharidosis type I, familial apolipoprotein E deficiency and atherosclerosis (ApoE), viral infections, and cancer. Other additional uses are described in more detail elsewhere herein.

Particular embodiments utilize a plasmid containing SEQ ID NOs: 18 and 19 which provides a destination plasmid into which sequences encoding active RNA interference (RNAi) sequences can be cloned. In particular embodiments, SEQ ID NO: 8 and/or SEQ ID NO: 9 are cloned between SEQ ID NO: 18 and SEQ ID NO: 19. Cloned between refers to a nucleotide sequence in line with and between the first and third sequence. In particular embodiments, the sequence cloned between two other sequences is immediately adjacent to the two other sequences. In particular embodiments, the sequence cloned between two other sequences is within 5,000, 1,000, 500, or 100 bp of both other sequences.

In particular embodiments, the viral vector is a lentiviral vector, a foamy viral vector, or an adenoviral vector, the CD33 blocking molecule is shRNA encoded by SEQ ID NO: 8 or SEQ ID NO: 9 and the therapeutic gene treats FA. In particular embodiments the therapeutic gene is FANCA. Particular embodiments utilize SEQ ID NO: 17 which provides a Fanconi destination plasmid into which sequences encoding active RNA interference (RNAi) sequences can be cloned. In particular embodiments, SEQ ID NO: 8 and/or SEQ ID NO: 9 are cloned into SEQ ID NO: 17. In particular embodiments, SEQ ID NO: 8 and/or SEQ ID NO: 9 are cloned between SEQ ID NO: 18 and SEQ ID NO: 19 with a therapeutic gene that treats an immune deficiency or cancer.

In particular embodiments, the viral vector is a lentiviral vector, a foamy viral vector, or an adenoviral vector, the CD33 blocking molecule is shRNA encoded by SEQ ID NO: 8 or SEQ ID NO: 9 and the therapeutic gene treats SCID. In particular embodiments, the therapeutic gene is γC.

In particular embodiments, the genetically-modified cells described herein are administered in combination with a treatment to target CD33-expressing cells using a CD33-targeting agent, such as an anti-CD33 antibody, an anti-CD33 immunotoxin (e.g., an antibody linked to a plant and/or bacterial toxin), an anti-CD33 antibody-drug conjugate (e.g., an antibody bound to a small molecule toxin), an anti-CD33 antibody-radioimmunoconjugate, an anti-CD33 bispecific antibody, an anti-CD33 bispecific antibody that binds CD33 and an immune activating epitope on an immune cell (e.g., a BiTE® (Amgen, Munich, Germany)), an anti-CD33 trispecific antibody, and/or an anti-CD33 CAR or TCR-modified T-cell.

Aspects of the current disclosure are now described in more supporting detail as follows: (I) HSC and HSPC Populations; (II) CD33 Blocking Molecules; (III) Optional Therapeutic Genes; (IV) Delivery and Expression of CD33 Blocking Molecules and Optional Therapeutic Genes; (V) CD33-Targeting Agents; (VI) Cell Formulations and CD33-Targeting Agent Compositions; (VII) Methods of Use; (VIII) Reference Levels Derived from Control Populations; (IX) Exemplary Embodiments; (X) Experimental Examples; and (XI) Closing Paragraphs.

(I) HSC AND HSPC POPULATIONS

As indicated, HSC are stem cells that can give rise to all blood cell types such as the white blood cells of the immune system (e.g., virus-fighting T cells and antibody-producing B cells), platelets, and red blood cells. In particular embodiments, HSC can be identified and/or sorted by the following marker profiles: CD34+; Lin−CD34+CD38−CD45RA−CD90+CD49f+ (HSC1); and CD34+CD38−CD45RA−CD90− CD49f+ (HSC2). Human HSC1 can be identified by the following profiles: CD34+/CD38−/CD45RA−/CD90+ or CD34+/CD45RA−/CD90+ and mouse LT-HSC can be identified by Lin−Sca1+ckit+CD150+CD48−Flt3−CD34− (where Lin represents the absence of expression of any marker of mature cells including CD3, CD4, CD8, CD11b, CD11c, NK1.1, Gr1, and TER119). In particular embodiments, HSC are identified by a CD164+ profile. In particular embodiments, HSC are identified by a CD34+/CD164+ profile. In particular embodiments, the CD34+/CD45RA−/CD90+ HSC population is selected. For additional information regarding HSC marker profiles, see WO2017/218948.

HSC differentiate into HSPC. HSPC can self-renew or can differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and lymphocyte-like cells called natural killer cells (NK-cells). For a general discussion of hematopoiesis and HSPC differentiation, see Chapter 17, Differentiated Cells and the Maintenance of Tissues, Alberts et al., 1989, Molecular Biology of the Cell, 2nd Ed., Garland Publishing, New York, NY; Chapter 2 of Regenerative Medicine, Department of Health and Human Services, Aug. 5, 2006, and Chapter 5 of Hematopoietic Stem Cells, 2009, Stem Cell Information, Department of Health and Human Services.

HSPC can be positive for a specific marker expressed in increased levels on HSPC relative to other types of hematopoietic cells. For example, such markers include CD34, CD43, CD45RO, CD45RA, CD59, CD90, CD109, CD117, CD133, CD166, HLA DR, or a combination thereof. Also, the HSPC can be negative for an expressed marker relative to other types of hematopoietic cells. For example, such markers include Lin, CD38, or a combination thereof. Preferably, HSPC are CD34+.

HSC and HSPC sources include umbilical cord blood, placental blood, bone marrow and peripheral blood (see U.S. Pat. Nos. 5,004,681; 7,399,633; and 7,147,626; Craddock et al., Blood. 90(12):4779-4788 (1997); Jin et al., Bone Marrow Transplant. 42(9):581-588 (2008); Jin et al., Bone Marrow Transplant. 42(7):455-459 (2008); Pelus, Curr. Opin. Hematol. 15(4):285-292 (2008); Papayannopoulou et al., Blood. 91:2231-2239 (1998); Tricot et al., Haematologica. 93(11):1739-1742 (2008); and Weaver et al., Bone Marrow Transplant. 27: S23-S29 (2001)), as well as fetal liver, and embryonic stem cells (ESC) and induced pluripotent stem cells (iPSCs) that can be differentiated into HSC. Methods regarding collection, anti-coagulation and processing, etc. of blood and tissue samples are well known in the art. See, for example, Alsever et al., J. Med. 41:126 (1941); De Gowin, et al., J. Am. Med. Assoc. 114-:850 (1940); Smith, et al., J. Thorne. Cardiovasc. Surg. 38:573 (1959); Rous and Turner, J. Exp. Med. 23(2): 219-237 (1916); and Hum, Calif. Med. 108(3):218-224 (1968). Stem cell sources of HSC and HSPC also include aortal-gonadal-mesonephros derived cells, lymph, liver, thymus, and spleen from age-appropriate donors. All collected stem cell sources of HSC and HSPC can be screened for undesirable components and discarded, treated, or used according to accepted current standards at the time. These stem cell sources can be steady state/naïve or primed with mobilizing or growth factor agents.

In order to avoid surgical procedures to perform a bone marrow harvest to isolate HSC or HSPC, approaches that harvest stem cells from the peripheral blood can be preferred. Mobilization is a process whereby stem cells are stimulated out of the bone marrow (BM) niche into the peripheral blood (PB), and likely proliferate in the PB. Mobilization allows for a larger frequency of stem cells within the PB minimizing the number of days of apheresis, reaching target number collection of stem cells, and minimizing discomfort to the donor. Agents that enhance mobilization can either enhance proliferation in the PB, or enhance migration from the BM to PB, or both. Mobilizing agents include cytotoxic drugs, cytokines, and/or small molecules. A historically used regimen is a combination of cyclophosphamide (Cy) plus granulocyte-colony stimulating factor (G-CSF) (Bonig et al., Stem Cells. 27(4):836-837 (2009)). Additional mobilizing agents include alpha4-integrin blockade with anti-functional antibodies and CXCR4 blockade with the small-molecule inhibitor plerixafor (also referred to as AMD3100). Plerixafor is a bicyclam molecule that specifically and reversibly blocks SDF-1 binding to CXCR4. Another protocol is the combined regimen of granulocyte-macrophage colony stimulating factor (GM-CSF) or G-CSF with plerixafor. In certain embodiments, plerixafor is used as a single agent for mobilization of HSPCs. Plerixafor is also known commercially under the trade names Mozobil, Revixil, UMK121, AMD3000, AMD3100, GZ316455, JM3100, and SDZSID791. In particular embodiments, the mobilizing agent is C4, a CXC chemokine ligand for the CXCR2 receptor. GRObeta rapidly mobilizes short- and long-term repopulating cells in mice and/or monkeys and synergistically enhances mobilization responses with G-CSF (Pelus and Fukuda, Exp. Hematol. 34(8):1010-1020 (2006)). Furthermore, GRObeta can be combined with antagonists of VLA4 to synergistically increase circulating HSPC numbers (Karpova et al., Blood. 129(21):2939-2949 (2017)).

HSC and/or HSPC can be collected and isolated from a sample using any appropriate technique. Appropriate collection and isolation procedures include magnetic separation; fluorescence activated cell sorting (FACS; Williams et al., Dev. Biol. 112(1):126-134 (1985); Lu et al., Exp. Hematol. 14(10):955-962 (1986); Lu et al., Blood. 68(1):126-133 (1986)); nanosorting based on fluorophore expression; affinity chromatography; cytotoxic agents joined to a monoclonal antibody or used in conjunction with a monoclonal antibody, e.g., complement and cytotoxins; "panning" with antibody attached to a solid matrix; selective agglutination using a lectin such as soybean (Reisner et al., Lancet. 2(8208-8209): 1320-1324 (1980)); immunomagnetic bead-based sorting or combinations of these techniques, etc. These techniques can also be used to assay for successful engraftment or manipulation of hematopoietic cells in vivo, for example for gene transfer, genetic editing or cell population expansion.

In particular embodiments, it is important to remove contaminating cell populations that would interfere with isolation of the intended cell population, such as red blood cells. Removing includes both biochemical and mechanical methods to remove the undesired cell populations. Examples include lysis of red blood cells using detergents, hetastarch, hetastarch with centrifugation, cell washing, cell washing with density gradient, Ficoll-hypaque, Sepx, Optipress, Filters, and other protocols that have been used both in the manufacture of HSC and/or gene therapies for research and therapeutic purposes.

In particular embodiments, a sample can be processed to select/enrich for CD34+ cells using anti-CD34 antibodies directly or indirectly conjugated to magnetic particles in connection with a magnetic cell separator, for example, the CliniMACS® Cell Separation System (Miltenyi Biotec, Bergisch Gladbach, Germany). See also, sec. 5.4.1.1 of U.S. Pat. No. 7,399,633 which describes enrichment of CD34+ HSC/HSPC from 1-2% of a normal bone marrow cell population to 50-80% of the population. HSC can also be selected to achieve the HSC profiles noted above, such as CD34+/CD45RA-/CD90+ or CD34+/CD38-/CD45RA-/CD90+.

Similarly, HSPC expressing CD43, CD45RO, CD45RA, CD59, CD90, CD109, CD117, CD133, CD166, HLA DR, or a combination thereof, can be enriched for using antibodies against these antigens. U.S. Pat. No. 5,877,299 describes additional appropriate hematopoietic antigens that can be used to isolate, collect, and enrich HSPC cells from samples.

Following isolation and/or enrichment, HSC or HSPC can be expanded in order to increase the number of HSC/HSPC. Isolation and/or expansion methods are described in, for example, U.S. Pat. Nos. 7,399,633 and 5,004,681; U.S. Patent Publication No. 2010/0183564; International Patent Publication Nos. (WO) WO2006/047569; WO2007/095594; WO 2011/127470; and WO 2011/127472; Varnum-Finney et al., 1993, Blood 101:1784-1789; Delaney et al., 2005, Blood 106:2693-2699; Ohishi et al., 2002, J. Clin. Invest. 110: 1165-1174; Delaney et al., 2010, Nature Med. 16(2): 232-236; and Chapter 2 of Regenerative Medicine, Department of Health and Human Services, August 2006, and the references cited therein. Each of the referenced methods of collection, isolation, and expansion can be used in particular embodiments of the disclosure.

Particular methods of expanding HSC/HSPC include expansion with a Notch agonist. For information regarding expansion of HSC/HSPC using Notch agonists, see sec. 5.1 and 5.3 of U.S. Pat. Nos. 7,399,633; 5,780,300; 5,648,464; 5,849,869; and 5,856,441; WO 1992/119734; Schlondorfi and Blobel, 1999, J. Cell Sci. 112:3603-3617; Olkkonen and Stenmark, 1997, Int. Rev. Cytol. 176:1-85; Kopan et al., 2009, Cell 137:216-233; Rebay et al., 1991, Cell 67:687-699 and Jarriault et al., 1998, Mol. Cell. Biol. 18:7423-7431.

Additional culture conditions can include expansion in the presence of one or more growth factors, such as: angiopoietin-like proteins (Angptls, e.g., Angptl2, Angptl3, Angptl7, Angptl5, and Mfap4); erythropoietin; fibroblast growth factor-1 (FGF-1); Flt-3 ligand (Flt-3L); G-CSF; GM-CSF; insulin growth factor-2 (IGF-2); interleukin-3 (IL-3); interleukin-6 (IL-6); interleukin-7 (IL-7); interleukin-11 (IL-11); stem cell factor (SCF; also known as the c-kit ligand or mast cell growth factor); thrombopoietin (TPO); and analogs thereof (wherein the analogs include any structural variants of the growth factors having the biological activity of the naturally occurring growth factor; see, e.g., WO 2007/1145227 and U.S. Patent Publication No. 2010/0183564).

As a particular example for expanding HSC/HSPC, the cells can be cultured on a plastic tissue culture dish containing immobilized Delta ligand and fibronectin and 50 ng/ml of each of SCF, Flt-3L and TPO.

(II) CD33 BLOCKING MOLECULES

As indicated, CD33 blocking molecules are provided to selectively protect therapeutic cells from CD33-targeting therapies. In particular embodiments, interfering RNA molecules that are homologous to target mRNA can lead to its degradation, a process referred to as RNA interference (RNAi) (Carthew, Curr. Opin. Cell. Biol. 13: 244-248 (2001)). RNAi occurs in cells naturally to remove foreign RNAs (e.g., viral RNAs). Natural RNAi proceeds via fragments cleaved from free double-strand RNA (dsRNA) which direct the degradative mechanism to other similar RNA sequences. Alternatively, RNAi can be manufactured, for example, to silence the expression of target genes. Exemplary RNAi molecules include small hairpin RNA (shRNA, also referred to as short hairpin RNA) and small interfering RNA (siRNA).

Without limiting the disclosure, and without being bound by theory, RNA interference is typically a two-step process. In the first step, the initiation step, input dsRNA is digested into 21-23 nucleotide (nt) siRNA, probably by the action of Dicer, a member of the ribonuclease (RNase) III family of dsRNA-specific ribonucleases, which processes (cleaves) dsRNA (introduced directly or via a transgene or a virus) in an ATP-dependent manner. Successive cleavage events degrade the RNA to 19-21 base pair (bp) duplexes (siRNA), each with 2-nucleotide 3' overhangs (Hutvagner and Zamore, Curr. Opin. Genet. Dev. 12: 225-232 (2002); Bernstein, Nature 409:363-366 (2001)).

In an effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and typically cleaves the mRNA into 12 nucleotide fragments from the 3' terminus of the siRNA (Hutvagner and Zamore, Curr. Opin. Genet. Dev. 12: 225-232 (2002); Hammond et al., Nat. Rev. Gen. 2:110-119 (2001); Sharp, Genes. Dev. 15:485-490 (2001)). Research indicates that each RISC contains a single siRNA and an RNase (Hutvagner and Zamore, Curr. Opin. Genet. Dev. 12: 225-232 (2002)).

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC (Hutvagner and Zamore, Curr. Opin. Genet. Dev. 12: 225-232 (2002); Hammond et al., Nat. Rev. Gen. 2:110-119 (2001); Sharp, Genes. Dev. 15:485-490 (2001)). RNAi is also described in Tuschl, Chem. Biochem. 2: 239-245 (2001); Cullen, Nat. Immunol. 3:597-599 (2002); and Brantl, Biochem. Biophys. Act. 1575:15-25 (2002).

Synthesis of RNAi molecules suitable for use with the present disclosure can be performed as follows. First, an mRNA sequence can be scanned downstream of the start codon of targeted CD33. Occurrence of each AA and the 3' adjacent 19 nucleotides is recorded as potential siRNA target sites. In particular embodiments, the siRNA target sites can be selected from the open reading frame, as untranslated regions (UTRs) are richer in regulatory protein binding sites. UTR-binding proteins and/or translation initiation complexes may interfere with binding of the siRNA endonuclease complex (Tuschl, Chem. Biochem. 2: 239-245 (2001)). It will be appreciated though, that siRNAs directed at untranslated regions may also be effective, as demonstrated for Glyceraldehyde 3-phosphate dehydrogenase (GAPDH) wherein siRNA directed at the 5' UTR mediated a 90% decrease in cellular GAPDH mRNA and completely abolished protein level. Second, potential target sites can be compared to an appropriate genomic database using any sequence alignment software, such as the Basic Local Alignment Search Tool (BLAST) software available from the National Center for Biotechnology Information (NCBI) server. Putative target sites which exhibit significant homology to other coding sequences can be filtered out.

Qualifying target sequences can be selected as templates for siRNA synthesis. Selected sequences can include those with low G/C content as these have been shown to be more effective in mediating gene silencing as compared to those with G/C content higher than 55%. Several target sites can be selected along the length of the target gene for evaluation. For better evaluation of the selected siRNAs, a negative control can be used. Negative control siRNA can include the same nucleotide composition as the siRNAs but lack significant homology to the genome. Thus, a scrambled nucleotide sequence of the siRNA may be used, provided it does not display any significant homology to other genes.

A sense strand is designed based on the sequence of the selected portion. The antisense strand is routinely the same length as the sense strand and includes complementary nucleotides. In particular embodiments, the strands are fully complementary and blunt-ended when aligned or annealed. In other embodiments, the strands align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can include nucleotides corresponding to the target gene sequence (or complement thereof). Alternatively, overhangs can include deoxyribonucleotides, for example deoxythymines (dTs), or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced. In particular embodiments, the base-pair strength is less due to fewer G:C base pairs between the 5' end of the first or antisense strand and the 3' end of the second or sense strand than between the 3' end of the first or antisense strand and the 5' end of the second or sense strand. In particular embodiments, the base pair strength is less due to at least one mismatched base pair between the 5' end of the first or antisense strand and the 3' end of the second or sense strand. Preferably, the mismatched base pair is selected from the group including G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair including a rare nucleotide, e.g., inosine (I). In particular embodiments, the base pair is selected from the group including an I:A, I:U and I:C. In yet another embodiment, the base pair strength is less due to at least one base pair including a modified nucleotide. In particular embodiments, the modified nucleotide is selected from, for example, 2-amino-G, 2-amino-A, 2,6-diamino-G, and 2,6-diamino-A.

ShRNAs are single-stranded polynucleotides with a hairpin loop structure. The single-stranded polynucleotide has a loop segment linking the 3' end of one strand in the double-stranded region and the 5' end of the other strand in the double-stranded region. The double-stranded region is formed from a first sequence that is hybridizable to a target sequence, such as a polynucleotide encoding CD33, and a second sequence that is complementary to the first sequence, thus the first and second sequence form a double stranded region to which the linking sequence connects the ends of to form the hairpin loop structure. The first sequence can be hybridizable to any portion of a polynucleotide encoding CD33. The double-stranded stem domain of the shRNA can include a restriction endonuclease site.

Transcription of shRNAs is initiated at a polymerase III (Pol III) promoter and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of 21-23 nucleotides (Brummelkamp et al., Science. 296(5567): 550-553 (2002); Lee et al., Nature Biotechnol. 20(5): 500-505 (2002); Miyagishi and Taira, Nature Biotechnol. 20(5): 497-500 (2002); Paddison et al., Genes & Dev. 16(8): 948-958 (2002); Paul et al., Nature Biotechnol. 20(5): 505-508 (2002); Sui, Proc. Natl. Acad. Sci. USA. 99(6): 5515-5520 (2002); Yu et al., Proc. Natl. Acad. Sci. USA. 99(9): 6047-6052 (2002)).

The stem-loop structure of shRNAs can have optional nucleotide overhangs, such as 2-bp overhangs, for example, 3' UU overhangs. While there may be variation, stems typically range from 15 to 49, 15 to 35, 19 to 35, 21 to 31 bp, or 21 to 29 bp, and the loops can range from 4 to 30 bp, for example, 4 to 23 bp. In particular embodiments, shRNA sequences include 45-65 bp; 50-60 bp; or 51, 52, 53, 54, 55, 56, 57, 58, or 59 bp. In particular embodiments, shRNA sequences include 52 or 55 bp. In particular embodiments siRNAs have 15-25 bp. In particular embodiments siRNAs have 16, 17, 18, 19, 20, 21, 22, 23, or 24 bp. In particular embodiments siRNAs have 19 bp. The skilled artisan will appreciate, however, that siRNAs having a length of less than 16 nucleotides or greater than 24 nucleotides can also function to mediate RNAi. Longer RNAi agents have been demonstrated to elicit an interferon or Protein kinase R (PKR) response in certain mammalian cells which may be undesirable. Preferably the RNAi agents do not elicit a PKR response (i.e., are of a sufficiently short length). However, longer RNAi agents may be useful, for example, in situations where the PKR response has been downregulated or dampened by alternative means.

Particular embodiments utilize one or more of SEQ ID NOs: 6-15 to encode CD33 blocking molecules. In particular embodiments CD33 blocking molecules are encoded by SEQ ID NO: 8 and/or SEQ ID NO: 9. Because SEQ ID NO: 8 and SEQ ID NO: 9 encode CD33 blocking molecules these sequences can also be considered CD33 blocking molecules.

(III) OPTIONAL THERAPEUTIC GENES

Particular examples of therapeutic genes and/or gene products to treat immune deficiencies can include genes associated with FA including: FancA, FancB, FancC, FancD1 (BRCA2), FancD2, FancE, FancF, FancG, FancI, FancJ (BRIP1), FancL, FancM, FancN (PALB2), FancO (RAD51C), FancP (SLX4), FancQ (ERCC4), FancR (RAD51), FancS (BRCA1), FancT (UBE2T), FancU (XRCC2), FancV (MAD2L2), and FancW (RFWD3). Exemplary genes and proteins associated with FA include: *Homo sapiens* FANCA coding sequence; *Homo sapiens* FANCC coding sequence; *Homo sapiens* FANCE coding sequence; *Homo sapiens* FANCF coding sequence; *Homo sapiens* FANCG coding sequence; *Homo sapiens* FANCA AA; *Homo sapiens* FANCC AA; *Homo sapiens* FANCE AA; *Homo sapiens* FANCF AA; and *Homo sapiens* FANCG AA.

Particular examples of therapeutic genes and/or gene products to treat immune deficiencies can include genes associated with SCID including: γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, and SLC46A1. Exemplary genes and proteins associated with SCID include: exemplary codon optimized Human γC DNA; exemplary native Human γC DNA; exemplary native canine γC DNA; exemplary human γC AA; and exemplary native canine γC AA (91% conserved with human). Exemplary genes and proteins associated with SCID include: *Homo sapiens* JAK3 coding sequence; *Homo sapiens* PNP coding sequence; *Homo sapiens* ADA coding sequence; *Homo sapiens* RAG1 coding sequence; *Homo sapiens* RAG2 coding sequence; *Homo sapiens* JAK3 AA; *Homo sapiens* PNP AA; *Homo sapiens* ADA AA; *Homo sapiens* RAG1 AA; and *Homo sapiens* RAG2 AA.

Additional exemplary therapeutic genes can include or encode for clotting and/or coagulation factors such as factor VIII (FVIII), FVII, von Willebrand factor (VWF), FI, FII, FV, FX, FXI, and FXIII).

Additional examples of therapeutic genes and/or gene products include those that can provide a therapeutically effective response against diseases related to red blood cells and clotting. In particular embodiments, the disease is a hemoglobinopathy like thalassemia, or a SCD/trait. Exemplary therapeutic genes include F8 and F9.

Particular examples of therapeutic genes and/or gene products include γ-globin; soluble CD40; CTLA; Fas L; antibodies to CD4, CD5, CD7, CD52, etc.; antibodies to IL1, IL2, IL6; an antibody to TCR specifically present on autoreactive T cells; IL4; IL10; IL12; IL13; IL1Ra, sIL1RI, sIL1RII; sTNFRI; sTNFRII; antibodies to TNF; P53, PTPN22, and DRB1*1501/DQB1*0602; globin family genes; WAS; phox; dystrophin; pyruvate kinase (PK); CLN3; ABCD1; arylsulfatase A (ARSA); SFTPB; SFTPC; NLX2.1; ABCA3; GATA1; ribosomal protein genes; TERC; CFTR; LRRK2; PARK2; PARK7; PINK1; SNCA; PSEN1; PSEN2; APP; SOD1; TDP43; FUS; ubiquilin 2; C9ORF72 and other therapeutic genes described herein.

Particular embodiments include inserting or altering a gene selected from ABLI, AKT1, APC, ARSB, BCL11A, BLC1, BLC6, BRCA1, BRIP1, C46, CAS9, C-CAM, CBFAI, CBL, CCR5, CD19, CDA, C-MYC, CRE, CSCR4, CSFIR, CTS-I, CYB5R3, DCC, DHFR, DLL1, DMD, EGFR, ERBA, ERBB, EBRB2, ETSI, ETS2, ETV6, FCC, FGR, FOX, FUSI, FYN, GALNS, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p2I, p27, p57, p73, PALB2, RAD51C, ras, at least one of RPL3 through RPL40, RPLP0, RPLP1, RPLP2, at least one of RPS2 through RPS30, RPSA, SGSH, SLX4, SOX2, VHL, and WT-I.

In addition to therapeutic genes and/or gene products, the transgene can also encode for therapeutic molecules, such as checkpoint inhibitor reagents, chimeric antigen receptor molecules specific to one or more cellular antigen (e.g. cancer antigen), and/or T-cell receptor specific to one or more cellular antigen (e.g. cancer antigen).

(IV) DELIVERY AND EXPRESSION OF CD33 BLOCKING MOLECULES AND OPTIONAL THERAPEUTIC Genes Cells can be genetically modified to express CD33 blocking molecules and optionally a therapeutic gene using any method known in the art.

Particular embodiments use a genetic construct or vector to deliver and express CD33 blocking molecules and optional therapeutic genes in cells. A genetic construct is an artificially produced combination of nucleotides to express particular intended molecules.

A "vector" is a nucleic acid molecule that is capable of transporting another nucleic acid molecule, such as a gene encoding a CD33 blocking molecule and optionally a therapeutic gene. Vectors include, e.g., plasmids, cosmids, viruses, and phage. Viral vectors refer to nucleic acid molecules that include virus-derived nucleic acid elements that facilitate transfer and expression of non-native genes within a cell. In particular embodiments, viral-mediated genetic modification can utilize, for example, retroviral vectors, lentiviral vectors, foamy viral vectors, adenoviral vectors, adeno-associated viral vectors, alpharetroviral vectors or gammaretroviral vectors. In particular embodiments, retroviral vectors (see Miller, et al., 1993, Meth. Enzymol. 217:581-599) can be used. In these embodiments, the gene to be expressed is cloned into the retroviral vector for its delivery into cells. In particular embodiments, a retroviral vector includes all of the cis-acting sequences necessary for the packaging and integration of the viral genome in the target cell, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, Biotherapy 6:291-302; Clowes, et al., 1994, J. Clin. Invest. 93:644-651; Kiem, et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Lentiviral vectors or "lentivirus" refers to a genus of retroviruses that are capable of infecting dividing and non-dividing cells and typically produce high viral titers. Lentiviral vectors have been employed in gene therapy for a number of diseases. For example, hematopoietic gene therapies using lentiviral vectors or gammaretroviral vectors have been used for x-linked adrenoleukodystrophy and β-thalassemia. Several examples of lentiviruses include HIV (including HIV type 1, and HIV type 2); equine infectious anemia virus; feline immunodeficiency virus (FIV); bovine immune deficiency virus (BIV); and simian immunodeficiency virus (SIV).

In particular embodiments, other retroviral vectors can be used in the practice of the methods of the invention. These include, e.g., vectors based on human foamy virus (HFV) or other viruses in the Spumavirus genera.

Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

FV vectors are also suitable for gene therapy applications because they can (1) accommodate large transgenes (>9 kb), (2) transduce slowly dividing cells efficiently, and (3) integrate as a provirus into the genome of target cells, thus enabling stable long-term expression of the transgene(s). FV vectors do need cell division for the pre-integration complex to enter the nucleus, however the complex is stable for at least 30 days and still infective. The intracellular half-life of the FV pre-integration complex is comparable to the one of lentiviruses and significantly higher than for gammaretroviruses, therefore FVes are also, similar to lentivirus vectors, able to transduce rarely dividing cells. FV vectors are natural self-inactivating vectors and characterized by the fact that they seem to have hardly any potential to activate neighboring genes. In addition, FV vectors can enter any cells known (although the receptor is not identified yet) and infectious vector particles can be concentrated 100-fold without loss of infectivity due to a stable envelope protein. FV vectors achieve high transduction efficiency in pluripotent hematopoietic stem cells and have been used in animal models to correct monogenetic diseases such as leukocyte adhesion deficiency (LAD) in dogs and FA in mice. FV vectors are also used in preclinical studies of β-thalassemia.

Point mutations can be made in FVes to render them integration incompetent. For example, foamy viruses can be rendered integration incompetent by introducing point mutations into the highly conserved DD35E catalytic core motif of the foamy virus integrase sequence. See, for example, Deyle D R et al. (2010) J. Virol. 84(18): 9341-9349. As another example, an FV vector can be rendered integration deficient by introducing point mutations into the Pol gene of the FV vector. FIG. 20 shows FV Pol coding sequence (SEQ ID NO: 104) and FV Pol amino acid sequence (SEQ ID NO: 105) with indicated nucleotides or amino acid residues, respectively, that can be mutated to render the FV vector integration deficient.

In particular embodiments, adenoviruses (e.g., adenovirus 5 (Ad5), adenovirus 35 (Ad35), adenovirus 11 (Ad11), adenovirus 26 (Ad26), adenovirus 48 (Ad48), adenovirus 50 (Ad50), Ad5/35++, and helper-dependent forms thereof (e.g., helper-dependent Ad5/35++ or helper dependent Ad35), adeno-associated viruses (AAV; see, e.g., U.S. Pat. No. 5,604,090), and alphaviruses can be used. See Kozarsky and Wilson, 1993, Current Opinion in Genetics and Development 3:499-503, Rosenfeld, et al., 1991, Science 252: 431-434; Rosenfeld, et al., 1992, Cell 68:143-155; Mastrangeli, et al., 1993, J. Clin. Invest. 91:225-234; Walsh, et al., 1993, Proc. Soc. Bioi. Med. 204:289-300; and Lundstrom, 1999, J. Recept. Signal Transduct. Res. 19: 673-686. Additional examples of viral vectors include those derived from cytomegaloviruses (CMV), flaviviruses, herpes viruses (e.g., herpes simplex), influenza viruses, papilloma viruses (e.g., human and bovine papilloma virus; see, e.g., U.S. Pat. No. 5,719,054), poxviruses, vaccinia viruses, modified vaccinia Ankara (MVA), NYVAC, or strains derived therefrom. Other examples include avipox vectors, such as a fowlpox vectors (e.g., FP9) or canarypox vectors (e.g., ALVAC and strains derived therefrom). As indicated, helper dependent forms of viral vectors may also be used.

Methods of using retroviral and lentiviral viral vectors and packaging cells for transducing mammalian host cells with viral particles including desired transgenes are described in, e.g., U.S. Pat. No. 8,119,772; Walchli, et al., 2011, PLoS One 6:327930; Zhao, et al., 2005, J. Immunol. 174:4415; Engels, et al., 2003, Hum. Gene Ther. 14:1155; Frecha, et al., 2010, Mol. Ther. 18:1748; and Verhoeyen, et al., 2009, Methods Mol. Biol. 506:97. Retroviral and lentiviral vector constructs and expression systems are also commercially available.

Although viral vectors are useful in the co-delivery of a CD33 blocking molecule and a therapeutic gene to ensure that only cells expressing the therapeutic gene are protected, other vectors or targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells. For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al. Nature Biotechnol. 25, 778-785 (2007); Bibikova, et al. Science 300, 764 (2003); Bibikova, et al. Genetics 161, 1169-1175 (2002); Wolfe, et al. Annu. Rev. Biophys. Biomol. Struct. 29, 183-212 (2000); Kim, et al. Proc. Natl. Acad. Sci. USA. 93, 1156-1160 (1996); and Miller, et al. The EM BO journal 4, 1609-1614 (1985).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biot, 2013, 14(I):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Other methods of gene delivery include use of artificial chromosome vectors such as mammalian artificial chromosomes (Vos, Curr. Opin. Genet. Dev. 8(3): 351-359, 1998) and yeast artificial chromosomes (YAC); liposomes (Tarahovsky and lvanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282). YAC are typically used when the inserted nucleic acids are too large for more conventional vectors (e.g., greater than 12 kb).

When targeted genome editing approaches are utilized, genes can be inserted within genomic safe harbors. Genomic safe harbor sites are intragenic or extragenic regions of the genome that are able to accommodate the predictable expression of newly integrated DNA without adverse effects on the host cell. A useful safe harbor must permit sufficient transgene expression to yield desired levels of the encoded molecule. A genomic safe harbor site also must not alter cellular functions. Methods for identifying genomic safe harbor sites are described in Sadelain et al., Nature Reviews (2012); 12:51-58; and Papapetrou et al., Nat Biotechnol. (2011) January; 29(1):73-8. In particular embodiments, a genomic safe harbor site meets one or more (one, two, three, four, or five) of the following criteria: (i) distance of at least 50 kb from the 5' end of any gene, (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the genome.

In particular embodiments, a genomic safe harbor meets criteria described herein and also demonstrates a 1:1 ratio of forward:reverse orientations of lentiviral integration further demonstrating the loci does not impact surrounding genetic material.

Particular genomic safe harbors sites include CCR5, HPRT, AAVS1, Rosa and albumin. See also, e.g., U.S. Pat. Nos. 7,951,925 and 8,110,379; U.S. Publication Nos. 20080159996; 201000218264; 20120017290; 20110265198; 20130137104; 20130122591; 20130177983 and 20130177960 for additional information and options for appropriate genomic safe harbor integration sites.

The vectors and genetic engineering approaches described herein are used to deliver genes to cells for expression. Delivery can utilize any appropriate technique, such as transfection, electroporation, microinjection, lipofection, calcium phosphate mediated transfection, infection with a viral or bacteriophage vector including the gene sequences, cell fusion, chromosome-mediated gene transfer, microcell-mediated gene transfer, spheroplast fusion, in vivo nanoparticle-mediated delivery, etc. Numerous techniques are known in the art for the introduction of foreign genes into cells (see e.g., Loeffler and Behr, 1993, Meth. Enzymol. 217:599-618; Cohen, et al., 1993, Meth. Enzymol. 217:618-644; Cline, 1985, Pharmac. Ther. 29:69-92) and may be used, provided that the necessary developmental and physiological functions of the recipient cells are not unduly disrupted. The technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes one or more CD33 blocking molecules and optionally one or more therapeutic proteins as described herein. Gene sequences encoding the molecule can be DNA or RNA. As appropriate for the given context, these nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The gene sequence can be readily prepared by synthetic or recombinant methods.

The definition of a gene includes various sequence polymorphisms; mutations; degenerate codons of the native sequence; sequences that may be introduced to provide codon preference in a specific cell type (e.g., codon optimized for expression in mammalian cells); and/or sequence variants wherein such alterations do not substantially affect the function of the encoded molecule. The term further can include all introns and other DNA sequences spliced from an mRNA transcript, along with variants resulting from alternative splice sites. Portions of complete gene sequences are referenced throughout the disclosure as is understood by one of ordinary skill in the art. Nucleotide sequences encoding other sequences disclosed herein can be readily determined by one of ordinary skill in the art.

The term "gene" may include not only coding sequences but also coding sequences operably linked to each other and relevant regulatory sequences such as promoters, enhancers, and termination regions. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions into a common reading frame.

These regulatory sequences can be eukaryotic or prokaryotic in nature. In particular embodiments, the regulatory sequence can result in the constitutive expression of the CD33 blocking molecule and optionally one or more therapeutic proteins upon entry of the vector into the cell. Alternatively, the regulatory sequences can include inducible sequences. Inducible regulatory sequences are well known to those skilled in the art and are those sequences that require the presence of an additional inducing factor to result in expression of the one or more molecules. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used.

In particular embodiments, the PGK promoter is used to drive expression of a CD33 blocking molecule and optionally a therapeutic gene. In particular embodiments, the PGK promoter is derived from the human gene encoding phosphoglycerate kinase (PGK). In particular embodiments, the PGK promoter includes binding sites for the Rap1p, Abf1p, and/or Gcr1p transcription factors. In particular embodiments, the PGK promoter includes 500 base pairs: Start (0); StyI (21); NspI-SphI (40); BpmI-Eco57MI (52); BaeGI-Bme1580I (63); AgeI (111); BsmBI-SpeI (246); BssS α I (252); BlpI (274); BsrDI (285); StuI (295); BglI (301); EaeI (308); AlwNI (350); EcoO109I-PpuMI (415); BspEI (420); BsmI (432); EarI (482); End (500). In particular embodiments, a PGK promoter includes SEQ ID NO: 106 in FIG. 20.

In particular embodiments, RNA polymerase III (also called Pol III) promoters can be used to drive expression of a CD33 blocking molecule and optionally a therapeutic gene. Pol III transcribes DNA to synthesize ribosomal 5S rRNA, tRNA, and other small RNAs. The Pol III promoters generally have well-defined initiation and stop sites and their transcripts lack poly(A) tails. The termination signal for these promoters is defined by the polythymidine tract, and the transcript is typically cleaved after the second uridine.

Cleavage at this position generates a 3' UU overhang in the expressed shRNA, which is similar to the 3' overhangs of synthetic siRNAs.

siRNA molecules can be transcribed from expression vectors which can facilitate stable expression of the siRNA transcripts once introduced into a host cell. These vectors are engineered to express shRNAs, which can be processed in vivo into siRNA molecules capable of carrying out gene-specific silencing (Brummelkamp et al., Science 296:550-553 (2002); Paddison et al., Genes Dev. 16:948-958 (2002); Paul et al., Nature Biotech. 20: 505-508 (2002); Yu et al., Proc. Natl. Acad. Sci. USA 99:6047-6052 (2002)).

In particular embodiments, a suitable siRNA expression vector encodes the sense and antisense siRNA under the regulation of separate Pol III promoters (Miyagishi and Taira, Nature Biotech. 20:497-500 (2002)). The siRNA, generated by this vector also includes a five thymidine (T5) termination signal.

In particular embodiments, the promoter will drive expression of the CD33 blocking molecule. In particular embodiments, the promoter will drive expression of the CD33 blocking molecule and a therapeutic gene. In particular embodiments, the promoter will be oriented in such a way that results in expression of the CD33 blocking molecule and therapeutic gene driven by the promoter.

Additional exemplary promoters are known in the art and include galactose inducible promoters, pGAL1, pGAL1-10, pGal4, and pGal10; cytochrome c promoter, pCYC1; and alcohol dehydrogenase 1 promoter, pADH1, EF1alpha.

In particular embodiments, the efficiency of integration, the size of the DNA sequence that can be integrated, and the number of copies of a DNA sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target DNA sequence.

A number of transposable elements have been described in the art that facilitate insertion of nucleic acids into the genome of vertebrates, including humans. Examples include Sleeping Beauty® (Regents of the University of Minnesota, Minneapolis, MN) (e.g., derived from the genome of salmonid fish); piggyBac® (Poseida Therapeutics, Inc. San Diego CA) (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Tribolium castaneum*) and spinON.

In particular embodiments, vectors provide cloning sites to facilitate transfer of the polynucleotide sequences. Such vector cloning sites include at least one restriction endonuclease recognition site positioned to facilitate excision and insertion, in reading frame, of polynucleotides segments. Any of the restriction sites known in the art can be utilized. Most commercially available vectors already contain multiple cloning site (MCS) or polylinker regions. In addition, genetic engineering techniques useful to incorporate new and unique restriction sites into a vector are known and routinely practiced by persons of ordinary skill in the art. A cloning site can involve as few as one restriction endonuclease recognition site to allow for the insertion or excision of a single polynucleotide fragment. More typically, two or more restriction sites are employed to provide greater control of for example, insertion (e.g., direction of insert), and greater flexibility of operation (e.g., the directed transfer of more than one polynucleotide fragment). Multiple restriction sites can be the same or different recognition sites.

In particular embodiments, the gene sequence encoding any of these sequences can have one or more restriction enzyme sites at the 5' and/or 3' ends of the coding sequence in order to provide for easy excision and replacement of the gene sequence encoding the sequence with another gene sequence encoding a different sequence. In particular embodiments, each of the restriction sites is unique in the vector and different from the other restriction sites. In particular embodiments, each of the restriction sites are identical to the other restriction sites.

In particular embodiments, for expression of shRNAs within cells, vectors containing either the polymerase III H1-RNA or U6 promoter, a cloning site for the stem-looped RNA insert, and a 4 5-thymidine transcription termination signal can be employed.

In particular embodiments, the pSUPER vector which contains polymerase-III H1-RNA gene promoter with a well-defined start of transcription and a termination signal including five thymidines in a row (T5) (Brummelkamp et al., Science 296:550-553 (2002)) is used. The cleavage of the transcript at the termination site is at a site following the second uridine, thus yielding a transcript which resembles the ends of synthetic siRNAs, which also contain nucleotide overhangs. siRNA is cloned such that it includes the sequence of interest. The resulting transcript folds back on itself to form a stem-loop structure, which mediates CD33 RNAi.

In particular embodiments, nucleotide sequences encoding one or more of SEQ ID NOs: 6-15 are cloned between SEQ ID NO: 18 and SEQ ID NO: 19 with a therapeutic gene.

In particular embodiments, the nucleic acid is stably integrated into the genome of a cell. In particular embodiments, the nucleic acid is stably maintained in a cell as a separate, episomal segment.

For additional information regarding procedures for genetic modification, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

(V) CD33-TARGETING AGENTS

Particular embodiments include targeting any residual and/or non-therapeutic cells that express CD33 with the use of a CD33-targeting agent. A CD33-targeting agent refers to a molecule, cell, drug, or combination thereof that targets CD33-expressing cells for cell death or to inhibit cell growth. Examples of CD33-targeting agents include anti-CD33 antibodies, anti-CD33 immunotoxins, anti-CD33 antibody-drug conjugates, anti-CD33 antibody-radioisotope conjugates), anti-CD33 multispecific antibodies (e.g. anti-CD33 bispecific antibodies, anti-CD33 bispecific antibodies that bind CD33 and an immune activating epitope on an immune cell (e.g., a CD3 as in BiTE®), anti-CD33 trispecific antibodies), and/or genetically modified cells expressing an anti-CD33 CAR or an engineered TCR. Each of these types of CD33-targeting agents include a binding domain that binds CD33, and most (except certain antibody forms) also include a linker. Accordingly, CD33 binding domains are described first and general description of linkers is provided next. Following this description of CD33 binding domains and linkers, more particular information regarding the different CD33-targeting agents are provided.

CD33-targeting agents can bind different forms and/or epitopes of CD33. For example, full length CD33 (CD33FL) is a transmembrane glycoprotein that is characterized by an amino-terminal, membrane-distant V-set immunoglobulin (Ig)-like domain and a membrane-proximal C2-set Ig-like domain in its extracellular portion. In addition to CD33FL, a splice variant that misses exon 2 (CD33ΔE2) has also been identified. Thus, CD33 refers to any native, mature CD33 which results from processing of a CD33 precursor protein in a cell (FIGS. 1A, 1B).

(V-a) CD33 Binding Domains.

Binding domains include any substance that binds to CD33 to form a complex. The choice of binding domain can depend upon the type and number of CD33 markers that define the surface of a target cell or the type of selected CD33-targeting agent. Examples of binding domains include cellular marker ligands, receptor ligands, antibodies, antibody binding domains, peptides, peptide aptamers, receptors (e.g., T cell receptors), or combinations and engineered fragments or formats thereof.

Antibodies are one example of binding domains and include whole antibodies or binding fragments of an antibody, e.g., Fv, Fab, Fab', F(ab')2, and single chain (sc) forms and fragments thereof that bind specifically CD33. Antibodies or antigen binding fragments can include all or a portion of polyclonal antibodies, monoclonal antibodies, human antibodies, humanized antibodies, synthetic antibodies, non-human antibodies, recombinant antibodies, chimeric antibodies, bispecific antibodies, mini bodies, and linear antibodies.

Antibodies are produced from two genes, a heavy chain gene and a light chain gene. Generally, an antibody includes two identical copies of a heavy chain, and two identical copies of a light chain. Within a variable heavy chain and variable light chain, segments referred to as complementary determining regions (CDRs) dictate epitope binding. Each heavy chain has three CDRs (i.e., CDRH1, CDRH2, and CDRH3) and each light chain has three CDRs (i.e., CDRL1, CDRL2, and CDRL3). CDR regions are flanked by framework residues (FR).

In particular embodiments, the CD33 binding domain can be derived from or include hP67.6 which is an anti-CD33 antibody used in the ADC, GO. In particular embodiments, the light chain of hP67.6 includes:

(SEQ ID NO: 39)
MSVPTQVLGLLLLWLTDARCDIQLTQSPSTLSASVGDRVTITCRASESL

DNYGIRFLTWFQQKPGKAPKLLMYAASNQGSGVPSRFSGSGSGTEFTLT

ISSLQPDDFATYYCQQTKEVPWSFGQGTKVEVKRT and the heavy chain of hP67.6 includes:

(SEQ ID NO: 40)
MEWSWVFLFFLSVTTGVHSEVQLVQSGAEVKKPGSSVKVSCKASGYTIT

DSNIHWVRQAPGQSLEWIGYIYPYNGGTDYNQKFKNRATLTVDNPTNTA

YMELSSLRSEDTDFYYCVNGNPWLAYWGQGTLVTVSSASTKGP.

In particular embodiments, the hP67.6 binding domain includes a variable light chain including a CDRL1 sequence including QSPSTLSASV (SEQ ID NO: 41), a CDRL2 sequence including DNYGIRFLTWFQQKPG (SEQ ID NO: 42), and a CDRL3 sequence including FTLTISSL (SEQ ID NO: 43). In particular embodiments, the hP67.6 binding domain includes a variable heavy chain including a CDRH1 sequence including VQSGAEVKKPG (SEQ ID NO: 44), a CDRH2 sequence including DSNIHWV (SEQ ID NO: 45), and a CDRH3 sequence including LTVDNPTNT (SEQ ID NO: 46).

In particular embodiments, the CD33 binding domain can be derived from or include h2H12EC which is the anti-CD33 antibody used in the ADC, SGN-CD33A. In particular embodiments, the h2H12EC binding domain includes a variable light chain including a CDRL1 sequence including NYDIN (SEQ ID NO: 98), a CDRL2 sequence including WIYPGDGSTKYNEKFKA (SEQ ID NO: 99), and a CDRL3 sequence including GYEDAMDY (SEQ ID NO: 100). In particular embodiments, the h2H12EC binding domain includes a variable heavy chain including a CDRH1 sequence including KASQDINSYLS (SEQ ID NO: 101), a CDRH2 sequence including RANRLVD (SEQ ID NO: 102), and a CDRH3 sequence including LQYDEFPLT (SEQ ID NO: 103).

Additional examples of anti-CD33 antibody heavy and light chains, as well as specific CDRs, include those described in U.S. Pat. No. 7,557,198. For instance, in particular embodiments, a light chain of a representative anti-CD33 antibody includes:

(SEQ ID NO: 47)
NIMLTQSPSSLAVSAGEKVTMSCKSSQSVFFSSSQKNYLAWYQQIPGQS

PKLLIYWASTRESGVPDRFTGSGSGTDFTLTISSVQSEDLAIYYCHQYL

SSRTFGGGTKLEIKR and a heavy chain of this representative anti-CD33 antibody includes:

(SEQ ID NO: 48)
QVQLQQPGAEVVKPGASVKMSCKASGYTFTSYYIHWIKQTPGQGLEWVG

VIYPGNDDISYNQKFKGKATLTADKSSTTAYMQLSSLTSEDSAVYYCAR

EVRLRYFDVWGAGTTVTVSS.

Additional examples of anti-CD33 antibody heavy and light chains, as well as specific CDRs, include those described in U.S. Pat. No. 7,557,198. In particular embodiments, the CD33 binding domain includes a variable light chain including a CDRL1 sequence including SYYIH (SEQ ID NO: 49), a CDRL2 sequence including VIYPGNDDISYNQKFXG (SEQ ID NO: 50) wherein X is K or Q, and a CDRL3 sequence including EVRLRYFDV (SEQ ID NO: 51). In particular embodiments, the CD33 binding domain includes a variable heavy chain including a CDRH1 sequence including KSSQSVFFSSSQKNYLA (SEQ ID NO: 52), a CDRH2 sequence including WASTRES (SEQ ID NO: 53), and a CDRH3 sequence including HQYLSSRT (SEQ ID NO: 54).

In some instances, it is beneficial for the binding domain to be derived from the same species it will ultimately be used in. For example, for use in humans, it may be beneficial for the antigen binding domain to include a human antibody, humanized antibody, or a fragment or engineered form thereof. Antibodies from human origin or humanized antibodies have lowered or no immunogenicity in humans and have a lower number of non-immunogenic epitopes compared to non-human antibodies. Antibodies and their engineered fragments will generally be selected to have a reduced level or no antigenicity in human subjects.

In particular embodiments, the binding domain includes a humanized antibody or an engineered fragment thereof. In particular embodiments, a non-human antibody is humanized, where one or more amino acid residues of the antibody are modified to increase similarity to an antibody naturally produced in a human or fragment thereof. These nonhuman amino acid residues are often referred to as "import" residues, which are typically taken from an "import" variable domain. As provided herein, humanized antibodies or antibody fragments include one or more CDRs from nonhuman immunoglobulin molecules and framework regions wherein the amino acid residues including the framework are derived completely or mostly from human germline. In one aspect, the antigen binding domain is humanized. A humanized antibody can be produced using a variety of techniques known in the art, including CDR-grafting (see, e.g., European Patent No. EP 239,400; WO 91/09967; and U.S. Pat. Nos. 5,225,539, 5,530,101, and 5,585,089), veneering or resurfacing (see, e.g., EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973), chain shuffling (see, e.g., U.S. Pat. No. 5,565,332), and techniques disclosed in, e.g., US 2005/0042664, US 2005/0048617, U.S. Pat. Nos. 6,407,213, 5,766,886, WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994). Often, framework residues in the framework regions will be substituted with the corresponding residue from the CDR donor antibody to alter, for example improve, cellular marker binding. These framework substitutions are identified by methods well-known in the art, e.g., by modeling of the interactions of the CDR and framework residues to identify framework residues important for cellular marker binding and sequence comparison to identify unusual framework residues at particular positions. (See, e.g., U.S. Pat. No. 5,585,089; and Riechmann et al., 1988, Nature, 332:323).

Antibodies with binding domains that specifically bind CD33 can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to CD33. For example, binding domains may be identified by screening a Fab phage library for Fab fragments that specifically bind CD33 (see Hoet et al., Nat. Biotechnol. 23:344, 2005). Phage display libraries of human antibodies are also available. Additionally, traditional strategies for hybridoma development using CD33 as an immunogen in convenient systems (e.g., mice, HuMAb mouse® (GenPharm Intl. Inc., Mountain View, CA), TC mouse® (Kirin Pharma Co. Ltd., Tokyo, JP), KM-mouse® (Medarex, Inc., Princeton, NJ), llamas, chicken, rats, hamsters, rabbits, etc.) can be used to develop binding domains. Once identified, the amino acid sequence of the antibody and gene sequence encoding the antibody can be isolated and/or determined.

As indicated, antibodies can be used as whole antibodies or binding fragments thereof, e.g., Fv, Fab, Fab', F(ab')2, and single chain (sc) forms and fragments thereof that specifically bind CD33.

In some instances, scFvs can be prepared according to methods known in the art (see, for example, Bird et al., (1988) Science 242:423-426 and Huston et al., (1988) Proc. Natl. Acad. Sci. USA 85:5879-5883). ScFv molecules can be produced by linking VH and VL regions of an antibody together using flexible polypeptide linkers. If a short polypeptide linker is employed (e.g., between 5-10 amino acids) intrachain folding is prevented. Interchain folding is also required to bring the two variable regions together to form a functional epitope binding site. For examples of linker orientations and sizes see, e.g., Hollinger et al. 1993 Proc Natl Acad. Sci. U.S.A. 90:6444-6448, US 2005/0100543, US 2005/0175606, US 2007/0014794, and WO2006/020258 and WO2007/024715. More particularly, linker sequences that are used to connect the VL and VH of an scFv are generally five to 35 amino acids in length. In particular embodiments, a VL-VH linker includes from five to 35, ten to 30 amino acids or from 15 to 25 amino acids. Variation in the linker length may retain or enhance activity, giving rise to superior efficacy in activity studies. scFV are commonly used as the binding domains of CAR discussed below.

Additional examples of antibody-based binding domain formats include scFv-based grababodies and soluble VH domain antibodies. These antibodies form binding regions using only heavy chain variable regions. See, for example, Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008.

In particular embodiments, a VL region in a binding domain of the present disclosure is derived from or based on a VL of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known monoclonal antibody. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

In particular embodiments, a binding domain VH region of the present disclosure can be derived from or based on a VH of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of a known monoclonal antibody. An insertion, deletion or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a binding domain includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from a monoclonal antibody or fragment or derivative thereof that specifically binds to a cellular marker of interest.

An alternative source of binding domains includes sequences that encode random peptide libraries or sequences that encode an engineered diversity of amino acids in loop regions of alternative non-antibody scaffolds, such as single chain (sc) T-cell receptor (scTCR) (see, e.g., Lake et al., Int. Immunol. 11:745, 1999; Maynard et al., J. Immunol. Methods 306:51, 2005; U.S. Pat. No. 8,361,794), fibrinogen domains (see, e.g., Weisel et al., Science 230:1388, 1985), Kunitz domains (see, e.g., U.S. Pat. No. 6,423,498), designed ankyrin repeat proteins (DARPins; Binz et al., J. Mol. Biol. 332:489, 2003 and Binz et al., Nat. Biotechnol. 22:575, 2004), fibronectin binding domains (adnectins or monobodies; Richards et al., J. Mol. Biol. 326:1475, 2003; Parker et al., Protein Eng. Des. Selec. 18:435, 2005 and Hackel et al. (2008) J. Mol. Biol. 381:1238-1252), cysteine-knot miniproteins (Vita et al., 1995, Proc. Nat'l. Acad. Sci. (USA) 92:6404-6408; Martin et al., 2002, Nat. Biotechnol. 21:71, 2002 and Huang et al. (2005) Structure 13:755, 2005), tetratricopeptide repeat domains (Main et al., Structure 11:497, 2003 and Cortajarena et al., ACS Chem. Biol. 3:161, 2008), leucine-rich repeat domains (Stumpp et al., J. Mol. Biol. 332:471, 2003), lipocalin domains (see, e.g., WO 2006/095164, Beste et al., Proc. Nat'l. Acad. Sci. (USA) 96:1898, 1999 and Schönfeld et al., Proc. Nat'l. Acad. Sci. (USA) 106:8198, 2009), V-like domains (see, e.g., US 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100:7779, 2003), mAb2 or Fc-region with antigen binding domain (Fcab™ (F-Star Biotechnology, Cambridge UK; see, e.g., WO 2007/098934 and WO 2006/072620), armadillo repeat proteins (see, e.g., Madhurantakam et al., Protein Sci. 21: 1015, 2012; WO 2009/040338), affilin (Ebersbach et al., J. Mol. Biol. 372: 172, 2007), affibody, avimers, knottins, fynomers, atrimers, cytotoxic T-lymphocyte associated protein-4 (Weidle et al., Cancer Gen. Proteo. 10:155, 2013), or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Plückthun, Curr. Opin. Biotechnol. 22:849, 2011).

Peptide aptamers include a peptide loop (which is specific for a cellular marker) attached at both ends to a protein scaffold. This double structural constraint increases the binding affinity of peptide aptamers to levels comparable to antibodies. The variable loop length is typically 8 to 20 amino acids and the scaffold can be any protein that is stable, soluble, small, and non-toxic. Peptide aptamer selection can be made using different systems, such as the yeast two-hybrid system (e.g., Gal4 yeast-two-hybrid system), or the LexA interaction trap system.

In particular embodiments, a binding domain is a scTCR including Vα/β and Cα/β chains (e.g., Vα-Cα, Vβ-Cβ, Vα-Vβ) or including a Vα-Cα, Vβ-Cβ, Vα-Vβ pair specific for a CD33 peptide-MHC complex.

In particular embodiments, engineered binding domains include Vα, Vβ, Cα, or Cβ regions derived from or based on a Vα, Vβ, Cα, or Cβ and includes one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the referenced Vα, Vβ, Cα, or Cβ. An insertion, deletion or substitution may be anywhere in a $V_L$, $V_H$, Vα, Vβ, Cα, or Cβ region, including at the amino- or carboxy-terminus or both ends of these regions, provided that each CDR includes zero changes or at most one, two, or three changes and provides a target binding domain containing a modified Vα, Vβ, Cα, or Cβ region can still specifically bind its target with an affinity and action similar to wild type.

In particular embodiments, engineered binding domains include a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a known or identified binding domain, wherein each CDR includes zero changes or at most one, two, or three changes, from a known or identified binding domain or fragment or derivative thereof that specifically binds to the targeted cellular marker.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

(V-B) LINKERS

As indicated, many CD33-targeting agents include linkers. Linkers can be used to achieve different outcomes depending on the particular CD33-targeting agent under consideration. A linker can include any chemical moiety that is capable of linking portions of a CD33-targeting agent. Linkers can be flexible, rigid, or semi-rigid, depending on the desired function of the linker.

For example, in particular embodiments, linkers provide flexibility and room for conformational movement between different components of CD33-targeting agents. Commonly used flexible linkers include linker sequence with the amino acids glycine and serine (Gly-Ser linkers). In particular embodiments, the linker sequence includes sets of glycine and serine repeats such as from one to ten repeats of $(Gly_xSer_y)_n$, wherein x and y are independently an integer from 0 to 10 provided that x and y are not both 0 and wherein n is an integer of 1, 2, 3, 4, 5, 6, 7, 8, 9 or 10). Particular examples include (Gly4Ser)n (SEQ ID NO: 20), (Gly3Ser)n(Gly4Ser)n (SEQ ID NO: 21), (Gly3Ser)n(Gly2Ser)n (SEQ ID NO: 22), or (Gly3Ser)n(Gly4Ser)1 (SEQ ID NO: 23). In particular embodiments, the linker is (Gly4Ser)4 (SEQ ID NO: 24), (Gly4Ser)3 (SEQ ID NO: 25), (Gly4Ser)2 (SEQ ID NO: 26), (Gly4Ser)1 (SEQ ID NO: 27), (Gly3Ser)2 (SEQ ID NO: 28), (Gly3Ser)1 (SEQ ID NO: 29), (Gly2Ser)2 (SEQ ID NO: 30) or (Gly2Ser)1, GGSGGGSGGSG (SEQ ID NO: 31), GGSGGGSGSG (SEQ ID NO: 32), or GGSGGGSG (SEQ ID NO: 33).

In some situations, flexible linkers may be incapable of maintaining a distance or positioning of CD33-targeting agent components needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

Spacer regions are a type of linker region that are used to create appropriate distances and/or flexibility from other linked components. In particular embodiments, the length of a spacer region can be customized for individual cellular markers on unwanted cells to optimize unwanted CD33-expressing cell recognition and destruction. The spacer can be of a length that provides for increased effectiveness of the CD33-targeting agent following CD33 binding, as compared to in the absence of the spacer. In particular embodiments, a spacer region length can be selected based upon the location of a cellular marker epitope, affinity of a binding domain for the epitope, and/or the ability of the CD33-targeting agent to mediate cell destruction following CD33 binding.

Spacer regions typically include those having 10 to 250 amino acids, 10 to 200 amino acids, 10 to 150 amino acids, 10 to 100 amino acids, 10 to 50 amino acids, or 10 to 25 amino acids. In particular embodiments, a spacer region is 12 amino acids, 20 amino acids, 21 amino acids, 26 amino acids, 27 amino acids, 45 amino acids, or 50 amino acids.

Exemplary spacer regions include all or a portion of an immunoglobulin hinge region. An immunoglobulin hinge region may be a wild-type immunoglobulin hinge region or an altered wild-type immunoglobulin hinge region. In certain embodiments, an immunoglobulin hinge region is a human immunoglobulin hinge region. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody.

An immunoglobulin hinge region may be an IgG, IgA, IgD, IgE, or IgM hinge region. An IgG hinge region may be an IgG1, IgG2, IgG3, or IgG4 hinge region. Sequences from IgG1, IgG2, IgG3, IgG4 or IgD can be used alone or in combination with all or a portion of a CH2 region; all or a portion of a CH3 region; or all or a portion of a CH2 region and all or a portion of a CH3 region.

Other examples of hinge regions used in fusion binding proteins described herein include the hinge region present in the extracellular regions of type 1 membrane proteins, such as CD8a, CD4, CD28 and CD7, which may be wild-type or variants thereof.

In particular embodiments, a spacer region includes a hinge region that includes a type II C-lectin interdomain (stalk) region or a cluster of differentiation (CD) molecule stalk region. A "stalk region" of a type II C-lectin or CD molecule refers to the portion of the extracellular domain of the type II C-lectin or CD molecule that is located between the C-type lectin-like domain (CTLD; e.g., similar to CTLD of natural killer cell receptors) and the hydrophobic portion (transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule includes amino acid residues 34-60, which are located between the hydrophobic portion (transmembrane domain) and CTLD (see Boyington et al., Immunity 10:15, 1999; for descriptions of other stalk regions, see also Beavil et al., Proc. Nat'l. Acad. Sci. USA 89:153, 1992; and Figdor et al., Nat. Rev. Immunol. 2:11, 2002). These type II C-lectin or CD molecules may also have junction amino acids (described below) between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an extracellular domain ranging from amino acids 94-233. The CTLD includes amino acids 119-231 and the stalk region includes amino acids 99-116, which may be flanked by additional junction amino acids. Other type II C-lectin or CD molecules, as well as their extracellular ligand-binding domains, stalk regions, and CTLDs are known in the art (see, e.g., GenBank Accession Nos. NP 001993.2; AAH07037.1; NP 001773.1; AAL65234.1; CAA04925.1; for the sequences of human CD23, CD69, CD72, NKG2A, and NKG2D and their descriptions, respectively).

In particular embodiments, a spacer region is (GGGGS)n (SEQ ID NO: 20) wherein n is an integer including, 1, 2, 3, 4, 5, 6, 7, 8, 9, or more. In particular embodiments, the spacer region is (EAAAK)n (SEQ ID NO: 36) wherein n is an integer including 1, 2, 3, 4, 5, 6, 7, 8, 9, or more.

Junction amino acids can be a short oligo- or protein linker, preferably between 2 and 9 amino acids (e.g., 2, 3, 4, 5, 6, 7, 8, or 9 amino acids) in length to form the linker. In particular embodiments, a glycine-serine doublet can be used as a suitable junction amino acid linker. In particular embodiments, a single amino acid, e.g., an alanine, a glycine, can be used as a suitable junction amino acid.

Linkers can be susceptible to cleavage (cleavable linker), such as, acid-induced cleavage, photo-induced cleavage, peptidase-induced cleavage, esterase-induced cleavage, and disulfide bond cleavage. Alternatively, linkers can be substantially resistant to cleavage (e.g., stable linker or non-cleavable linker). In some aspects, the linker is a procharged linker, a hydrophilic linker, or a dicarboxylic acid-based linker.

(V-C) EXAMPLES OF CD33-TARGETING AGENTS

CD33-targeting agents include molecules that result in the destruction of CD33-expressing cells. Examples of CD33- targeting agents include anti-CD33 antibodies; anti-CD33 immunotoxins; anti-CD33 antibody-drug conjugates; anti-CD33 antibody-radioisotope conjugates; anti-CD33 multispecific antibodies (e.g. bi- and trispecific antibodies); and/or immune cells expressing CARs or engineered TCRs that specifically bind CD33. Anti-CD33 antibodies are described above in relation to binding domains.

(V-C-I) ANTI-CD33 ANTIBODY CONJUGATES

Anti-CD33 antibody conjugates are artificial molecules that include a molecule conjugated to a CD33 binding domain. Anti-CD33 antibody conjugates include anti-CD33 immunotoxins, ADCs, and radioisotope conjugates.

Anti-CD33 immunotoxins are artificial molecules that include a toxin linked to a CD33 binding domain. In particular embodiments, immunotoxins selectively deliver an effective dose of a cytotoxin to non-genetically modified CD33-expressing cells.

To prepare immunotoxins, linker-cytotoxin conjugates can be made by conventional methods analogous to those described by Doronina et al. (Bioconjugate Chem. 17: 114-124, 2006). Immunotoxins containing CD33 binding domains can be prepared by standard methods for cysteine conjugation, such as by methods analogous to that described in Hamblett et al., Clin. Cancer Res. 10:7063-7070, 2004; Doronina et al., Nat. Biotechnol. 21(7): 778-784, 2003; and Francisco et al., Blood 102:1458-1465. 2003.

Immunotoxins with multiple (e.g., four) cytotoxins per binding domain can be prepared by partial reduction of the binding domain with an excess of a reducing reagent such as dithiothreitol (DTT) or tris(2-carboxyethyl)phosphine (TCEP) at 37° C. for 30 min, then the buffer can be exchanged by elution through SEPHADEX G-25 resin with 1 mM DTPA (diethylene triamine penta-acetic acid) in Dulbecco's phosphate-buffered saline (DPBS). The eluent can be diluted with further DPBS, and the thiol concentration of the binding domain can be measured using 5,5'-dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting immunotoxin mixture can be purified on SEPHADEX G-25 equilibrated in PBS to remove unreacted linker-cytotoxin conjugate, desalted if desired, and purified by size-exclusion chromatography. The resulting immunotoxin can then be sterile filtered, for example, through a 0.2 µm filter, and can be lyophilized if desired for storage.

Frequently used plant toxin drugs are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and *Pseudomonas* exotoxin (PE). Kreitman, Current Pharmaceutical Biotechnology 2:313-325 (2001). The toxin may also be an antibody or other peptide. Anti-CD33 ADCs include a CD33 binding domain linked to a cytotoxic drug that results in the bound cell's destruction. ADCs allow for the targeted delivery of a drug moiety to a selected cell, and, in particular embodiments intracellular accumulation therein, where systemic administration of unconjugated drugs may result in unacceptable levels of toxicity to normal cells (Polakis P. (2005) Current Opinion in Pharmacology 5:382-387).

ADC can include targeted drugs which combine properties of both antibodies and cytotoxic drugs by targeting potent cytotoxic drugs to antigen-expressing cells (Teicher, B. A. (2009) Current Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res. 41:98-107). See also Kamath & Iyer (Pharm Res. 32(11): 3470-3479, 2015), which describes considerations for the development of ADCs.

ADC compounds of the disclosure include those with anti-CD33 cell activity. In particular embodiments, the ADC compounds include a CD33 binding domain conjugated, i.e. covalently attached, to the drug moiety.

Examples of drugs useful to include within the ADC format include taxol, taxane, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other appropriate toxins include, for example, CC-1065 and analogues thereof, the duocarmycins. Additional examples include maytansinoid (including monomethyl auristatin E [MMAE]; vedotin), dolastatin, auristatin, calicheamicin, pyrrolobenzodiazepine (PBD) dimer, indolino-benzodiazepine dimer, nemorubicin and its derivatives, PNU-159682, anthracycline, *vinca* alkaloid, trichothecene, camptothecin, elinafide, and stereoisomers, isosteres, analogs, and derivatives thereof that have cytotoxic activity.

The drug may be obtained from essentially any source; it may be synthetic or a natural product isolated from a selected source, e.g., a plant, bacterial, insect, mammalian or fungal source. The drug may also be a synthetically modified natural product or an analogue of a natural product.

Exemplary ADCs that target CD33 include GO (which includes the recombinant humanized IgG4 anti-CD33 hP67.6 antibody linked to the cytotoxic antitumor antibiotic calicheamicin; U.S. Pat. No. 5,773,001), lintuzumab (SGN-33; HuM195; Caron et al., Can. Res. 52:6761-6767, 1992), SGN-CD33A (the antibody portion of which is h2H12EC a.k.a h2H12d; see US 2013/0309223), and IMGN779.

Anti-CD33 antibody-radioisotope conjugates include a CD33 binding domain linked to a cytotoxic radioisotope for use in nuclear medicine. Nuclear medicine refers to the diagnosis and/or treatment of conditions by administering radioactive isotopes (radioisotopes or radionuclides) to a subject. Therapeutic nuclear medicine is often referred to as radiation therapy or radioimmunotherapy (RIT).

Examples of radioactive isotopes that can be conjugated to CD33 binding domains include iodine-131, indium-111, yttrium-90, and lutetium-177, as well as alpha-emitting radionuclides such as astatine-211 or bismuth-212, bismuth-213, or actinium-225. Methods for preparing radioimmunoconjugates are established in the art. Examples of radioimmunotoxins are commercially available, including Zevalin® (RIT Oncology, Seattle, WA), and similar methods can be used to prepare radioimmunotoxins using the binding domains of the disclosure.

Examples of radionuclides that are useful for radiation therapy include $^{225}$AC and $^{227}$Th. $^{225}$AC is a radionuclide with the half-life of ten days. As $^{225}$AC decays the daughter isotopes $^{221}$Fr, $^{213}$Bi, and $^{209}$Pb are formed. $^{227}$Th has a half-life of 19 days and forms the daughter isotope $^{223}$Ra.

Additional examples of useful radioisotopes include $^{228}$Ac, $^{111}$Ag, $^{124}$Am, $^{74}$As, $^{209}$At, $^{194}$Au, $^{128}$Ba, $^{7}$Be, $^{206}$Bi, $^{245}$Bk, $^{246}$Bk, $^{76}$Br, $^{11}$C, $^{47}$Ca, $^{254}$Cf, $^{242}$Cm, $^{51}$Cr, $^{67}$Cu, $^{153}$Dy, $^{157}$Dy, $^{159}$Dy, $^{165}$Dy, $^{166}$Dy, $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{68}$Ge, $^{170}$Hf, $^{171}$Hf, $^{193}$Hg, $^{193}$mHg, $^{160}$mHo, $^{130}$I, $^{135}$I, $^{114}$mIn, $^{185}$Ir, $^{42}$K, $^{43}$K, $^{76}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$P, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{93}$Y, $^{169}$Yb, $^{175}$Yb, $^{65}$Zn, $^{71}$mZn, $^{86}$Zr, $^{95}$Zr, and/or $^{97}$Zr.

(V-C-II) ANTI-CD33 BISPECIFIC & TRISPECIFIC ANTIBODIES

Anti-CD33 bispecific antibodies bind at least two epitopes wherein at least one of the epitopes is located on CD33. Anti-CD33 trispecific antibodies bind at least 3 epitopes, wherein at least one of the epitopes is located on CD33.

Some examples of bispecific antibodies have two heavy chains (each having three heavy chain CDRs, followed by (N-terminal to C-terminal) a CH1 domain, a hinge, a CH2 domain, and a CH3 domain), and two immunoglobulin light chains that confer antigen-binding specificity through association with each heavy chain. However, additional architectures can be used, including bispecific antibodies in which the light chain(s) associate with each heavy chain but do not (or minimally) contribute to antigen-binding specificity, or that can bind one or more of the epitopes bound by the heavy chain antigen-binding regions, or that can associate with each heavy chain and enable binding of one or both of the heavy chains to one or both epitopes. Other forms of bispecific antibodies include the single chain "Janusins" described in Traunecker et al. (Embo Journal, 10, 3655-3659, 1991).

Bispecific antibodies can be prepared as full-length antibodies or antibody fragments (for example, F(ab')2 bispecific antibodies).

Methods for making bispecific antibodies are also described in Millstein et al. Nature 305:37-39, 1983; WO 1993/008829; and Traunecker et al., EMBO J. 10:3655-3659, 1991. In particular embodiments, bispecific antibodies can be prepared using chemical linkage. For example, Brennan et al. (Science 229: 81, 1985) describes a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated then are converted to thionitrobenzoate (TNB) derivatives. One of the Fab'-TNB derivatives then is reconverted to the Fab'-thiol by reduction with mercaptoethylamine and is mixed with an equimolar amount of the other Fab'-TNB derivative to form the bispecific antibody.

In particular embodiments, CD33-targeting agents include bi- or trispecific immune cell engaging antibody constructs. An example of a bi- or trispecific immune cell engaging antibody construct includes those which bind both CD33 and an immune cell (e.g., T-cell) activating epitope, with the goal of bringing immune cells to CD33-expressing cells to destroy the CD33-expressing cells. See, for example, US 2008/0145362. Such constructs are referred to herein as immune-activating bi- or tri-specifics or I-ABTS). In particular embodiments, I-ABTS include AMG330, AMG673, and AMV-564. BiTEs® are one form of I-ABTS. Immune cells that can be targeted for localized activation by I-ABTS within the current disclosure include, for example, T-cells, natural killer (NK) cells, and macrophages which are discussed in more detail herein. Bispecific immune cell engaging antibody constructs, including I-ABTS utilize bispecific binding domains, such as bispecific antibodies to target CD33-expressing cells and immune cells. The binding domain that binds CD33 and the binding domain that binds and activates an immune cell may be joined through a linker, as described elsewhere herein.

T-cell activation can be mediated by two distinct signals: those that initiate antigen-dependent primary activation and provide a T-cell receptor like signal (primary cytoplasmic signaling sequences) and those that act in an antigen-independent manner to provide a secondary or co-stimulatory signal (secondary cytoplasmic signaling sequences). I-ABTS disclosed herein can target any T-cell activating epitope that upon binding induces T-cell activation. Examples of such T-cell activating epitopes are on T-cell markers including CD2, CD3, CD7, CD27, CD28, CD30, CD40, CD83, 4-1BB (CD 137), OX40, lymphocyte function-associated antigen-1 (LFA-1), LIGHT, NKG2C, and B7-H3.

Several different subsets of T-cells have been discovered, each with a distinct function. For example, a majority of T-cells have a TCR existing as a complex of several proteins. The actual T-cell receptor is composed of two separate peptide chains, which are produced from the independent T-cell receptor α and β (TCRα and TCRβ) genes and are called α- and β-TCR chains.

CD3 is a primary signal transduction element of T-cell receptors. CD3 is composed of a group of invariant proteins called gamma (γ), delta (δ), epsilon (ε), zeta (ζ) and eta (η) chains. The γ, δ, and ε chains are structurally-related, each containing an Ig-like extracellular constant domain followed by a transmembrane region and a cytoplasmic domain of more than 40 amino acids. The ζ and η chains have a distinctly different structure: both have a very short extracellular region of only 9 amino acids, a transmembrane region and a long cytoplasmic tail including 113 and 115 amino acids in the ζ and η chains, respectively. The invariant protein chains in the CD3 complex associate to form non-covalent heterodimers of the ε chain with a γ chain (εγ) or with a δ chain (εδ) or of the ζ and η chain (ζη), or a disulfide-linked homodimer of two ζ chains (ζζ). 90% of the CD3 complex incorporate the ζζ homodimer.

The cytoplasmic regions of the CD3 chains include a motif designated the immunoreceptor tyrosine-based activation motif (ITAM). This motif is found in a number of other receptors including the Ig-α/Ig-β heterodimer of the B-cell receptor complex and Fc receptors for IgE and IgG. The ITAM sites associate with cytoplasmic tyrosine kinases and participate in signal transduction following TCR-mediated triggering. In CD3, the γ, δ and ε chains each contain a single copy of ITAM, whereas the ζ and η chains harbor three ITAMs in their long cytoplasmic regions. Indeed, the ζ and η chains have been ascribed a major role in T-cell activation signal transduction pathways.

In particular embodiments, the CD3 binding domain (e.g., scFv) of an I-ABTS is derived from the OKT3 antibody (also utilized in blinatumomab). The OKT3 antibody is described in detail in U.S. Pat. No. 5,929,212. It includes a variable light chain including a CDRL1 sequence including SASSSVSYMN (SEQ ID NO: 55), a CDRL2 sequence including RWIYDTSKLAS (SEQ ID NO: 56), and a CDRL3 sequence including QQWSSNPFT (SEQ ID NO:

57). In particular embodiments, the CD3 T-cell activating epitope binding domain is a human or humanized binding domain (e.g., scFv) including a variable heavy chain including a CDRH1 sequence including KASGYTFTRYTMH (SEQ ID NO: 58), a CDRH2 sequence including INPSR-GYTNYNQKFKD (SEQ ID NO: 59), and a CDRH3 sequence including YYDDHYCLDY (SEQ ID NO: 60).

The following sequence is an scFv derived from OKT3 which retains the capacity to bind CD3:

```
(SEQ ID NO: 61)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSSSGGGGSGGGGSGGGGSQIVLTQSPAIMS

ASPGEKVTMTCSASSSVSYMNWYQQKSGTSPKRWIYDTSKLASGVPAHF

RGSGSGTSYSLTISGMEAEDAATYYCQQWSSNPFTFGSGTKLEINR.
```

It may also be used as a CD3 binding domain.

In particular embodiments, the CD3 T-cell activating epitope binding domain is a human or humanized binding domain (e.g., scFv) including a variable light chain including a CDRL1 sequence including QSLVHNNGNTY (SEQ ID NO: 62), a CDRL2 sequence including KVS, and a CDRL3 sequence including GQGTQYPFT (SEQ ID NO: 63). In particular embodiments, the CD3 T-cell activating epitope binding domain is a human or humanized binding domain (e.g., scFv) including a variable heavy chain including a CDRH1 sequence including GFTFTKAW (SEQ ID NO: 64), a CDRH2 sequence including IKDKSNSYAT (SEQ ID NO: 65), and a CDRH3 sequence including RGVYYALSPFDY (SEQ ID NO: 66). These reflect CDR sequences of the 20G6-F3 antibody.

In particular embodiments, the CD3 T-cell activating epitope binding domain is a human or humanized binding domain (e.g., scFv) including a variable light chain including a CDRL1 sequence including QSLVHDNGNTY (SEQ ID NO: 67), a CDRL2 sequence including KVS, and a CDRL3 sequence including GQGTQYPFT (SEQ ID NO: 63). In particular embodiments, the CD3 T-cell activating epitope binding domain is a human or humanized binding domain (e.g., scFv) including a variable heavy chain including a CDRH1 sequence including GFTFSNAW (SEQ ID NO: 69), a CDRH2 sequence including IKARSNNYAT (SEQ ID NO: 70), and a CDRH3 sequence including RGTYYASKPFDY (SEQ ID NO: 71). These reflect CDR sequences of the 4B4-D7 antibody.

In particular embodiments, the CD3 T-cell activating epitope binding domain is a human or humanized binding domain (e.g., scFv) including a variable light chain including a CDRL1 sequence including QSLEHNNGNTY (SEQ ID NO: 72), a CDRL2 sequence including KVS, and a CDRL3 sequence including GQGTQYPFT (SEQ ID NO: 63). In particular embodiments, the CD3 T-cell activating epitope binding domain is a human or humanized binding domain (e.g., scFv) including a variable heavy chain including a CDRH1 sequence including GFTFSNAW (SEQ ID NO: 69), a CDRH2 sequence including IKDKSNNYAT (SEQ ID NO: 75), and a CDRH3 sequence including RYVHYGIGYAMDA (SEQ ID NO: 76). These reflect CDR sequences of the 4E7-C9 antibody.

In particular embodiments, the CD3 T-cell activating epitope binding domain is a human or humanized binding domain (e.g., scFv) including a variable light chain including a CDRL1 sequence including QSLVHTNGNTY (SEQ ID NO: 77), a CDRL2 sequence including KVS, and a CDRL3 sequence including GQGTHYPFT (SEQ ID NO: 78). In particular embodiments, the CD3 T-cell activating epitope binding domain is a human or humanized binding domain (e.g., scFv) including a variable heavy chain including a CDRH1 sequence including GFTFTNAW (SEQ ID NO: 79), a CDRH2 sequence including KDKSNNYAT (SEQ ID NO: 80), and a CDRH3 sequence including RYVHYRFAYALDA (SEQ ID NO: 81). These reflect CDR sequences of the 18F5-H10 antibody.

Additional examples of anti-CD3 antibodies, binding domains, and CDRs can be found in WO2016/116626. TR66 may also be used. WO 2015/036583 describes a bispecific antibody construct that binds to CD33 and CD3.

CD28 is a surface glycoprotein present on 80% of peripheral T-cells in humans and is present on both resting and activated T-cells. CD28 binds to B7-1 (CD80) and B7-2 (CD86) and is the most potent of the known co-stimulatory molecules (June et al., Immunol. Today 15:321, 1994; Linsley et al., Ann. Rev. Immunol. 11:191, 1993). In particular embodiments, the CD28 binding domain (e.g., scFv) is derived from CD80, CD86 or the 9D7 antibody. Additional antibodies that bind CD28 include 9.3, KOLT-2, 15E8, 248.23.2, and EX5.3D10. Further, 1YJD provides a crystal structure of human CD28 in complex with the Fab fragment of a mitogenic antibody (5.11A1). In particular embodiments, antibodies that do not compete with 9D7 are selected.

In particular embodiments, a CD28 binding domain is derived from TGN1412. In particular embodiments, the variable heavy chain of TGN1412 includes:

```
(SEQ ID NO: 37)
QVQLVQSGAEVKKPGASVKVSCKASGYTFTSYYIHWVRQAPGQGLEWIG

CIYPGNVNTNYNEKFKDRATLTVDTSISTAYMELSRLRSDDTAVYFCTR

SHYGLDWNFDVWGQGTTVTVSS
``` and the variable light chain of TGN1412 includes:

```
(SEQ ID NO: 38)
DIQMTQSPSSLSASVGDRVTITCHASQNIYVWLNWYQQKPGKAPKLLIY

KASNLHTGVPSRFSGSGSGTDFTLTISSLQPEDFATYYCQQGQTYPYTF

GGGTKVEIK.
```

In particular embodiments, the CD28 binding domain includes a variable light chain including a CDRL1 sequence including HASQNIYVWLN (SEQ ID NO: 68), CDRL2 sequence including KASNLHT (SEQ ID NO: 73), and CDRL3 sequence including QQGQTYPYT (SEQ ID NO: 74), a variable heavy chain including a CDRH1 sequence including GYTFTSYYIH (SEQ ID NO: 90), a CDRH2 sequence including CIYPGNVNTNYNEK (SEQ ID NO: 91), and a CDRH3 sequence including SHYGLDWNFDV (SEQ ID NO: 92).

In particular embodiments, the CD28 binding domain including a variable light chain including a CDRL1 sequence including HASQNIYVWLN (SEQ ID NO: 68), a CDRL2 sequence including KASNLHT (SEQ ID NO: 73), and a CDRL3 sequence including QQGQTYPYT (SEQ ID NO: 74) and a variable heavy chain including a CDRH1 sequence including SYYIH (SEQ ID NO: 49), a CDRH2 sequence including CIYPGNVNTNYNEKFKD (SEQ ID NO: 94), and a CDRH3 sequence including SHY-GLDWNFDV (SEQ ID NO: 92).

Activated T-cells express 4-1BB (CD137). In particular embodiments, the 4-1BB binding domain includes a variable light chain including a CDRL1 sequence including RASQSVS (SEQ ID NO: 95), a CDRL2 sequence including ASNRAT (SEQ ID NO: 108), and a CDRL3 sequence including QRSNWPPALT (SEQ ID NO: 109) and a variable heavy chain including a CDRH1 sequence including YYWS (SEQ ID NO: 110), a CDRH2 sequence including INH, and a CDRH3 sequence including YGPGNYDWYFDL (SEQ ID NO: 111).

In particular embodiments, the 4-1BB binding domain includes a variable light chain including a CDRL1 sequence including SGDNIGDQYAH (SEQ ID NO: 112), a CDRL2 sequence including QDKNRPS (SEQ ID NO: 113), and a CDRL3 sequence including ATYTGFGSLAV (SEQ ID NO: 114) and a variable heavy chain including a CDRH1 sequence including GYSFSTYWIS (SEQ ID NO: 115), a CDRH2 sequence including KIYPGDSYTNYSPS (SEQ ID NO: 116) and a CDRH3 sequence including GYGIFDY (SEQ ID NO: 35).

Particular embodiments disclosed herein include immune cell binding domains that bind epitopes on CD8. In particular embodiments, the CD8 binding domain (e.g., scFv) is derived from the OKT8 antibody. For example, in particular embodiments, the CD8 T-cell activating epitope binding domain is a human or humanized binding domain (e.g., scFv) including a variable light chain including a CDRL1 sequence including RTSRSISQYLA (SEQ ID NO: 82), a CDRL2 sequence including SGSTLQS (SEQ ID NO: 83), and a CDRL3 sequence including QQHNENPLT (SEQ ID NO: 84). In particular embodiments, the CD8 T-cell activating epitope binding domain is a human or humanized binding domain (e.g., scFv) including a variable heavy chain including a CDRH1 sequence including GFNIKD (SEQ ID NO: 85), a CDRH2 sequence including RIDPANDNT (SEQ ID NO: 86), and a CDRH3 sequence including GYGYYVFDH (SEQ ID NO: 87). These reflect CDR sequences of the OKT8 antibody.

In particular embodiments, an immune cell binding domain is a scTCR including $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or including $V_\alpha$-$C_\alpha$, $V_\beta$-$C_\beta$, $V_\alpha$-$V_\beta$ pair specific for a target epitope of interest. In particular embodiments, T-cell activating epitope binding domains can be derived from or based on a $V\alpha$, $V\beta$, $C\alpha$, or $C\beta$ of a known TCR (e.g., a high-affinity TCR).

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3.

In particular embodiments NK cells are targeted for localized activation by I-ABTS. NK cells can induce apoptosis or cell lysis by releasing granules that disrupt cellular membranes and can secrete cytokines to recruit other immune cells.

Examples of activating proteins expressed on the surface of NK cells include NKG2D, CD8, CD16, KIR2DL4, KIR2DS1, KIR2DS2, KIR3DS1, NKG2C, NKG2E, NKG2D, and several members of the natural cytotoxicity receptor (NCR) family. Examples of NCRs that activate NK cells upon ligand binding include NKp30, NKp44, NKp46, NKp80, and DNAM-1.

Examples of commercially available antibodies that bind to an NK cell receptor and induce and/or enhance activation of NK cells include: 5C6 and 1D11, which bind and activate NKG2D (available from BioLegend® San Diego, CA); mAb 33, which binds and activates KIR2DL4 (available from BioLegend®); P44-8, which binds and activates NKp44 (available from BioLegend®); SKI, which binds and activates CD8; and 3G8 which binds and activates CD16.

In particular embodiments, the I-ABTS can bind to and block an NK cell inhibitory receptor to enhance NK cell activation. Examples of NK cell inhibitory receptors that can be bound and blocked include KIR2DL1, KIR2DL2/3, KIR3DL1, NKG2A, and KLRG1. In particular embodiments, a binding domain that binds and blocks the NK cell inhibitory receptors KIR2DL1 and KIR2DL2/3 includes a variable light chain region of the sequence:

```
                                          (SEQ ID NO: 88)
EIVLTQSPVTLSLSPGERATLSCRASQSVSSYLAWYQQKPGQAPRLLIY

DASNRATGIPARFSGSGSGTDFTLTISSLEPEDFAVYYCQQRSNWMYTF

GQGTKLEIKRT
``` and a variable heavy chain region of the sequence:

```
                                          (SEQ ID NO: 89)
QVQLVQSGAEVKKPGSSVKVSCKASGGTFSFYAISWVRQAPGQGLEWMG

GFIPIFGAANYAQKFQGRVTITADESTSTAYMELSSLRSDDTAVYYCAR

IPSGSYYYDYDMDVWGQGTTVTVSS.
```

Additional NK cell activating antibodies are described in WO/2005/0003172 and U.S. Pat. No. 9,415,104.

Macrophages (and their precursors, monocytes) reside in every tissue of the body (in certain instances as microglia, Kupffer cells and osteoclasts) where they engulf apoptotic cells, pathogens and other non-self-components.

The I-ABTS can be designed to bind to a protein expressed on the surface of macrophages. Examples of activating proteins expressed on the surface of macrophages (and their precursors, monocytes) include CD11b, CD11c, CD64, CD68, CD119, CD163, CD206, CD209, F4/80, IFGR2, Toll-like receptors (TLRs) 1-9, IL-4Rα, and MARCO. Commercially available antibodies that bind to proteins expressed on the surface of macrophages include M1/70, which binds and activates CD11b (available from BioLegend); KP1, which binds and activates CD68 (available from ABCAM, Cambridge, United Kingdom); and ab87099, which binds and activates CD163 (available from ABCAM).

Anti-CD33 tri-specific antibodies are artificial proteins that simultaneously bind to three different types of antigens, wherein at least one of the antigens is CD33. Tri-specific antibodies are described in, for example, WO2016/105450, WO 2010/028796; WO 2009/007124; WO 2002/083738; US 2002/0051780; and WO 2000/018806.

When CD33-targeting agents are based on antibodies, binding domains, or similar proteins derived therefrom, modifications that provide different administration benefits can be useful. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live. While the disclosure below describes these modifications in terms of their application to antibodies, when applicable to another particular anti-CD33 binding domain format (e.g., an scFv, bispecific antibodies), the modifications can also be applied to these other formats.

In particular embodiments the antibodies can be mutated to increase the half-life of the antibodies in serum. M428L/N434S is a pair of mutations that increase the half-life of antibodies in serum, as described in Zalevsky et al., Nature Biotechnology 28, 157-159, 2010.

In particular embodiments the antibodies can be mutated to increase their affinity for Fc receptors. Exemplary mutations that increase the affinity for Fc receptors include: G236A/S239D/A330L/I332E (GASDALIE). Smith et al., Proceedings of the National Academy of Sciences of the United States of America, 109(16), 6181-6186, 2012. In particular embodiments, an antibody variant includes an Fc region with one or more amino acid substitutions which improve ADCC, e.g., substitutions at positions 298, 333, and/or 334 of the Fc region (EU numbering of residues). In particular embodiments, alterations are made in the Fc region that result in altered C1q binding and/or Complement Dependent Cytotoxicity (CDC), e.g., as described in U.S. Pat. No. 6,194,551, WO 99/51642, and Idusogie et al., J. Immunol. 164: 4178-4184, 2000.

Antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at position 297 in the Fc region (Eu numbering of Fc region residues); however, Asn297 may also be located ±3 amino acids upstream or downstream of position 297, i.e., between positions 294 and 300, due to minor sequence variations in antibodies. Such fucosylation variants may have improved ADCC function. See, e.g., WO2000/61739; WO 2001/29246; WO2002/031140; US2002/0164328; WO2003/085119; WO2003/084570; US2003/0115614; US2003/0157108; US2004/0093621; US2004/0110704; US2004/0132140; US2004/0110282; US2004/0109865; WO2005/035586; WO2005/035778; WO2005/053742; Okazaki et al. J. Mol. Biol. 336:1239-1249 (2004); and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545, 1986, and knockout cell lines, such as alpha-1,6-fucosyltransferase gene, FUT8, knockout CHO cells (see, e.g., Yamane-Ohnuki et al., Biotech. Bioeng. 87: 614, 2004; Kanda et al., Biotechnol. Bioeng., 94(4):680-688, 2006; and WO2003/085107).

In particular embodiments, modified antibodies include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N—X—S/T motifs during expression in mammalian cells) or modified by synthetic means. The modified amino acid can be within the sequence or at the terminal end of a sequence. Modifications also include nitrited constructs.

PEGylation particularly is a process by which polyethylene glycol (PEG) polymer chains are covalently conjugated to other molecules such as proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the half-lives of proteins in the body (Abuchowski, A. et al., Cancer Biochem. Biophys., 1984, 7:175-186; Hershfield, M. S. et al., N. Engl. J. Medicine, 1987, 316:589-596; and Meyers, F. J. et al., Clin. Pharmacol. Ther., 49:307-313, 1991). The attachment of PEG to proteins not only protects the molecules against enzymatic degradation, but also reduces their clearance rate from the body. The size of PEG attached to a protein has significant impact on the half-life of the protein. The ability of PEGylation to decrease clearance is generally not a function of how many PEG groups are attached to the protein, but the overall molecular weight of the altered protein. Usually the larger the PEG is, the longer the in vivo half-life of the attached protein. In addition, PEGylation can also decrease protein aggregation (Suzuki et al., Biochem. Bioph. Acta 788:248, 1984), alter protein immunogenicity (Abuchowski et al., J. Biol. Chem. 252: 3582, 1977), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

(V-C-III) ANTI-CD33 CARS OR TCRS

CD33-targeting agents also include immune cells expressing CAR or TCR that specifically bind CD33. Methods to genetically modify cells to express an exogenous gene are described above in section (IV).

CAR refer to proteins including several distinct subcomponents. The subcomponents include at least an extracellular component, a transmembrane domain, and an intracellular component. Within the current disclosure, the extracellular component includes a binding domain that binds CD33. When the binding domain binds CD33, the intracellular component signals the immune cell to destroy the bound cell. Binding domains that specifically bind CD33 are described above.

The intracellular or otherwise the cytoplasmic signaling components of CAR are responsible for activation of the cell in which the CAR is expressed. The term "intracellular signaling components" or "intracellular components" is thus meant to include any portion of the intracellular domain sufficient to transduce an activation signal. Intracellular components of expressed CAR can include effector domains. An effector domain is an intracellular portion of a fusion protein or receptor that can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response, such as co-stimulatory domains.

Effector domains can provide for activation of at least one function of a modified cell upon binding to the cellular marker expressed by a CD33-expressing cell. Activation of the modified cell can include one or more of differentiation, proliferation and/or activation or other effector functions. In particular embodiments, an effector domain can include an intracellular signaling component including a T cell receptor and a co-stimulatory domain which can include the cytoplasmic sequence from a co-receptor or co-stimulatory molecule.

An effector domain can include one, two, three or more receptor signaling domains, intracellular signaling components (e.g., cytoplasmic signaling sequences), co-stimulatory domains, or combinations thereof. Exemplary effector domains include signaling and stimulatory domains selected from: 4-1BB (CD137), CARD11, CD3γ, CD3δ, CD3ε, CD3ζ, CD27, CD28, CD79A, CD79B, DAP10, FcRα, FcRβ (FcεR1b), FcRγ, Fyn, HVEM (LIGHTR), ICOS, LAG3, LAT, Lck, LRP, NKG2D, NOTCH1, pTα, PTCH2, OX40, ROR2, Ryk, SLAMF1, Slp76, TCRα, TCRβ, TRIM, Wnt, Zap70, or any combination thereof. In particular embodiments, exemplary effector domains include signaling and co-stimulatory domains selected from: CD86, FcγRIIa, DAP12, CD30, CD40, PD-1, lymphocyte function-associated antigen-1 (LFA-1), CD2, CD7, LIGHT, NKG2C, B7-H3, a ligand that specifically binds with CD83, CDS, ICAM-1, GITR, BAFFR, SLAMF7, NKp80 (KLRF1), CD127, CD160, CD19, CD4, CD8α, CD8β, IL2Rβ, IL2Rγ, IL7Rα, ITGA4, VLA1, CD49a, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Ly108), SLAM (CD150, IPO-3), BLAME (SLAMF8), SELPLG (CD162), LTBR, GADS, PAG/Cbp, NKp44, NKp30, or NKp46.

Intracellular signaling component sequences that act in a stimulatory manner may include iTAMs. Examples of iTAMs including primary cytoplasmic signaling sequences include those derived from CD3γ, CD3δ, CD3ε, CD3ζ, CD5, CD22, CD66d, CD79a, CD79b, and common FcRγ (FCER1G), FcγRIIa, FcRβ (Fcε Rib), DAP10, and DAP12. In particular embodiments, variants of CD3ζ retain at least one, two, three, or all ITAM regions.

Additional examples of intracellular signaling components include the cytoplasmic sequences of the CD3ζ chain, and/or co-receptors that act in concert to initiate signal transduction following binding domain engagement.

A co-stimulatory domain is a domain whose activation can be required for an efficient lymphocyte response to cellular marker binding. Some molecules are interchangeable as intracellular signaling components or co-stimulatory domains. Examples of costimulatory domains include CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83. Further examples of such co-stimulatory domain molecules include CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, ITGAM, CDI Ib, ITGAX, CD11c, ITGBI, CD29, ITGB2, CD18, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, and CD19a.

In particular embodiments, the intracellular signaling component includes (i) all or a portion of the signaling domain of CD3, (ii) all or a portion of the signaling domain of 4-1BB, or (iii) all or a portion of the signaling domain of CD3 and 4-1BB.

Intracellular components may also include one or more of a protein of a Wnt signaling pathway (e.g., LRP, Ryk, or ROR2), NOTCH signaling pathway (e.g., NOTCH1, NOTCH2, NOTCH3, or NOTCH4), Hedgehog signaling pathway (e.g., PTCH or SMO), receptor tyrosine kinases (RTKs) (e.g., epidermal growth factor (EGF) receptor family, fibroblast growth factor (FGF) receptor family, hepatocyte growth factor (HGF) receptor family, insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, or muscle specific kinase (MuSK) receptor family); G-protein-coupled receptors, GPCRs (Frizzled or Smoothened); serine/threonine kinase receptors (BMPR or TGFR); or cytokine receptors (IL1R, IL2R, IL7R, or IL15R).

As indicated, transmembrane domains within a CAR molecule, often serving to connect the extracellular component and intracellular component through the cell membrane. The transmembrane domain can anchor the expressed molecule in the modified cell's membrane.

The transmembrane domain can be derived either from a natural and/or a synthetic source. When the source is natural, the transmembrane domain can be derived from any membrane-bound or transmembrane protein. Transmembrane domains can include at least the transmembrane region(s) of the α, β or ζ chain of a T-cell receptor, CD28, CD27, CD3 epsilon, CD45, CD4, CD5, CD8, CD9, CD16, CD22; CD33, CD37, CD64, CD80, CD86, CD134, CD137 and CD154. In particular embodiments, a transmembrane domain may include at least the transmembrane region(s) of, e.g., KIRDS2, OX40, CD2, CD27, LFA-1 (CD 11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7R a, ITGA1, VLA1, CD49a, ITGA4, IA4, CD49D, ITGA6, VLA-6, CD49f, ITGAD, CDI Id, ITGAE, CD103, ITGAL, CDI Ia, ITGAM, CDI Ib, ITGAX, CDI Ic, ITGB1, CD29, ITGB2, CD18, ITGB7, TNFR2, DNAM1(CD226), SLAMF4 (CD244, 2B4), CD84, CD96 (Tactile), CEACAM1, CRT AM, Ly9(CD229), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, or NKG2C. In particular embodiments, a variety of human hinges can be employed as well including the human Ig (immunoglobulin) hinge (e.g., an IgG4 hinge, an IgD hinge), a GS linker (e.g., a Gly-Ser linker described herein), a KIR2DS2 hinge or a CD8a hinge.

In particular embodiments, a transmembrane domain has a three-dimensional structure that is thermodynamically stable in a cell membrane, and generally ranges in length from 15 to 30 amino acids. The structure of a transmembrane domain can include an α helix, a β barrel, a β sheet, a β helix, or any combination thereof.

A transmembrane domain can include one or more additional amino acids adjacent to the transmembrane region, e.g., one or more amino acid within the extracellular region of the CAR (e.g., up to 15 amino acids of the extracellular region) and/or one or more additional amino acids within the intracellular region of the CAR (e.g., up to 15 amino acids of the intracellular components). In one aspect, the transmembrane domain is from the same protein that the signaling domain, co-stimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins to minimize interactions with other unintended members of the receptor complex. In one aspect, the transmembrane domain is capable of homodimerization with another CAR on the cell surface of a CAR-expressing cell. In a different aspect, the amino acid sequence of the transmembrane domain may be modified or substituted so as to minimize interactions with the binding domains of the native binding partner present in the same CAR-expressing cell.

CAR and TCR expressed by genetically modified immune cells often additionally include spacer regions. Spacer regions can position the binding domain away from the immune cell (e.g., T cell) surface to enable proper cell/cell contact, antigen binding and activation (Patel et al., Gene Therapy 6: 412-419 (1999)). As indicated, an extracellular spacer region of a fusion binding protein is generally located between a hydrophobic portion or transmembrane domain and the extracellular binding domain, and the spacer region length may be varied to maximize antigen recognition (e.g., tumor recognition) based on the selected target molecule, selected binding epitope, or antigen-binding domain size and affinity (see, e.g., Guest et al., J. Immunother. 28:203-11 (2005); PCT Publication No. WO 2014/031687).

Junction amino acids can be a linker which can be used to connect the sequences of CAR domains when the distance provided by a spacer is not needed and/or wanted. Junction amino acids are short amino acid sequences that can be used to connect co-stimulatory intracellular signaling components. In particular embodiments, junction amino acids are 9 amino acids or less.

In particular embodiments, CAR targeting CD33-expressing cells includes the sequence set forth in SEQ ID NOs: 144 and 145. Exemplary methods to produce CD33 CAR T-cells are described in WO2018/US34743.

In particular embodiments, cells genetically modified to express a CAR or TCR can additionally express one or more tag cassettes, transduction markers, and/or suicide switches. In some embodiments, the transduction marker and/or suicide switch is within the same construct but is expressed as a separate molecule on the cell surface. Tag cassettes and transduction markers can be used to activate, promote proliferation of, detect, enrich for, isolate, track, deplete and/or eliminate cells genetically modified to express a CAR or TCR in vitro, in vivo and/or ex vivo. "Tag cassette" refers to a unique synthetic peptide sequence affixed to, fused to, or that is part of a CD33-targeting agent, to which a cognate binding molecule (e.g., ligand, antibody, or other binding partner) is capable of specifically binding where the binding property can be used to activate, promote proliferation of, detect, enrich for, isolate, track, deplete and/or eliminate the tagged protein and/or cells expressing the tagged protein. Transduction markers can serve the same purposes but are derived from naturally occurring molecules and are often expressed using a skipping element that separates the transduction marker from the rest of the CD33-targeting agent.

Tag cassettes that bind cognate binding molecules include, for example, His tag (SEQ ID NO: 146), Flag tag (SEQ ID NO: 147), Xpress tag (SEQ ID NO: 148), Avi tag (SEQ ID NO: 149), Calmodulin tag (SEQ ID NO: 150), Polyglutamate tag, HA tag (SEQ ID NO: 151), Myc tag (SEQ ID NO: 152), Softag 1 (SEQ ID NO: 153), Softag 3 (SEQ ID NO: 154), and V5 tag (SEQ ID NO: 155).

Conjugate binding molecules that specifically bind tag cassette sequences disclosed herein are commercially available. For example, His tag antibodies are commercially available from suppliers including Life Technologies, Pierce Antibodies, and GenScript. Flag tag antibodies are commercially available from suppliers including Pierce Antibodies, GenScript, and Sigma-Aldrich. Xpress tag antibodies are commercially available from suppliers including Pierce Antibodies, Life Technologies and GenScript. Avi tag antibodies are commercially available from suppliers including Pierce Antibodies, IsBio, and Genecopoeia. Calmodulin tag antibodies are commercially available from suppliers including Santa Cruz Biotechnology, Abcam, and Pierce Antibodies. HA tag antibodies are commercially available from suppliers including Pierce Antibodies, Cell Signaling Technology and Abcam. Myc tag antibodies are commercially available from suppliers including Santa Cruz Biotechnology, Abcam, and Cell Signaling Technology.

Transduction markers may be selected from at least one of a truncated CD19 (tCD19; see Budde et al., Blood 122: 1660, 2013); a truncated human epidermal growth factor (tEGFR; see Wang et al., Blood 118: 1255, 2011); an extracellular domain of human CD34; and/or RQR8 which combines target epitopes from CD34 (see Fehse et al, Mol. Therapy 1(5 Pt 1); 448-456, 2000) and CD20 antigens (see Philip et al, Blood 124: 1277-1278).

In particular embodiments, a polynucleotide encoding an iCaspase9 construct (iCasp9) may be inserted into a CD33-targeting agent nucleotide construct as a suicide switch.

Control features may be present in multiple copies or can be expressed as distinct molecules with the use of a skipping element. For example, a CAR can have one, two, three, four or five tag cassettes and/or one, two, three, four, or five transduction markers could also be expressed. For example, embodiments can include a CD33-targeting agent having two Myc tag cassettes, or a His tag and an HA tag cassette, or a HA tag and a Softag 1 tag cassette, or a Myc tag and a SBP tag cassette. In particular embodiments, a transduction marker includes tEFGR. Exemplary transduction markers and cognate pairs are described in U.S. Ser. No. 13/463,247.

One advantage of including at least one control feature in cells genetically modified to express a CAR or TCR is that, if necessary or beneficial, the cells can be depleted following administration to a subject using the cognate binding molecule to a tag cassette.

In certain embodiments, CD33-targeting agents may be detected or tracked in vivo by using antibodies that bind with specificity to a control feature (e.g., anti-Tag antibodies), or by other cognate binding molecules that specifically bind the control feature, which binding partners for the control feature are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu, et al., Theranostics 2:3, 2012).

Thus, CD33-targeting agents expressing at least one control feature can be more readily identified, isolated, sorted, tracked, and/or eliminated as compared to a CD33-targeting agent without a tag cassette.

(VI) CELL FORMULATIONS AND CD33-TARGETING AGENT COMPOSITIONS

Therapeutic cell formulations and CD33-targeting agent compositions can be formulated for administration to subjects. In particular embodiments, cell-based formulations are administered to subjects as soon as reasonably possible following their initial formulation. In particular embodiments, formulations and/or compositions can be frozen (e.g., cryopreserved or lyophilized) prior to administration to a subject.

For example, as is understood by one of ordinary skill in the art, the freezing of cells can be destructive (see Mazur, P., 1977, Cryobiology 14:251-272) but there are numerous procedures available to prevent such damage. For example, damage can be avoided by (a) use of a cryoprotective agent, (b) control of the freezing rate, and/or (c) storage at a temperature sufficiently low to minimize degradative reactions. Exemplary cryoprotective agents include dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In particular embodiments, DMSO can be used. Addition of plasma (e.g., to a concentration of 20-25%) can augment the protective effects of DMSO. After addition of DMSO, cells can be kept at 0° C. until freezing, because DMSO concentrations of 1% can be toxic at temperatures above 4° C.

In the cryopreservation of cells, slow controlled cooling rates can be critical and different cryoprotective agents (Rapatz et al., 1968, Cryobiology 5(1): 18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1): 17-32; and Mazur, 1970, Science 168:939-949 for effects of cooling velocity on survival of stem cells and on their transplantation potential). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling.

In particular embodiments, DMSO-treated cells can be pre-cooled on ice and transferred to a tray containing chilled methanol which is placed, in turn, in a mechanical refrigerator (e.g., Harris® (Thermo Fisher Scientific Inc., Waltham, MA) or Revco® (Thermo Fisher Scientific Inc., Waltham, MA)) at −80° C. Thermocouple measurements of the methanol bath and the samples indicate a cooling rate of 1° to 3° C./minute can be preferred. After at least two hours, the specimens can have reached a temperature of −80° C. and can be placed directly into liquid nitrogen (−196° C.).

After thorough freezing, the cells can be rapidly transferred to a long-term cryogenic storage vessel. In a preferred embodiment, samples can be cryogenically stored in liquid nitrogen (−196° C.) or vapor (−1° C.). Such storage is facilitated by the availability of highly efficient liquid nitrogen refrigerators.

Further considerations and procedures for the manipulation, cryopreservation, and long-term storage of cells, can be found in the following exemplary references: U.S. Pat. Nos. 4,199,022; 3,753,357; and 4,559,298; Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186; Livesey and Linner, 1987, Nature 327:255; Linner et al., 1986, J. Histochem. Cytochem. 34(9):1123-1135; Simione, 1992, J. Parenter. Sci. Technol. 46(6):226-32).

Following cryopreservation, frozen cells can be thawed for use in accordance with methods known to those of ordinary skill in the art. Frozen cells are preferably thawed quickly and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed on ice.

In particular embodiments, methods can be used to prevent cellular clumping during thawing. Exemplary methods include: the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

As is understood by one of ordinary skill in the art, if a cryoprotective agent that is toxic to humans is used, it should be removed prior to therapeutic use. DMSO has no serious toxicity.

Exemplary carriers and modes of administration of cells are described at pages 14-15 of U.S. Patent Publication No. 2010/0183564. Additional pharmaceutical carriers are described in Remington: The Science and Practice of Pharmacy, 21st Edition, David B. Troy, ed., Lippicott Williams & Wilkins (2005).

In particular embodiments, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs, Chicago, IL), Plasma-Lyte A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within cell-based formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells. In cell-based formulations disclosed herein, cells are generally in a volume of a liter or less, 500 ml or less, 250 ml or less, or 100 ml or less. Hence the density of administered cells is typically greater than $10^4$ cells/ml, $10^7$ cells/ml or $10^8$ cells/ml.

Therapeutically effective amounts of protein-based compounds within CD33 targeting compositions can include 0.1 to 5 pg or µg/mL or L, or from 0.5 to 1 pg or µg/mL or L. In other examples, a dose can include 1 pg or µg/mL or L, 15 pg or µg/mL or L, 30 pg or µg/mL or L, 50 pg or µg/mL or L, 55 pg or µg/mL or L, 70 pg or µg/mL or L, 90 pg or µg/mL or L, 150 pg or µg/mL or L, 350 pg or µg/mL or L, 500 pg or µg/mL or L, 750 pg or µg/mL or L, 1000 pg or µg/mL or L, 0.1 to 5 mg/mL or L or from 0.5 to 1 mg/mL or L. In other examples, a dose can include 1 mg/mL or L, 10 mg/mL or L, 30 mg/mL or L, 50 mg/mL or L, 70 mg/mL or L, 100 mg/mL or L, 300 mg/mL or L, 500 mg/mL or L, 700 mg/mL or L, 1000 mg/mL or L or more.

Cell formulations and CD33 targeting compositions can be prepared for administration by, for example, injection, infusion, perfusion, or lavage. CD33-targeting agent compositions can also be prepared as oral, inhalable, or implantable compositions.

(VII) METHODS OF USE

The formulations and compositions disclosed herein can be used for treating subjects (humans, veterinary animals (dogs, cats, reptiles, birds, etc.), livestock (horses, cattle, goats, pigs, chickens, etc.), and research animals (monkeys, rats, mice, fish, etc.). In particular embodiments, subjects are human patients. Treating subjects includes delivering therapeutically effective amounts. Therapeutically effective amounts include those that provide effective amounts, prophylactic treatments, and/or therapeutic treatments.

An "effective amount" is the amount of a formulation necessary to result in a desired physiological change in a subject. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose and amount of a therapeutic formulation and/or composition administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts of cell-based compositions can include $10^4$ to $10^9$ cells/kg body weight, or $10^3$ to $10^{11}$ cells/kg body weight. Exemplary doses may include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

Therapeutically effective amounts of protein-based compounds within CD33 targeting compositions can include 0.1 to 5 pg or µg/kg, or from 0.5 to 1 µg/kg. In other examples, a dose can include 1 pg or µg/kg, 15 pg or µg/kg, 30 pg or µg/kg, 50 pg or µg/kg, 55 pg or µg/kg, 70 pg or µg/kg, 90 pg or µg/kg, 150 pg or µg/kg, 350 pg or µg/kg, 500 pg or µg/kg, 750 pg or µg/kg, 1000 pg or µg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be administered through any appropriate administration route such as by, injection, infusion, perfusion, and more particularly by administration by one or more of bone marrow, intravenous, intradermal, intraarterial, intranodal, intralymphatic, intraperitoneal injection, infusion, or perfusion). Administration of CD33-targeting agents can additionally be through oral administration, inhalation, or implantation.

Therapeutically effective amounts can be achieved by administering single or multiple doses during the course of a treatment regimen, depending on, for example, the particular treatment protocol being implemented. In particular embodiments, the treatment protocol may be dictated by a clinical trial protocol or an FDA-approved treatment protocol.

In particular embodiments, methods of the present disclosure can be used to treat acquired thrombocytopenia, acute lymphoblastic leukemia (ALL), acute myelogenous leukemia (AML), adrenoleukodystrophy, agnogenic myeloid metaplasia, AIDS, amegakaryocytosis/congenital thrombocytopenia, aplastic anemia, ataxia telangiectasia, β-thalassemia major, Chediak-Higashi syndrome, chronic granulomatous disease, chronic lymphocytic leukemia (CLL), chronic myelogenous leukemia (CML), chronic myelomonocytic leukemia, common variable immune deficiency (CVID), complement disorders, congenital agammaglobulinemia, Diamond Blackfan syndrome, diffuse large B-cell lymphoma, Fabry disease (alpha-galactosidase A), familial erythrophagocytic lymphohistiocytosis, Fanconi's anemia, fetal maternal incompatibility, follicular lymphoma, Gaucher disease (glucocerebrosidase), hemolytic anemia, Hodgkin's lymphoma, Hurler's syndrome, hyper IgM, IgG subclass deficiency, hypogammaglobulinemia, immune thrombocytopenia purpura, juvenile myelomonocytic leukemia, leukemia, lymphoma, May-Hegglin syndrome, metachromatic leukodystrophy, mucopolysaccharidoses, mucopolysaccharidosis type I (alpha-L-Iduronidase), multiple myeloma (MM), myelodysplastic syndrome (MDS or myelodysplasia), myelofibrosis, non-Hodgkin's lymphoma (NHL), paroxysmal nocturnal hemoglobinuria (PNH), Pompe disease, primary immunodeficiency diseases with antibody deficiency, pure red cell aplasia, refractory anemia, SCID, selective IgA deficiency, severe aplastic anemia, Shwachmann-Diamond-Blackfan anemia, sickle cell disease, specific antibody deficiency, systemic lupus erythematosus (SLE), thrombocytopenia, Wiskott-Aldridge syndrome, and X-linked agammaglobulinemia (XLA).

Additional exemplary cancers that may be treated include solid tumors, astrocytoma, atypical teratoid rhabdoid tumor, brain and central nervous system (CNS) cancer, breast cancer, carcinosarcoma, chondrosarcoma, chordoma, choroid plexus carcinoma, choroid plexus papilloma, clear cell sarcoma of soft tissue, gastrointestinal stromal tumor, glioblastoma, HBV-induced hepatocellular carcinoma, head and neck cancer, kidney cancer, lung cancer, malignant rhabdoid tumor, medulloblastoma, melanoma, meningioma, mesothelioma, neuroglial tumor, not otherwise specified (NOS) sarcoma, oligoastrocytoma, oligodendroglioma, osteosarcoma, ovarian cancer, ovarian clear cell adenocarcinoma, ovarian endomethrioid adenocarcinoma, ovarian serous adenocarcinoma, pancreatic cancer, pancreatic ductal adenocarcinoma, pancreatic endocrine tumor, pineoblastoma, prostate cancer, renal cell carcinoma, renal medullo carcinoma, rhabdomyosarcoma, sarcoma, schwannoma, skin squamous cell carcinoma, and stem cell cancer.

As indicated previously, FA is an inherited genetic disease characterized by fragile bone marrow cells and the inability to repair DNA damage, which accumulates in repopulating stem cells, resulting in eventual bone marrow failure. This disease can arise through mutations in any of a family of Fanconi-associated genes, with the most common of these mutations occurring in either the FANCA, FANCC, or FANCG genes. The current treatment protocol for patients is a bone marrow transplant from a matched donor, ideally from a sibling. However, the majority of patients will not have an appropriately matched sibling donor, and transplants from alternative donors are still associated with substantial toxicity and morbidity. For these patients, ongoing trials use an autologous transplant combined with new gene therapy approaches to introduce a corrected form of the mutated gene through collection and modification of the patient's own hematopoietic stem cells (e.g., NCT01331018).

Another compounding problem for transplant recipients is the conditioning regimen used to prepare the marrow compartment for infused cells to engraft. Since chemotherapy or other DNA damaging agents are not well tolerated in these patients due to their underlying disease condition, in autologous transplants, gene modified cells are re-administered without prior conditioning. While safer, avoidance of conditioning potentially prevents efficient engraftment of corrected cells into the marrow niche where they can begin contributing to hematopoietic development. In the allogeneic transplant setting initial conditioning regimens included TBI and cyclophosphamide (Cy), however, significant mortality was observed secondary to graft-versus-host disease (GVHD) and Cy toxicity including hemorrhagic cystitis, mucositis, and cardiac failure. For this reason, reduced-intensity conditioning (RIC) is now used for FA patients which includes low-dose Cy, fludarabine, and anti-thymocyte globulin. Although overall survival has improved using RIC, late complications continue to be an issue whether associated with conditioning, GVHD, or from disease-related complications.

For the reasons noted above, FA is an ideal candidate for autologous gene therapy, wherein the patient's own HSC can be supplied a functional FA gene, thereby diminishing GVHD risk. Importantly, the rationale for autologous genetic correction, even in a small number of cells, is supported by the spontaneous correction of the mutated FA gene documented in a few FA patients and resulting improvement in hematologic parameters. This "somatic mosaicism" occurs in single cell clones that can then sustain hematopoiesis over years without the requirement for marrow conditioning. A number of preclinical studies have demonstrated in vitro gene delivery by viral vectors, resulting in FA phenotype correction as demonstrated by protection from DNA crosslinking agents, such as mitomycin C (MMC). Integrating retroviral vectors encoding FANCA or FANCC cDNA were used to transduce FA murine hematopoietic progenitor cells, restore resistance of colony forming cells to MMC, and repopulate murine homozygous deficient models. As a result, several clinical trials have been conducted. All of these trials have attempted collection of FA patient HSPC by selecting $CD34^+$ cells for ex vivo gene transfer and subsequent reinfusion to limit off-target transduction for reasons of both safety and efficacy. One important remaining obstacle with autologous gene therapy is the presence of residual FA hematopoiesis that can result in myeloid malignancy, a scenario that could be minimized with the inclusion of the disclosed strategy to eliminate non-corrected or host FA cells. The current disclosure and treatment methods address this concern.

In particular embodiments, therapeutic efficacy can be observed through mouse models of FA transplantation that have been used to study ex vivo gene therapy of HSPCs. One such model includes a functional knockout of the FANCA gene, resulting in fragile marrow of these mice that are thus unable to form healthy colonies when bone marrow is plated in outgrowth assays in the presence of even low levels of MMC, a DNA damaging agent. Healthy heterozygote littermates exhibit bone marrow colony forming potential regardless of MMC presence, whereas FANCA mice are demonstrated to have a significant decrease in colony forming potential with increasing MMC concentration. This mimics the clinical setting where patient stem cells exhibit a similar phenotype when exposed to DNA damaging agents. The use of low-dose Cy for bone marrow transplant in this mouse model has been demonstrated. Without some form of preconditioning prior to transplant, donor cells can home to the bone marrow; however, they do not contribute to peripheral hematopoiesis. This underscores the need to both clear FANCA-deficient stem cell populations and promote engraftment and hematopoietic development of transplanted donor or gene-corrected autologous cell populations.

In particular embodiments, therapeutic efficacy for FA (and other immune deficiency disorders) can be observed through lymphocyte reconstitution, improved clonal diversity and thymopoiesis, reduced infections, and/or improved patient outcome. Therapeutic efficacy can also be observed through one or more of weight gain and growth, improved gastrointestinal function (e.g., reduced diarrhea), reduced upper respiratory symptoms, reduced fungal infections of the mouth (thrush), reduced incidences and severity of pneumonia, reduced meningitis and blood stream infections, and reduced ear infections. In particular embodiments, treating FA with methods of the present disclosure include increasing resistance of BM derived cells to mitomycin C (MMC). In particular embodiments, the resistance of BM derived cells to MMC can be measured by a cell survival assay in methylcellulose and MMC.

In particular embodiments, methods of the present disclosure can be used to treat SCID-X1. In particular embodiments, methods of the present disclosure can be used to treat SCID (e.g., JAK 3 kinase deficiency SCID, purine nucleoside phosphorylase (PNP) deficiency SCID, adenosine deaminase (ADA) deficiency SCID, MHC class II deficiency or recombinase activating gene (RAG) deficiency SCID). In particular embodiments, therapeutic efficacy can be observed through lymphocyte reconstitution, improved clonal diversity and thymopoiesis, reduced infections, and/or improved patient outcome. Therapeutic efficacy can also be observed through one or more of weight gain and growth, improved gastrointestinal function (e.g., reduced diarrhea), reduced upper respiratory symptoms, reduced fungal infections of the mouth (thrush), reduced incidences and severity of pneumonia, reduced meningitis and blood stream infections, and reduced ear infections. In particular embodiments, treating SCID-X1 with methods of the present disclosure include restoring functionality to the γC-dependent signaling pathway. The functionality of the γC-dependent signaling pathway can be assayed by measuring tyrosine phosphorylation of effector molecules STAT3 and/or STAT5 following in vitro stimulation with IL-21 and/or IL-2, respectively. Tyrosine phosphorylation of STAT3 and/or STAT5 can be measured by intracellular antibody staining.

Particular embodiments include treatment of secondary, or acquired, immune deficiencies such as immune deficiencies caused by trauma, viruses, chemotherapy, toxins, and pollution. As previously indicated, acquired immunodeficiency syndrome (AIDS) is an example of a secondary immune deficiency disorder caused by a virus, the human immunodeficiency virus (HIV), in which a depletion of T lymphocytes renders the body unable to fight infection. Thus, as another example, a gene can be selected to provide a therapeutically effective response against an infectious disease. In particular embodiments, the infectious disease is human immunodeficiency virus (HIV). The therapeutic gene may be, for example, a gene rendering immune cells resistant to HIV infection, or which enables immune cells to effectively neutralize the virus via immune reconstitution, polymorphisms of genes encoding proteins expressed by immune cells, genes advantageous for fighting infection that are not expressed in the patient, genes encoding an infectious agent, receptor or coreceptor; a gene encoding ligands for receptors or coreceptors; viral and cellular genes essential for viral replication including; a gene encoding ribozymes, antisense RNA, small interfering RNA (siRNA) or decoy RNA to block the actions of certain transcription factors; a gene encoding dominant negative viral proteins, intracellular antibodies, intrakines and suicide genes. Exemplary therapeutic genes and gene products include α2β1; αvβ3; αvβ5; αvβ63; BOB/GPR15; Bonzo/STRL-33/TYM-STR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC; and laminin receptor. A therapeutically effective amount for the treatment of HIV, for example, may increase the immunity of a subject against HIV, ameliorate a symptom associated with AIDS or HIV, or induce an innate or adaptive immune response in a subject against HIV. An immune response against HIV may include antibody production and result in the prevention of AIDS and/or ameliorate a symptom of AIDS or HIV infection of the subject or decrease or eliminate HIV infectivity and/or virulence.

In particular embodiments, methods of the present disclosure can be used to treat hypogammaglobulinemia. Hypogammaglobulinemia is caused by a lack of B-lymphocytes and is characterized by low levels of antibodies in the blood. Hypogammaglobulinemia can occur in patients with chronic lymphocytic leukemia (CLL), multiple myeloma (MM), non-Hodgkin's lymphoma (NHL) and other relevant malignancies as a result of both leukemia-related immune dysfunction and therapy-related immunosuppression. Patients with acquired hypogammaglobulinemia secondary to such hematological malignancies, and those patients receiving post-HSPC transplantation are susceptible to bacterial infections. The deficiency in humoral immunity is largely responsible for the increased risk of infection-related morbidity and mortality in these patients, especially by encapsulated microorganisms. For example, *Streptococcus pneumoniae, Haemophilus influenzae*, and *Staphylococcus aureus*, as well as *Legionella* and *Nocardia* spp. are frequent bacterial pathogens that cause pneumonia in patients with CLL. Opportunistic infections such as *Pneumocystis carinii*, fungi, viruses, and mycobacteria also have been observed. The number and severity of infections in these patients can be significantly reduced by administration of immune globulin (Griffiths H et al. (1989) Blood 73: 366-368; Chapel H M et al. (1994) Lancet 343: 1059-1063).

In particular embodiments, a therapeutically effective treatment induces or increases expression of fetal hemoglobin (HbF), induces or increases production of hemoglobin and/or induces or increases production of β-globin. In particular embodiments, a therapeutically effective treatment improves blood cell function, and/or increases oxygenation of cells.

In the context of cancers, therapeutically effective amounts have an anti-cancer effect. An anti-cancer effect can be quantified by observing a decrease in the number of cancer cells, a decrease in the number of metastases, a decrease in cancer volume, an increase in life expectancy, induction of apoptosis of cancer cells, induction of cancer cell death, inhibition of cancer cell proliferation, inhibition of tumor (e.g., solid tumor) growth, prevention of metastasis, prolongation of a subject's life, and/or reduction of relapse or re-occurrence of the cancer following treatment.

In particular embodiments, methods of the present disclosure can restore BM function in a subject in need thereof. In particular embodiments, restoring BM function can include improving BM repopulation with gene corrected cells as compared to a subject in need thereof that is not administered a therapy described herein. Improving BM repopulation with gene corrected cells can include increasing the percentage of cells that are gene corrected. In particular embodiments, the cells are selected from white blood cells and BM derived cells. In particular embodiments, the percentage of cells that are gene corrected can be measured using an assay selected from quantitative real time PCR and flow cytometry.

In particular embodiments, methods of the present disclosure can restore T-cell mediated immune responses in a subject in need thereof. Restoration of T-cell mediated immune responses can include restoring thymic output and/or restoring normal T lymphocyte development.

In particular embodiments, methods of the present disclosure can improve the kinetics and/or clonal diversity of lymphocyte reconstitution in a subject in need thereof. In particular embodiments, improving the kinetics of lymphocyte reconstitution can include increasing the number of circulating T lymphocytes to within a range of a reference level derived from a control population. In particular embodiments, improving the kinetics of lymphocyte reconstitution can include increasing the absolute CD3+ lymphocyte count to within a range of a reference level derived from a control population. A range of can be a range of values observed in or exhibited by normal (i.e., non-immunocompromised) subjects for a given parameter. In particular embodiments, improving the kinetics of lymphocyte reconstitution can include reducing the time required to reach normal lymphocyte counts as compared to a subject in need thereof not administered a therapy described herein. In particular embodiments, improving the kinetics of lymphocyte reconstitution can include increasing the frequency of gene corrected lymphocytes as compared to a subject in need thereof not administered a therapy described herein. In particular embodiments, improving the kinetics of lymphocyte reconstitution can include increasing diversity of clonal repertoire of gene corrected lymphocytes in the subject as compared to a subject in need thereof not administered a gene therapy described herein. Increasing diversity of clonal repertoire of gene corrected lymphocytes can include increasing the number of unique retroviral integration site (RIS) clones as measured by a RIS analysis.

In particular embodiments, restoring thymic output can include restoring the frequency of CD3+ T cells expressing CD45RA in peripheral blood to a level comparable to that of a reference level derived from a control population. In particular embodiments, restoring thymic output can include restoring the number of T cell receptor excision circles (TRECs) per $10^6$ maturing T cells to a level comparable to that of a reference level derived from a control population. The number of TRECs per $10^6$ maturing T cells can be determined as described in Kennedy D R et al. (2011) Vet Immunol Immunopathol 142: 36-48.

In particular embodiments, restoring normal T lymphocyte development includes restoring the ratio of CD4+ cells: CD8+ cells to 2. In particular embodiments, restoring normal T lymphocyte development includes detecting the presence of αβ TCR in circulating T-lymphocytes. The presence of αβ TCR in circulating T-lymphocytes can be detected, for example, by flow cytometry using antibodies that bind an α and/or β chain of a TCR. In particular embodiments, restoring normal T lymphocyte development includes detecting the presence of a diverse TCR repertoire comparable to that of a reference level derived from a control population. TCR diversity can be assessed by TCRVβ spectratyping, which analyzes genetic rearrangement of the variable region of the TCRβ gene. Robust, normal spectratype profiles can be characterized by a Gaussian distribution of fragments sized across 17 families of TCRVβ segments. In particular embodiments, restoring normal T lymphocyte development includes restoring T-cell specific signaling pathways. Restoration of T-cell specific signaling pathways can be assessed by lymphocyte proliferation following exposure to the T cell mitogen phytohemagglutinin (PHA). In particular embodiments, restoring normal T lymphocyte development includes restoring white blood cell count, neutrophil cell count, monocyte cell count, lymphocyte cell count, and/or platelet cell count to a level comparable to a reference level derived from a control population.

In particular embodiments, methods of the present disclosure can normalize primary and secondary antibody responses to immunization in a subject in need thereof. Normalizing primary and secondary antibody responses to immunization can include restoring B-cell and/or T-cell cytokine signaling programs functioning in class switching and memory response to an antigen. Normalizing primary and secondary antibody responses to immunization can be measured by a bacteriophage immunization assay. In particular embodiments, restoration of B-cell and/or T-cell cytokine signaling programs can be assayed after immunization with the T-cell dependent neoantigen bacteriophage ψX174. In particular embodiments, normalizing primary and secondary antibody responses to immunization can include increasing the level of IgA, IgM, and/or IgG in a subject in need thereof to a level comparable to a reference level derived from a control population. In particular embodiments, normalizing primary and secondary antibody responses to immunization can include increasing the level of IgA, IgM, and/or IgG in a subject in need thereof to a level greater than that of a subject in need thereof not administered a gene therapy described herein. The level of IgA, IgM, and/or IgG can be measured by, for example, an immunoglobulin test. In particular embodiments, the immunoglobulin test includes antibodies binding IgG, IgA, IgM, kappa light chain, lambda light chain, and/or heavy chain. In particular embodiments, the immunoglobulin test includes serum protein electrophoresis, immunoelectrophoresis, radial immunodiffusion, nephelometry and turbidimetry. Commercially available immunoglobulin test kits include MININEPH™ (Binding site, Birmingham, UK), and immunoglobulin test systems from Dako (Glostrup, Denmark) and Dade Behring (Marburg, Germany). In particular embodiments, a sample that can be used to measure immunoglobulin levels includes a blood sample, a plasma sample, a cerebrospinal fluid sample, and a urine sample.

In particular embodiments, therapeutically effective amounts may provide function to immune and other blood cells, reduce or eliminate an immune-mediated condition; and/or reduce or eliminate a symptom of the immune-mediated condition.

In particular embodiments, particular methods of use include the treatment of conditions wherein corrected cells have a selective advantage over non-corrected cells. For example, in FA and SCID, corrected cells have an advantage and only transducing the therapeutic gene into a "few" HSPCs is sufficient for therapeutic efficacy.

(VIII) REFERENCE LEVELS DERIVED FROM CONTROL POPULATIONS

Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 0-2 years) and non-immunocompromised status. In particular embodiments, a normal control population includes individuals that are age-matched to a test subject and non-immune compromised. In particular embodiments, age-matched includes, e.g., 0-6 months old; 0-2 years old; 0-10 years old; 10-15 years old, 60-65 years old, 70-85 years old, etc., as is clinically relevant under the circumstances. In particular embodiments, a control population can include those that have an immune deficiency and have not been administered a therapeutically effective amount In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular data point, where the data point is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

(IX) EXEMPLARY EMBODIMENTS

1. A genetic construct encoding a CD33 blocking molecule that reduces expression of CD33.
2. A genetic construct of embodiment 1 wherein the CD33 blocking molecule results in RNA-interference.
3. A genetic construct of embodiment 1 or 2 wherein the CD33 blocking molecule includes shRNA or siRNA.
4. A genetic construct of any of embodiments 1-3 wherein the CD33 blocking molecule includes shRNA encoded by SEQ ID NO: 8 or SEQ ID NO: 9.
5. A genetic construct of any of embodiments 1-3 wherein the CD33 blocking molecule includes siRNA encoded by SEQ ID NO: 11, SEQ ID NO: 12, SEQ ID NO: 13, SEQ ID NO: 14, or SEQ ID NO: 15.
6. A genetic construct of any of embodiments 1-5, wherein the CD33 blocking molecule includes a wobble base pair.
7. A genetic construct of any of embodiments 1-6 wherein the genetic construct is within a viral vector.
8. A genetic construct of an of embodiments 1-7, wherein the viral vector is a lentiviral vector, a foamy viral vector, or an adenoviral vector that optionally includes a PGK promoter.
9. A genetic construct of any of embodiments 1-8, further including a therapeutic gene.
10. A genetic construct of embodiment 9, wherein the therapeutic gene includes FancA, FancB, FancC, FancD1, FancD2, FancE, FancF, FancG, FancI, FancJ, FancL, FancM, FancN, FancO, FancP, FancQ, FancR, FancS, FancT, FancU, FancV, or FancW or encodes a checkpoint inhibitor, a gene editing molecule, a chimeric antigen receptor that specifically binds a cellular antigen (e.g. a cancer antigen or a viral antigen), and/or a T-cell receptor that specifically binds a cellular antigen (e.g. a cancer antigen or a viral antigen).
11. A genetic construct of embodiment 9, wherein the therapeutic gene includes γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, or SLC46A1.
12. A genetic construct of embodiment 9, wherein the therapeutic gene includes factor VIII (FVIII), FVII, von Willebrand factor (VWF), FI, FII, FV, FX, FXI, or FXIII).
13. A genetic construct of embodiment 9, wherein the therapeutic gene includes F8 or F9.
14. A genetic construct of embodiment 9, wherein the therapeutic gene includes γ-globin; soluble CD40; CTLA; Fas L; antibodies to CD4, CD5, CD7, CD52, etc.; antibodies to IL1, IL2, IL6; an antibody to TCR specifically present on autoreactive T cells; 1L4; IL10; IL12; IL13; IL1Ra, sIL1RI, sIL1RII; sTNFRI; sTN-FRII; antibodies to TNF; P53, PTPN22, and DRB1*1501/DQB1*0602; globin family genes; WAS; phox; dystrophin; pyruvate kinase (PK); CLN3; ABCD1; arylsulfatase A (ARSA); SFTPB; SFTPC; NLX2.1; ABCA3; GATA1; ribosomal protein genes;

TERC; CFTR; LRRK2; PARK2; PARK7; PINK1; SNCA; PSEN1; PSEN2; APP; SOD1; TDP43; FUS; ubiquilin 2; or C9ORF72.

15. A genetic construct of embodiment 9,wherein the therapeutic gene includes ABLI, AKT1, APC, ARSB, BCL11A, BLC1, BLC6, BRCA1, BRCA2, BRIP1, C46, CAS9, C-CAM, CBFAI, CBL, CCR5, CD19, CDA, C-MYC, CRE, CSCR4, CSFIR, CTS-I, CYB5R3, DCC, DHFR, DLL1, DMD, EGFR, ERBA, ERBB, EBRB2, ETSI, ETS2, ETV6, FCC, FGR, FOX, FUSI, FYN, GALNS, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LYN, MCC, MDM2, MGMT, MLL, MMACI, MYB, MEN-I, MEN-11, MYC, NAGLU, NANOG, NF-1, NF-2, NKX2.1, NOTCH, OCT4, p16, p2I, p27, p57, p73, PALB2, RAD51C, ras, at least one of RPL3 through RPL40, RPLP0, RPLP1, RPLP2, at least one of RPS2 through RPS30, RPSA, SGSH, SLX4, SOX2, VHL, or WT-1.

16. A genetic construct of any of embodiments 1-15 including a nucleotide encoding an shRNA or siRNA CD33 blocking molecule (e.g., SEQ ID NOs: 8 or 9) cloned between SEQ ID NO: 18 and SEQ ID NO: 19.

17. A cell genetically modified by the genetic construct of any of embodiments 1-16.

18. A cell of embodiment 17 wherein the cell is a hematopoietic stem and progenitor cell (HSPC).

19. A cell of embodiment 17 wherein the cell is a $CD34^+CD45RA^-CD90^+$ HSC.

20. A population of cells genetically modified by a genetic construct of any of embodiments 1-16.

21. A population of embodiment 20, wherein cells in the population are HSPC and/or $CD34^+CD45RA^-CD90^+$ HSC.

22. A cell formulation including a cell or population of any of embodiments 17-21 and a pharmaceutically acceptable carrier.

23. A kit including a genetic construct, cell, population of cells or cell formulation according to any of embodiments 1-22 and a CD33-targeting agent.

24. A kit of embodiment 23 wherein the CD33-targeting agent includes an anti-CD33 antibody, an anti-CD33 immunotoxin, an anti-CD33 antibody-drug conjugate, an anti-CD33 antibody-radioisotope conjugate, an anti-CD33 bispecific antibody, an anti-CD33 bispecific immune cell engaging antibody, an anti-CD33 trispecific antibody, and/or an anti-CD33 chimeric antigen receptor (CAR) with one or more binding domains.

25. A kit of embodiment 23 or 24 wherein the CD33-targeting agent includes Hp67.6, lintuzumab, SGN-CD33A, and/or AMG 330.

26. A kit of any of embodiments 23-25 wherein the CD33-targeting agent includes a binding domain derived from Hp67.6, lintuzumab, SGN-CD33A, and/or AMG 330.

27. A kit of any of embodiments 23-26 wherein the CD33-targeting agent includes the CDRs of Hp67.6, lintuzumab, SGN-CD33A, and/or AMG 330 and/or a sequence combination of
a variable light chain including SEQ ID NO: 39 and a variable heavy chain including SEQ ID NO: 40;
a variable light chain including SEQ ID NO: 47 and a variable heavy chain including SEQ ID NO: 48;
a variable light chain including a CDRL1 of SEQ ID NO: 41, a CDRL2 of SEQ ID NO: 42, and a CDRL3 of SEQ ID NO: 43 and a variable heavy chain including a CDRH1 of SEQ ID NO: 44, a CDRH2 of SEQ ID NO: 45, and a CDRH3 of SEQ ID NO: 46;
a variable light chain including a CDRL1 of SEQ ID NO: 49, a CDRL2 of SEQ ID NO: 50, and a CDRL3 of SEQ ID NO: 51 and a variable heavy chain including a CDRH1 of SEQ ID NO: 52, a CDRH2 of SEQ ID NO: 53, and a CDRH3 of SEQ ID NO: 54; and/or
a variable light chain including a CDRL1 of SEQ ID NO: 98, a CDRL2 of SEQ ID NO: 99, and a CDRL3 of SEQ ID NO: 100 and a variable heavy chain including a CDRH1 of SEQ ID NO: 101, a CDRH2 of SEQ ID NO: 102, and a CDRH3 of SEQ ID NO: 103.

28. A kit of any of embodiments 23-27 wherein the CD33-targeting agent includes an antibody-drug conjugate or an antibody-radioisotope conjugate wherein the drug or radioisotope are selected from taxol, taxane, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, maytansinoid, dolastatin, auristatin, calicheamicin, pyrrolobenzodiazepine, nemorubicin PNU-159682, anthracycline, vinca alkaloid, trichothecene, CC1065, camptothecin, elinafide, actinomycin D, 1-dehydrotestosterone, glucocorticoids, procaine, tetracaine, lidocaine, propranolol, puromycin, ricin, CC-1065, duocarmycin, diphtheria toxin, snake venom, cobra venom, mistletoe lectin, modeccin, pokeweed antiviral protein, saporin, Bryodin 1, bouganin, gelonin, *Pseudomonas* exotoxin, iodine-131, indium-111, yttrium-90, lutetium-177, astatine-211, bismuth-212, and/or bismuth-213 and/or wherein the antibody-drug conjugate includes GO.

29. A kit of any of embodiments 23-28 wherein the CD33-targeting agent includes a linker.

30. A kit of any of embodiments 23-29 wherein the CD33-targeting agent includes a bispecific antibody including a combination of binding variable chains or a binding CDR combination of Hp67.6, lintuzumab, SGN-CD33A, and/or AMG 330 and/or a sequence combination of a variable light chain including SEQ ID NO: 39 and a variable heavy chain including SEQ ID NO: 40;
a variable light chain including SEQ ID NO: 47 and a variable heavy chain including SEQ ID NO: 48;
a variable light chain including a CDRL1 of SEQ ID NO: 41, a CDRL2 of SEQ ID NO: 42, and a CDRL3 of SEQ ID NO: 43 and a variable heavy chain including a CDRH1 of SEQ ID NO: 44, a CDRH2 of SEQ ID NO: 45, and a CDRH3 of SEQ ID NO: 46;
a variable light chain including a CDRL1 of SEQ ID NO: 49, a CDRL2 of SEQ ID NO: 50, and a CDRL3 of SEQ ID NO: 51 and a variable heavy chain including a CDRH1 of SEQ ID NO: 52, a CDRH2 of SEQ ID NO: 53, and a CDRH3 of SEQ ID NO: 54; and/or
a variable light chain including a CDRL1 of SEQ ID NO: 98, a CDRL2 of SEQ ID NO: 99, and a CDRL3 of SEQ ID NO: 100 and a variable heavy chain including a CDRH1 of SEQ ID NO: 101, a CDRH2 of SEQ ID NO: 102, and a CDRH3 of SEQ ID NO: 103.

31. A kit of any of embodiments 23-30 wherein the CD33-targeting agent includes a bispecific antibody including at least one binding domain that activates an immune cell.
32. A kit of embodiment 31, wherein the immune cell is a T-cell, natural killer (NK) cell, or a macrophage.
33. A kit of embodiment 31 or 32, wherein the binding domain that activates an immune cell binds CD3, CD28, CD8, NKG2D, CD8, CD16, KIR2DL4, KIR2DS1, KIR2DS2, KIR3DS1, NKG2C, NKG2E, NKG2D, NKp30, NKp44, NKp46, NKp80, DNAM-1, CD11b, CD11c, CD64, CD68, CD119, CD163, CD206, CD209, F4/80, IFGR2, Toll-like receptors 1-9, IL-4Rα, or MARCO.
34. A kit of any of embodiments 31-33, wherein the binding domain that activates an immune cell includes a variable light chain including a CDRL1 of SEQ ID NO: 55, a CDRL2 of SEQ ID NO: 56, and a CDRL3 sequence of SEQ ID NO: 57 and a variable heavy chain including a CDRH1 of SEQ ID NO: 58, a CDRH2 of SEQ ID NO: 59, and a CDRH3 of SEQ ID NO: 60.
35. A kit of any of embodiments 31-34, wherein the binding domain that activates an immune cell includes SEQ ID NO: 61.
36. A kit of any of embodiments 31-35, wherein the binding domain that activates an immune cell includes a variable light chain including a CDRL1 of SEQ ID NO: 62, a CDRL2 of KVS, and a CDRL3 sequence of SEQ ID NO: 63 and a variable heavy chain including a CDRH1 of SEQ ID NO: 64, a CDRH2 of SEQ ID NO: 65, and a CDRH3 of SEQ ID NO: 66.
37. A kit of any of embodiments 31-36, wherein the binding domain that activates an immune cell includes a variable light chain including a CDRL1 of SEQ ID NO: 67, a CDRL2 of KVS, and a CDRL3 sequence of SEQ ID NO: 63 and a variable heavy chain including a CDRH1 of SEQ ID NO: 69, a CDRH2 of SEQ ID NO: 70, and a CDRH3 of SEQ ID NO: 71.
38. A kit of any of embodiments 31-37, wherein the binding domain that activates an immune cell includes a variable light chain including a CDRL1 of SEQ ID NO: 72, a CDRL2 of KVS, and a CDRL3 sequence of SEQ ID NO: 63 and a variable heavy chain including a CDRH1 of SEQ ID NO: 69, a CDRH2 of SEQ ID NO: 75, and a CDRH3 of SEQ ID NO: 76.
39. A kit of any of embodiments 31-38, wherein the binding domain that activates an immune cell includes a variable light chain including a CDRL1 of SEQ ID NO: 77, a CDRL2 of KVS, and a CDRL3 sequence of SEQ ID NO: 78 and a variable heavy chain including a CDRH1 of SEQ ID NO: 79, a CDRH2 of SEQ ID NO: 80, and a CDRH3 of SEQ ID NO: 81.
40. A kit of any of embodiments 31-39, wherein the binding domain that activates an immune cell includes a variable light chain including a CDRL1 of SEQ ID NO: 82, a CDRL2 of SEQ ID NO: 83, and a CDRL3 sequence of SEQ ID NO: 84 and a variable heavy chain including a CDRH1 of SEQ ID NO: 85, a CDRH2 of SEQ ID NO: 86, and a CDRH3 of SEQ ID NO: 87.
41. A kit of any of embodiments 31-40, wherein the binding domain that activates an immune cell includes a TCR.
42. A kit of any of embodiments 31-41, wherein the binding domain that activates an immune cell includes a variable light chain including SEQ ID NO: 88 and a variable heavy chain including SEQ ID NO: 89.
43. A kit of any of embodiments 31-42, wherein the binding domains of the bispecific antibody are joined through a linker.
44. A kit of any of embodiments 23-43, wherein the CD33-targeting agent includes a chimeric antigen receptor (CAR) including one or more binding domains.
45. A kit of embodiment 44, wherein the CAR includes an anti-CD33 binding domain and a binding domain of any of embodiments 31-42.
46. A kit of embodiment 44 or 45, wherein the effector domain of the CAR is selected from 4-1BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.
47. A kit of any of embodiments 44-46, wherein the CAR includes a cytoplasmic signaling sequence derived from CD3 zeta, FcR gamma, CD3 gamma, CD3 delta, CD3 epsilon, CD5, CD22, CD79a, CD79b, or CD66d.
48. A kit of any of embodiments 44-47, wherein the CAR includes an intracellular signaling domain and a costimulatory signaling region.
49. A kit of embodiment 48, wherein the costimulatory signaling region includes the intracellular domain of CD27, CD28, 4-1BB, OX40, CD30, CD40, lymphocyte function-associated antigen-1, CD2, CD7, LIGHT, NKG2C, or B7-H3.
50. A kit of any of embodiments 44-49, wherein the CAR includes a spacer region.
51. A kit of any of embodiments 44-50, wherein the CAR includes a transmembrane domain.
52. A method of genetically-modifying a cell to provide a therapeutic gene and to have reduced CD33 expression including exposing the cell to an effective amount of a genetic construct of any of embodiments 1-16.
53. A method of protecting a cell from an anti-CD33 treatment including genetically-modifying the cell with a genetic construct of any of embodiments 1-16.
54. A method of embodiment 53, wherein the cell is a therapeutic cell.
55. A method of embodiment 53 or 54, wherein the protecting is in vivo.
56. A method for treating a subject in need thereof with a cell formulation of embodiment 22 including administering a therapeutically effective amount of the cell formulation to the subject thereby treating the subject.
57. A method of embodiment 56, wherein the treating provides a therapeutically effective treatment against a primary immune deficiency.
58. A method of embodiment 56, wherein the treating provides a therapeutically effective treatment against a secondary immune deficiency.
59. A method of embodiment 56, wherein the treating provides a therapeutically effective treatment for a disorder including: FA, SCID, Pompe disease, Gaucher disease, Fabry disease, Mucopolysaccharidosis type I, familial apolipoprotein E deficiency and atherosclerosis (ApoE), viral infections, and cancer.
60. A method of any of embodiments 56-59 further including administering to the subject a CD33-targeting agent.
61. A method of embodiment 60, wherein the CD33-targeting agent includes an anti-CD33 antibody, an anti-CD33 immunotoxin, an anti-CD33 antibody-drug conjugate, an anti-CD33 antibody-radioisotope conjugate, an anti-CD33 bispecific antibody, an anti-CD33 bispecific immune cell engaging antibody, an anti-CD33 trispecific antibody, and/or an anti-CD33 chimeric antigen receptor (CAR) described in any of the preceding exemplary embodiments.

(X) EXPERIMENTAL EXAMPLES

A novel strategy to selectively protect therapeutic cells by reducing CD33 expression in the therapeutic cells and targeting non-therapeutic cells with anti-CD33 therapy is described. The selective protection results in the enrichment of the therapeutic cells while simultaneously targeting and reducing diseased, malignant, and/or non-therapeutic CD33 expressing cells within a subject.

Figure 4:
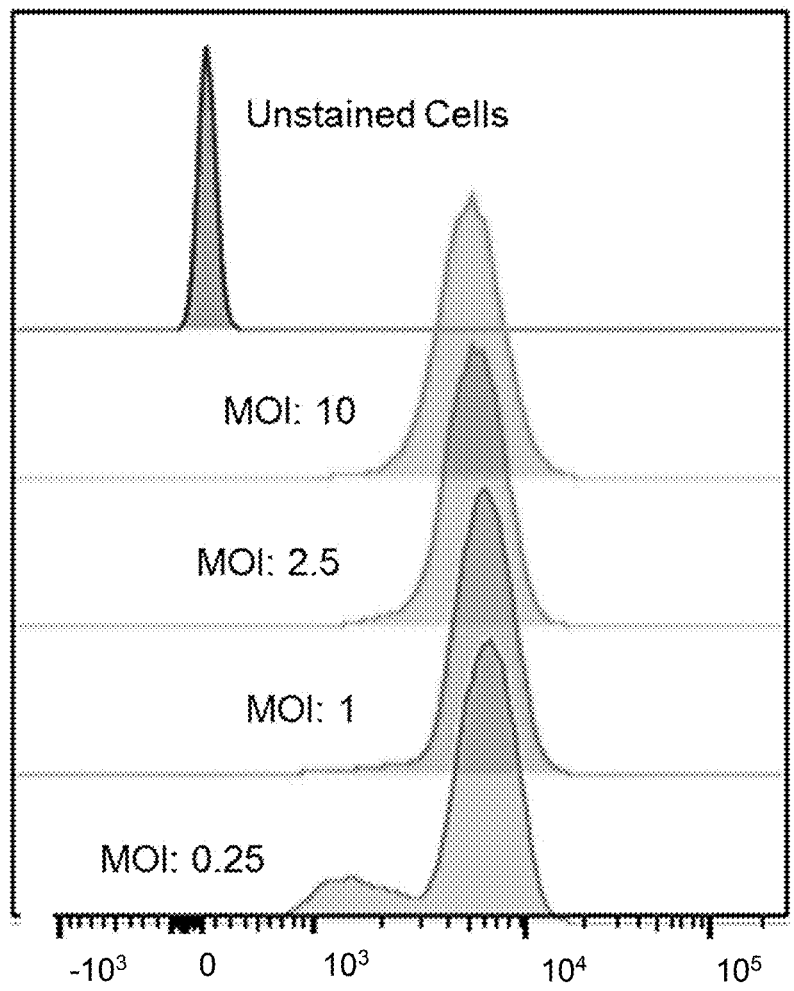
FIG. 4. Efficient shRNA-mediated CD33 knockdown in the AML cell line ML1 (acute myeloblastic leukemia). ML1 cells were transduced with increasing multiplicities of infection (MOI) of control or shRNA-containing lentiviral vectors, and surface CD33 expression measured after 1 week. ML1 cells transduced with lentiviral vector including shRNA4 or shRNA5 show a dose dependent reduction in CD33 expression.
Figure 5:
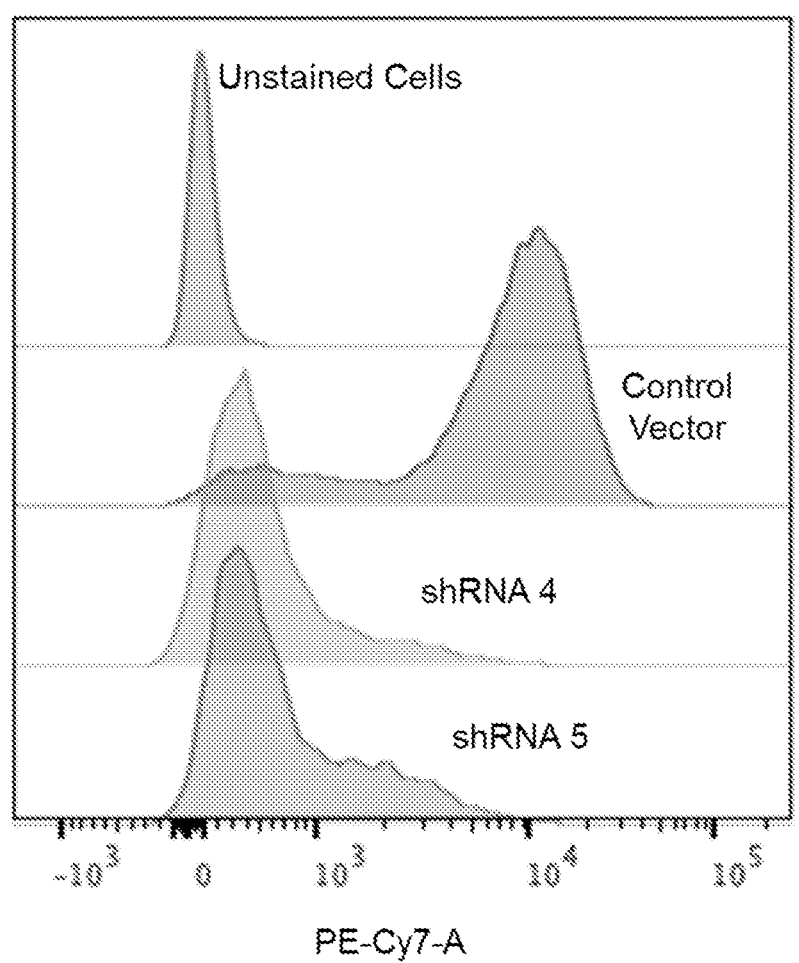
FIG. 5. Efficient knockdown of CD33 in human CD34+ hematopoietic stem and progenitor cells (HSPCs) using shRNA4, shRNA5, or a control vector. CD33 surface expression was measured by flow cytometry on day 9 after transduction.
Figure 6:
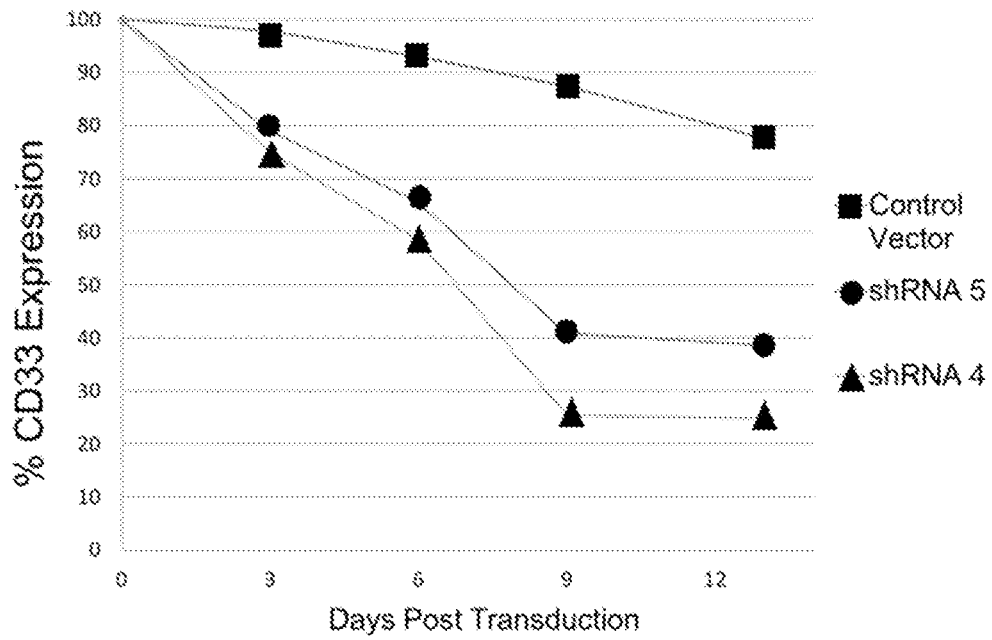
FIG. 6. Time course of CD33 surface expression in human CD34+ HSPCs treated with shRNA4 (triangle), shRNA5 (circle), or control vector (square) lentiviral vectors.
Figure 16:
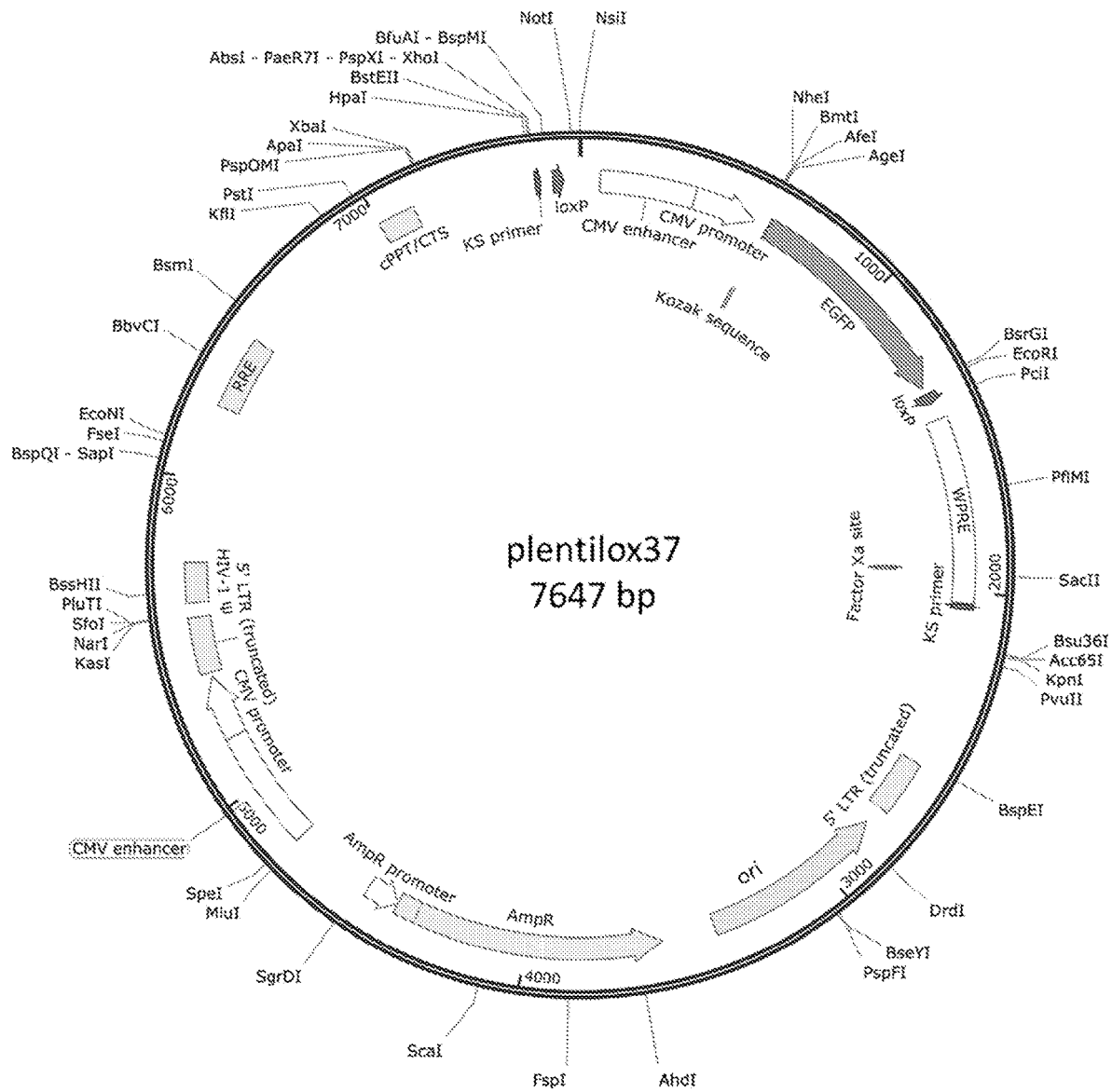
FIG. 16. Plasmid map of the lentilox 3.7 lentiviral vector used for delivery and screening of CD33 shRNA activity.

Results. CD33 shRNA4 and shRNA5 strongly reduce CD33 surface expression in the ML1 cell line. To identify a CD33 shRNA that is capable of downregulating CD33 surface expression, five shRNA sequences with predicted interference activity against CD33 coding region (FIG. 3) were cloned into lentiviral transfer plasmid pLentiLox 3.7 (FIG. 16). ML1 cells were transduced with the resulting VSV-G pseudotyped lentiviral vectors at different multiplicity of infections (MOIs). Transduced cells were analyzed by flow cytometry 3 to 7 days post treatment to determine transduction efficiency as measured by GFP expression and CD33 knockdown as determined by surface antibody staining. As shown in FIG. 4, treatment with CD33 shRNA4 and shRNA5 drastically reduced CD33 expression in ML1 cells while CD33 shRNA1 and shRNA6 did not show any activity. In summary, these results validated the activity of two CD33 shRNA molecules in the ML1 myeloid cell line.

Figure 7:
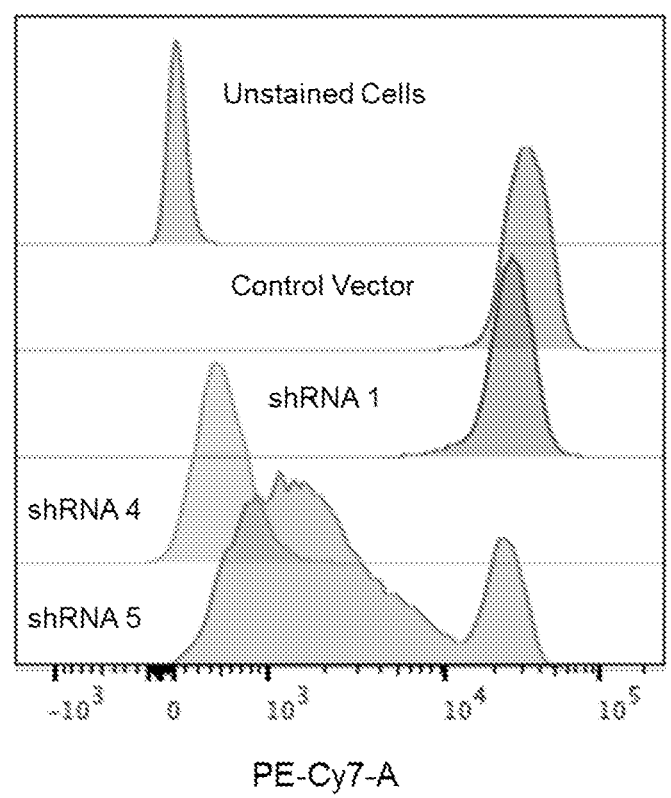
FIG. 7. Efficient knockdown of CD33 in ML1 cells treated with shRNA1, shRNA4, shRNA5, and a control vector was assessed using flow cytometry. These cells were subsequently tested for sensitivity to GO treatment in FIG. 8.
Figure 8:
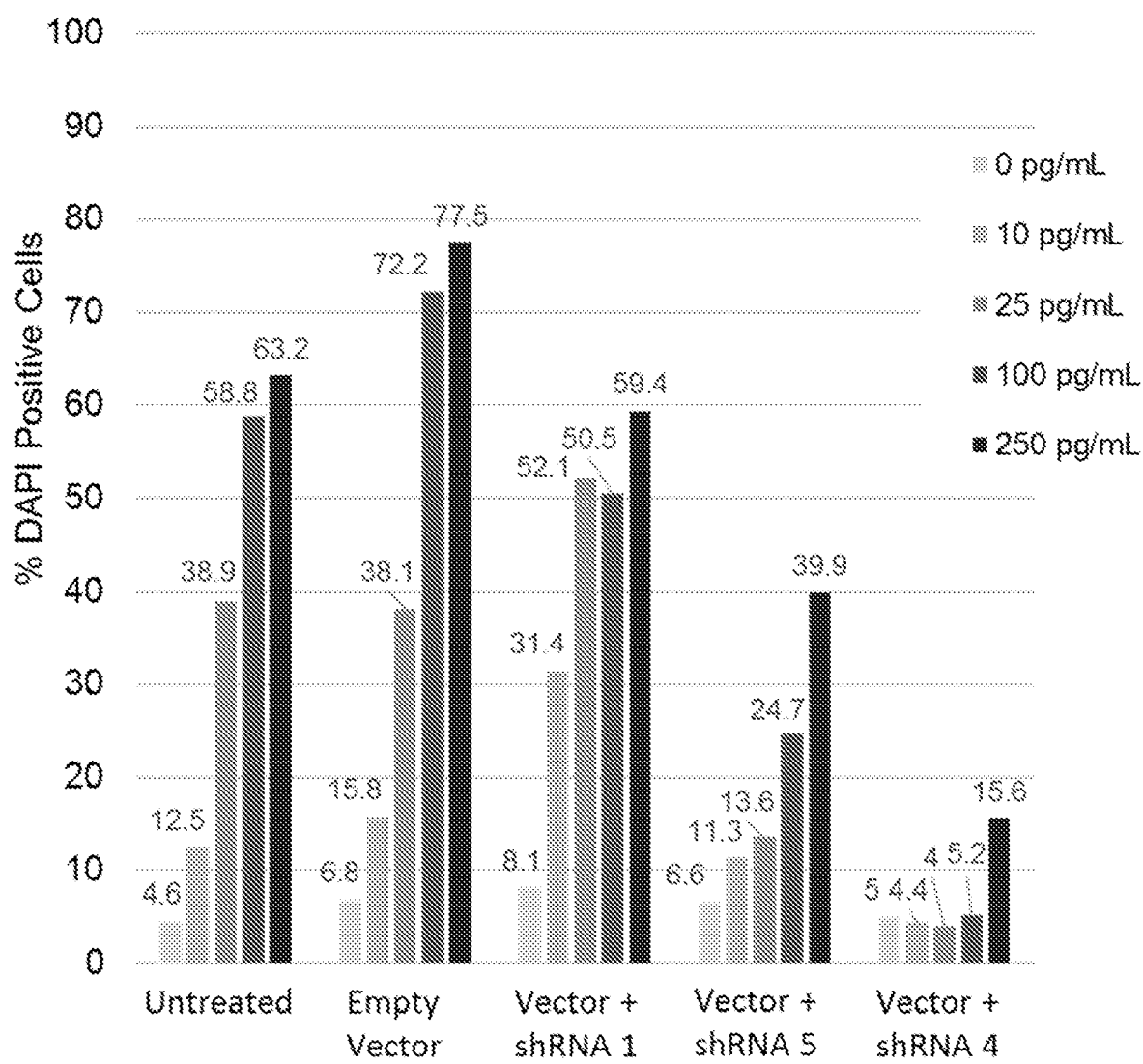
FIG. 8. Gemtuzumab ozogamicin (GO)-induced toxicity in ML1 cells left untreated or treated with an empty vector, shRNA1, shRNA4, or shRNA5. Cytotoxicity was measured by DAPI (4',6-diamidino-2-phenylindole) staining after exposure to increasing concentrations of GO for 3 days. Frequency of DAPI positive cells is shown on the top of each bar. Transduction with lentiviral vector including shRNA4 or shRNA5 protected cells from the cytotoxic effects of GO.

In vitro protection of CD33 shRNA-modified ML1 cells from GO cytotoxicity. To determine if cells in which surface expression of CD33 was efficiently downregulated by the shRNA could be protected from cytotoxicity of the CD33-directed drug GO, ML1 cells modified with the control lentiviral vector or with shRNA1, shRNA4 or shRNA5 were treated with GO in vitro and cytotoxicity was evaluated by staining with a live/dead dye. Effective protection was found for cells treated with shRNA4 (FIG. 8) as compared to shRNA5, which correlated with more effective CD33 downregulation (FIG. 7). In contrast, ML1 cells left untreated or treated with the control vector were effectively killed by GO.

shRNA-mediated CD33 knockdown in human CD34+ cells. Having validated the activity of CD33 shRNA in the ML1 cell line, CD33 shRNA activity was assessed in human CD34+ HSPCs, which have important therapeutic relevance. Similar to the results from ML1 cells, both shRNA4 and shRNA5 successfully reduced CD33 surface expression in human fetal liver (FL) CD34+ cells in a dose dependent manner (FIGS. 5, 6, and 9B-9C). shRNA4 was selected for further studies for the modification of human adult CD34+ cells. While transduction efficiency was lower in adult CD34+ as compared to FLCD34+ (FIG. 9A bottom row), the levels of CD33 knockdown achieved in transduced (i.e. GFP+) cells were comparable between both cell types (FIG. 9C).

In vitro selection of CD33 shRNA-modified CD34+ cells following GO treatment. Since shRNA-modified cells are protected from GO-cytotoxicity, it was hypothesized that this CD33-based strategy can be used to select for gene-modified cells in vitro or in vivo. shRNA-modified human CD34+ cells were thus treated with GO to determine if they have a selective advantage as compared to non-modified cells under these conditions. An increase in GFP+ cells was found in both shRNA-treated adult and FL CD34+ cells indicating that gene modified cells could be selected in vitro (FIG. 10, line with triangles). In contrast, no selection was seen for cells modified with the control vector (FIG. 10, line with squares), confirming that this effect is dependent on shRNA-mediated CD33 knockdown activity.

Figures 11A, 11B:
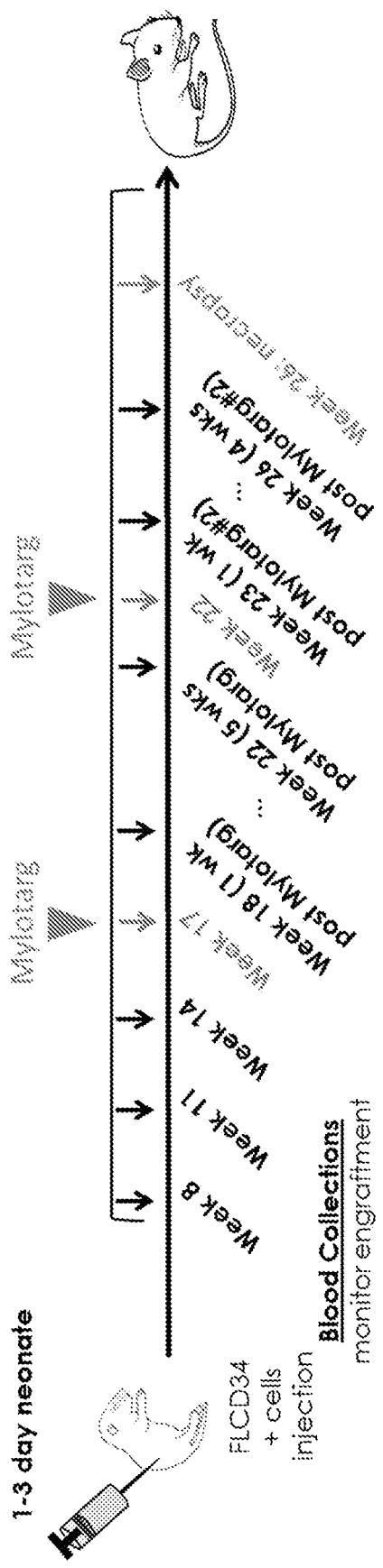
FIGS. 11A, 11B. Engraftment of shRNA-modified human CD34+ cells in the mouse xenotransplantation model. (11A) Table showing the two experimental groups in which mice were transplanted with either human CD34+ cells modified with the control or shRNA 4 lentiviral vectors or a pLL 'empty' vector. Cells were transplanted at a dose of 0.5 million cells per mouse. 6 mice per group were transplanted and 2 per group were treated with GO after stable engraftment. (11B) Timeline of transplantation experiment with blood collections to monitor engraftment and times of GO administration.
Figure 12A:
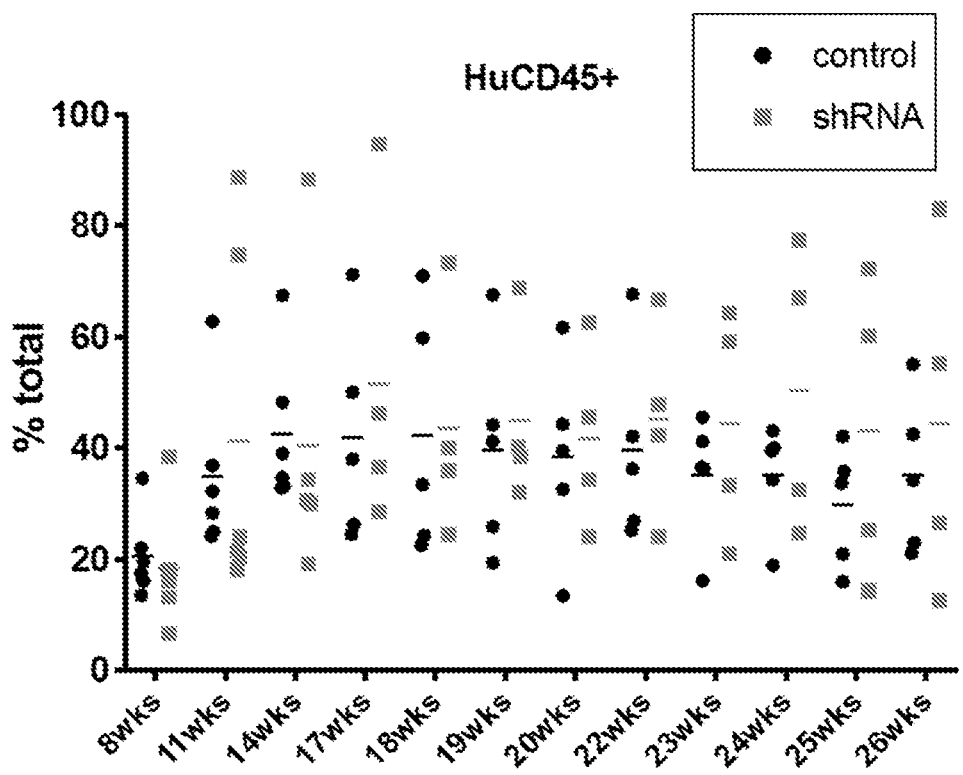
FIGS. 12A, 12B. Comparable engraftment of control-(circle) and shRNA-(square) modified human CD34+ cells in mice. (12A) Human cell engraftment as determined by human CD45+ expression from peripheral blood of transplanted mice at different time points post-transplantation. (12B) Engraftment of gene-modified cells as determined by GFP expression within human CD45+ cells in both control (circle) and shRNA (square) modified human CD34+ cells.
Figure 12B:
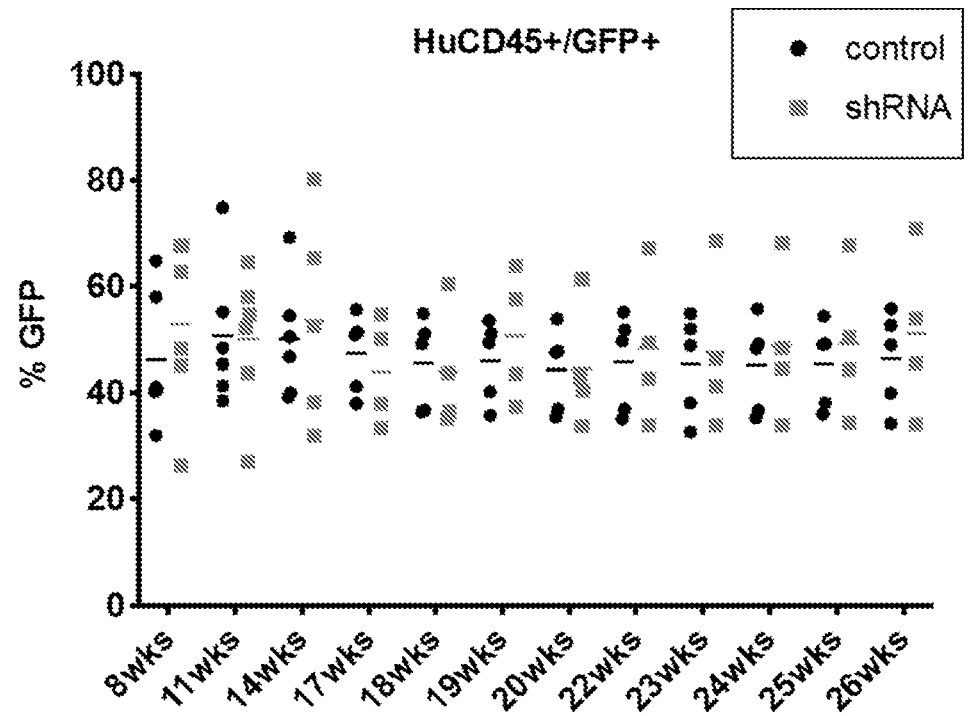
Figure 13A:
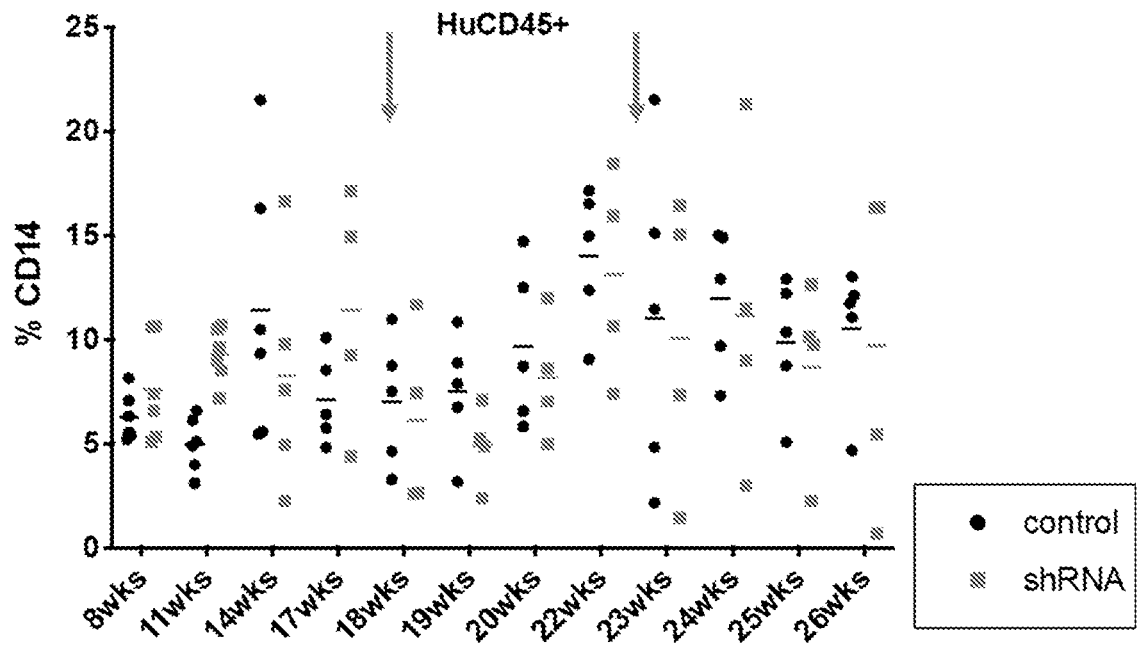
FIGS. 13A, 13B. shRNA-mediated CD33 knockdown is maintained in vivo. (13A) Frequency of CD14+ monocyte within human CD45+ cells measured in peripheral blood of all engrafted mice over time. Arrows show times of GO treatment in 2 mice per cohort. (13B) Frequency of CD33 expression within CD14+/GFP+ cells in both animal cohorts. Arrows show times of GO treatment in 2 mice per cohort.
Figure 13B:
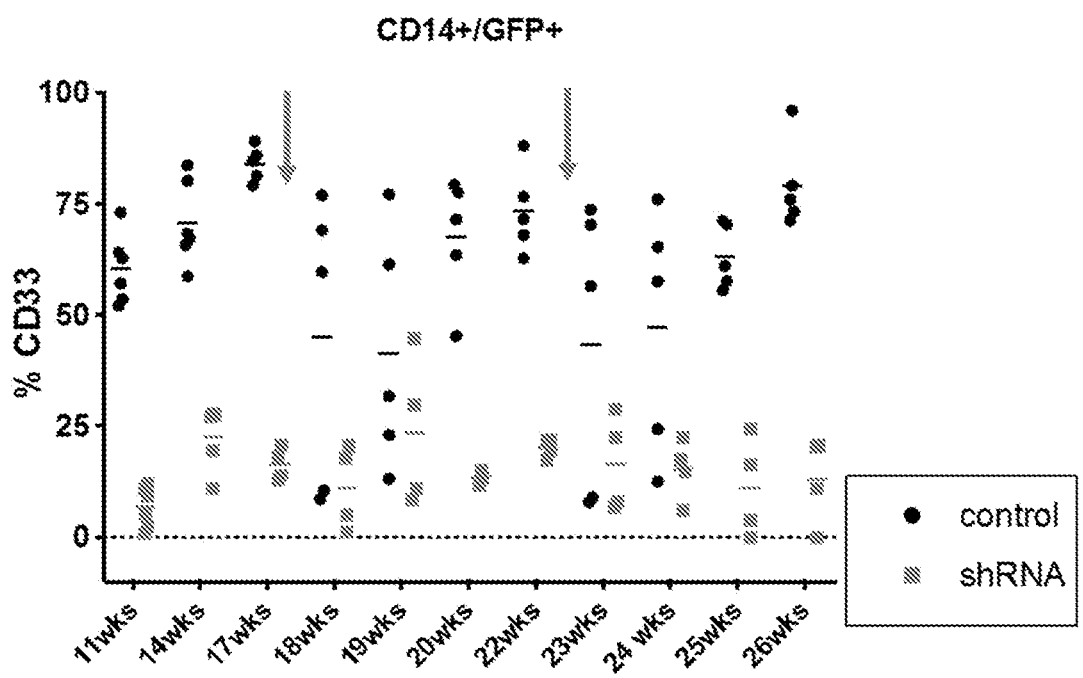

Efficient engraftment of CD33 shRNA-modified human CD34+ cells in the mouse xenotransplantation model. To assess engraftment and the multilineage differentiation potential of shRNA-modified human stem cells, NSG neonate mice were transplanted with human FL CD34+ cells transduced with the control lentiviral vector or with the CD33 shRNA vector (n=6 for each group, FIGS. 11A, 11B). Engraftment and multilineage differentiation were tracked from peripheral blood of transplanted mice within a time span of 26 weeks and no difference in engrafted human CD45+ cells was observed between each experimental group (FIG. 12A). Importantly, the frequency of gene-modified, GFP+, human CD45+ cells was also comparable between the control and shRNA-treated group (FIG. 12B), indicating that expression of the CD33 shRNA in CD34+ stem cells did not impact engraftment in this model. CD14+ monocytes derived from engrafted CD34+ cells were produced at comparable frequencies averaging 5% to 15% of total human cells in both experimental groups (FIG. 13A). Similarly, the frequencies of T- and B-lymphocytes were comparable between both groups, confirming that expression of the shRNA did not affect CD34+ stem cell multilineage differentiation potential. As expected, CD33 expression within CD14+ monocytes was significantly reduced in transduced monocytes from the shRNA group as compared to the control group (FIG. 13B) for the entire duration of the experiment. In summary, these results demonstrate normal engraftment and differentiation of shRNA-modified human CD34+, with persistent knockdown of CD33 surface expression in the mouse transplantation model.

Figure 14A:
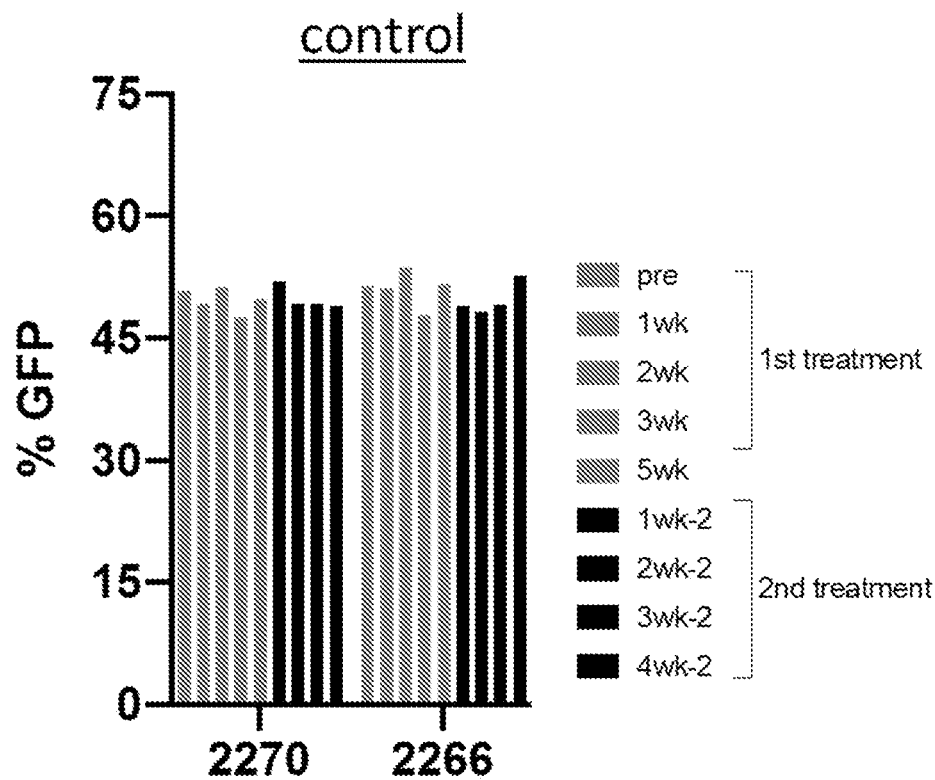
FIGS. 14A, 14B. In vivo selection for CD33 shRNA-modified cells following two rounds of GO treatment in engrafted mice. (14A) Weekly measurement of the frequency of gene modified cells as determined by GFP+ human CD45+ cells in two mice from the control group after two rounds of GO administered in vivo and separated by 5 weeks. (14B) Weekly measurement of the frequency of gene modified cells as determined by GFP+ human CD45+ cells in two mice from the CD33 shRNA group after two rounds of GO administered in vivo and separated by 5 weeks.
Figure 14B:
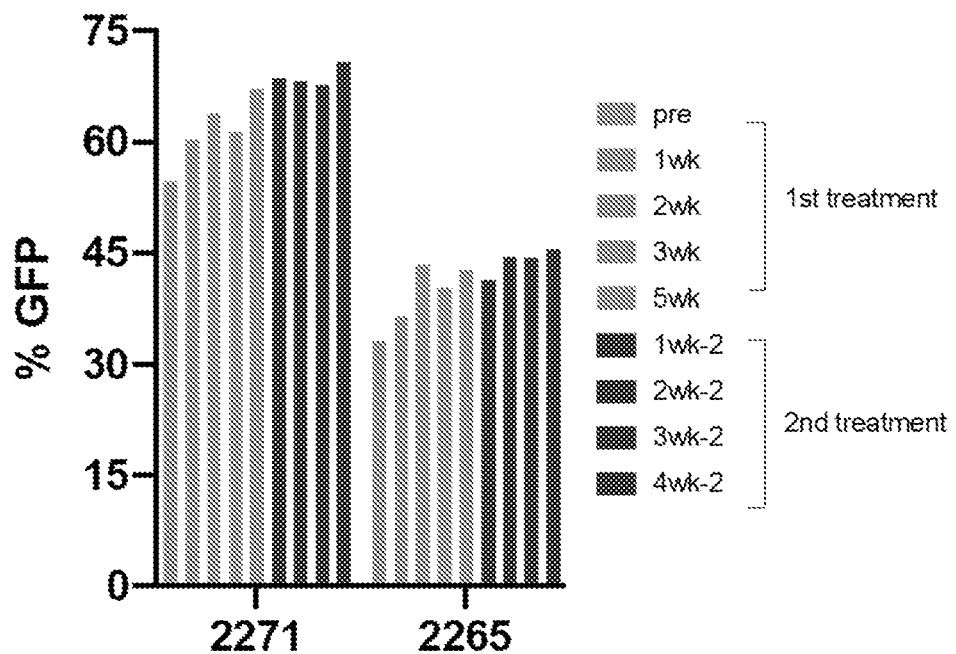
Figure 15A:
FIGS. 15A, 15B. (15A) Schematic of proposed viral vector. This exemplary viral vector results in expression of both a therapeutic gene (TG) and a GFP reporter driven by unique constitutive promoters alongside an shRNA sequence under the control of the U6 transcription promoter. Exemplary promoters include phosphoglycerate kinase (PGK) and elongation factor-1α (EF1α). (15B) Schematics of additional TG viral vectors into which a CD33 blocking molecule can be incorporated. Exemplary viral vectors include the validated therapeutic gene with lentiviral (LV) vector, foamy viral (FV) vector, and foamy viral vector with enhanced GFP (eGFP). Vectors also include long terminal repeats (LTR) at both the 5' and 3' ends and in particular embodiments, a Woodchuck Hepatitis Virus Posttranscriptional Regulatory Element (wpre).
Figure 15B:
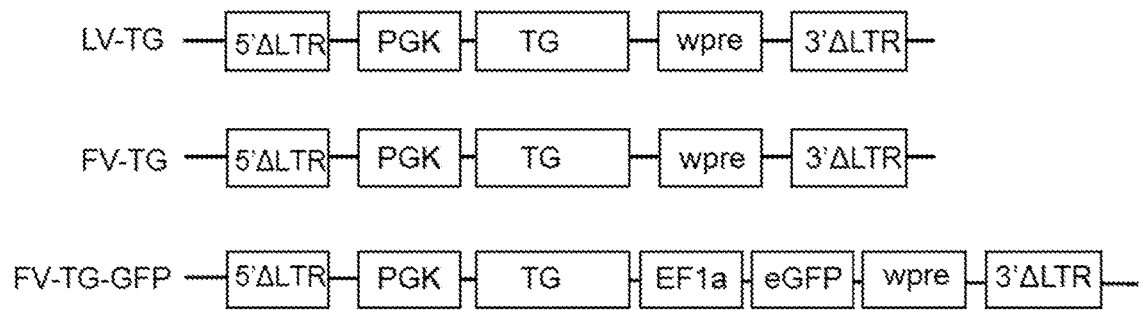

In vivo selection of CD33 shRNA-modified cells after GO treatment. The mouse transplantation model offers a unique opportunity to determine if CD33-directed drugs can select for CD33 shRNA-modified cells in vivo. GO was administered in two mice per group at 17 weeks and 22 weeks post transplantation (FIGS. 11A, 11B), and the frequency of GFP+ human CD45+ cells was monitored weekly after each administration. GFP+ cells steadily increased in the shRNA group from 55%-70% in one animal and from 30-45% in the other animal (FIG. 14B). In contrast, the frequency of GFP+ cells remained constant in the two animals from the control group (FIG. 14A). These results confirmed that cells expressing CD33 shRNA have a selective advantage after GO treatment in vivo. This selection strategy has the potential to increase the number of cells containing the gene-modification in vivo, which have important therapeutic benefits and can be used for the treatment of a variety of hematopoietic and immune disorders after stem cell gene therapy.

Methods. Cloning of CD33 shRNA target sequence into pLentiLox 3.7 and generation of corresponding VSV-G lentiviral vector. Single stranded oligonucleotides corresponding to the shRNA target sequences were ordered through Integrated DNA Technologies (IDT, Coralville IA) with 5' phosphate modification and PAGE purified (FIG. 3). The format of the sense oligo is 5'T-($GN_{18}$)-(TTCAAGAGA)-($N_{18}C$)-TTTTTTC (SEQ ID NO: 93) and the antisense oligo is the sequence complement of the sense but with additional nucleotides at the 5' end to generate a XhoI restriction site overhang. The N18 represents an 18-nucleotide sequence corresponding to the shRNA target sequence.

Sense and antisense oligonucleotides were annealed to form double stranded DNA molecules and cloned in the pLentiLox 3.7 plasmid immediately following the U6 promoter using XhoI/HpaI restriction sites.

Second-generation LVs were produced by three plasmid-polyethylenimine transfection in HEK 293T-cells. HEK 293T-cells were cultured in Dulbecco's modified Eagle medium (DMEM) supplemented with 10% Hyclone Cosmic Calf serum (Thermo Fischer Scientific, Waltham, MA), 1% sodium pyruvate, nonessential aminoacids, L-Glutamine, and 1% penicillin/streptomycin. For LV production in 15-cm plates, cells were plated on 0.1% gelatin at a density of $1.8 \times 10^7$ cells/plate and transfected with 27 µg transfer vector construct (pLentiLox 3.7 containing the different CD33 shRNA sequences), 6 µg pMDLg-pRRE, 12 µg pRSC-Rev, and 6 µg pMD2.G for VSV-G pseudotyped LV. The next day, cells were washed with 1× Dulbecco's phosphate buffered saline (Thermo Fischer Scientific) and treated with 15 ml media containing 10 mmol/1 sodium butyrate (Sigma-Aldrich, St. Louis, MO) for 8 hours. Cell supernatant was harvested and combined with two additional harvests carried out over a time span of 48 hours. The supernatant was filtered through a 0.8 µm-pore-size filter, concentrated 100-fold by centrifugation for 15-20 hours at 4° C. at 5,000×g, and stored at −80° C. The titer of the vector preparations was determined by adding different amounts of LV to the human fibrosarcoma cell line HT1080. HT1080 cells were grown in DMEM supplemented with 10% fetal bovine serum (FBS), 1% penicillin/streptomycin and were plated at $1 \times 10^5$ cells/ml in a 12-well plate one day before transduction. For 100× concentrated LV, volumes used in the transduction were 1, 0.3, 0.1, 0.03 µl following serial dilutions of the vector. Protamine sulfate was added to the cells at a final concentration of 8 µg/ml. Since the pLentilox 3.7 transfer vector contains a GFP reporter, cells were analyzed by flow cytometry 3 days post transduction and the percentage of GFP-expressing cells was used to calculate the number of infectious units (IU) per ml of vector.

Transduction of ML1 cells and human CD34+ cells with CD33 shRNA lentiviral vectors. All LV transductions were performed in presence of 8 µg/ml protamine sulfate. ML1 cells were cultured in RPMI medium with 10% FBS, 1% penicillin/streptomycin. Adult human CD34$^+$ cells were collected from volunteers under an institutional review board-approved protocol. Human fetal liver CD34+ cells were enriched by immunomagnetic separation from tissue obtained from Advance Bioscience Resources Inc. (ABR, Alameda, CA). CD34+ cells were cultured in StemSpan™ serum-free expansion medium II (SFEM II) (StemCell Technologies, Vancouver, Canada) supplemented with penicillin/streptomycin (Life Technologies, Carlsbad, CA), Stem cell factor (PeproTech, Rocky Hill, NJ), Thrombopoietin (PeproTech), and FLT3-L (Miltenyi Biotec, Auburn, CA). For transduction, cells were plated on CH-296 fibronectin (Takara, New York, NY) at 2 µg/ml, and exposed to the vector at various MOI as determined by HT1080 titer.

In vitro cytotoxicity and selection assays. Drug-induced cytotoxicity was quantified as described previously by Laszlo et al., Oncotarget, 7:43281-43294 (2016). Briefly, parental and shRNA-modified ML1 cells were incubated in 96-well round bottom plates with and without gemtuzumab ozogamicin (GO, Pfizer, New York, NY) for 3 days followed by flow cytometric quantification of cell numbers and cell viability, using 4',6-diamidino-2-phenylindole (DAPI) to detect non-viable cells. In the selection assay, human CD34+ cells were grown as described above and were treated with 10 ng/ul GO for 12 hours.

Engraftment of NSG mice with shRNA-modified human CD34+ cells and in vivo selection following GO treatment. For in vivo assessment of engineered HSPCs, NOD.CgPrkdcscidIl2rgtm1Wjl/Szj (NOD SCID gamma/, NSG) neonate mice were infused with $5.0 \times 10^5$ human CD34+ cells and peripheral blood and tissue samples were collected and processed as described by Haworth et al., Mol Ther. Methods Clin. Dev., 6: 17-30 (2017). Flow cytometry staining was performed with human CD45-PerCP (Clone 2D1), mouse CD45.1/CD45.2-V500 (Clone 30-F11), CD3-FITC or -APC (Clone UCHT1), CD4-V450 (Clone RPA-T4), CD20-PE (Clone 2H7), CD14-APC or -PE-Cy7 (Clone M5E2), CD34-APC (Clone 581) (all from BD Biosciences, San Jose, CA), and CD33-PE (Clone AC104.3E3, Miltenyi Biotec). In vivo selection of CD33 shRNA-modified cells with GO was assessed by injecting mice intravenously with GO at a dose of 0.1 mg/kg.

(XI) CLOSING PARAGRAPHS

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gin), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

In particular embodiments, the disclosure provides proteins that bind with a cognate binding molecule with an association rate constant or $k_{on}$ rate of not more than $10^7$ $M^{-1}$ $s^{-1}$, less than $5\times10^6$ $M^{-1}$ $s^{-1}$, less than $2.5\times10^6$ $M^{-1}$ $s^{-1}$, less than $2\times10^6$ $M^{-1}$ $s^{-1}$, less than $1.5\times10^6$ $M^{-1}$ $s^{-1}$, less than $10^6$ $M^{-1}$ $s^{-1}$, less than $5\times10^5$ $M^{-1}$ $s^{-1}$, less than $2.5\times10^5$ $M^{-1}$ $s^{-1}$, less than $2\times10^5$ $M^{-1}$ $s^{-1}$, less than $1.5\times10^5$ $M^{-1}$ $s^{-1}$, less than $10^5$ $M^{-1}$ $s^{-1}$, less than $5\times10^4$ $M^{-1}$ $s^{-1}$, less than $2.5\times10^4$ $M^{-1}$ $s^{-1}$, less than $2\times10^4$ $M^{-1}$ $s^{-1}$, less than $1.5\times10^4$ $M^{-1}$ $s^{-1}$, less than $10^4$ $M^{-1}$ $s^{-1}$, less than $10^3$ $M^{-1}$ $s^{-1}$, less than $10^2$ $M^{-1}$ $s^{-1}$, or in a range of $10^2$ $M^{-1}$ $s^{-1}$ to $10^7$ $M^{-1}$ $s^{-1}$, in a range of $10^3$ $M^{-1}$ $s^{-1}$ to $10^6$ $M^{-1}$ $s^{-1}$, in a range of $10^4$ $M^{-1}$ $s^{-1}$ to $10^5$ $M^{-1}$ $s^{-1}$, or in a range of $10^3$ $M^{-1}$ $s^{-1}$ to $10^7$ $M^{-1}$ $s^{-1}$.

In particular embodiments, the disclosure provides proteins that bind with a cognate binding molecule a $k_{off}$ rate of not less than 0.5 $s^{-1}$, not less than 0.25 $s^{-1}$, not less than 0.2

$s^{-1}$, not less than 0.1 $s^{-1}$, not less than $5 \times 10^{-2}$ $s^{-1}$, not less than $2.5 \times 10^{-2}$ $s^{-1}$, not less than $2 \times 10^{-2}$ $s^{-1}$, not less than $1.5 \times 10^{-2}$ $s^{-1}$, not less than $10^{-2}$ $s^{-1}$, not less than $5 \times 10^{-3}$ $s^{-1}$, not less than $2.5 \times 10^{-3}$ $s^{-1}$, not less than $2 \times 10^{-3}$ $s^{-1}$, not less than $1.5 \times 10^{-3}$ $s^{-1}$, not less than $10^{-3}$ $s^{-1}$, not less than $5 \times 10^{-4}$ $s^{-1}$, not less than $2.5 \times 10^{-4}$ $s^{-1}$, not less than $2 \times 10^{-4}$ $s^{-1}$, not less than $1.5 \times 10^{-4}$ $s^{-1}$, not less than $10^{-4}$ $s^{-1}$, not less than $5 \times 10^{-5}$ $s^{-1}$, not less than $2.5 \times 10^{-5}$ $s^{-1}$, not less than $2 \times 10^{-5}$ $s^{-1}$, not less than $1.5 \times 10^{-5}$ $s^{-1}$, not less than $10^{-5}$ $s^{-1}$, not less than $5 \times 10^{-6}$ $s^{-1}$, not less than $2.5 \times 10^{-6}$ $s^{-1}$, not less than $2 \times 10^{-6}$ $s^{-1}$, not less than $1.5 \times 10^{-6}$ $s^{-1}$, not less than $10^{-6}$ $s^{-1}$, or in a range of 0.5 to $10^{-6}$ $s^{-1}$, in a range of $10^{-2}$ $s^{-1}$ to $10^{-5}$ $s^{-1}$, or in a range of $10^{-3}$ $s^{-1}$ to $10^{-4}$ $s^{-1}$.

In particular embodiments, the disclosure provides proteins that bind with a cognate binding molecule with an affinity constant or $K_a$ ($k_{on}/k_{off}$) of, either before and/or after modification, less than $10^6$ $M^{-1}$, less than $5 \times 10^5$ $M^{-1}$, less than $2.5 \times 10^5$ $M^{-1}$, less than $2 \times 10^5$ $M^{-1}$, less than $1.5 \times 10^5$ $M^{-1}$, less than $10^5$ $M^{-1}$, less than $5 \times 10^4$ $M^{-1}$, less than $2.5 \times 10^4$ $M^{-1}$, less than $2 \times 10^4$ $M^{-1}$, less than $1.5 \times 10^4$ $M^{-1}$, less than $10^4$ $M^{-1}$, less than $5 \times 10^3$ $M^{-1}$, less than $2.5 \times 10^3$ $M^{-1}$, less than $2 \times 10^3$ $M^{-1}$, less than $1.5 \times 10^3$ $M^{-1}$, less than $10^3$ $M^{-1}$, less than 500 $M^{-1}$, less than 250 $M^{-1}$, less than 200 $M^{-1}$, less than 150 $M^{-1}$, less than 100 $M^{-1}$, less than 50 $M^{-1}$, less than 25 $M^{-1}$, less than 20 $M^{-1}$, less than 15 $M^{-1}$, or less than 10 $M^{-1}$, or in a range of 10 $M^{-1}$ to $10^6$ $M^{-1}$, in a range of $10^2$ $M^{-1}$ to $10^5$ $M^{-1}$, or in a range of $10^3$ $M^{-1}$ to $1 \times 10^4$ $M^{-1}$.

In particular embodiments, the disclosure provides proteins that bind with a cognate binding molecule with a dissociation constant or $K_d$ ($k_{off}/k_{on}$) of, either before and/or after modification, not less than 0.05 M, not less than 0.025 M, not less than 0.02 M, not less than 0.01 M, not less than $5 \times 10^{-3}$ M, not less than $2.5 \times 10^{-3}$ M, not less than $2 \times 10^{-3}$ M, not less than $1.5 \times 10^{-3}$ M, not less than $10^{-3}$ M, not less than $5 \times 10^{-4}$ M, not less than $2.5 \times 10^{-4}$ M, not less than $2 \times 10^{-4}$ M, not less than $1.5 \times 10^{-4}$ M, not less than $10^{-4}$ M, not less than $5 \times 10^{-5}$ M, not less than $2.5 \times 10^{-5}$ M, not less than $2 \times 10^{-5}$ M, not less than $1.5 \times 10^{-5}$ M, not less than $10^{-5}$ M, not less than $5 \times 10^{-6}$ M, not less than $2.5 \times 10^{-6}$ M, not less than $2 \times 10^{-6}$ M, not less than $1.5 \times 10^{-6}$ M, not less than $10^{-6}$ M, or not less than $10^{-7}$ M, or in a range of 0.05 M to $10^{-7}$ M, in a range of $5 \times 10^{-3}$ M to $10^{-6}$ M, or in a range of $10^{-4}$ M to $10^{-7}$ M.

When antibody residues are provided, the assignment of amino acids to each domain is in accordance with Kabat Sequences of Proteins of Immunological Interest (National Institutes of Health, Bethesda, Md. (1987 and 1991)) unless otherwise specified.

Unless otherwise indicated, aspects of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in resistance to a CD33 targeting therapy in cells genetically modified with a viral vector including a therapeutic gene and a CD33 blocking molecule as disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The invention claimed is:

1. A genetic construct comprising a CD33 blocking molecule selected from SEQ ID NO: 8 or SEQ ID NO: 9.

2. The genetic construct of claim 1, wherein the genetic construct is within a viral vector.

3. The genetic construct of claim 2, wherein the viral vector is a lentiviral vector, a foamy viral vector, or an adenoviral vector that optionally comprises a PGK promoter.

4. The genetic construct of claim 1, further comprising a therapeutic gene.

5. The genetic construct of claim 4, wherein the therapeutic gene:
   (i) comprises FancA, FancB, FancC, FancD1, FancD2, FancE, FancF, FancG, FancI, FancJ, FancL, FancM, FancN, FancO, FancP, FancQ, FancR, FancS, FancT, FancU, FancV, or FancW; or
   (ii) encodes a checkpoint inhibitor, a gene editing molecule, a chimeric antigen receptor that specifically binds a cellular antigen or a T-cell receptor that specifically binds a cellular antigen; or
   (iii) comprises γC, JAK3, IL7RA, RAG1, RAG2, DCLRE1C, PRKDC, LIG4, NHEJ1, CD3D, CD3E, CD3Z, CD3G, PTPRC, ZAP70, LCK, AK2, ADA, PNP, WHN, CHD7, ORAI1, STIM1, CORO1A, CIITA, RFXANK, RFX5, RFXAP, RMRP, DKC1, TERT, TINF2, DCLRE1B, or SLC46A1; or (iv) comprises factor VIII (FVIII), FVII, von Willebrand factor (VWF), FI, FII, FV, FX, FXI, or FXIII); or (v) comprises F8 or F9; or (vi) comprises γ-globin; soluble CD40; CTLA; Fas L; an antibody to CD4, CD5, CD7, CD52; an antibody to IL1, IL2, IL6; an antibody to TCR specifically present on autoreactive T cells; IL4; IL10; IL12; IL13; IL1Ra, sIL1RI; sIL1RII; sTNFRI; sTNFRII; an antibody to TNF; P53, PTPN22, and DRB1*1501/DQB1*0602; globin family genes; WAS; phox; dystrophin; pyruvate kinase (PK); CLN3; ABCD1; arylsulfatase A (ARSA); SFTPB; SFTPC; NLX2.1; ABCA3; GATA1; ribosomal protein genes; TERC; CFTR; LRRK2; PARK2; PARK7; PINK1; SNCA; PSEN1; PSEN2; APP; SOD1; TDP43; FUS; ubiquilin 2; or C9ORF72; or (vii) comprises ABLI, AKT1, APC, ARSB, BCL11A, BLC1, BLC6, BRCA1, BRCA2, BRIP1, C46, CAS9, C-CAM, CBFAI, CBL, CCR5, CD19, CDA, C-MYC, CRE, CSCR4, CSFIR, CTS-I, CYB5R3, DCC, DHFR, DLL1, DMD, EGFR, ERBA, ERBB, EBRB2, ETSI, ETS2, ETV6, FCC, FGR, FOX, FUSI, FYN, GALNS, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p21, p27, p57, p73, PALB2, RAD51C, ras, at least one of RPL3 through RPL40, RPLPO, RPLP1, RPLP2, at least one of RPS2 through RPS30, RPSA, SGSH, SLX4, SOX2, VHL, or WT-I; or (viii) any two or more of (i)-(vii).

6. The genetic construct of claim 1, cloned between SEQ ID NO: 18 and SEQ ID NO: 19.

7. The genetic construct of claim 1, wherein the CD33 blocking molecule comprises a wobble base pair.

8. A kit comprising a genetic construct of claim 1 and a CD33-targeting agent.

9. The kit of claim 8, wherein the CD33-targeting agent comprises:

(i) an anti-CD33 antibody, an anti-CD33 immunotoxin, an anti-CD33 antibody-drug conjugate, an anti-CD33 antibody-radioisotope conjugate, an anti-CD33 bispecific antibody, an anti-CD33 bispecific immune cell engaging antibody, an anti-CD33 trispecific antibody, and/or an anti-CD33 chimeric antigen receptor (CAR) with one or more binding domains; or (ii) Hp67.6, lintuzumab, SGN-CD33A, and/or AMG 330; or (iii) a binding domain derived from Hp67.6, lintuzumab, SGN-CD33A, and/or AMG 330; or (iv) the CDRs of Hp67.6, lintuzumab, SGN-CD33A, and/or AMG 330 and/or a sequence combination of
a variable light chain comprising SEQ ID NO: 39 and a variable heavy chain comprising SEQ ID NO: 40;
a variable light chain comprising SEQ ID NO: 47 and a variable heavy chain comprising SEQ ID NO: 48;
a variable light chain comprising a CDRL1 of SEQ ID NO: 41, a CDRL2 of SEQ ID NO: 42, and a CDRL3 of SEQ ID NO: 43 and a variable heavy chain comprising a CDRH1 of SEQ ID NO: 44, a CDRH2 of SEQ ID NO: 45, and a CDRH3 of SEQ ID NO: 46;
a variable light chain comprising a CDRL1 of SEQ ID NO: 49, a CDRL2 of SEQ ID NO: 50, and a CDRL3 of SEQ ID NO: 51 and a variable heavy chain comprising a CDRH1 of SEQ ID NO: 52, a CDRH2 of SEQ ID NO: 53, and a CDRH3 of SEQ ID NO: 54; and/or
a variable light chain comprising a CDRL1 of SEQ ID NO: 98, a CDRL2 of SEQ ID NO: 99, and a CDRL3 of SEQ ID NO: 100 and a variable heavy chain comprising a CDRH1 of SEQ ID NO: 101, a CDRH2 of SEQ ID NO: 102, and a CDRH3 of SEQ ID NO: 103; or (v) an antibody-drug conjugate or an antibody-radioisotope conjugate wherein the drug or radioisotope are selected from taxol, taxane, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, maytansinoid, dolastatin, auristatin, calicheamicin, pyrrolobenzodiazepine, nemorubicin PNU-159682, anthracycline, vinca alkaloid, trichothecene, CC1065, camptothecin, elinafide, actinomycin D, 1-dehydrotestosterone, glucocorticoids, procaine, tetracaine, lidocaine, propranolol, puromycin, ricin, CC-1065, duocarmycin, diphtheria toxin, snake venom, cobra venom, mistletoe lectin, modeccin, pokeweed antiviral protein, saporin, Bryodin 1, bouganin, gelonin, *Pseudomonas* exotoxin, iodine-131, indium-111, yttrium-90, lutetium-177, astatine-211, bismuth-212, and/or bismuth-213, and/or wherein the antibody-drug conjugate comprises gemtuzumab ozogamicin (GO); or (vi) a linker; or (vii) a bispecific antibody comprising a combination of binding variable chains or a binding CDR combination of Hp67.6, lintuzumab, SGN-CD33A, and/or AMG 330 and/or a sequence combination of
a variable light chain comprising SEQ ID NO: 39 and a variable heavy chain comprising SEQ ID NO: 40;
a variable light chain comprising SEQ ID NO: 47 and a variable heavy chain comprising SEQ ID NO: 48;
a variable light chain comprising a CDRL1 of SEQ ID NO: 41, a CDRL2 of SEQ ID NO: 42, and a CDRL3 of SEQ ID NO: 43 and a variable heavy chain comprising a CDRH1 of SEQ ID NO: 44, a CDRH2 of SEQ ID NO: 45, and a CDRH3 of SEQ ID NO: 46;
a variable light chain comprising a CDRL1 of SEQ ID NO: 49, a CDRL2 of SEQ ID NO: 50, and a CDRL3 of SEQ ID NO: 51 and a variable heavy chain comprising a CDRH1 of SEQ ID NO: 52, a CDRH2 of SEQ ID NO: 53, and a CDRH3 of SEQ ID NO: 54; and/or
a variable light chain comprising a CDRL1 of SEQ ID NO: 98, a CDRL2 of SEQ ID NO: 99, and a CDRL3 of SEQ ID NO: 100 and a variable heavy chain comprising a CDRH1 of SEQ ID NO: 101, a CDRH2 of SEQ ID NO: 102, and a CDRH3 of SEQ ID NO: 103; or (viii) any two or more of (i)-(vii).

10. The kit of claim 8, wherein the CD33-targeting agent comprises a bispecific antibody comprising at least one binding domain that activates an immune cell.

11. The kit of claim 10, wherein the binding domain that activates an immune cell:

(i) binds CD3, CD28, CD8, NKG2D, CD8, CD16, KIR2DL4, KIR2DS1, KIR2DS2, KIR3DS1, NKG2C, NKG2E, NKG2D, NKp30, NKp44, NKp46, NKp80, DNAM-1, CD11b, CD11c, CD64, CD68, CD119, CD163, CD206, CD209, F4/80, IFGR2, Toll-like receptors 1-9, IL-4Rα, or MARCO; or (ii) comprises a variable light chain comprising a CDRL1 of SEQ ID NO: 55, a CDRL2 of SEQ ID NO: 56, and a CDRL3 sequence of SEQ ID NO: 57 and a variable heavy chain comprising a CDRH1 of SEQ ID NO: 58, a CDRH2 of SEQ ID NO: 59, and a CDRH3 of SEQ ID NO: 60; or (iii) comprises SEQ ID NO: 61; or (iv) comprises a variable light chain comprising a CDRL1 of SEQ ID NO: 62, a CDRL2 of KVS, and a CDRL3 sequence of SEQ ID NO: 63 and a variable heavy chain comprising a CDRH1 of SEQ ID NO: 64, a CDRH2 of SEQ ID NO: 65, and a CDRH3 of SEQ ID NO: 66; or (v) comprises a variable light chain comprising a CDRL1 of SEQ ID NO: 67, a CDRL2 of KVS, and a CDRL3 sequence of SEQ ID NO: 63 and a variable heavy chain comprising a CDRH1 of SEQ ID NO: 69, a CDRH2 of SEQ ID NO: 70, and a CDRH3 of SEQ ID NO: 71; or (vi) comprises a variable light chain comprising a CDRL1 of SEQ ID NO: 72, a CDRL2 of KVS, and a CDRL3 sequence of SEQ ID NO: 63 and a variable heavy chain comprising a CDRH1 of SEQ ID NO: 69, a CDRH2 of SEQ ID NO: 75, and a CDRH3 of SEQ ID NO: 76; or (vii) comprises a variable light chain comprising a CDRL1 of SEQ ID NO: 77, a CDRL2 of KVS, and a CDRL3 sequence of SEQ ID NO: 78 and a variable heavy chain comprising a CDRH1 of SEQ ID NO: 79, a CDRH2 of SEQ ID NO: 80, and a CDRH3 of SEQ ID NO: 81; or (viii) comprises a variable light chain comprising a CDRL1 of SEQ ID NO: 82, a CDRL2 of SEQ ID NO: 83, and a CDRL3 sequence of SEQ ID NO: 84 and a variable heavy chain comprising a CDRH1 of SEQ ID NO: 85, a CDRH2 of SEQ ID NO: 86, and a CDRH3 of SEQ ID NO: 87;

(ix) comprises a TCR; or (x) comprises a variable light chain comprising SEQ ID NO: 88 and a variable heavy chain comprising SEQ ID NO: 89; or (xi) any two or more of (i)-(x).

12. The kit of claim 8, wherein the CD33-targeting agent comprises a chimeric antigen receptor (CAR) comprising one or more binding domains.

13. The kit of claim 12, wherein:

(i) the CAR comprises an anti-CD33 binding domain and a binding domain that activates an immune cell; or (ii) the CAR comprises an effector domain selected from 4-1BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTa, TCRa, TCRB, TRIM, Zap70, PTCH2, or any combination thereof; or (iii) the CAR comprises a cytoplasmic signaling sequence derived from CD3 zeta, FcR gamma, CD3 gamma, CD3 delta, CD3 epsilon, CD5, CD22, CD79a, CD79b, or CD66d;

(iv) the CAR comprises an intracellular signaling domain and a costimulatory signaling region; or (v) the CAR comprises a spacer region; or (vi) the CAR comprises a transmembrane domain;

(vii) the CAR comprises a costimulatory signaling region comprises the intracellular domain of CD27, CD28, 4-1BB, OX40, CD30, CD40, lymphocyte function-associated antigen-1, CD2, CD7, LIGHT, NKG2C, or B7-H3; or (viii) any two or more of (i)-(vii).

14. A method of genetically-modifying a cell to provide a therapeutic gene and to have reduced CD33 expression, the method comprising exposing the cell to an effective amount of a genetic construct of claim 4.

15. A method of protecting a cell from an anti-CD33 treatment comprising genetically-modifying the cell with a genetic construct of claim 1.

16. The method of claim 15, wherein:

the cell is a therapeutic cell; and/or the protecting is in vivo.

* * * * *

SEQUENCE LISTING

```
<160> NUMBER OF SEQ ID NOS: 155

<210> SEQ ID NO 1
<211> LENGTH: 282
<212> TYPE: PRT
<213> ORGANISM: Macaca fascicularis

<400> SEQUENCE: 1

Met Pro Leu Leu Leu Leu Pro Leu Leu Trp Ala Gly Ala Leu Ala Met
1               5                   10                  15

Asp Pro Arg Val Arg Leu Glu Val Gln Glu Ser Val Thr Val Gln Glu
            20                  25                  30

Gly Leu Cys Val Leu Val Pro Cys Thr Phe Phe His Pro Val Pro Tyr
        35                  40                  45

His Thr Arg Asn Ser Pro Val His Gly Tyr Trp Phe Arg Glu Gly Ala
    50                  55                  60

Ile Val Ser Leu Asp Ser Pro Val Ala Thr Asn Lys Leu Asp Gln Glu
65                  70                  75                  80

Val Gln Glu Glu Thr Gln Gly Arg Phe Arg Leu Leu Gly Asp Pro Ser
                85                  90                  95

Arg Asn Asn Cys Ser Leu Ser Ile Val Asp Ala Arg Arg Arg Asp Asn
            100                 105                 110

Gly Ser Tyr Phe Phe Arg Met Glu Lys Gly Ser Thr Lys Tyr Ser Tyr
        115                 120                 125

Lys Ser Thr Gln Leu Ser Val His Val Thr Asp Leu Thr His Arg Pro
    130                 135                 140
```

Gln Ile Leu Ile Pro Gly Ala Leu Asp Pro Asp His Ser Lys Asn Leu
145                 150                 155                 160

Thr Cys Ser Val Pro Trp Ala Cys Glu Gln Gly Thr Pro Pro Ile Phe
            165                 170                 175

Ser Trp Met Ser Ala Ala Pro Thr Ser Leu Gly Leu Arg Thr Thr His
        180                 185                 190

Ser Ser Val Leu Ile Ile Thr Pro Arg Pro Gln Asp His Gly Thr Asn
    195                 200                 205

Leu Thr Cys Gln Val Lys Phe Pro Gly Ala Gly Val Thr Thr Glu Arg
210                 215                 220

Thr Ile Gln Leu Asn Val Ser Tyr Ala Ser Gln Asn Pro Arg Thr Asp
225                 230                 235                 240

Ile Phe Leu Gly Asp Gly Ser Arg Lys Ala Arg Lys Gln Gly Val
                245                 250                 255

Val Gln Gly Ala Ile Gly Gly Ala Gly Val Thr Val Leu Leu Ala Leu
                260                 265                 270

Cys Leu Cys Leu Ile Phe Phe Thr Val Gln
                275                 280

<210> SEQ ID NO 2
<211> LENGTH: 283
<212> TYPE: PRT
<213> ORGANISM: Homo sapiens

<400> SEQUENCE: 2

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

```
Gly Ile Phe Pro Gly Asp Ser Gly Lys Gln Glu Thr Arg Ala Gly
                245                 250                 255

Val Val His Gly Ala Ile Gly Ala Gly Val Thr Ala Leu Leu Ala
            260                 265                 270

Leu Cys Leu Cys Leu Ile Phe Phe Ile Val Gln
            275                 280

<210> SEQ ID NO 3
<211> LENGTH: 267
<212> TYPE: PRT
<213> ORGANISM: Mus musculus

<400> SEQUENCE: 3

Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
            20                  25                  30

Glu Gly Leu Cys Val His Val Pro Cys Ser Val Phe Tyr Pro Ser Ile
        35                  40                  45

Lys Leu Thr Leu Gly Pro Val Thr Gly Ser Trp Leu Arg Lys Gly Val
    50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
            100                 105                 110

Gly Met Tyr Phe Phe Arg Val Val Arg Glu Pro Phe Val Arg Tyr Ser
        115                 120                 125

Tyr Lys Lys Ser Gln Leu Ser Leu His Val Thr Ser Leu Ser Arg Thr
    130                 135                 140

Pro Asp Ile Ile Ile Pro Gly Thr Leu Glu Ala Gly Tyr Pro Ser Asn
145                 150                 155                 160

Leu Thr Cys Ser Val Pro Trp Ala Cys Glu Gln Gly Thr Pro Pro Thr
                165                 170                 175

Phe Ser Trp Met Ser Thr Ala Leu Thr Ser Leu Ser Arg Thr Thr
            180                 185                 190

Asp Ser Ser Val Leu Thr Phe Thr Pro Gln Pro Gln Asp His Gly Thr
        195                 200                 205

Lys Leu Thr Cys Leu Val Thr Phe Ser Gly Ala Gly Val Thr Val Glu
    210                 215                 220

Arg Thr Ile Gln Leu Asn Val Thr Arg Lys Ser Gly Gln Met Arg Glu
225                 230                 235                 240

Leu Val Leu Val Ala Val Gly Glu Ala Thr Val Lys Leu Leu Ile Leu
                245                 250                 255

Gly Leu Cys Leu Val Phe Leu Ile Val Met Phe
            260                 265

<210> SEQ ID NO 4
<211> LENGTH: 481
<212> TYPE: PRT
<213> ORGANISM: Artificial Sequence
<220> FEATURE:
<223> OTHER INFORMATION: Full-length CD33

<400> SEQUENCE: 4
```

```
Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
50                  55                  60

Ala Ile Ile Ser Arg Asp Ser Pro Val Ala Thr Asn Lys Leu Asp Gln
65                  70                  75                  80

Glu Val Gln Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Gly Gly Ser Gly Cys Lys Pro Cys Ile Cys Thr Val Pro Glu Val Ser
            260                 265                 270

Ser Val Phe Ile Phe Pro Pro Lys Pro Lys Asp Val Leu Thr Ile Thr
    275                 280                 285

Leu Thr Pro Lys Val Thr Cys Val Val Asp Ile Ser Lys Asp Asp
    290                 295                 300

Pro Glu Val Gln Phe Ser Trp Phe Val Asp Asp Val Glu Val His Thr
305                 310                 315                 320

Ala Gln Thr Gln Pro Arg Glu Glu Gln Phe Asn Ser Thr Phe Arg Ser
            325                 330                 335

Val Ser Glu Leu Pro Ile Met His Gln Asp Trp Leu Asn Gly Lys Glu
            340                 345                 350

Phe Lys Cys Arg Val Asn Ser Ala Ala Phe Pro Ala Pro Ile Glu Lys
        355                 360                 365

Thr Ile Ser Lys Thr Lys Gly Arg Pro Lys Ala Pro Gln Val Tyr Thr
370                 375                 380

Ile Pro Pro Pro Lys Glu Gln Met Ala Lys Asp Lys Val Ser Leu Thr
385                 390                 395                 400

Cys Met Ile Thr Asp Phe Phe Pro Glu Asp Ile Thr Val Glu Trp Gln
                405                 410                 415

Trp Asn Gly Gln Pro Ala Glu Asn Tyr Lys Asn Thr Gln Pro Ile Met
```

```
                420             425             430
Asn Thr Asn Gly Ser Tyr Phe Val Tyr Ser Lys Leu Asn Val Gln Lys
            435             440             445

Ser Asn Trp Glu Ala Gly Asn Thr Phe Thr Cys Ser Val Leu His Glu
            450             455             460

Gly Leu His Asn His His Thr Glu Lys Ser Leu Ser His Ser Pro Gly
465             470             475             480

Lys

<210> SEQ ID NO 5
<211> LENGTH: 244
<212> TYPE: PRT
<213> ORGANISM: Artificial Sequence
<220> FEATURE:
<223> OTHER INFORMATION: CD33deltaE2

<400> SEQUENCE: 5

Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Gly Gly Ser Gly Cys Lys Pro Cys Ile Cys Thr Val Pro Glu Val
    130                 135                 140

Ser Ser Val Phe Ile Phe Pro Pro Lys Pro Lys Asp Val Leu Thr Ile
145                 150                 155                 160

Thr Leu Thr Pro Lys Val Thr Cys Val Val Asp Ile Ser Lys Asp
                165                 170                 175

Asp Pro Glu Val Gln Phe Ser Trp Phe Val Asp Asp Val Glu Val His
            180                 185                 190

Thr Ala Gln Thr Gln Pro Arg Glu Glu Gln Phe Asn Ser Thr Phe Arg
        195                 200                 205

Ser Val Ser Glu Leu Pro Ile Met His Gln Asp Trp Leu Asn Gly Lys
    210                 215                 220

Glu Phe Lys Cys Arg Val Asn Ser Ala Ala Phe Pro Ala Pro Ile Glu
225                 230                 235                 240

Lys Thr Ile Ser

<210> SEQ ID NO 6
<211> LENGTH: 55
<212> TYPE: DNA
<213> ORGANISM: Artificial Sequence
<220> FEATURE:
<223> OTHER INFORMATION: sequence encoding shRNA1 that targets CD33

<400> SEQUENCE: 6
```
tgccattata tccagggact ttcaagagaa gtccctggat ataatggctt ttttc            55

<210> SEQ ID NO 7
<211> LENGTH: 52
<212> TYPE: DNA
<213> ORGANISM: Artificial Sequence
<220> FEATURE:
<223> OTHER INFORMATION: sequence encoding shRNA3 that targets CD33

<400> SEQUENCE: 7
tggatgagga gctgcattat ttcagaataa tgcagctcct catcctttt tc               52

<210> SEQ ID NO 8
<211> LENGTH: 55
<212> TYPE: DNA
<213> ORGANISM: Artificial Sequence
<220> FEATURE:
<223> OTHER INFORMATION: sequence encoding shRNA4 that targets CD33

<400> SEQUENCE: 8
tgttcatact tctttcggat ttcaagagaa tccgaaagaa gtatgaactt ttttc           55

<210> SEQ ID NO 9
<211> LENGTH: 55
<212> TYPE: DNA
<213> ORGANISM: Artificial Sequence
<220> FEATURE:
<223> OTHER INFORMATION: sequence encoding shRNA5 that targets CD33

<400> SEQUENCE: 9
tggagagagg aagtaccaaa ttcaagagat tggtacttc ctctctcctt ttttc            55

<210> SEQ ID NO 10
<211> LENGTH: 55
<212> TYPE: DNA
<213> ORGANISM: Artificial Sequence
<220> FEATURE:
<223> OTHER INFORMATION: sequence encoding shRNA6 that targets CD33

<400> SEQUENCE: 10
tgggaaggag ccattatatc ttcaagagag atataatggc tccttccctt ttttc           55

<210> SEQ ID NO 11
<211> LENGTH: 19
<212> TYPE: DNA
<213> ORGANISM: Artificial Sequence
<220> FEATURE:
<223> OTHER INFORMATION: sequence encoding siRNA that targets CD33

<400> SEQUENCE: 11
gccattatat ccagggact                                                   19

<210> SEQ ID NO 12
<211> LENGTH: 19
<212> TYPE: DNA
<213> ORGANISM: Artificial Sequence
<220> FEATURE:
<223> OTHER INFORMATION: sequence encoding siRNA that targets CD33

<400> SEQUENCE: 12
ggatgaggag ctgcattat                                                   19

<210> SEQ ID NO 13
<211> LENGTH: 19
<212> TYPE: DNA

```
<213> ORGANISM: Artificial Sequence
<220> FEATURE:
<223> OTHER INFORMATION: sequence encoding siRNA that targets CD33

<400> SEQUENCE: 13
gttcatactt ctttcggat                                                 19

<210> SEQ ID NO 14
<211> LENGTH: 19
<212> TYPE: DNA
<213> ORGANISM: Artificial Sequence
<220> FEATURE:
<223> OTHER INFORMATION: sequence encoding siRNA that targets CD33

<400> SEQUENCE: 14
ggagagagga agtaccaaa                                                 19

<210> SEQ ID NO 15
<211> LENGTH: 19
<212> TYPE: DNA
<213> ORGANISM: Artificial Sequence
<220> FEATURE:
<223> OTHER INFORMATION: sequence encoding siRNA that targets CD33

<400> SEQUENCE: 15
gggaaggagc cattatatc                                                 19

<210> SEQ ID NO 16
<211> LENGTH: 7650
<212> TYPE: DNA
<213> ORGANISM: Artificial Sequence
<220> FEATURE:
<223> OTHER INFORMATION: Plasmid used to clone or test shRNA (pLL37)

<400> SEQUENCE: 16
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt cgctgcttc gcgatgtacg ggccagatat acgcgttgac     240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg cccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
```

```
ttttgactag cggaggctag aaggagagag atgggtgcga gagcgtcagt attaagcggg    1200
ggagaattag atcgcgatgg gaaaaaattc ggttaaggcc aggggaaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ccgcgctga tcttcagacc tggaggagga    1560
gatatgaggg acaattggag aagtgaatta tataaatata aagtagtaaa aattgaacca    1620
ttaggagtag cacccaccaa ggcaaagaga agtggtgc agagagaaaa aagagcagtg    1680
ggaataggag ctttgttcct tgggttcttg ggagcagcag gaagcactat gggcgcagcg    1740
tcaatgacgc tgacggtaca ggccagacaa ttattgtctg gtatagtgca gcagcagaac    1800
aatttgctga gggctattga ggcgcaacag catctgttgc aactcacagt ctggggcatc    1860
aagcagctcc aggcaagaat cctggctgtg gaaagatacc taaaggatca acagctcctg    1920
gggatttggg gttgctctgg aaaactcatt tgcaccactg ctgtgccttg gaatgctagt    1980
tggagtaata aatctctgga acagatttgg aatcacacga cctggatgga gtgggacaga    2040
gaaattaaca attacacaag cttaatacac tccttaattg aagaatcgca aaaccagcaa    2100
gaaaagaatg aacaagaatt attggaatta gataaatggg caagtttgtg gaattggttt    2160
aacataacaa attggctgtg gtatataaaa ttattcataa tgatagtagg aggcttggta    2220
ggtttaagaa tagttttttgc tgtactttct atagtgaata gagttaggca gggatattca    2280
ccattatcgt ttcagaccca cctcccaacc ccgaggggac ccgacaggcc cgaaggaata    2340
gaagaagaag gtggagagag agacagagac agatccattc gattagtgaa cggatcggca    2400
ctgcgtgcgc caattctgca gacaaatggc agtattcatc cacaatttta aaagaaaagg    2460
ggggattggg gggtacagtg caggggaaag aatagtagac ataatagcaa cagacataca    2520
aactaaagaa ttacaaaaac aaattacaaa aattcaaaat tttcgggttt attacaggga    2580
cagcagagat ccagtttggt tagtaccggg cccgctctag agatccgacg ccgccatctc    2640
taggcccgcg ccggcccct cgcacagact tgtgggagaa gctcggctac tcccctgccc    2700
cggttaattt gcatataata tttcctagta actatagagg cttaatgtgc gataaaagac    2760
agataatctg ttcttttaa tactagctac atttacatg ataggcttgg atttctataa    2820
gagatacaaa tactaaatta ttattttaaa aaacagcaca aaaggaaact caccctaact    2880
gtaaagtaat tgtgtgtttt gagactataa atatcccttg gagaaaagcc ttgttaacgc    2940
gcggtgaccc tcgaggtcga cggtatcgat aagctcgctt cacgagattc cagcaggtcg    3000
agggacctaa taacttcgta tagcatacat tatacgaagt tatattaagg gttccaagct    3060
taagcggccg cgtggataac cgtattaccg ccatgcatta gttattaata gtaatcaatt    3120
acggggtcat tagttcatag cccatatatg gagttccgcg ttacataact tacggtaaat    3180
ggcccgcctg gctgaccgcc caacgacccc cgcccattga cgtcaataat gacgtatgtt    3240
cccatagtaa cgccaatagg gactttccat tgacgtcaat gggtggagta tttacggtaa    3300
actgcccact tggcagtaca tcaagtgtat catatgccaa gtacgccccc tattgacgtc    3360
aatgacggta aatggcccgc ctggcattat gcccagtaca tgaccttatg gactttcct    3420 acttggcagt acatctacgt attagtcatc gctattacca tggtgatgcg gttttggcag    3480
```

```
tacatcaatg ggcgtggata gcggtttgac tcacggggat ttccaagtct ccaccccatt    3540
gacgtcaatg ggagtttgtt ttggcaccaa aatcaacggg actttccaaa atgtcgtaac    3600
aactccgccc cattgacgca aatgggcggt aggcgtgtac ggtgggaggt ctatataagc    3660
agagctggtt tagtgaaccg tcagatccgc tagcgctacc ggtcgccacc atggtgagca    3720
agggcgagga gctgttcacc ggggtggtgc ccatcctggt cgagctggac ggcgacgtaa    3780
acggccacaa gttcagcgtg tccggcgagg gcgagggcga tgccacctac ggcaagctga    3840
ccctgaagtt catctgcacc accggcaagc tgcccgtgcc ctggcccacc ctcgtgacca    3900
ccctgaccta cggcgtgcag tgcttcagcc gctaccccga ccacatgaag cagcacgact    3960
tcttcaagtc cgccatgccc gaaggctacg tccaggagcg caccatcttc ttcaaggacg    4020
acggcaacta caagacccgc gccgaggtga agttcgaggg cgacaccctg gtgaaccgca    4080
tcgagctgaa gggcatcgac ttcaaggagg acggcaacat cctggggcac aagctggagt    4140
acaactacaa cagccacaac gtctatatca tggccgacaa gcagaagaac ggcatcaagg    4200
tgaacttcaa gatccgccac aacatcgagg acggcagcgt gcagctcgcc gaccactacc    4260
agcagaacac ccccatcggc gacggccccg tgctgctgcc cgacaaccac tacctgagca    4320
cccagtccgc cctgagcaaa gaccccaacg agaagcgcga tcacatggtc ctgctggagt    4380
tcgtgaccgc cgccgggatc actctcggca tggacgagct gtacaagtag gaattcgtcg    4440
agggacctaa taacttcgta tagcatacat tatacgaagt tatacatgtt taagggttcc    4500
ggttccacta ggtacaattc gatatcaagc ttatcgataa tcaacctctg gattacaaaa    4560
tttgtgaaag attgactggt attcttaact atgttgctcc ttttacgcta tgtggatacg    4620
ctgctttaat gcctttgtat catgctattg cttcccgtat ggctttcatt ttctcctcct    4680
tgtataaatc ctggttgctg tctctttatg aggagttgtg gcccgttgtc aggcaacgtg    4740
gcgtggtgtg cactgtgttt gctgacgcaa ccccCactgg ttggggcatt gccaccacct    4800
gtcagctcct ttccgggact ttcgctttcc cctccctat tgccacgcg gaactcatcg    4860
ccgcctgcct tgcccgctgc tggacagggg ctcggctgtt gggcactgac aattccgtgg    4920
tgttgtcggg gaaatcatcg tcctttcctt ggctgctcgc ctgtgttgcc acctggattc    4980
tgcgcgggac gtccttctgc tacgtccctt cggccctcaa tccagcggac cttccttccc    5040
gcggcctgct gccggctctg cggcctcttc cgcgtcttcg ccttcgccct cagacgagtc    5100
ggatctccct ttgggccgcc tccccgcatc gataccgtcg acctcgatcg agacctagaa    5160
aaacatggag caatcacaag tagcaataca gcagctacca atgctgattg tgcctggcta    5220
gaagcacaag aggaggagga ggtgggtttt ccagtcacac ctcaggtacc tttaagacca    5280
atgacttaca aggcagctgt agatcttagc cactttttaa agaaaagggg ggactggaa    5340
gggctaattc actcccaacg aagacaagat atccttgatc tgtggatcta ccacacacaa    5400
ggctacttcc ctgattggca gaactacaca ccagggccag ggatcagata tccactgacc    5460
tttggatggt gctacaagct agtaccagtt gagcaagaga aggtagaaga agccaatgaa    5520
ggagagaaca cccgcttgtt acaccctgtg agcctgcatg ggatggatga cccggagaga    5580
gaagtattag agtggaggtt tgacagccgc ctagcatttc atcacatggc ccgagagctg    5640
catccggact gtactgggtc tctctggtta gaccagatct gagcctggga gctctctggc    5700
taactaggga acccactgct taagcctcaa taaagcttgc cttgagtgct tcaagtagtg    5760
tgtgcccgtc tgttgtgtga ctctggtaac tagagatccc tcagaccctt ttagtcagtg    5820
tggaaaatct ctagcagcat gtgagcaaaa ggccagcaaa aggccaggaa ccgtaaaaag    5880
```

```
gccgcgttgc tggcgttttt ccataggctc cgcccccctg acgagcatca caaaaatcga   5940
cgctcaagtc agaggtggcg aaacccgaca ggactataaa gataccaggc gtttccccct   6000
ggaagctccc tcgtgcgctc tcctgttccg accctgccgc ttaccggata cctgtccgcc   6060
tttctcccct cgggaagcgt ggcgctttct catagctcac gctgtaggta tctcagttcg   6120
gtgtaggtcg ttcgctccaa gctgggctgt gtgcacgaac cccccgttca gcccgaccgc   6180
tgcgccttat ccggtaacta tcgtcttgag tccaacccgg taagacacga cttatcgcca   6240
ctggcagcag ccactggtaa caggattagc agagcgaggt atgtaggcgg tgctacagag   6300
ttcttgaagt ggtggcctaa ctacggctac actagaagaa cagtatttgg tatctgcgct   6360
ctgctgaagc cagttacctt cggaaaaaga gttggtagct cttgatccgg caaacaaacc   6420
accgctggta gcggtggttt ttttgtttgc aagcagcaga ttacgcgcag aaaaaaagga   6480
tctcaagaag atcctttgat cttttctacg ggtctgacg ctcagtggaa cgaaaactca   6540
cgttaaggga ttttggtcat gagattatca aaaaggatct tcacctagat ccttttaaat   6600
taaaaatgaa gttttaaatc aatctaaagt atatatgagt aaacttggtc tgacagttac   6660
caatgcttaa tcagtgaggc acctatctca gcgatctgtc tatttcgttc atccatagtt   6720
gcctgactcc ccgtcgtgta gataactacg atacgggagg gcttaccatc tggccccagt   6780
gctgcaatga taccgcgaga cccacgctca ccggctccag atttatcagc aataaaccag   6840
ccagccggaa gggccgagcg cagaagtggt cctgcaactt tatccgcctc catccagtct   6900
attaattgtt gccgggaagc tagagtaagt agttcgccag ttaatagttt gcgcaacgtt   6960
gttgccattg ctacaggcat cgtggtgtca cgctcgtcgt ttggtatggc ttcattcagc   7020
tccggttccc aacgatcaag gcgagttaca tgatccccca tgttgtgcaa aaaagcggtt   7080
agctccttcg gtcctccgat cgttgtcaga agtaagttgg ccgcagtgtt atcactcatg   7140
gttatggcag cactgcataa ttctcttact gtcatgccat ccgtaagatg cttttctgtg   7200
actggtgagt actcaaccaa gtcattctga gaatagtgta tgcggcgacc gagttgctct   7260
tgcccggcgt caatacggga taataccgcg ccacatagca gaactttaaa agtgctcatc   7320
attggaaaac gttcttcggg gcgaaaactc tcaaggatct taccgctgtt gagatccagt   7380
tcgatgtaac ccactcgtgc acccaactga tcttcagcat cttttacttt caccagcgtt   7440
tctgggtgag caaaaacagg aaggcaaaat gccgcaaaaa agggaataag ggcgacacgg   7500
aaatgttgaa tactcatact cttcctttt caatattatt gaagcattta tcagggttat   7560
tgtctcatga gcggatacat atttgaatgt atttagaaaa ataaacaaat aggggttccg   7620
cgcacatttc cccgaaaagt gccacctgac                                     7650
```

<210> SEQ ID NO 17
<211> LENGTH: 11045
<212> TYPE: DNA
<213> ORGANISM: Artificial Sequence
<220> FEATURE:
<223> OTHER INFORMATION: Fanconi destination plasmid in which the active
    shRNAs can be cloned

<400> SEQUENCE: 17

```
caggtggcac ttttcgggga aatgtgcgcg gaacccctat ttgtttattt ttctaaatac     60
attcaaatat gtatccgctc atgagacaat aaccctgata aatgcttcaa taatattgaa    120
aaaggaagag tatgagtatt caacatttcc gtgtcgccct tattcccttt tttgcggcat    180
tttgccttcc tgtttttgct cacccagaaa cgctggtgaa agtaaaagat gctgaagatc    240
```

```
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttt gcacaacatg ggggatcatg     600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt cattttaat ttaaaaggat ctaggtgaag atccttttg     1080
ataatctcat gaccaaaatc ccttaacgtg agttttcgtt ccactgagcg tcagaccccg   1140
tagaaaagat caaaggatct cttgagatc ctttttttct gcgcgtaatc tgctgcttgc    1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca gggggggcgga  1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg aagtaaggt ggtacgatcg     2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
```

```
actagagatc cctcagaccc ttttagtcag tgtggaaaat ctctagcagt ggcgcccgaa    2640
cagggacctg aaagcgaaag ggaaaccaga gctctctcga cgcaggactc ggcttgctga    2700
agcgcgcacg gcaagaggcg aggggcggcg actggtgagt acgccaaaaa ttttgactag    2760
cggaggctag aaggagagag atgggtgcga gagcgtcagt attaagcggg ggagaattag    2820
atcgcgatgg gaaaaaattc ggttaaggcc agggggaaag aaaaaatata aattaaaaca    2880
tatagtatgg gcaagcaggg agctagaacg attcgcagtt aatcctggcc tgttagaaac    2940
atcagaaggc tgtagacaaa tactgggaca gctacaacca tcccttcaga caggatcaga    3000
agaacttaga tcattatata atacagtagc aaccctctat tgtgtgcatc aaaggataga    3060
gataaaagac accaaggaag ctttagacaa gatagaggaa gagcaaaaca aaagtaagac    3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat tggaatcaca cgacctggat ggagtgggac agagaaatta caattacac     3660 aagcttaata cactccttaa ttgaagaatc gcaaaaccag caagaaaaga atgaacaaga    3720
attattggaa ttagataaat gggcaagttt gtggaattgg tttaacataa caattggct     3780 gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
gagagacaga gacagatcca ttcgattagt gaacggatct cgacggtatc ggttaacttt    4020
taaaagaaaa gggggggattg gggggtacag tgcaggggaa agaatagtag acataatagc    4080
aacagacata caaactaaag aattacaaaa acaaattaca aaattcaaa attttccgat      4140 cacgagacta gcctcgagaa gcttgatatc gaattcccac ggggttgggg ttgcgccttt    4200
tccaaggcag ccctgggttt gcgcagggac gcggctgctc tgggcgtggt tccgggaaac    4260
gcagcggcgc cgaccctggg tctcgcacat tcttcacgtc cgttcgcagc gtcacccgga    4320
tcttcgccgc taccctttgtg ggccccccgg cgacgcttcc tgctccgccc ctaagtcggg    4380
aaggttcctt gcggttcgcg gcgtgccgga cgtgacaaac ggaagccgca cgtctcacta    4440
gtaccctcgc agacggacag cgccagggag caatggcagc gcgccgaccg cgatgggctg    4500
tggccaatag cggctgctca gcggggcgcg ccgagagcag cggccgggaa ggggcggtgc    4560
gggaggcggg gtgtggggcg gtagtgtggg ccctgttcct gcccgcgcgg tgttccgcat    4620
tctgcaagcc tccggagcgc acgtcggcag tcggctccct cgttgaccga atcaccgacc    4680
tctctcccca gggggatcca ccggtccgcc aaggccatgt ccgactcgtg ggtcccgaac    4740
tccgcctcgg gccaggaccc aggggccgc cggagggcct gggccgagct gctggcggga    4800
agggtcaaga gggaaaaata taatcctgaa agggcacaga aattaaagga atcagctgtg    4860
cgcctcctgc gaagccatca ggacctgaat gccctttttgc ttgaggtaga aggtccactg    4920
tgtaaaaaat tgtctctcag caaagtgatt gactgtgaca gttctgaggc ctatgctaat    4980
```

```
cattctagtt catttatagg ctctgctttg caggatcaag cctcaaggct gggggttccc      5040
gtgggtattc tctcagccgg gatggttgcc tctagcgtgg gacagatctg cacggctcca      5100
gcggagacca gtcaccctgt gctgctgact gtggagcaga gaaagaagct gtcttccctg      5160
ttagagtttg ctcagtattt attggcacac agtatgttct cccgtctttc cttctgtcaa      5220
gaattatgga aaatacagag ttctttgttg cttgaagcgg tgtggcatct tcacgtacaa      5280
ggcattgtga gcctgcaaga gctgctgaaa agccatcccg acatgcatgc tgtgggatcg      5340
tggctcttca ggaatctgtg ctgcctttgt gaacagatgg aagcatcctg ccagcatgct      5400
gacgtcgcca gggccatgct ttctgatttt gttcaaatgt ttgttttgag gggatttcag      5460
aaaaactcag atctgagaag aactgtggag cctgaaaaaa tgccgcaggt cacggttgat      5520
gtactgcaga gaatgctgat ttttgcactt gacgctttgg ctgctggagt acaggaggag      5580
tcctccactc acaagatcgt gaggtgctgg ttcgagtgt tcagtggaca cacgcttggc       5640
agtgtaattt ccacagatcc tctgaagagg ttcttcagtc ataccctgac tcagatactc      5700
actcacagcc ctgtgctgaa agcatctgat gctgttcaga tgcagagaga gtggagcttt      5760
gcgcggacac accctctgct cacctcactg taccgcaggc tctttgtgat gctgagtgca      5820
gaggagttgg ttggccattt gcaagaagtt ctggaaacgc aggaggttca ctggcagaga      5880
gtgctctcct ttgtgtctgc cctggttgtc tgctttccag aagcgcagca gctgcttgaa      5940
gactgggtgg cgcgtttgat ggcccaggca ttcgagagct gccagctgga cagcatggtc      6000
actgcgttcc tggttgtgcg ccaggcagca ctggagggcc cctctgcgtt cctgtcatat      6060
gcagactggt tcaaggcctc ctttgggagc acacgaggct accatggctg cagcaagaag      6120
gccctggtct tcctgtttac gttcttgtca gaactcgtgc cttttgagtc tccccggtac      6180
ctgcaggtgc acattctcca cccacccctg gttccagca agtaccgctc cctcctcaca      6240
gactacatct cattggccaa gacacggctg ccgacctca aggtttctat agaaaacatg       6300
ggactctacg aggatttgtc atcagctggg gacattactg agcccacag ccaagctctt       6360 caggatgttg aaaaggccat catggtgttt gagcatacgg ggaacatccc agtcaccgtc      6420
atggaggcca gcatattcag gaggccttac tacgtgtccc acttcctccc cgccctgctc      6480
acacctcgag tgctccccaa gtccctgac tcccgtgtgg cgtttataga gtctctgaag       6540
agagcagata aaatccccc atctctgtac tccacctact gccaggcctg ctctgctgct      6600
gaagagaagc cagaagatgc agccctggga gtgagggcag aacccaactc tgctgaggag      6660
cccctgggac agctcacagc tgcactggga gagctgagag cctccatgac agaccccagc      6720
cagcgtgatg ttatatcggc acaggtggca gtgatttctg aaagactgag ggctgtcctg      6780
ggccacaatg aggatgacag cagcgttgag atatcaaaga ttcagctcag catcaacacg      6840
ccgagactgg agccacggga acacattgct gtggacctcc tgctgacgtc tttctgtcag      6900
aacctgatgg ctgcctccag tgtcgctccc ccggagaggc agggtccctg gctgccctc       6960 ttcgtgagga ccatgtgtgg acgtgtgctc cctgcagtgc tcacccggct ctgccagctg      7020
ctccgtcacc agggcccgag cctgagtgcc ccacatgtgc tggggttggc tgccctggcc      7080
gtgcacctgg gtgagtccag gtctgcgctc ccagaggtga atgtgggtcc tcctgcacct      7140
ggtgctggcc ttcctgtccc tgcgctcttt gacagcctcc tgacctgtag gacgagggat      7200
tccttgttct ctgcctgaa attttgtaca gcagcaattt cttactctct ctgcaagttt       7260
tcttcccagt cacgagatac tttgtgcagc tgcttatctc caggccttat taaaaagttt      7320
```

```
cagttcctca tgttcagatt gttctcagag gcccgacagc ctctttctga ggaggacgta    7380
gccagccttt cctggagacc cttgcacctt ccttctgcag actggcagag agctgccctc    7440
tctctctgga cacacagaac cttccgagag gtgttgaaag aggaagatgt tcacttaact    7500
taccaagact ggttacacct ggagctggaa attcaacctg aagctgatgc tctttcagat    7560
actgaacggc aggacttcca ccagtgggcg atccatgagc actttctccc tgagtcctcg    7620
gcttcagggg gctgtgacgg agacctgcag gctgcgtgta ccattcttgt caacgcactg    7680
atggatttcc accaaagctc aaggagttat gaccactcag aaaattctga tttggtcttt    7740
ggtggccgca caggaaatga ggatattatt tccagattgc aggagatggt agctgacctg    7800
gagctgcagc aagacctcat agtgcctctc ggccacaccc cttcccagga gcacttcctc    7860
tttgagattt tccgcagacg gctccaggct ctgacaagcg ggtggagcgt ggctgccagc    7920
cttcagagac agagggagct gctaatgtac aaacggatcc tcctccgcct gccttcgtct    7980
gtcctctgcg gcagcagctt ccaggcagaa cagcccatca ctgccagatg cgagcagttc    8040
ttccacttgg tcaactctga gatgagaaac ttctgctccc acggaggtgc cctgacacag    8100
gacatcactg cccacttctt caggggcctc ctgaacgcct gtctgcggag cagagacccc    8160
tccctgatgg tcgacttcat actggccaag tgccagacga aatgcccctt aattttgacc    8220
tctgctctgg tgtggtggcc gagcctggag cctgtgctgc tctgccggtg gaggagacac    8280
tgccagagcc cgctgccccg ggaactgcag aagctacaag aaggccggca gtttgccagc    8340
gatttcctct cccctgaggc tgcctcccca gcacccaacc cggactggct ctcagctgct    8400
gcactgcact ttgcgattca acaagtcagg gaagaaaaca tcaggaagca gctaaagaag    8460
ctggactgcg agagagagga gctattggtt ttccttttct tcttctcctt gatgggcctg    8520
ctgtcgtcac atctgacctc aaatagcacc acagacctgc caaaggcttt ccacgtttgt    8580
gcagcaatcc tcgagtgttt agagaagagg aagatatcct ggctggcact ctttcagttg    8640
acagagagtg acctcaggct ggggcggctc ctcctccgtg tggcccccgga tcagcacacc    8700 aggctgctgc cttttcgcttt ttacagtctt ctctcctact tccatgaaga cgcggccatc    8760
agggaagagg ccttcctgca tgttgctgtg gacatgtact tgaagctggt ccagctcttc    8820
gtggctgggg atacaagcac agtttcacct ccagctggca ggagcctgga gctcaagggt    8880
cagggcaacc ccgtggaact gataacaaaa gctcgtcttt ttctgctgca gttaataccT    8940
cggtgcccga aaagagcttt ctcacacgtg gcagagctgc tggctgatcg tggggactgc    9000
gacccagagg tgagcgccgc cctccagagc agacagcagg ctgcccctga cgctgacctg    9060
tcccaggagc ctcatctctt ctgacgggac ctgcgtttaa acgaattcga gcatcttacc    9120
gccatttatt cccatatttg ttctgttttt cttgatttgg gtatacattt aaatgttaat    9180
aaaacaaaat ggtggggcaa tcatttacat ttttagggat atgtaattac tagttcaggt    9240
gtattgccac aagacaaaca tgttaagaaa ctttcccgtt atttacgctc tgttcctgtt    9300
aatcaacctc tggattacaa aatttgtgaa agattgactg atattcttaa ctatgttgct    9360
ccttttacgc tgtgtggata tgctgcttta tagcctctgt atctagctat tgcttcccgt    9420
acggctttcg ttttctcctc cttgtataaa tcctggttgc tgtctctttt agaggagttg    9480
tggcccgttg tccgtcaacg tggcgtggtg tgctctgtgt ttgctgacgc aaccccccact    9540 ggctggggca ttgccaccac ctgtcaactc ctttctggga ctttcgcttt ccccctcccg    9600
atcgccacgg cagaactcat cgccgcctgc cttgcccgct gctggacagg gctaggttg    9660 ctgggcactg ataattccgt ggtgttgtcc gaagtcgacc tcgagggggg gcccggtacc    9720
```

| | | | | |
|---|---|---|---|---|
| tttaagacca | atgacttaca | aggcagctgt | agatcttagc | cacttttttaa | aagaaaaggg | 9780 |
| gggactggaa | gggctaattc | actcccaacg | aagacaagat | ctgcttttg | cttgtactgg | 9840 |
| gtctctctgg | ttagaccaga | tctgagcctg | ggagctctct | ggctaactag | ggaacccact | 9900 |
| gcttaagcct | caataaagct | tgccttgagt | gcttcaagta | gtgtgtgccc | gtctgttgtg | 9960 |
| tgactctggt | aactagagat | ccctcagacc | cttttagtca | gtgtggaaaa | tctctagcag | 10020 |
| tagtagttca | tgtcatctta | ttattcagta | tttataactt | gcaaagaaat | gaatatcaga | 10080 |
| gagtgagagg | aacttgttta | ttgcagctta | taatggttac | aaataaagca | atagcatcac | 10140 |
| aaatttcaca | aataaagcat | tttttcact | gcattctagt | tgtggtttgt | ccaaactcat | 10200 |
| caatgtatct | tatcatgtct | ggctctagct | atcccgcccc | taactccgcc | cagttccgcc | 10260 |
| cattctccgc | cccatggctg | actaattttt | tttatttatg | cagaggccga | ggccgcctcg | 10320 |
| gcctctgagc | tattccagaa | gtagtgagga | ggcttttttg | gaggcctagg | cttttgcgtc | 10380 |
| gagacgtacc | caattcgccc | tatagtgagt | cgtattacgc | gcgctcactg | gccgtcgttt | 10440 |
| tacaacgtcg | tgactgggaa | aaccctggcg | ttacccaact | taatcgcctt | gcagcacatc | 10500 |
| cccctttcgc | cagctggcgt | aatagcgaag | aggcccgcac | cgatcgccct | tcccaacagt | 10560 |
| tgcgcagcct | gaatggcgaa | tggcgcgacg | cgccctgtag | cggcgcatta | agcgcggcgg | 10620 |
| gtgtggtggt | tacgcgcagc | gtgaccgcta | cacttgccag | cgccctagcg | cccgctcctt | 10680 |
| tcgctttctt | cccttccttt | ctcgccacgt | tcgccggctt | tccccgtcaa | gctctaaatc | 10740 |
| gggggctccc | tttagggttc | cgatttagtg | ctttacggca | cctcgacccc | aaaaaacttg | 10800 |
| attagggtga | tggttcacgt | agtgggccat | cgccctgata | gacggttttt | cgccctttga | 10860 |
| cgttggagtc | cacgttcttt | aatagtggac | tcttgttcca | aactggaaca | acactcaacc | 10920 |
| ctatctcggt | ctattctttt | gatttataag | ggattttgcc | gatttcggcc | tattggttaa | 10980 |
| aaaatgagct | gatttaacaa | aaatttaacg | cgaattttaa | caaaatatta | acgtttacaa | 11040 |
| tttcc | | | | | | 11045 |

<210> SEQ ID NO 18
<211> LENGTH: 4716
<212> TYPE: DNA
<213> ORGANISM: Artificial Sequence
<220> FEATURE:
<223> OTHER INFORMATION: Part of destination plasmid

<400> SEQUENCE: 18

| | | | | | | |
|---|---|---|---|---|---|---|
| caggtggcac | ttttcgggga | aatgtgcgcg | gaacccctat | ttgtttattt | ttctaaatac | 60 |
| attcaaatat | gtatccgctc | atgagacaat | aaccctgata | aatgcttcaa | taatattgaa | 120 |
| aaaggaagag | tatgagtatt | caacatttcc | gtgtcgccct | tattcccttt | tttgcggcat | 180 |
| tttgccttcc | tgttttgct | cacccagaaa | cgctggtgaa | agtaaaagat | gctgaagatc | 240 |
| agttgggtgc | acgagtgggt | tacatcgaac | tggatctcaa | cagcggtaag | atccttgaga | 300 |
| gttttcgccc | cgaagaacgt | tttccaatga | tgagcacttt | taaagttctg | ctatgtggcg | 360 |
| cggtattatc | ccgtattgac | gccgggcaag | agcaactcgg | tcgccgcata | cactattctc | 420 |
| agaatgactt | ggttgagtac | tcaccagtca | cagaaaagca | tcttacggat | ggcatgacag | 480 |
| taagagaatt | atgcagtgct | gccataacca | tgagtgataa | cactgcggcc | aacttacttc | 540 |
| tgacaacgat | cggaggaccg | aaggagctaa | ccgcttttt | gcacaacatg | ggggatcatg | 600 |
| taactcgcct | tgatcgttgg | gaaccggagc | tgaatgaagc | cataccaaac | gacgagcgtg | 660 |

-continued

| | | | | | |
|---|---|---|---|---|---|
| acaccacgat | gcctgtagca | atggcaacaa | cgttgcgcaa | actattaact | ggcgaactac | 720 |
| ttactctagc | ttcccggcaa | caattaatag | actggatgga | ggcggataaa | gttgcaggac | 780 |
| cacttctgcg | ctcggcccttt | ccggctggct | ggtttattgc | tgataaatct | ggagccggtg | 840 |
| agcgtgggtc | tcgcggtatc | attgcagcac | tggggccaga | tggtaagccc | tcccgtatcg | 900 |
| tagttatcta | cacgacgggg | agtcaggcaa | ctatggatga | acgaaataga | cagatcgctg | 960 |
| agataggtgc | ctcactgatt | aagcattggt | aactgtcaga | ccaagtttac | tcatatatac | 1020 |
| tttagattga | tttaaaactt | cattttttaat | ttaaaaggat | ctaggtgaag | atccttttttg | 1080 |
| ataatctcat | gaccaaaatc | ccttaacgtg | agttttcgtt | ccactgagcg | tcagaccccg | 1140 |
| tagaaaagat | caaaggatct | tcttgagatc | ctttttttct | gcgcgtaatc | tgctgcttgc | 1200 |
| aaacaaaaaa | accaccgcta | ccagcggtgg | tttgtttgcc | ggatcaagag | ctaccaactc | 1260 |
| tttttccgaa | ggtaactggc | ttcagcagag | cgcagatacc | aaatactgtc | cttctagtgt | 1320 |
| agccgtagtt | aggccaccac | ttcaagaact | ctgtagcacc | gcctacatac | ctcgctctgc | 1380 |
| taatcctgtt | accagtggct | gctgccagtg | gcgataagtc | gtgtcttacc | gggttggact | 1440 |
| caagacgata | gttaccggat | aaggcgcagc | ggtcgggctg | aacggggggt | tcgtgcacac | 1500 |
| agcccagctt | ggagcgaacg | acctacaccg | aactgagata | cctacagcgt | gagctatgag | 1560 |
| aaagcgccac | gcttcccgaa | gggagaaagg | cggacaggta | tccggtaagc | ggcagggtcg | 1620 |
| gaacaggaga | gcgcacgagg | gagcttccag | ggggaaacgc | ctggtatctt | tatagtcctg | 1680 |
| tcgggtttcg | ccacctctga | cttgagcgtc | gatttttgtg | atgctcgtca | ggggggcgga | 1740 |
| gcctatggaa | aaacgccagc | aacgcggcct | ttttacggtt | cctggccttt | tgctggcctt | 1800 |
| ttgctcacat | gttctttcct | gcgttatccc | ctgattctgt | ggataaccgt | attaccgcct | 1860 |
| ttgagtgagc | tgataccgct | cgccgcagcc | gaacgaccga | gcgcagcgag | tcagtgagcg | 1920 |
| aggaagcgga | agagcgccca | atacgcaaac | cgcctctccc | cgcgcgttgg | ccgattcatt | 1980 |
| aatgcagctg | gcacgacagg | tttcccgact | ggaaagcggg | cagtgagcgc | aacgcaatta | 2040 |
| atgtgagtta | gctcactcat | taggcacccc | aggctttaca | ctttatgctt | ccggctcgta | 2100 |
| tgttgtgtgg | aattgtgagc | ggataacaat | ttcacacagg | aaacagctat | gaccatgatt | 2160 |
| acgccaagcg | cgcaattaac | cctcactaaa | gggaacaaaa | gctggagctg | caagcttaat | 2220 |
| gtagtcttat | gcaatactct | tgtagtcttg | caacatggta | acgatgagtt | agcaacatgc | 2280 |
| cttacaagga | gagaaaaagc | accgtgcatg | ccgattggtg | gaagtaaggt | ggtacgatcg | 2340 |
| tgccttatta | ggaaggcaac | agacgggtct | gacatggatt | ggacgaacca | ctgaattgcc | 2400 |
| gcattgcaga | gatattgtat | ttaagtgcct | agctcgatac | aataaacggg | tctctctggt | 2460 |
| tagaccagat | ctgagcctgg | gagctctctg | gctaactagg | gaacccactg | cttaagcctc | 2520 |
| aataaagctt | gccttgagtg | cttcaagtag | tgtgtgcccg | tctgttgtgt | gactctggta | 2580 |
| actagagatc | cctcagaccc | ttttagtcag | tgtggaaaat | ctctagcagt | ggcgcccgaa | 2640 |
| cagggacctg | aaagcgaaag | ggaaaccaga | gctctctcga | cgcaggactc | ggcttgctga | 2700 |
| agcgcgcacg | gcaagaggcg | aggggcggcg | actggtgagt | acgccaaaaa | ttttgactag | 2760 |
| cggaggctag | aaggagagag | atgggtgcga | gagcgtcagt | attaagcggg | ggagaattag | 2820 |
| atcgcgatgg | gaaaaaattc | ggttaaggcc | aggggggaaag | aaaaaatata | aattaaaaca | 2880 |
| tatagtatgg | gcaagcaggg | agctagaacg | attcgcagtt | aatcctggcc | tgttagaaac | 2940 |
| atcagaaggc | tgtagacaaa | tactgggaca | gctacaacca | tcccttcaga | caggatcaga | 3000 |
| agaacttaga | tcattatata | atacagtagc | aaccctctat | tgtgtgcatc | aaaggataga | 3060 |

```
gataaaagac accaaggaag ctttagacaa gatagaggaa gagcaaaaca aaagtaagac    3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat tggaatcaca cgacctggat ggagtgggac agagaaatta acaattacac    3660
aagcttaata cactccttaa ttgaagaatc gcaaaaccag caagaaaaga atgaacaaga    3720
attattggaa ttagataaat gggcaagttt gtggaattgg tttaacataa caaattggct    3780
gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
gagagacaga gacagatcca ttcgattagt gaacggatct cgacggtatc ggttaacttt    4020
taaaagaaaa gggggggattg gggggtacag tgcaggggaa agaatagtag acataatagc    4080
aacagacata caaactaaag aattacaaaa acaaattaca aaaattcaaa attttccgat    4140
cacgagacta gcctcgagaa gcttgatatc gaattcccac ggggttgggg ttgcgccttt    4200
tccaaggcag ccctgggttt gcgcagggac gcggctgctc tgggcgtggt tccgggaaac    4260
gcagcggcgc cgaccctggg tctcgcacat tcttcacgtc cgttcgcagc gtcacccgga    4320
tcttcgccgc tacccttgtg ggccccccgg cgacgcttcc tgctccgccc ctaagtcggg    4380
aaggttcctt gcggttcgcg gcgtgccgga cgtgacaaac ggaagccgca cgtctcacta    4440
gtaccctcgc agacgacag cgccaggag caatggcagc gcgccgaccg cgatgggctg    4500
tggccaatag cggctgctca gcggggcgcg ccgagagcag cggccgggaa ggggcggtgc    4560
gggaggcggg gtgtggggcg gtagtgtggg ccctgttcct gcccgcgcgg tgttccgcat    4620
tctgcaagcc tccggagcgc acgtcggcag tcggctccct cgttgaccga atcaccgacc    4680
tctctcccca gggggatcca ccggtccgcc aaggcc                              4716
```

<210> SEQ ID NO 19
<211> LENGTH: 1961
<212> TYPE: DNA
<213> ORGANISM: Artificial Sequence
<220> FEATURE:
<223> OTHER INFORMATION: Part of destination plasmid

<400> SEQUENCE: 19

```
cgggacctgc gtttaaacga attcgagcat cttaccgcca tttattccca tatttgttct     60
gtttttcttg atttgggtat acatttaaat gttaataaaa caaatggtg gggcaatcat    120 ttacatttt agggatatgt aattactagt tcaggtgtat tgccacaaga caaacatgtt    180
aagaaacttt ccgttatttt acgctctgtt cctgttaatc aacctctgga ttacaaaatt    240
tgtgaaagat tgactgatat tcttaactat gttgctcctt ttacgctgtg tggatatgct    300
gctttatagc ctctgtatct agctattgct tcccgtacgg ctttcgtttt ctcctccttg    360
```

```
tataaatcct  ggttgctgtc  tcttttagag  gagttgtggc  ccgttgtccg  tcaacgtggc        420
gtggtgtgct  ctgtgtttgc  tgacgcaacc  cccactggct  ggggcattgc  caccacctgt        480
caactccttt  ctgggacttt  cgctttcccc  ctcccgatcg  ccacggcaga  actcatcgcc        540
gcctgccttg  cccgctgctg  gacagggggct aggttgctgg  gcactgataa  ttccgtggtg        600
ttgtccgaag  tcgacctcga  gggggggccc  ggtacccttta agaccaatga  cttacaaggc        660
agctgtagat  cttagccact  ttttaaaaga  aaaggggga   ctggaagggc  taattcactc        720
ccaacgaaga  caagatctgc  tttttgcttg  tactgggtct  ctctggttag  accagatctg        780
agcctgggag  ctctctggct  aactagggaa  cccactgctt  aagcctcaat  aaagcttgcc        840
ttgagtgctt  caagtagtgt  gtgcccgtct  gttgtgtgac  tctggtaact  agagatccct        900
cagacccttt  tagtcagtgt  ggaaaatctc  tagcagtagt  agttcatgtc  atcttattat        960
tcagtattta  aacttgcaa   agaaatgaat  atcagagagt  gagaggaact  tgtttattgc       1020
agcttataat  ggttacaaat  aaagcaatag  catcacaaat  ttcacaaata  aagcattttt       1080
ttcactgcat  tctagttgtg  gtttgtccaa  actcatcaat  gtatcttatc  atgtctggct       1140
ctagctatcc  cgcccctaac  tccgcccagt  tccgcccatt  ctccgcccca  tggctgacta       1200
atttttttta  tttatgcaga  ggccgaggcc  gcctcggcct  ctgagctatt  ccagaagtag       1260
tgaggaggct  tttttggagg  cctaggcttt  tgcgtcgaga  cgtacccaat  tcgccctata       1320
gtgagtcgta  ttacgcgcgc  tcactggccg  tcgttttaca  acgtcgtgac  tgggaaaacc       1380
ctggcgttac  ccaacttaat  cgccttgcag  cacatccccc  tttcgccagc  tggcgtaata       1440
gcgaagaggc  ccgcaccgat  cgcccttccc  aacagttgcg  cagcctgaat  ggcgaatggc       1500
gcgacgcgcc  ctgtagcggc  gcattaagcg  cggcgggtgt  ggtggttacg  cgcagcgtga       1560
ccgctacact  tgccagcgcc  ctagcgcccg  ctcctttcgc  tttcttccct  tcctttctcg       1620
ccacgttcgc  cggctttccc  cgtcaagctc  taaatcgggg  gctccctta   gggttccgat       1680 ttagtgcttt  acggcacctc  gaccccaaaa  aacttgatta  gggtgatggt  tcacgtagtg       1740
ggccatcgcc  ctgatagacg  gttttcgcc   ctttgacgtt  ggagtccacg  ttctttaata       1800
gtggactctt  gttccaaact  ggaacaacac  tcaaccctat  ctcggtctat  tcttttgatt       1860
tataagggat  tttgccgatt  tcggcctatt  ggttaaaaaa  tgagctgatt  taacaaaaat       1920
ttaacgcgaa  ttttaacaaa  atattaacgt  ttacaatttc  c                            1961
```

<210> SEQ ID NO 20
<211> LENGTH: 5
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(5)
<223> OTHER INFORMATION: The (GlyGlyGlyGlySer) sequence as a whole is
      repeated n times, wherein n is an integer including 1, 2, 3, 4, 5,
      6, 7, 8, 9, or more.

<400> SEQUENCE: 20

Gly Gly Gly Gly Ser
1               5

<210> SEQ ID NO 21
<211> LENGTH: 9
<212> TYPE: PRT
<213> ORGANISM: Artificial Sequence
<220> FEATURE:

```
<223> OTHER INFORMATION: GlySer linker
<220> FEATURE:
<221> NAME/KEY: MISC_FEATURE
<222> LOCATION: (1)..(4)
<223> OTHER INFORMATION: The (GlyGlyGlySer) sequence is repeated n
      times, wherein n is an integer including 1, 2, 3, 4, 5, 6, 7, 8,
      9, or more.
<220> FEATURE:
<221> NAME/KEY: MISC_FEATURE
<222> LOCATION: (5)..(9)
<223> OTHER INFORMATION: The (GlyGlyGlyGlySer) sequence is repeated n
      times, wherein n is an integer including 1, 2, 3, 4, 5, 6, 7, 8,
      9, or more.

<400> SEQUENCE: 21

Gly Gly Gly Ser Gly Gly Gly Gly Ser
1               5

<210> SEQ ID NO 22
<211> LENGTH: 7
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: The (GlyGlyGlySer) sequence as a whole is
      repeated n times, wherein n is an integer including 1, 2, 3, 4, 5,
      6, 7, 8, 9, or more.
<220> FEATURE:
<221> NAME/KEY: MISC_FEATURE
<222> LOCATION: (5)..(7)
<223> OTHER INFORMATION: The (GlyGlySer) sequence as a whole is repeated
      n times, wherein n is an integer including 1, 2, 3, 4, 5, 6, 7, 8,
      9, or more.

<400> SEQUENCE: 22

Gly Gly Gly Ser Gly Gly Ser
1               5

<210> SEQ ID NO 23
<211> LENGTH: 9
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(4)
<223> OTHER INFORMATION: The (GlyGlyGlySer) sequence as a whole is
      repeated n times, wherein n is an integer including 1, 2, 3, 4, 5,
      6, 7, 8, 9, or more. Then the sequence is followed by the rest of
      the sequence (GlyGlyGlyGlySer).

<400> SEQUENCE: 23

Gly Gly Gly Ser Gly Gly Gly Gly Ser
1               5

<210> SEQ ID NO 24
<211> LENGTH: 20
<212> TYPE: PRT
<213> ORGANISM: Artificial Sequence
<220> FEATURE:
<223> OTHER INFORMATION: GlySer linker

<400> SEQUENCE: 24

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 25
<211> LENGTH: 15
<212> TYPE: PRT
<213> ORGANISM: Artificial Sequence
<220> FEATURE:
<223> OTHER INFORMATION: GlySer linker

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 10
<212> TYPE: PRT
<213> ORGANISM: Artificial Sequence
<220> FEATURE:
<223> OTHER INFORMATION: GlySer linker

<400> SEQUENCE: 26

Gly Gly Gly Gly Ser Gly Gly Gly Gly Ser
1               5                   10

<210> SEQ ID NO 27
<211> LENGTH: 5
<212> TYPE: PRT
<213> ORGANISM: Artificial Sequence
<220> FEATURE:
<223> OTHER INFORMATION: GlySer linker

<400> SEQUENCE: 27

Gly Gly Gly Gly Ser
1               5

<210> SEQ ID NO 28
<211> LENGTH: 8
<212> TYPE: PRT
<213> ORGANISM: Artificial Sequence
<220> FEATURE:
<223> OTHER INFORMATION: GlySer linker

<400> SEQUENCE: 28

Gly Gly Gly Ser Gly Gly Gly Ser
1               5

<210> SEQ ID NO 29
<211> LENGTH: 4
<212> TYPE: PRT
<213> ORGANISM: Artificial Sequence
<220> FEATURE:
<223> OTHER INFORMATION: GlySer linker

<400> SEQUENCE: 29

Gly Gly Gly Ser
1

<210> SEQ ID NO 30
<211> LENGTH: 6
<212> TYPE: PRT
<213> ORGANISM: Artificial Sequence
<220> FEATURE:
<223> OTHER INFORMATION: GlySer linker

<400> SEQUENCE: 30

Gly Gly Ser Gly Gly Ser
1               5
```

```
<210> SEQ ID NO 31
<211> LENGTH: 11
<212> TYPE: PRT
<213> ORGANISM: Artificial Sequence
<220> FEATURE:
<223> OTHER INFORMATION: GlySer linker

<400> SEQUENCE: 31

Gly Gly Ser Gly Gly Gly Ser Gly Gly Ser Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: GlySer linker

<400> SEQUENCE: 32

Gly Gly Ser Gly Gly Gly Ser Gly Ser Gly
1               5                   10

<210> SEQ ID NO 33
<211> LENGTH: 8
<212> TYPE: PRT
<213> ORGANISM: Artificial Sequence
<220> FEATURE:
<223> OTHER INFORMATION: GlySer linker

<400> SEQUENCE: 33

Gly Gly Ser Gly Gly Gly Ser Gly
1               5

<210> SEQ ID NO 34

<400> SEQUENCE: 34

000

<210> SEQ ID NO 35
<211> LENGTH: 7
<212> TYPE: PRT
<213> ORGANISM: Artificial Sequence
<220> FEATURE:
<223> OTHER INFORMATION: CDRH3 of anti-4-1BB antibody

<400> SEQUENCE: 35

Gly Tyr Gly Ile Phe Asp Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: Spacer Region
<220> FEATURE:
<221> NAME/KEY: MISC_FEATURE
<222> LOCATION: (1)..(5)
<223> OTHER INFORMATION: The sequence as a whole is repeated n times,
      wherein n is an integer including 1, 2, 3, 4, 5, 6, 7, 8, 9, or
      more.

<400> SEQUENCE: 36

Glu Ala Ala Ala Lys
1               5
```

```
<210> SEQ ID NO 37
<211> LENGTH: 120
<212> TYPE: PRT
<213> ORGANISM: Artificial Sequence
<220> FEATURE:
<223> OTHER INFORMATION: Variable heavy chain of TGN1412

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
                100                 105                 110

Gly Thr Thr Val Thr Val Ser Ser
            115                 120

<210> SEQ ID NO 38
<211> LENGTH: 107
<212> TYPE: PRT
<213> ORGANISM: Artificial Sequence
<220> FEATURE:
<223> OTHER INFORMATION: Variable light chain of TGN1412

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
                20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
                100                 105

<210> SEQ ID NO 39
<211> LENGTH: 133
<212> TYPE: PRT
<213> ORGANISM: Artificial Sequence
<220> FEATURE:
<223> OTHER INFORMATION: variable light chain of gemtuzumab

<400> SEQUENCE: 39

Met Ser Val Pro Thr Gln Val Leu Gly Leu Leu Leu Leu Trp Leu Thr
1               5                   10                  15

Asp Ala Arg Cys Asp Ile Gln Leu Thr Gln Ser Pro Ser Thr Leu Ser
                20                  25                  30
```

```
Ala Ser Val Gly Asp Arg Val Thr Ile Thr Cys Arg Ala Ser Glu Ser
            35                  40                  45

Leu Asp Asn Tyr Gly Ile Arg Phe Leu Thr Trp Phe Gln Gln Lys Pro
 50                  55                  60

Gly Lys Ala Pro Lys Leu Leu Met Tyr Ala Ala Ser Asn Gln Gly Ser
 65                  70                  75                  80

Gly Val Pro Ser Arg Phe Ser Gly Ser Gly Ser Gly Thr Glu Phe Thr
                 85                  90                  95

Leu Thr Ile Ser Ser Leu Gln Pro Asp Asp Phe Ala Thr Tyr Tyr Cys
            100                 105                 110

Gln Gln Thr Lys Glu Val Pro Trp Ser Phe Gly Gln Gly Thr Lys Val
            115                 120                 125

Glu Val Lys Arg Thr
            130

<210> SEQ ID NO 40
<211> LENGTH: 141
<212> TYPE: PRT
<213> ORGANISM: Artificial Sequence
<220> FEATURE:
<223> OTHER INFORMATION: variable heavy chain of gemtuzumab

<400> SEQUENCE: 40

Met Glu Trp Ser Trp Val Phe Leu Phe Phe Leu Ser Val Thr Thr Gly
 1               5                  10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Ile
            35                  40                  45

Thr Asp Ser Asn Ile His Trp Val Arg Gln Ala Pro Gly Gln Ser Leu
 50                  55                  60

Glu Trp Ile Gly Tyr Ile Tyr Pro Tyr Asn Gly Gly Thr Asp Tyr Asn
 65                  70                  75                  80

Gln Lys Phe Lys Asn Arg Ala Thr Leu Thr Val Asp Asn Pro Thr Asn
                 85                  90                  95

Thr Ala Tyr Met Glu Leu Ser Ser Leu Arg Ser Glu Asp Thr Asp Phe
            100                 105                 110

Tyr Tyr Cys Val Asn Gly Asn Pro Trp Leu Ala Tyr Trp Gly Gln Gly
            115                 120                 125

Thr Leu Val Thr Val Ser Ser Ala Ser Thr Lys Gly Pro
130                 135                 140

<210> SEQ ID NO 41
<211> LENGTH: 10
<212> TYPE: PRT
<213> ORGANISM: Artificial Sequence
<220> FEATURE:
<223> OTHER INFORMATION: CDRL1 sequence of gemtuzumab

<400> SEQUENCE: 41

Gln Ser Pro Ser Thr Leu Ser Ala Ser Val
 1               5                  10

<210> SEQ ID NO 42
<211> LENGTH: 16
<212> TYPE: PRT
<213> ORGANISM: Artificial Sequence
<220> FEATURE:
<223> OTHER INFORMATION: CDRL2 sequence of gemtuzumab
```

-continued

<400> SEQUENCE: 42

Asp Asn Tyr Gly Ile Arg Phe Leu Thr Trp Phe Gln Gln Lys Pro Gly
1               5                   10                  15

<210> SEQ ID NO 43
<211> LENGTH: 8
<212> TYPE: PRT
<213> ORGANISM: Artificial Sequence
<220> FEATURE:
<223> OTHER INFORMATION: CDRL3 sequence of gemtuzumab

<400> SEQUENCE: 43

Phe Thr Leu Thr Ile Ser Ser Leu
1               5

<210> SEQ ID NO 44
<211> LENGTH: 11
<212> TYPE: PRT
<213> ORGANISM: Artificial Sequence
<220> FEATURE:
<223> OTHER INFORMATION: CDRH1 sequence of gemtuzumab

<400> SEQUENCE: 44

Val Gln Ser Gly Ala Glu Val Lys Lys Pro Gly
1               5                   10

<210> SEQ ID NO 45
<211> LENGTH: 7
<212> TYPE: PRT
<213> ORGANISM: Artificial Sequence
<220> FEATURE:
<223> OTHER INFORMATION: CDRH2 sequence of gemtuzumab

<400> SEQUENCE: 45

Asp Ser Asn Ile His Trp Val
1               5

<210> SEQ ID NO 46
<211> LENGTH: 9
<212> TYPE: PRT
<213> ORGANISM: Artificial Sequence
<220> FEATURE:
<223> OTHER INFORMATION: CDRH3 sequence of gemtuzumab

<400> SEQUENCE: 46

Leu Thr Val Asp Asn Pro Thr Asn Thr
1               5

<210> SEQ ID NO 47
<211> LENGTH: 113
<212> TYPE: PRT
<213> ORGANISM: Artificial Sequence
<220> FEATURE:
<223> OTHER INFORMATION: variable light chain of a representative anti-
      CD33 antibody

<400> SEQUENCE: 47

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val

```
                50                  55                  60
Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
                100                 105                 110

Arg

<210> SEQ ID NO 48
<211> LENGTH: 118
<212> TYPE: PRT
<213> ORGANISM: Artificial Sequence
<220> FEATURE:
<223> OTHER INFORMATION: variable heavy chain of a representative anti-
      CD33 antibody

<400> SEQUENCE: 48

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
        50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
                100                 105                 110

Thr Val Thr Val Ser Ser
            115

<210> SEQ ID NO 49
<211> LENGTH: 5
<212> TYPE: PRT
<213> ORGANISM: Artificial Sequence
<220> FEATURE:
<223> OTHER INFORMATION: CDRL1 of an anti-CD33 antibody

<400> SEQUENCE: 49

Ser Tyr Tyr Ile His
1               5

<210> SEQ ID NO 50
<211> LENGTH: 17
<212> TYPE: PRT
<213> ORGANISM: Artificial Sequence
<220> FEATURE:
<223> OTHER INFORMATION: CDRL2 of an anti-CD33 antibody
<220> FEATURE:
<221> NAME/KEY: misc_feature
<222> LOCATION: (16)..(16)
<223> OTHER INFORMATION: Xaa can be any naturally occurring amino acid

<400> SEQUENCE: 50

Val Ile Tyr Pro Gly Asn Asp Asp Ile Ser Tyr Asn Gln Lys Phe Xaa
1               5                   10                  15

Gly
```

```
<210> SEQ ID NO 51
<211> LENGTH: 9
<212> TYPE: PRT
<213> ORGANISM: Artificial Sequence
<220> FEATURE:
<223> OTHER INFORMATION: CDRL3 of an anti-CD33 antibody

<400> SEQUENCE: 51

Glu Val Arg Leu Arg Tyr Phe Asp Val
1               5

<210> SEQ ID NO 52
<211> LENGTH: 17
<212> TYPE: PRT
<213> ORGANISM: Artificial Sequence
<220> FEATURE:
<223> OTHER INFORMATION: CDRH1 of an anti-CD33 antibody

<400> SEQUENCE: 52

Lys Ser Ser Gln Ser Val Phe Phe Ser Ser Gln Lys Asn Tyr Leu
1               5                   10                  15

Ala

<210> SEQ ID NO 53
<211> LENGTH: 7
<212> TYPE: PRT
<213> ORGANISM: Artificial Sequence
<220> FEATURE:
<223> OTHER INFORMATION: CDRH2 of an anti-CD33 antibody

<400> SEQUENCE: 53

Trp Ala Ser Thr Arg Glu Ser
1               5

<210> SEQ ID NO 54
<211> LENGTH: 8
<212> TYPE: PRT
<213> ORGANISM: Artificial Sequence
<220> FEATURE:
<223> OTHER INFORMATION: CDRH3 of an anti-CD33 antibody

<400> SEQUENCE: 54

His Gln Tyr Leu Ser Ser Arg Thr
1               5

<210> SEQ ID NO 55
<211> LENGTH: 10
<212> TYPE: PRT
<213> ORGANISM: Artificial Sequence
<220> FEATURE:
<223> OTHER INFORMATION: CDRL1 of OKT3 antibody

<400> SEQUENCE: 55

Ser Ala Ser Ser Ser Val Ser Tyr Met Asn
1               5                   10

<210> SEQ ID NO 56
<211> LENGTH: 11
<212> TYPE: PRT
<213> ORGANISM: Artificial Sequence
<220> FEATURE:
<223> OTHER INFORMATION: CDRL2 of OKT3 antibody

<400> SEQUENCE: 56

Arg Trp Ile Tyr Asp Thr Ser Lys Leu Ala Ser
```

```
<210> SEQ ID NO 57
<211> LENGTH: 9
<212> TYPE: PRT
<213> ORGANISM: Artificial Sequence
<220> FEATURE:
<223> OTHER INFORMATION: CDRL3 of OKT3 antibody

<400> SEQUENCE: 57

Gln Gln Trp Ser Ser Asn Pro Phe Thr
1               5

<210> SEQ ID NO 58
<211> LENGTH: 13
<212> TYPE: PRT
<213> ORGANISM: Artificial Sequence
<220> FEATURE:
<223> OTHER INFORMATION: CDRH1 of CD3 T-cell activating epitope (OKT3
      antibody)

<400> SEQUENCE: 58

Lys Ala Ser Gly Tyr Thr Phe Thr Arg Tyr Thr Met His
1               5                   10

<210> SEQ ID NO 59
<211> LENGTH: 16
<212> TYPE: PRT
<213> ORGANISM: Artificial Sequence
<220> FEATURE:
<223> OTHER INFORMATION: CDRH2 of CD3 T-cell activating epitope (OKT3
      antibody)

<400> SEQUENCE: 59

Ile Asn Pro Ser Arg Gly Tyr Thr Asn Tyr Asn Gln Lys Phe Lys Asp
1               5                   10                  15

<210> SEQ ID NO 60
<211> LENGTH: 10
<212> TYPE: PRT
<213> ORGANISM: Artificial Sequence
<220> FEATURE:
<223> OTHER INFORMATION: CDRH3 of CD3 T-cell activating epitope (OKT3
      antibody)

<400> SEQUENCE: 60

Tyr Tyr Asp Asp His Tyr Cys Leu Asp Tyr
1               5                   10

<210> SEQ ID NO 61
<211> LENGTH: 242
<212> TYPE: PRT
<213> ORGANISM: Artificial Sequence
<220> FEATURE:
<223> OTHER INFORMATION: scFv derived from OKT3 which retains the
      capacity to bind CD3

<400> SEQUENCE: 61

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly
        115                 120                 125

Gly Ser Gly Gly Gly Ser Gln Ile Val Leu Thr Gln Ser Pro Ala
    130                 135                 140

Ile Met Ser Ala Ser Pro Gly Glu Lys Val Thr Met Thr Cys Ser Ala
145                 150                 155                 160

Ser Ser Ser Val Ser Tyr Met Asn Trp Tyr Gln Gln Lys Ser Gly Thr
                165                 170                 175

Ser Pro Lys Arg Trp Ile Tyr Asp Thr Ser Lys Leu Ala Ser Gly Val
            180                 185                 190

Pro Ala His Phe Arg Gly Ser Gly Ser Gly Thr Ser Tyr Ser Leu Thr
        195                 200                 205

Ile Ser Gly Met Glu Ala Glu Asp Ala Ala Thr Tyr Tyr Cys Gln Gln
    210                 215                 220

Trp Ser Ser Asn Pro Phe Thr Phe Gly Ser Gly Thr Lys Leu Glu Ile
225                 230                 235                 240

Asn Arg

<210> SEQ ID NO 62
<211> LENGTH: 11
<212> TYPE: PRT
<213> ORGANISM: Artificial Sequence
<220> FEATURE:
<223> OTHER INFORMATION: CDRL1 of CD3 T-cell activating epitope (20G6-F3
      antibody)

<400> SEQUENCE: 62

Gln Ser Leu Val His Asn Asn Gly Asn Thr Tyr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: CDRL3 of CD3 T-cell activating epitope (20G6-F3
      antibody)

<400> SEQUENCE: 63

Gly Gln Gly Thr Gln Tyr Pro Phe Thr
1               5

<210> SEQ ID NO 64
<211> LENGTH: 8
<212> TYPE: PRT
<213> ORGANISM: Artificial Sequence
<220> FEATURE:
<223> OTHER INFORMATION: CDRH1 of CD3 T-cell activating epitope (20G6-F3
      antibody)

<400> SEQUENCE: 64

Gly Phe Thr Phe Thr Lys Ala Trp
1               5
```

```
<210> SEQ ID NO 65
<211> LENGTH: 10
<212> TYPE: PRT
<213> ORGANISM: Artificial Sequence
<220> FEATURE:
<223> OTHER INFORMATION: CDRH2 of CD3 T-cell activating epitope (20G6-F3
      antibody)

<400> SEQUENCE: 65

Ile Lys Asp Lys Ser Asn Ser Tyr Ala Thr
1               5                   10

<210> SEQ ID NO 66
<211> LENGTH: 12
<212> TYPE: PRT
<213> ORGANISM: Artificial Sequence
<220> FEATURE:
<223> OTHER INFORMATION: CDRH3 of CD3 T-cell activating epitope (20G6-F3
      antibody)

<400> SEQUENCE: 66

Arg Gly Val Tyr Tyr Ala Leu Ser Pro Phe Asp Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: CDRL1 of CD3 T-cell activating epitope (4B4-D7
      antibody)

<400> SEQUENCE: 67

Gln Ser Leu Val His Asp Asn Gly Asn Thr Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: CDRL1 of TGN1412

<400> SEQUENCE: 68

His Ala Ser Gln Asn Ile Tyr Val Trp Leu Asn
1               5                   10

<210> SEQ ID NO 69
<211> LENGTH: 8
<212> TYPE: PRT
<213> ORGANISM: Artificial Sequence
<220> FEATURE:
<223> OTHER INFORMATION: CDRH1 of CD3 T-cell activating epitope (4B4-D7
      antibody) and (4E7-C9 antibody)

<400> SEQUENCE: 69

Gly Phe Thr Phe Ser Asn Ala Trp
1               5

<210> SEQ ID NO 70
<211> LENGTH: 10
<212> TYPE: PRT
<213> ORGANISM: Artificial Sequence
<220> FEATURE:
<223> OTHER INFORMATION: CDRH2 of CD3 T-cell activating epitope (4B4-D7
      antibody)

<400> SEQUENCE: 70
```

Ile Lys Ala Arg Ser Asn Asn Tyr Ala Thr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: CDRH3 of CD3 T-cell activating epitope (4B4-D7
      antibody)

<400> SEQUENCE: 71

Arg Gly Thr Tyr Tyr Ala Ser Lys Pro Phe Asp Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: CDRL1 of CD3 T-cell activating epitope (4E7-C9
      antibody)

<400> SEQUENCE: 72

Gln Ser Leu Glu His Asn Asn Gly Asn Thr Tyr
1               5                   10

<210> SEQ ID NO 73
<211> LENGTH: 7
<212> TYPE: PRT
<213> ORGANISM: Artificial Sequence
<220> FEATURE:
<223> OTHER INFORMATION: CDRL2 of TGN1412

<400> SEQUENCE: 73

Lys Ala Ser Asn Leu His Thr
1               5

<210> SEQ ID NO 74
<211> LENGTH: 9
<212> TYPE: PRT
<213> ORGANISM: Artificial Sequence
<220> FEATURE:
<223> OTHER INFORMATION: CDRL3 of TGN1412

<400> SEQUENCE: 74

Gln Gln Gly Gln Thr Tyr Pro Tyr Thr
1               5

<210> SEQ ID NO 75
<211> LENGTH: 10
<212> TYPE: PRT
<213> ORGANISM: Artificial Sequence
<220> FEATURE:
<223> OTHER INFORMATION: CDRH2 of CD3 T-cell activating epitope (4E7-C9
      antibody)

<400> SEQUENCE: 75

Ile Lys Asp Lys Ser Asn Asn Tyr Ala Thr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: CDRH3 of CD3 T-cell activating epitope (4E7-C9
      antibody)

```
<400> SEQUENCE: 76

Arg Tyr Val His Tyr Gly Ile Gly Tyr Ala Met Asp Ala
1               5                   10

<210> SEQ ID NO 77
<211> LENGTH: 11
<212> TYPE: PRT
<213> ORGANISM: Artificial Sequence
<220> FEATURE:
<223> OTHER INFORMATION: CDRL1 of CD3 T-cell activating epitope (18F5-
      H10 antibody)

<400> SEQUENCE: 77

Gln Ser Leu Val His Thr Asn Gly Asn Thr Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: CDRL3 of CD3 T-cell activating epitope (18F5-
      H10 antibody)

<400> SEQUENCE: 78

Gly Gln Gly Thr His Tyr Pro Phe Thr
1               5

<210> SEQ ID NO 79
<211> LENGTH: 8
<212> TYPE: PRT
<213> ORGANISM: Artificial Sequence
<220> FEATURE:
<223> OTHER INFORMATION: CDRH1 of CD3 T-cell activating epitope (18F5-
      H10 antibody)

<400> SEQUENCE: 79

Gly Phe Thr Phe Thr Asn Ala Trp
1               5

<210> SEQ ID NO 80
<211> LENGTH: 9
<212> TYPE: PRT
<213> ORGANISM: Artificial Sequence
<220> FEATURE:
<223> OTHER INFORMATION: CDRH2 of CD3 T-cell activating epitope (18F5-
      H10 antibody)

<400> SEQUENCE: 80

Lys Asp Lys Ser Asn Asn Tyr Ala Thr
1               5

<210> SEQ ID NO 81
<211> LENGTH: 13
<212> TYPE: PRT
<213> ORGANISM: Artificial Sequence
<220> FEATURE:
<223> OTHER INFORMATION: CDRH3 of CD3 T-cell activating epitope (18F5-
      H10 antibody)

<400> SEQUENCE: 81

Arg Tyr Val His Tyr Arg Phe Ala Tyr Ala Leu Asp Ala
1               5                   10

<210> SEQ ID NO 82
<211> LENGTH: 11
```

```
<212> TYPE: PRT
<213> ORGANISM: Artificial Sequence
<220> FEATURE:
<223> OTHER INFORMATION: CDRL1 of OKT8 antibody

<400> SEQUENCE: 82

Arg Thr Ser Arg Ser Ile Ser Gln Tyr Leu Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: CDRL2 of OKT8 antibody

<400> SEQUENCE: 83

Ser Gly Ser Thr Leu Gln Ser
1               5

<210> SEQ ID NO 84
<211> LENGTH: 9
<212> TYPE: PRT
<213> ORGANISM: Artificial Sequence
<220> FEATURE:
<223> OTHER INFORMATION: CDRL3 of OKT8 antibody

<400> SEQUENCE: 84

Gln Gln His Asn Glu Asn Pro Leu Thr
1               5

<210> SEQ ID NO 85
<211> LENGTH: 6
<212> TYPE: PRT
<213> ORGANISM: Artificial Sequence
<220> FEATURE:
<223> OTHER INFORMATION: CDRH1 of OKT8 antibody

<400> SEQUENCE: 85

Gly Phe Asn Ile Lys Asp
1               5

<210> SEQ ID NO 86
<211> LENGTH: 9
<212> TYPE: PRT
<213> ORGANISM: Artificial Sequence
<220> FEATURE:
<223> OTHER INFORMATION: CDRH2 of OKT8 antibody

<400> SEQUENCE: 86

Arg Ile Asp Pro Ala Asn Asp Asn Thr
1               5

<210> SEQ ID NO 87
<211> LENGTH: 9
<212> TYPE: PRT
<213> ORGANISM: Artificial Sequence
<220> FEATURE:
<223> OTHER INFORMATION: CDRH3 of OKT8 antibody

<400> SEQUENCE: 87

Gly Tyr Gly Tyr Tyr Val Phe Asp His
1               5

<210> SEQ ID NO 88
<211> LENGTH: 109
<212> TYPE: PRT
```

```
<213> ORGANISM: Artificial Sequence
<220> FEATURE:
<223> OTHER INFORMATION: variable light chain of antibody that binds
      KIR2DL1 and KIR2DL2/3

<400> SEQUENCE: 88

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105

<210> SEQ ID NO 89
<211> LENGTH: 123
<212> TYPE: PRT
<213> ORGANISM: Artificial Sequence
<220> FEATURE:
<223> OTHER INFORMATION: variable heavy chain of antibody that binds
      KIR2DL1 and KIR2DL2/3

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 90
<211> LENGTH: 10
<212> TYPE: PRT
<213> ORGANISM: Artificial Sequence
<220> FEATURE:
<223> OTHER INFORMATION: CDRH1 of TGN1412

<400> SEQUENCE: 90

Gly Tyr Thr Phe Thr Ser Tyr Tyr Ile His
1               5                   10

<210> SEQ ID NO 91
<211> LENGTH: 14
```

```
<212> TYPE: PRT
<213> ORGANISM: Artificial Sequence
<220> FEATURE:
<223> OTHER INFORMATION: CDRH2 of TGN1412

<400> SEQUENCE: 91

Cys Ile Tyr Pro Gly Asn Val Asn Thr Asn Tyr Asn Glu Lys
1               5                   10

<210> SEQ ID NO 92
<211> LENGTH: 11
<212> TYPE: PRT
<213> ORGANISM: Artificial Sequence
<220> FEATURE:
<223> OTHER INFORMATION: CDRH3 of anti-CD28 antibody

<400> SEQUENCE: 92

Ser His Tyr Gly Leu Asp Trp Asn Phe Asp Val
1               5                   10

<210> SEQ ID NO 93
<211> LENGTH: 55
<212> TYPE: DNA
<213> ORGANISM: Artificial Sequence
<220> FEATURE:
<223> OTHER INFORMATION: Sense oligo format
<220> FEATURE:
<221> NAME/KEY: misc_feature
<222> LOCATION: (3)..(20)
<223> OTHER INFORMATION: nnnnnnnnnnnnnnnnnn represents an 18 nucleotide
      sequence corresponding to the shRNA target sequence
<220> FEATURE:
<221> NAME/KEY: misc_feature
<222> LOCATION: (30)..(47)
<223> OTHER INFORMATION: nnnnnnnnnnnnnnnnnn represents an 18 nucleotide
      sequence corresponding to the shRNA target sequence

<400> SEQUENCE: 93
tgnnnnnnnn nnnnnnnnnn ttcaagagan nnnnnnnnnn nnnnnnnctt ttttc           55

<210> SEQ ID NO 94
<211> LENGTH: 17
<212> TYPE: PRT
<213> ORGANISM: Artificial Sequence
<220> FEATURE:
<223> OTHER INFORMATION: CDRH2 of anti-CD28 antibody

<400> SEQUENCE: 94

Cys Ile Tyr Pro Gly Asn Val Asn Thr Asn Tyr Asn Glu Lys Phe Lys
1               5                   10                  15

Asp

<210> SEQ ID NO 95
<211> LENGTH: 7
<212> TYPE: PRT
<213> ORGANISM: Artificial Sequence
<220> FEATURE:
<223> OTHER INFORMATION: CDRL1 of anti-4-1BB antibody

<400> SEQUENCE: 95

Arg Ala Ser Gln Ser Val Ser
1               5

<210> SEQ ID NO 96

<400> SEQUENCE: 96

000
```

<210> SEQ ID NO 97

<400> SEQUENCE: 97

000

<210> SEQ ID NO 98
<211> LENGTH: 5
<212> TYPE: PRT
<213> ORGANISM: Artificial Sequence
<220> FEATURE:
<223> OTHER INFORMATION: CDRL1 of h2H12d

<400> SEQUENCE: 98

Asn Tyr Asp Ile Asn
1               5

<210> SEQ ID NO 99
<211> LENGTH: 17
<212> TYPE: PRT
<213> ORGANISM: Artificial Sequence
<220> FEATURE:
<223> OTHER INFORMATION: CDRL2 of h2H12d

<400> SEQUENCE: 99

Trp Ile Tyr Pro Gly Asp Gly Ser Thr Lys Tyr Asn Glu Lys Phe Lys
1               5                   10                  15

Ala

<210> SEQ ID NO 100
<211> LENGTH: 8
<212> TYPE: PRT
<213> ORGANISM: Artificial Sequence
<220> FEATURE:
<223> OTHER INFORMATION: CDRL3 of h2H12d

<400> SEQUENCE: 100

Gly Tyr Glu Asp Ala Met Asp Tyr
1               5

<210> SEQ ID NO 101
<211> LENGTH: 11
<212> TYPE: PRT
<213> ORGANISM: Artificial Sequence
<220> FEATURE:
<223> OTHER INFORMATION: CDRH1 of h2H12d

<400> SEQUENCE: 101

Lys Ala Ser Gln Asp Ile Asn Ser Tyr Leu Ser
1               5                   10

<210> SEQ ID NO 102
<211> LENGTH: 7
<212> TYPE: PRT
<213> ORGANISM: Artificial Sequence
<220> FEATURE:
<223> OTHER INFORMATION: CDRH2 of h2H12d

<400> SEQUENCE: 102

Arg Ala Asn Arg Leu Val Asp
1               5

<210> SEQ ID NO 103
<211> LENGTH: 9
<212> TYPE: PRT

<213> ORGANISM: Artificial Sequence
<220> FEATURE:
<223> OTHER INFORMATION: CDRH3 of h2H12d

<400> SEQUENCE: 103

Leu Gln Tyr Asp Glu Phe Pro Leu Thr
1               5

<210> SEQ ID NO 104
<211> LENGTH: 3417
<212> TYPE: DNA
<213> ORGANISM: Artificial Sequence
<220> FEATURE:
<223> OTHER INFORMATION: FV Pol gene

<400> SEQUENCE: 104

| | | | | | |
|---|---|---|---|---|---|
| atgaatcccc | tccaactgtt | gcagcctctg | cccgcagaga | tcaaagggac | taaactgctg | 60 |
| gctcattggg | actctggagc | aaccataaca | tgcataccag | aaagcttcct | tgaggacgag | 120 |
| cagcctatca | aaaaacatt | gattaagacg | atccacgggg | aaaagcagca | gaacgtgtat | 180 |
| tacgttacct | taaggtgaa | gggccggaaa | gtcgaggccg | aggtcattgc | ctctccatac | 240 |
| gaatacattc | tgctctcacc | caccgacgtg | ccatggttga | cccagcagcc | tcttcagctg | 300 |
| actatcctgg | tccctttgca | ggagtaccag | gaaaagattc | tgagcaagac | ggcgcttccc | 360 |
| gaagatcaga | aacagcagct | gaagaccctc | ttcgtgaaat | acgataatct | ctggcagcac | 420 |
| tgggaaaacc | aggtgggcca | tcggaagatt | cgaccccaca | atatcgccac | gggcgactat | 480 |
| ccacctaggc | ctcagaagca | gtatcccatc | aacccaaaag | caaaaccaag | catccagatc | 540 |
| gtcatcgatg | atttgcttaa | gcaaggagtg | ctcaccccac | aaaatagcac | tatgaacacc | 600 |
| ccagtgtacc | ccgtgcccaa | accggacggc | agatggagaa | tggtattgga | ctatcgcgaa | 660 |
| gttaacaaaa | ccatacctt | gaccgcagcc | cagaatcaac | acagcgccgg | catcttggct | 720 |
| acgatcgtga | gacagaagta | caaaacaact | ctcgatctgg | ccaacggctt | tgggctcac | 780 |
| ccaatcactc | cagagagcta | ctggcttacc | gcctttacat | ggcagggaa | caatactgt | 840 |
| tggacccggc | tgcctcaggg | gttcttgaat | tcacccgcac | tgtttacagc | tgacgtcgtt | 900 |
| gatctgctga | agaaatccc | caatgtgcag | gtatacgtgg | acgacatcta | tctttcccac | 960 |
| gacgatccaa | aagagcatgt | tcagcagctc | gaaaaagttt | tccagatcct | gctgcaggct | 1020 |
| ggttatgtcg | tctcactcaa | gaagtctgag | ataggacaaa | agactgtgga | gtttctggga | 1080 |
| tttaacatca | ccaaggaagg | acggggattg | actgatacgt | tcaagactaa | gctgctcaac | 1140 |
| attactcctc | ccaaggatct | taagcagctg | cagagtattc | ttggcttgct | caattttgcc | 1200 |
| cggaattta | tccctaactt | cgctgagctt | gttcagcccc | tgtataatct | gatagcctcc | 1260 |
| gccaagggta | gtacatcga | atggagcgag | gagaatacta | aacagttgaa | catggtgatt | 1320 |
| gaggcactta | acactgcctc | caacttggag | gaacgactgc | cagagcagcg | acttgtgatt | 1380 |
| aaagtgaaca | cctcaccaag | tgcggggtac | gtgcgctact | acaacgagac | aggcaaaaag | 1440 |
| cccataatgt | acctgaacta | tgtcttctca | aaagctgagc | tcaagtttag | catgctcgag | 1500 |
| aagctgctta | ctaccatgca | caaggccctg | ataaaggcca | tggaccttgc | catggggcaa | 1560 |
| gaaatcctcg | tgtacagccc | catcgttttcc | atgacgaaga | tccagaaaac | accactgccc | 1620 |
| gaacgaaagg | ccttgcctat | cagatggatt | acttggatga | cctaccttga | ggaccccgc | 1680 |
| atccagtttc | attatgataa | gaccctgcct | gaactgaaac | acatcccaga | cgtgtacacc | 1740 |
| tccagtcagt | ccccagtcaa | gcacccttct | caatatgaag | gagtgtttta | taccgatggg | 1800 |

```
agtgccatca aatcccctga ccccacaaaa agtaacaacg ccggtatggg tatcgtccac   1860
gcgacctata agcccgagta tcaggtactg aaccagtggt ccatcccgct ggggaatcat   1920
accgcccaga tggcggaaat tgccgcagtc gagtttgcct gcaaaaaggc attgaaaatc   1980
ccagggcctg tcctggtcat caccgactct ttctacgtag ccgagtcagc caataaggaa   2040
ctgcccctatt ggaaaagtaa tggcttcgtg aacaacaaga agaagccact gaaacatatt   2100
agcaaatgga atctattgc cgagtgtctg tctatgaagc ccgacatcac tatccagcac   2160
gaaaagggcc atcagcccac caacactagt atccatacgg agggaaacgc tctggccgat   2220
aagctagcca ctcaagggag ttacgtcgtg aactgcaaca ccaagaaacc taaccttgac   2280
gccgaattgg accaattgct gcagggacat tacataaagg ctaccccaa gcagtatacc   2340
tattttctgg aagacggcaa ggtaaaagtg tcccggccag agggcgtcaa gatcatcccg   2400
ccacaaagcg acagacagaa aatcgttctg caggcccaca acctcgctca tactgggcgc   2460
gaagctactc tgctcaagat tgccaatctg tattggtggc cgaatatgag aaaagacgtc   2520
gtaaagcaac tggggcgctg tcagcagtgt ttgatcacta acgcaagtaa caaagcaagt   2580
gggccgattc ttcgaccaga ccgccctcag aaaccgttcg ataagttttt tatagattac   2640
attggacctc tgcctcccag tcaaggctac ctctacgtgc tggtagtggt cgatggcatg   2700
acgggattca catggctgta cccgaccaag gcgccgagta cttccgcgac ggtcaagagc   2760
cttaacgttc tcacctccat agctatcccc aaagttatcc actccgacca gggcgcagct   2820
ttcaccagct ctaccttcgc ggagtgggcc aaagagaggg ggattcactt ggaattctca   2880
acgccttacc accccaatc tagcggaaag gtcgagagaa aaaattcaga tatcaaaaga   2940
ctgttgacca agctgcttgt tggccgccct acaaagtggt atgacctcct gcctgtcgtc   3000
cagctggcac tgaacaacac ctacagcccc gtgctcaagt atacacctca tcagttgctg   3060
tttggtattg atagtaacac tcctttcgca aatcaggata cgttggatct cactcgcgaa   3120
gaagagctca gtttgctgca ggagatacgc acgagtctgt accacccttc cactcctccc   3180
acttctagta ggtcttggtc tccagttgtg ggacagcttg ttcaggaaag agtcgcccgg   3240
cccgcatcac tgcggccccg gtggcacaaa ccgtctactg tactgaaggt gctcaaccca   3300
cggacggtgg taatccttga ccatctcgga aacaaccgga cagtgtcaat cgataacctc   3360
aagccaacct cccaccaaaa cggcacaacc aatgacacag ccacaatgga tcattag     3417
```

<210> SEQ ID NO 105
<211> LENGTH: 1138
<212> TYPE: PRT
<213> ORGANISM: Artificial Sequence
<220> FEATURE:
<223> OTHER INFORMATION: sequence encoded by FV Pol gene

<400> SEQUENCE: 105

```
Met Asn Pro Leu Gln Leu Leu Gln Pro Leu Pro Ala Glu Ile Lys Gly
1               5                   10                  15

Thr Lys Leu Leu Ala His Trp Asp Ser Gly Ala Thr Ile Thr Cys Ile
            20                  25                  30

Pro Glu Ser Phe Leu Glu Asp Glu Gln Pro Ile Lys Lys Thr Leu Ile
        35                  40                  45

Lys Thr Ile His Gly Glu Lys Gln Gln Asn Val Tyr Tyr Val Thr Phe
    50                  55                  60

Lys Val Lys Gly Arg Lys Val Glu Ala Glu Val Ile Ala Ser Pro Tyr
65                  70                  75                  80
```

-continued

```
Glu Tyr Ile Leu Leu Ser Pro Thr Asp Val Pro Trp Leu Thr Gln Gln
                 85                  90                  95

Pro Leu Gln Leu Thr Ile Leu Val Pro Leu Gln Glu Tyr Gln Glu Lys
            100                 105                 110

Ile Leu Ser Lys Thr Ala Leu Pro Glu Asp Gln Lys Gln Gln Leu Lys
            115                 120                 125

Thr Leu Phe Val Lys Tyr Asp Asn Leu Trp Gln His Trp Glu Asn Gln
        130                 135                 140

Val Gly His Arg Lys Ile Arg Pro His Asn Ile Ala Thr Gly Asp Tyr
145                 150                 155                 160

Pro Pro Arg Pro Gln Lys Gln Tyr Pro Ile Asn Pro Lys Ala Lys Pro
                165                 170                 175

Ser Ile Gln Ile Val Ile Asp Asp Leu Leu Lys Gln Gly Val Leu Thr
            180                 185                 190

Pro Gln Asn Ser Thr Met Asn Thr Pro Val Tyr Pro Val Pro Lys Pro
            195                 200                 205

Asp Gly Arg Trp Arg Met Val Leu Asp Tyr Arg Glu Val Asn Lys Thr
        210                 215                 220

Ile Pro Leu Thr Ala Ala Gln Asn Gln His Ser Ala Gly Ile Leu Ala
225                 230                 235                 240

Thr Ile Val Arg Gln Lys Tyr Lys Thr Thr Leu Asp Leu Ala Asn Gly
                245                 250                 255

Phe Trp Ala His Pro Ile Thr Pro Glu Ser Tyr Trp Leu Thr Ala Phe
            260                 265                 270

Thr Trp Gln Gly Lys Gln Tyr Cys Trp Thr Arg Leu Pro Gln Gly Phe
        275                 280                 285

Leu Asn Ser Pro Ala Leu Phe Thr Ala Asp Val Val Asp Leu Leu Lys
        290                 295                 300

Glu Ile Pro Asn Val Gln Val Tyr Val Asp Asp Ile Tyr Leu Ser His
305                 310                 315                 320

Asp Asp Pro Lys Glu His Val Gln Gln Leu Glu Lys Val Phe Gln Ile
                325                 330                 335

Leu Leu Gln Ala Gly Tyr Val Val Ser Leu Lys Lys Ser Glu Ile Gly
            340                 345                 350

Gln Lys Thr Val Glu Phe Leu Gly Phe Asn Ile Thr Lys Glu Gly Arg
        355                 360                 365

Gly Leu Thr Asp Thr Phe Lys Thr Lys Leu Leu Asn Ile Thr Pro Pro
    370                 375                 380

Lys Asp Leu Lys Gln Leu Gln Ser Ile Leu Gly Leu Leu Asn Phe Ala
385                 390                 395                 400

Arg Asn Phe Ile Pro Asn Phe Ala Glu Leu Val Gln Pro Leu Tyr Asn
                405                 410                 415

Leu Ile Ala Ser Ala Lys Gly Lys Tyr Ile Glu Trp Ser Glu Glu Asn
            420                 425                 430

Thr Lys Gln Leu Asn Met Val Ile Glu Ala Leu Asn Thr Ala Ser Asn
        435                 440                 445

Leu Glu Glu Arg Leu Pro Glu Gln Arg Leu Val Ile Lys Val Asn Thr
    450                 455                 460

Ser Pro Ser Ala Gly Tyr Val Arg Tyr Tyr Asn Glu Thr Gly Lys Lys
465                 470                 475                 480

Pro Ile Met Tyr Leu Asn Tyr Val Phe Ser Lys Ala Glu Leu Lys Phe
                485                 490                 495

Ser Met Leu Glu Lys Leu Leu Thr Thr Met His Lys Ala Leu Ile Lys
```

```
                500                 505                 510
Ala Met Asp Leu Ala Met Gly Gln Glu Ile Leu Val Tyr Ser Pro Ile
            515                 520                 525

Val Ser Met Thr Lys Ile Gln Lys Thr Pro Leu Pro Glu Arg Lys Ala
            530                 535                 540

Leu Pro Ile Arg Trp Ile Thr Trp Met Thr Tyr Leu Glu Asp Pro Arg
545                 550                 555                 560

Ile Gln Phe His Tyr Asp Lys Thr Leu Pro Glu Leu Lys His Ile Pro
                565                 570                 575

Asp Val Tyr Thr Ser Ser Gln Ser Pro Val Lys His Pro Ser Gln Tyr
            580                 585                 590

Glu Gly Val Phe Tyr Thr Asp Gly Ser Ala Ile Lys Ser Pro Asp Pro
            595                 600                 605

Thr Lys Ser Asn Asn Ala Gly Met Gly Ile Val His Ala Thr Tyr Lys
            610                 615                 620

Pro Glu Tyr Gln Val Leu Asn Gln Trp Ser Ile Pro Leu Gly Asn His
625                 630                 635                 640

Thr Ala Gln Met Ala Glu Ile Ala Ala Val Glu Phe Ala Cys Lys Lys
                645                 650                 655

Ala Leu Lys Ile Pro Gly Pro Val Leu Val Ile Thr Asp Ser Phe Tyr
            660                 665                 670

Val Ala Glu Ser Ala Asn Lys Glu Leu Pro Tyr Trp Lys Ser Asn Gly
            675                 680                 685

Phe Val Asn Asn Lys Lys Lys Pro Leu Lys His Ile Ser Lys Trp Lys
            690                 695                 700

Ser Ile Ala Glu Cys Leu Ser Met Lys Pro Asp Ile Thr Ile Gln His
705                 710                 715                 720

Glu Lys Gly His Gln Pro Thr Asn Thr Ser Ile His Thr Glu Gly Asn
                725                 730                 735

Ala Leu Ala Asp Lys Leu Ala Thr Gln Gly Ser Tyr Val Val Asn Cys
            740                 745                 750

Asn Thr Lys Lys Pro Asn Leu Asp Ala Glu Leu Asp Gln Leu Leu Gln
            755                 760                 765

Gly His Tyr Ile Lys Gly Tyr Pro Lys Gln Tyr Thr Tyr Phe Leu Glu
            770                 775                 780

Asp Gly Lys Val Lys Val Ser Arg Pro Glu Gly Val Lys Ile Ile Pro
785                 790                 795                 800

Pro Gln Ser Asp Arg Gln Lys Ile Val Leu Gln Ala His Asn Leu Ala
                805                 810                 815

His Thr Gly Arg Glu Ala Thr Leu Leu Lys Ile Ala Asn Leu Tyr Trp
            820                 825                 830

Trp Pro Asn Met Arg Lys Asp Val Val Lys Gln Leu Gly Arg Cys Gln
            835                 840                 845

Gln Cys Leu Ile Thr Asn Ala Ser Asn Lys Ala Ser Gly Pro Ile Leu
            850                 855                 860

Arg Pro Asp Arg Pro Gln Lys Pro Phe Asp Lys Phe Phe Ile Asp Tyr
865                 870                 875                 880

Ile Gly Pro Leu Pro Pro Ser Gln Gly Tyr Leu Tyr Val Leu Val Val
                885                 890                 895

Val Asp Gly Met Thr Gly Phe Thr Trp Leu Tyr Pro Thr Lys Ala Pro
            900                 905                 910

Ser Thr Ser Ala Thr Val Lys Ser Leu Asn Val Leu Thr Ser Ile Ala
            915                 920                 925
```

```
Ile Pro Lys Val Ile His Ser Asp Gln Gly Ala Ala Phe Thr Ser Ser
    930                 935                 940

Thr Phe Ala Glu Trp Ala Lys Glu Arg Gly Ile His Leu Glu Phe Ser
945                 950                 955                 960

Thr Pro Tyr His Pro Gln Ser Ser Gly Lys Val Glu Arg Lys Asn Ser
                965                 970                 975

Asp Ile Lys Arg Leu Leu Thr Lys Leu Leu Val Gly Arg Pro Thr Lys
            980                 985                 990

Trp Tyr Asp Leu Leu Pro Val Val Gln Leu Ala Leu Asn Asn Thr Tyr
        995                 1000                1005

Ser Pro Val Leu Lys Tyr Thr Pro His Gln Leu Leu Phe Gly Ile
    1010                1015                1020

Asp Ser Asn Thr Pro Phe Ala Asn Gln Asp Thr Leu Asp Leu Thr
    1025                1030                1035

Arg Glu Glu Glu Leu Ser Leu Leu Gln Glu Ile Arg Thr Ser Leu
    1040                1045                1050

Tyr His Pro Ser Thr Pro Pro Thr Ser Ser Arg Ser Trp Ser Pro
    1055                1060                1065

Val Val Gly Gln Leu Val Gln Glu Arg Val Ala Arg Pro Ala Ser
    1070                1075                1080

Leu Arg Pro Arg Trp His Lys Pro Ser Thr Val Leu Lys Val Leu
    1085                1090                1095

Asn Pro Arg Thr Val Val Ile Leu Asp His Leu Gly Asn Asn Arg
    1100                1105                1110

Thr Val Ser Ile Asp Asn Leu Lys Pro Thr Ser His Gln Asn Gly
    1115                1120                1125

Thr Thr Asn Asp Thr Ala Thr Met Asp His
    1130                1135

<210> SEQ ID NO 106
<211> LENGTH: 511
<212> TYPE: DNA
<213> ORGANISM: Artificial Sequence
<220> FEATURE:
<223> OTHER INFORMATION: PGK Promoter

<400> SEQUENCE: 106
ggggttgggg ttgcgccttt tccaaggcag ccctgggttt gcgcagggac gcggctgctc    60
tgggcgtggt tccgggaaac gcagcggcgc cgaccctggg tctcgcacat tcttcacgtc   120
cgttcgcagc gtcaccccga tcttcgccgc tacccttgtg ggccccccgg cgacgcttcc   180
tgctccgccc ctaagtcggg aaggttcctt gcggttcgcg cgtgccgga cgtgacaaac    240 ggaagccgca cgtctcacta gtaccctcgc agacggacag cgccaggag caatggcagc    300 gcgccgaccg cgatgggctg tggccaatag cggctgctca gcggggcgcg ccgagagcag   360
cggccgggaa gggggcggtgc gggaggcggg gtgtggggcg gtagtgtggg ccctgttcct   420
gcccgcgcgg tgttccgcat tctgcaagcc tccggagcgc acgtcggcag tcggctccct   480
cgttgaccga atcaccgacc tctctcccca g                                   511

<210> SEQ ID NO 107
<211> LENGTH: 363
<212> TYPE: PRT
<213> ORGANISM: Homo sapiens

<400> SEQUENCE: 107
```

Met Ala Gln Thr Pro Ala Phe Asp Lys Pro Lys Val Glu Leu His Val
1               5                   10                  15

His Leu Asp Gly Ser Ile Lys Pro Glu Thr Ile Leu Tyr Tyr Gly Arg
            20                  25                  30

Arg Arg Gly Ile Ala Leu Pro Ala Asn Thr Ala Glu Gly Leu Leu Asn
        35                  40                  45

Val Ile Gly Met Asp Lys Pro Leu Thr Leu Pro Asp Phe Leu Ala Lys
    50                  55                  60

Phe Asp Tyr Tyr Met Pro Ala Ile Ala Gly Cys Arg Glu Ala Ile Lys
65              70                  75                  80

Arg Ile Ala Tyr Glu Phe Val Glu Met Lys Ala Lys Leu Gly Val Val
                85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

Val Val Ala Leu Val Gly Gln Gly Leu Gln Gly Glu Arg Asp Phe
    130                 135                 140

Gly Val Lys Ala Arg Ser Ile Leu Cys Cys Met Arg His Gln Pro Asn
145             150                 155                 160

Trp Ser Pro Lys Val Val Glu Leu Cys Lys Lys Tyr Gln Gln Gln Thr
            165                 170                 175

Val Val Ala Ile Asp Leu Ala Gly Asp Glu Thr Ile Pro Gly Ser Ser
        180                 185                 190

Leu Leu Pro Gly His Val Gln Ala Tyr Gln Glu Ala Val Lys Ser Gly
        195                 200                 205

Ile His Arg Thr Val His Ala Gly Glu Val Gly Ser Ala Glu Val Val
210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
            245                 250                 255

Met His Phe Glu Ile Cys Pro Trp Ser Ser Tyr Leu Thr Gly Ala Trp
        260                 265                 270

Lys Pro Asp Thr Glu His Ala Val Ile Arg Leu Lys Asn Asp Gln Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
            325                 330                 335

Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
        355                 360

<210> SEQ ID NO 108
<211> LENGTH: 6
<212> TYPE: PRT
<213> ORGANISM: Artificial Sequence
<220> FEATURE:
<223> OTHER INFORMATION: CDRL2 of anti-4-1BB antibody

<400> SEQUENCE: 108

Ala Ser Asn Arg Ala Thr
1               5

<210> SEQ ID NO 109
<211> LENGTH: 10
<212> TYPE: PRT
<213> ORGANISM: Artificial Sequence
<220> FEATURE:
<223> OTHER INFORMATION: CDRL3 of anti-4-1BB antibody

<400> SEQUENCE: 109

Gln Arg Ser Asn Trp Pro Pro Ala Leu Thr
1               5                   10

<210> SEQ ID NO 110
<211> LENGTH: 4
<212> TYPE: PRT
<213> ORGANISM: Artificial Sequence
<220> FEATURE:
<223> OTHER INFORMATION: CDRH1 of anti-4-1BB antibody

<400> SEQUENCE: 110

Tyr Tyr Trp Ser
1

<210> SEQ ID NO 111
<211> LENGTH: 12
<212> TYPE: PRT
<213> ORGANISM: Artificial Sequence
<220> FEATURE:
<223> OTHER INFORMATION: CDRH3 of anti-4-1BB antibody

<400> SEQUENCE: 111

Tyr Gly Pro Gly Asn Tyr Asp Trp Tyr Phe Asp Leu
1               5                   10

<210> SEQ ID NO 112
<211> LENGTH: 11
<212> TYPE: PRT
<213> ORGANISM: Artificial Sequence
<220> FEATURE:
<223> OTHER INFORMATION: CDRL1 of anti-4-1BB antibody

<400> SEQUENCE: 112

Ser Gly Asp Asn Ile Gly Asp Gln Tyr Ala His
1               5                   10

<210> SEQ ID NO 113
<211> LENGTH: 7
<212> TYPE: PRT
<213> ORGANISM: Artificial Sequence
<220> FEATURE:
<223> OTHER INFORMATION: CDRL2 of anti-4-1BB antibody

<400> SEQUENCE: 113

Gln Asp Lys Asn Arg Pro Ser
1               5

<210> SEQ ID NO 114
<211> LENGTH: 11
<212> TYPE: PRT
<213> ORGANISM: Artificial Sequence
<220> FEATURE:
<223> OTHER INFORMATION: CDRL3 of anti-4-1BB antibody

<400> SEQUENCE: 114

Ala Thr Tyr Thr Gly Phe Gly Ser Leu Ala Val

<210> SEQ ID NO 115
<211> LENGTH: 10
<212> TYPE: PRT
<213> ORGANISM: Artificial Sequence
<220> FEATURE:
<223> OTHER INFORMATION: CDRH1 of anti-4-1BB antibody

<400> SEQUENCE: 115

Gly Tyr Ser Phe Ser Thr Tyr Trp Ile Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: CDRH2 of anti-4-1BB antibody

<400> SEQUENCE: 116

Lys Ile Tyr Pro Gly Asp Ser Tyr Thr Asn Tyr Ser Pro Ser
1               5                   10

<210> SEQ ID NO 117
<211> LENGTH: 4368
<212> TYPE: DNA
<213> ORGANISM: Homo sapiens

<400> SEQUENCE: 117

```
atgtccgact cgtgggtccc gaactccgcc tcgggccagg acccaggggg ccgccggagg      60
gcctgggccg agctgctggc gggaagggtc aagagggaaa aatataatcc tgaaagggca     120
cagaaattaa aggaatcagc tgtgcgcctc ctgcgaagcc atcaggacct gaatgccctt     180
ttgcttgagg tagaaggtcc actgtgtaaa aaattgtctc tcagcaaagt gattgactgt     240
gacagttctg aggcctatgc taatcattct agttcattta taggctctgc tttgcaggat     300
caagcctcaa ggctgggggt tcccgtgggt attctctcag ccgggatggt tgcctctagc     360
gtgggacaga tctgcacggc tccagcggag accagtcacc ctgtgctgct gactgtggag     420
cagagaaaga agctgtcttc cctgttagag tttgctcagt atttattggc acacagtatg     480
ttctcccgtc tttccttctg tcaagaatta tggaaaatac agagttcttt gttgcttgaa     540
gcggtgtggc atcttcacgt acaaggcatt gtgagcctgc aagagctgct ggaaagccat     600
cccgacatgc atgctgtggg atcgtggctc ttcaggaatc tgtgctgcct ttgtgaacag     660
atggaagcat cctgccagca tgctgacgtc gccagggcca tgctttctga ttttgttcaa     720
atgtttgttt tgagggattt tcagaaaaac tcagatctga aagaactgtg ggagcctgaa     780
aaaatgccgc aggtcacggt tgatgtactg cagagaatgc tgattttgtgc acttgacgct     840
ttggctgctg gagtacagga ggagtcctcc actcacaaga tcgtgaggtg ctggttcgga     900
gtgttcagtg gacacacgct tggcagtgta atttccacag atcctctgaa gaggttcttc     960
agtcataccc tgactcagat actcactcac agccctgtgc tgaaagcatc tgatgctgtt    1020
cagatgcaga gagagtggag ctttgcgcgg acacaccctc tgctcacctc actgtaccgc    1080
aggctctttg tgatgctgag tgcagaggag ttggttggcc atttgcaaga agttctggaa    1140
acgcaggagg ttcactggca gagagtgctc tcctttgtgt ctgccctggt tgtctgcttt    1200
ccagaagcgc agcagctgct tgaagactgg gtggcgcgtt tgatgcccca ggcattcgag    1260
agctgccagc tggacagcat ggtcactgcg ttcctggttg tgcgccaggc agcactggag    1320
```

```
ggcccctctg cgttcctgtc atatgcagac tggttcaagg cctcctttgg gagcacacga   1380
ggctaccatg gctgcagcaa gaaggccctg gtcttcctgt ttacgttctt gtcagaactc   1440
gtgccttttg agtctccccg gtacctgcag gtgcacattc tccacccacc cctggttccc   1500
agcaagtacc gctccctcct cacagactac atctcattgg ccaagacacg gctggccgac   1560
ctcaaggttt ctatagaaaa catgggactc tacgaggatt tgtcatcagc tggggacatt   1620
actgagcccc acagccaagc tcttcaggat gttgaaaagg ccatcatggt gtttgagcat   1680
acggggaaca tcccagtcac cgtcatggag gccagcatat tcaggaggcc ttactacgtg   1740
tcccacttcc tccccgccct gctcacacct cgagtgctcc ccaaagtccc tgactcccgt   1800
gtggcgttta tagagtctct gaagagagca gataaaatcc cccatctct gtactccacc    1860
tactgccagg cctgctctgc tgctgaagag aagccagaag atgcagccct gggagtgagg   1920
gcagaaccca actctgctga ggagcccctg gacagctca cagctgcact gggagagctg     1980
agagcctcca tgacagaccc cagccagcgt gatgttatat cggcacaggt ggcagtgatt   2040
tctgaaagac tgagggctgt cctgggccac aatgaggatg acagcagcgt tgagatatca   2100
aagattcagc tcagcatcaa cacgccgaga ctggagccac gggaacacat tgctgtggac   2160
ctcctgctga cgtctttctg tcagaacctg atggctgcct ccagtgtcgc tcccccggag   2220
aggcagggtc cctgggctgc cctcttcgtg aggaccatgt gtggacgtgt gctccctgca   2280
gtgctcaccc ggctctgcca gctgctccgt caccagggcc cgagcctgag tgccccacat   2340
gtgctggggt tggctgccct ggccgtgcac ctgggtgagt ccaggtctgc gctcccagag   2400
gtggatgtgg gtcctcctgc acctggtgct ggccttcctg tccctgcgct ctttgacagc   2460
ctcctgacct gtaggacgag ggattccttg ttcttctgcc tgaaattttg tacagcagca   2520
atttcttact ctctctgcaa gttttcttcc cagtcacgag atactttgtg cagctgctta   2580
tctccaggcc ttattaaaaa gtttcagttc ctcatgttca gattgttctc agaggcccga   2640
cagcctcttt ctgaggagga cgtagccagc ctttcctgga gacccttgca ccttccttct   2700
gcagactggc agagagctgc cctctctctc tggacacaca gaaccttccg agaggtgttg   2760
aaagaggaag atgttcactt aacttaccaa gactggttac acctggagct ggaaattcaa   2820
cctgaagctg atgctctttc agatactgaa cggcaggact tccaccagtg ggcgatccat   2880
gagcactttc tccctgagtc ctcggcttca gggggctgtg acggagacct gcaggctgcg   2940
tgtaccattc ttgtcaacgc actgatggat ttccaccaaa gctcaaggag ttatgaccac   3000
tcagaaaatt ctgatttggt ctttggtggc cgcacaggaa atgaggatat tatttccaga   3060
ttgcaggaga tggtagctga cctggagctg cagcaagacc tcatagtgcc tctcggccac   3120
accccttccc aggagcactt cctctttgag attttccgca gacggctcca ggctctgaca   3180
agcgggtgga gcgtggctgc cagccttcag agacagaggg agctgctaat gtacaaacgg   3240
atcctcctcc gcctgccttc gtctgtcctc tgcggcagca gcttccaggc agaacagccc   3300
atcactgcca gatgcgagca gttcttccac ttggtcaact ctgagatgag aaacttctgc   3360
tcccacggag gtgccctgac acaggacatc actgccccact tcttcagggg cctcctgaac   3420
gcctgtctgc ggagcagaga cccctccctg atggtcgact tcatactggc caagtgccag   3480
acgaaatgcc ccttaatttt gacctctgct ctggtgtggt ggccgagcct ggagcctgtg   3540
ctgctctgcc ggtggaggag acactgccag agccgctgc cccgggaact gcagaagcta    3600
caagaaggcc ggcagtttgc cagcgatttc ctctcccctg aggctgcctc cccagcaccc   3660
```

| | |
|---|---|
| aacccggact ggctctcagc tgctgcactg cactttgcga ttcaacaagt cagggaagaa | 3720 |
| aacatcagga agcagctaaa gaagctggac tgcgagagag aggagctatt ggttttcctt | 3780 |
| ttcttcttct ccttgatggg cctgctgtcg tcacatctga cctcaaatag caccacagac | 3840 |
| ctgccaaagg cttccacgt ttgtgcagca atcctcgagt gtttagagaa gaggaagata | 3900 |
| tcctggctgg cactctttca gttgacagag agtgacctca ggctggggcg ctcctcctc | 3960 |
| cgtgtggccc cggatcagca caccaggctg ctgcctttcg cttttttacag tcttctctcc | 4020 |
| tacttccatg aagacgcggc catcagggaa gaggccttcc tgcatgttgc tgtggacatg | 4080 |
| tacttgaagc tggtccagct cttcgtggct ggggatacaa gcacagtttc acctccagct | 4140 |
| ggcaggagcc tggagctcaa gggtcagggc aaccccgtgg aactgataac aaaagctcgt | 4200 |
| cttttctgc tgcagttaat acctcggtgc ccgaaaaaga gcttctcaca cgtggcagag | 4260 |
| ctgctggctg atcgtgggga ctgcgaccca gaggtgagcg ccgccctcca gagcagacag | 4320 |
| caggctgccc ctgacgctga cctgtcccag gagcctcatc tcttctga | 4368 |

<210> SEQ ID NO 118
<211> LENGTH: 1677
<212> TYPE: DNA
<213> ORGANISM: Homo sapiens

<400> SEQUENCE: 118

| | |
|---|---|
| atggctcaag attcagtaga tctttcttgt gattatcagt tttggatgca gaagctttct | 60 |
| gtatgggatc aggcttccac tttggaaacc cagcaagaca cctgtcttca cgtggctcag | 120 |
| ttccaggagt tcctaaggaa gatgtatgaa gccttgaaag atgtggattc taatacagtc | 180 |
| attgaaagat tccccacaat tggtcaactg ttggcaaaag cttgttggaa tccttttatt | 240 |
| ttagcatatg atgaaagcca aaaaattcta atatggtgct tatgttgtct aattaacaaa | 300 |
| gaaccacaga attctggaca atcaaaactt aactcctgga tacagggtgt attatctcat | 360 |
| atactttcag cactcagatt tgataaagaa gttgctcttt tcactcaagg tcttgggtat | 420 |
| gcacctatag attactatcc tggtttgctt aaaaatatgg ttttatcatt agcgtctgaa | 480 |
| ctcagagaga atcatcttaa tggatttaac actcaaaggc gaatggctcc cgagcgagtg | 540 |
| gcgtccctgt cacgagtttg tgtcccactt attaccctga cagatgttga cccctggtg | 600 |
| gaggctctcc tcatctgtca tggacgtgaa cctcaggaaa tcctccagcc agagttcttt | 660 |
| gaggctgtaa cgaggccat tttgctgaag aagatttctc tccccatgtc agctgtagtc | 720 |
| tgcctctggc ttcggcacct tcccagcctt gaaaaagcaa tgctgcatct ttttgaaaag | 780 |
| ctaatctcca gtgagagaaa ttgtctgaga aggatcgaat gctttataaa agattcatcg | 840 |
| ctgcctcaag cagcctgcca ccctgccata ttccggggttg ttgatgagat gttcaggtgt | 900 |
| gcactcctgg aaaccgatgg ggccctggaa atcatagcca ctattcaggt gtttacgcag | 960 |
| tgctttgtag aagctctgga gaaagcaagc aagcagctgc ggtttgcact caagacctac | 1020 |
| tttccttaca cttctccatc tcttgccatg gtgctgctgc aagaccctca agatatccct | 1080 |
| cggggacact ggctccagac actgaagcat atttctgaac tgctcagaga agcagttgaa | 1140 |
| gaccagactc atgggtcctg cggaggtccc tttgagagct ggttcctgtt cattcacttc | 1200 |
| ggaggatggg ctgagatggt ggcagagcaa ttactgatgt cggcagccga acccccacg | 1260 |
| gccctgctgt ggctcttggc cttctactac ggccccgtg atgggaggca gcagagagca | 1320 |
| cagactatg tccaggtgaa ggccgtgctg gccacctcc tggcaatgtc cagaagcagc | 1380 |
| agcctctcag cccaggacct gcagacggta gcaggacagg gcacagacac agacctcaga | 1440 |

```
gctcctgcac aacagctgat caggcacctt ctcctcaact tcctgctctg ggctcctgga   1500
ggccacacga tcgcctggga tgtcatcacc ctgatggctc acactgctga gataactcac   1560
gagatcattg gctttcttga ccagaccttg tacagatgga atcgtcttgg cattgaaagc   1620
cctagatcag aaaaactggc ccgagagctc cttaaagagc tgcgaactca agtctag     1677
```

<210> SEQ ID NO 119
<211> LENGTH: 1611
<212> TYPE: DNA
<213> ORGANISM: Homo sapiens

<400> SEQUENCE: 119

```
atggcgacac cggacgcggg gctccctggg gctgagggcg tggagccggc gccctgggcg     60
cagctggagg ccccgcccg cctcctgctg caggcgctgc aggcggggcc tgaggggggcg   120 cggcgcggcc tggggggtgct ccgggcgctg ggcagccgcg gctgggagcc cttcgactgg   180
ggtcgcttgc tcgaggccct gtgccggag gagccggtcg tgcaggggcc tgacggccgt   240
ctggagctga accactgtt gctgcgattg ccccggatat gccagaggaa cctgatgtcc   300
ctgctgatgg ccgttcggcc atcgctgccg gaaagtgggc tcctctctgt gctgcagatt   360
gcccagcagg acctagcccc tgacccagat gcctggctcc gtgccctggg ggaattgctg   420
cgaagggatt tgggggtggg gacctccatg gaggagcctt ctccactgtc tgaaagatgc   480
cagagacagc tccaaagtct atgtaggggg ctgggcctgg ggggcaggag gttgaaatcc   540
ccccaggctc cagaccctga agaagaggag aacaggggact cccagcagcc tgggaaacgc   600
agaaaggact cagaggaaga ggctgccagt cctgaggggga agagggtccc caaaagatta   660
cggtgttggg aagaggaaga agatcatgag aaggagagac ccgaacataa gtcactggaa   720
tccctggcag atggaggaag tgcatctcct attaaggacc agcctgtcat ggcagttaag   780
actggcgagg acggttcgaa tctggatgat gctaaaggtc tggctgagag tttggagttg   840
cccaaagcta tccaggacca gcttcccagg ctgcagcagc tgctgaagac cttggaggag   900
gggttagagg gattggagga tgccccccca gttgagctac agcttcttca cgaatgtagt   960
cccagccaga tggacttgct gtgtgcccag ctgcagctcc ctcagctctc agacctcggt  1020
ctcctgcggc tctgcacctg gctgctggcc ctttcacctg atctcagcct cagcaatgct  1080
actgtgctga ccagaagcct cttttcttga cggatcctct ccttgacttc ctcagcctcc  1140
cgcctgctta caactgccct gacctccttc tgtgccaaat atacataccc tgtctgcagc  1200
gccctccttg accctgtgct ccaggcccca ggcacaggtc tgctcaaac agagttactg  1260 tgttgccttg tgaagatgga gtccctggag ccagatgcac aggttctaat gctgggacag  1320
atcttggagc tgccctggaa ggaggaaact ttcttggtgt tgcagtcact cctagagcgg  1380
caggtggaga tgaccctga gaagttcagt gtcttaatgg agaagctctg taaaaagggg  1440
ctggcagcca ccacctccat ggcctatgcc aagctcatgc tgacagtgat gaccaagtat  1500
caggctaaca tcactgagac ccagaggctg ggcctggcta tgggccctaga acctaacacc  1560 accttcctga ggaagtccct gaaggccgcc ttgaaacatt tgggcccctg a           1611
```

<210> SEQ ID NO 120
<211> LENGTH: 1125
<212> TYPE: DNA
<213> ORGANISM: Homo sapiens

<400> SEQUENCE: 120

| | |
|---|---:|
| atggaatccc ttctgcagca cctggatcgc ttttccgagc ttctggcggt ctcaagcact | 60 |
| acctacgtca gcacctggga ccccgccacc gtgcgccggg ccttgcagtg ggcgcgctac | 120 |
| ctgcgccaca tccatcggcg ctttggtcgg catggcccca ttcgcacggc tctggagcgg | 180 |
| cggctgcaca accagtggag gcaagagggc ggctttgggc ggggtccagt tccgggatta | 240 |
| gcgaacttcc aggccctcgg tcactgtgac gtcctgctct ctctgcgcct gctggagaac | 300 |
| cgggccctcg gggatgcagc tcgttaccac ctggtgcagc aactcttttcc cggcccgggc | 360 |
| gtccgggacg ccgatgagga gacactccaa gagagcctgg cccgccttgc ccgccggcgg | 420 |
| tctgcggtgc acatgctgcg cttcaatggc tatagagaga acccaaatct ccaggaggac | 480 |
| tctctgatga agacccaggc ggagctgctg ctggagcgtc tgcaggaggt ggggaaggcc | 540 |
| gaagcggagc gtcccgccag gtttctcagc agcctgtggg agcgcttgcc tcagaacaac | 600 |
| ttcctgaagg tgatagcggt ggcgctgttg cagccgcctt tgtctcgtcg gccccaagaa | 660 |
| gagttggaac ccggcatcca caaatcacct ggagagggga gccaagtgct agtccactgg | 720 |
| cttctgggga attcggaagt ctttgctgcc ttttgtcgcg ccctcccagc cgggcttttg | 780 |
| actttagtga ctagccgcca cccagcgctg tctcctgtct atctgggtct gctaacagac | 840 |
| tggggtcaac gtttgcacta tgaccttcag aaaggcattt gggttggaac tgagtcccaa | 900 |
| gatgtgccct gggaggagtt gcacaatagg tttcaaagcc tctgtcaggc ccctccacct | 960 |
| ctgaaagata aagttctaac tgccctggag acctgtaaag cgcaggatgg agattttgaa | 1020 |
| gtacctggtc ttagcatctg gacagacctc ttattagctc ttcgtagtgg tgcatttagg | 1080 |
| aaaagacaag ttttgggtct cagcgcaggc ctcagttctg tatag | 1125 |

<210> SEQ ID NO 121
<211> LENGTH: 1869
<212> TYPE: DNA
<213> ORGANISM: Homo sapiens

<400> SEQUENCE: 121

| | |
|---|---:|
| atgtcccgcc agaccacctc tgtgggctcc agctgcctgg acctgtggag ggaaaagaat | 60 |
| gaccggctcg ttcgacaggc caaggtggct cagaactccg gtctgactct gaggcgacag | 120 |
| cagttggctc aggatgcact ggaagggctc agagggctcc tccatagtct gcaagggctc | 180 |
| cctgcagctg ttcctgttct tcccttggag ctgactgtca cctgcaactt cattatcctg | 240 |
| agggcaagct ggcccagggg tttcacagag gatcaggccc aggatatcca gcggagccta | 300 |
| gagagagtgc tggagacaca ggagcagcag gggcccaggt tggaacaggg gctcagggag | 360 |
| ctgtgggact ctgtccttcg tgcttcctgc cttctgccgg agctgctgtc tgccctgcac | 420 |
| cgcctggttg gcctgcaggc tgccctctgg ttgagtgctg accgtcttgg ggacctggcc | 480 |
| ttgttactag agaccctgaa tggcagccag agtggagcct ctaaggatct gctgttactt | 540 |
| ctgaaaactt ggagtccccc agctgaggaa ttagatgctc cattgaccct gcaggatgcc | 600 |
| cagggattga aggatgtcct cctgacagca tttgcctacc gccaaggtct ccaggagctg | 660 |
| atcacaggga acccagacaa ggcactaagc agccttcatg aagcggcctc aggcctgtgt | 720 |
| ccacggcctg tgttggtcca ggtgtacaca gcactgggt cctgtcaccg taagatggga | 780 |
| aatccacaga gagcactgtt gtacttggtt gcagccctga agagggatc agcctggggt | 840 |
| cctccacttc tggaggcctc taggctctat cagcaactgg gggacacaac agcagagctg | 900 |
| gagagtctgg agctgctagt tgaggccttg aatgtcccat gcagttccaa agccccgcag | 960 |
| tttctcattg aggtagaatt actactgcca ccacctgacc tagcctcacc ccttcattgt | 1020 |

-continued

```
ggcactcaga gccagaccaa gcacatacta gcaagcaggt gcctacagac ggggagggca   1080
ggagacgctg cagagcatta cttggacctg ctggccctgt tgctggatag ctcggagcca   1140
aggttctccc cacccccctc ccctccaggg ccctgtatgc ctgaggtgtt tttggaggca   1200
gcggtagcac tgatccaggc aggcagagcc caagatgcct tgactctatg tgaggagttg   1260
ctcagccgca catcatctct gctacccaag atgtcccggc tgtgggaaga tgccagaaaa   1320
ggaaccaagg aactgccata ctgcccactc tgggtctctg ccacccacct gcttcagggc   1380
caggcctggg ttcaactggg tgcccaaaaa gtggcaatta gtgaatttag caggtgcctc   1440
gagctgctct tccgggccac acctgaggaa aagaacaag gggcagcttt caactgtgag   1500
cagggatgta agtcagatgc ggcactgcag cagcttcggg cagccgccct aattagtcgt   1560
ggactggaat gggtagccag cggccaggat accaaagcct tacaggactt cctcctcagt   1620
gtgcagatgt gcccaggtaa tcgagacact tactttcacc tgcttcagac tctgaagagg   1680
ctagatcgga gggatgaggc cactgcactc tggtggaggc tggagcccca aactaagggg   1740
tcacatgaag atgctctgtg gtctctcccc ctgtacctag aaagctattt gagctggatc   1800
cgtccctctg atcgtgacgc cttccttgaa gaatttcgga catctctgcc aaagtcttgt   1860
gacctgtag                                                           1869
```

<210> SEQ ID NO 122
<211> LENGTH: 1455
<212> TYPE: PRT
<213> ORGANISM: Homo sapiens

<400> SEQUENCE: 122

```
Met Ser Asp Ser Trp Val Pro Asn Ser Ala Ser Gly Gln Asp Pro Gly
1               5                   10                  15

Gly Arg Arg Arg Ala Trp Ala Glu Leu Leu Ala Gly Arg Val Lys Arg
                20                  25                  30

Glu Lys Tyr Asn Pro Glu Arg Ala Gln Lys Leu Lys Glu Ser Ala Val
            35                  40                  45

Arg Leu Leu Arg Ser His Gln Asp Leu Asn Ala Leu Leu Leu Glu Val
        50                  55                  60

Glu Gly Pro Leu Cys Lys Lys Leu Ser Leu Ser Lys Val Ile Asp Cys
65                  70                  75                  80

Asp Ser Ser Glu Ala Tyr Ala Asn His Ser Ser Phe Ile Gly Ser
                85                  90                  95

Ala Leu Gln Asp Gln Ala Ser Arg Leu Gly Val Pro Val Gly Ile Leu
            100                 105                 110

Ser Ala Gly Met Val Ala Ser Val Gly Gln Ile Cys Thr Ala Pro
        115                 120                 125

Ala Glu Thr Ser His Pro Val Leu Leu Thr Val Glu Gln Arg Lys Lys
        130                 135                 140

Leu Ser Ser Leu Leu Glu Phe Ala Gln Tyr Leu Ala His Ser Met
145                 150                 155                 160

Phe Ser Arg Leu Ser Phe Cys Gln Glu Leu Trp Lys Ile Gln Ser Ser
                165                 170                 175

Leu Leu Leu Glu Ala Val Trp His Leu His Val Gln Gly Ile Val Ser
            180                 185                 190

Leu Gln Glu Leu Leu Glu Ser His Pro Asp Met His Ala Val Gly Ser
        195                 200                 205

Trp Leu Phe Arg Asn Leu Cys Cys Leu Cys Glu Gln Met Glu Ala Ser
```

```
                210                 215                 220
Cys Gln His Ala Asp Val Ala Arg Ala Met Leu Ser Asp Phe Val Gln
225                 230                 235                 240

Met Phe Val Leu Arg Gly Phe Gln Lys Asn Ser Asp Leu Arg Arg Thr
                245                 250                 255

Val Glu Pro Glu Lys Met Pro Gln Val Thr Val Asp Val Leu Gln Arg
                260                 265                 270

Met Leu Ile Phe Ala Leu Asp Ala Leu Ala Ala Gly Val Gln Glu Glu
                275                 280                 285

Ser Ser Thr His Lys Ile Val Arg Cys Trp Phe Gly Val Phe Ser Gly
                290                 295                 300

His Thr Leu Gly Ser Val Ile Ser Thr Asp Pro Leu Lys Arg Phe Phe
305                 310                 315                 320

Ser His Thr Leu Thr Gln Ile Leu Thr His Ser Pro Val Leu Lys Ala
                325                 330                 335

Ser Asp Ala Val Gln Met Gln Arg Glu Trp Ser Phe Ala Arg Thr His
                340                 345                 350

Pro Leu Leu Thr Ser Leu Tyr Arg Arg Leu Phe Val Met Leu Ser Ala
                355                 360                 365

Glu Glu Leu Val Gly His Leu Gln Glu Val Leu Glu Thr Gln Glu Val
                370                 375                 380

His Trp Gln Arg Val Leu Ser Phe Val Ser Ala Leu Val Cys Phe
385                 390                 395                 400

Pro Glu Ala Gln Gln Leu Leu Glu Asp Trp Val Ala Arg Leu Met Ala
                405                 410                 415

Gln Ala Phe Glu Ser Cys Gln Leu Asp Ser Met Val Thr Ala Phe Leu
                420                 425                 430

Val Val Arg Gln Ala Ala Leu Glu Gly Pro Ser Ala Phe Leu Ser Tyr
                435                 440                 445

Ala Asp Trp Phe Lys Ala Ser Phe Gly Ser Thr Arg Gly Tyr His Gly
                450                 455                 460

Cys Ser Lys Lys Ala Leu Val Phe Leu Phe Thr Phe Leu Ser Glu Leu
465                 470                 475                 480

Val Pro Phe Glu Ser Pro Arg Tyr Leu Gln Val His Ile Leu His Pro
                485                 490                 495

Pro Leu Val Pro Ser Lys Tyr Arg Ser Leu Leu Thr Asp Tyr Ile Ser
                500                 505                 510

Leu Ala Lys Thr Arg Leu Ala Asp Leu Lys Val Ser Ile Glu Asn Met
                515                 520                 525

Gly Leu Tyr Glu Asp Leu Ser Ser Ala Gly Asp Ile Thr Glu Pro His
                530                 535                 540

Ser Gln Ala Leu Gln Asp Val Glu Lys Ala Ile Met Val Phe Glu His
545                 550                 555                 560

Thr Gly Asn Ile Pro Val Thr Val Met Glu Ala Ser Ile Phe Arg Arg
                565                 570                 575

Pro Tyr Tyr Val Ser His Phe Leu Pro Ala Leu Leu Thr Pro Arg Val
                580                 585                 590

Leu Pro Lys Val Pro Asp Ser Arg Val Ala Phe Ile Glu Ser Leu Lys
                595                 600                 605

Arg Ala Asp Lys Ile Pro Pro Ser Leu Tyr Ser Thr Tyr Cys Gln Ala
                610                 615                 620

Cys Ser Ala Ala Glu Glu Lys Pro Glu Asp Ala Ala Leu Gly Val Arg
625                 630                 635                 640
```

-continued

```
Ala Glu Pro Asn Ser Ala Glu Pro Leu Gly Gln Leu Thr Ala Ala
            645             650                 655

Leu Gly Glu Leu Arg Ala Ser Met Thr Asp Pro Ser Gln Arg Asp Val
        660                 665                 670

Ile Ser Ala Gln Val Ala Val Ile Ser Glu Arg Leu Arg Ala Val Leu
            675                 680                 685

Gly His Asn Glu Asp Ser Ser Val Glu Ile Ser Lys Ile Gln Leu
        690                 695                 700

Ser Ile Asn Thr Pro Arg Leu Glu Pro Arg Glu His Ile Ala Val Asp
705                 710                 715                 720

Leu Leu Leu Thr Ser Phe Cys Gln Asn Leu Met Ala Ala Ser Ser Val
                725                 730                 735

Ala Pro Pro Glu Arg Gln Gly Pro Trp Ala Ala Leu Phe Val Arg Thr
            740                 745                 750

Met Cys Gly Arg Val Leu Pro Ala Val Leu Thr Arg Leu Cys Gln Leu
        755                 760                 765

Leu Arg His Gln Gly Pro Ser Leu Ser Ala Pro His Val Leu Gly Leu
    770                 775                 780

Ala Ala Leu Ala Val His Leu Gly Glu Ser Arg Ser Ala Leu Pro Glu
785                 790                 795                 800

Val Asp Val Gly Pro Pro Ala Pro Gly Ala Gly Leu Pro Val Pro Ala
                805                 810                 815

Leu Phe Asp Ser Leu Leu Thr Cys Arg Thr Arg Asp Ser Leu Phe Phe
            820                 825                 830

Cys Leu Lys Phe Cys Thr Ala Ala Ile Ser Tyr Ser Leu Cys Lys Phe
        835                 840                 845

Ser Ser Gln Ser Arg Asp Thr Leu Cys Ser Cys Leu Ser Pro Gly Leu
    850                 855                 860

Ile Lys Lys Phe Gln Phe Leu Met Phe Arg Leu Phe Ser Glu Ala Arg
865                 870                 875                 880

Gln Pro Leu Ser Glu Glu Asp Val Ala Ser Leu Ser Trp Arg Pro Leu
                885                 890                 895

His Leu Pro Ser Ala Asp Trp Gln Arg Ala Ala Leu Ser Leu Trp Thr
            900                 905                 910

His Arg Thr Phe Arg Glu Val Leu Lys Glu Glu Asp Val His Leu Thr
        915                 920                 925

Tyr Gln Asp Trp Leu His Leu Glu Leu Glu Ile Gln Pro Glu Ala Asp
    930                 935                 940

Ala Leu Ser Asp Thr Glu Arg Gln Asp Phe His Gln Trp Ala Ile His
945                 950                 955                 960

Glu His Phe Leu Pro Glu Ser Ser Ala Ser Gly Gly Cys Asp Gly Asp
                965                 970                 975

Leu Gln Ala Ala Cys Thr Ile Leu Val Asn Ala Leu Met Asp Phe His
            980                 985                 990

Gln Ser Ser Arg Ser Tyr Asp His  Ser Glu Asn Ser Asp Leu Val Phe
        995                 1000                1005

Gly Gly Arg Thr Gly Asn Glu  Asp Ile Ile Ser Arg  Leu Gln Glu
    1010                1015                1020

Met Val Ala Asp Leu Glu Leu  Gln Gln Asp Leu Ile  Val Pro Leu
    1025                1030                1035

Gly His Thr Pro Ser Gln Glu  His Phe Leu Phe Glu  Ile Phe Arg
    1040                1045                1050
```

```
Arg Arg Leu Gln Ala Leu Thr Ser Gly Trp Ser Val Ala Ala Ser
1055              1060              1065

Leu Gln Arg Gln Arg Glu Leu Met Tyr Lys Arg Ile Leu Leu
1070              1075              1080

Arg Leu Pro Ser Ser Val Leu Cys Gly Ser Ser Phe Gln Ala Glu
1085              1090              1095

Gln Pro Ile Thr Ala Arg Cys Glu Gln Phe Phe His Leu Val Asn
1100              1105              1110

Ser Glu Met Arg Asn Phe Cys Ser His Gly Gly Ala Leu Thr Gln
1115              1120              1125

Asp Ile Thr Ala His Phe Phe Arg Gly Leu Leu Asn Ala Cys Leu
1130              1135              1140

Arg Ser Arg Asp Pro Ser Leu Met Val Asp Phe Ile Leu Ala Lys
1145              1150              1155

Cys Gln Thr Lys Cys Pro Leu Ile Leu Thr Ser Ala Leu Val Trp
1160              1165              1170

Trp Pro Ser Leu Glu Pro Val Leu Leu Cys Arg Trp Arg Arg His
1175              1180              1185

Cys Gln Ser Pro Leu Pro Arg Glu Leu Gln Lys Leu Gln Glu Gly
1190              1195              1200

Arg Gln Phe Ala Ser Asp Phe Leu Ser Pro Glu Ala Ala Ser Pro
1205              1210              1215

Ala Pro Asn Pro Asp Trp Leu Ser Ala Ala Ala Leu His Phe Ala
1220              1225              1230

Ile Gln Gln Val Arg Glu Glu Asn Ile Arg Lys Gln Leu Lys Lys
1235              1240              1245

Leu Asp Cys Glu Arg Glu Glu Leu Leu Val Phe Leu Phe Phe Phe
1250              1255              1260

Ser Leu Met Gly Leu Leu Ser Ser His Leu Thr Ser Asn Ser Thr
1265              1270              1275

Thr Asp Leu Pro Lys Ala Phe His Val Cys Ala Ala Ile Leu Glu
1280              1285              1290

Cys Leu Glu Lys Arg Lys Ile Ser Trp Leu Ala Leu Phe Gln Leu
1295              1300              1305

Thr Glu Ser Asp Leu Arg Leu Gly Arg Leu Leu Leu Arg Val Ala
1310              1315              1320

Pro Asp Gln His Thr Arg Leu Leu Pro Phe Ala Phe Tyr Ser Leu
1325              1330              1335

Leu Ser Tyr Phe His Glu Asp Ala Ala Ile Arg Glu Glu Ala Phe
1340              1345              1350

Leu His Val Ala Val Asp Met Tyr Leu Lys Leu Val Gln Leu Phe
1355              1360              1365

Val Ala Gly Asp Thr Ser Thr Val Ser Pro Ala Gly Arg Ser
1370              1375              1380

Leu Glu Leu Lys Gly Gln Gly Asn Pro Val Glu Leu Ile Thr Lys
1385              1390              1395

Ala Arg Leu Phe Leu Leu Gln Leu Ile Pro Arg Cys Pro Lys Lys
1400              1405              1410

Ser Phe Ser His Val Ala Glu Leu Leu Ala Asp Arg Gly Asp Cys
1415              1420              1425

Asp Pro Glu Val Ser Ala Ala Leu Gln Ser Arg Gln Gln Ala Ala
1430              1435              1440

Pro Asp Ala Asp Leu Ser Gln Glu Pro His Leu Phe
```

<210> SEQ ID NO 123
<211> LENGTH: 558
<212> TYPE: PRT
<213> ORGANISM: Homo sapiens

<400> SEQUENCE: 123

Met Ala Gln Asp Ser Val Asp Leu Ser Cys Asp Tyr Gln Phe Trp Met
1               5                   10                  15

Gln Lys Leu Ser Val Trp Asp Gln Ala Ser Thr Leu Glu Thr Gln Gln
            20                  25                  30

Asp Thr Cys Leu His Val Ala Gln Phe Gln Glu Phe Leu Arg Lys Met
        35                  40                  45

Tyr Glu Ala Leu Lys Glu Met Asp Ser Asn Thr Val Ile Glu Arg Phe
50                  55                  60

Pro Thr Ile Gly Gln Leu Leu Ala Lys Ala Cys Trp Asn Pro Phe Ile
65                  70                  75                  80

Leu Ala Tyr Asp Glu Ser Gln Lys Ile Leu Ile Trp Cys Leu Cys Cys
                85                  90                  95

Leu Ile Asn Lys Glu Pro Gln Asn Ser Gly Gln Ser Leu Asn Ser
            100                 105                 110

Trp Ile Gln Gly Val Leu Ser His Ile Leu Ser Ala Leu Arg Phe Asp
            115                 120                 125

Lys Glu Val Ala Leu Phe Thr Gln Gly Leu Gly Tyr Ala Pro Ile Asp
130                 135                 140

Tyr Tyr Pro Gly Leu Leu Lys Asn Met Val Leu Ser Leu Ala Ser Glu
145                 150                 155                 160

Leu Arg Glu Asn His Leu Asn Gly Phe Asn Thr Gln Arg Arg Met Ala
                165                 170                 175

Pro Glu Arg Val Ala Ser Leu Ser Arg Val Cys Val Pro Leu Ile Thr
            180                 185                 190

Leu Thr Asp Val Asp Pro Leu Val Glu Ala Leu Leu Ile Cys His Gly
        195                 200                 205

Arg Glu Pro Gln Glu Ile Leu Gln Pro Glu Phe Phe Glu Ala Val Asn
210                 215                 220

Glu Ala Ile Leu Leu Lys Lys Ile Ser Leu Pro Met Ser Ala Val Val
225                 230                 235                 240

Cys Leu Trp Leu Arg His Leu Pro Ser Leu Glu Lys Ala Met Leu His
                245                 250                 255

Leu Phe Glu Lys Leu Ile Ser Ser Glu Arg Asn Cys Leu Arg Arg Ile
            260                 265                 270

Glu Cys Phe Ile Lys Asp Ser Ser Leu Pro Gln Ala Ala Cys His Pro
        275                 280                 285

Ala Ile Phe Arg Val Val Asp Glu Met Phe Arg Cys Ala Leu Leu Glu
290                 295                 300

Thr Asp Gly Ala Leu Glu Ile Ile Ala Thr Ile Gln Val Phe Thr Gln
305                 310                 315                 320

Cys Phe Val Glu Ala Leu Glu Lys Ala Ser Lys Gln Leu Arg Phe Ala
                325                 330                 335

Leu Lys Thr Tyr Phe Pro Tyr Thr Ser Pro Ser Leu Ala Met Val Leu
            340                 345                 350

Leu Gln Asp Pro Gln Asp Ile Pro Arg Gly His Trp Leu Gln Thr Leu
        355                 360                 365

-continued

Lys His Ile Ser Glu Leu Leu Arg Glu Ala Val Glu Asp Gln Thr His
370                 375                 380

Gly Ser Cys Gly Gly Pro Phe Glu Ser Trp Phe Leu Phe Ile His Phe
385                 390                 395                 400

Gly Gly Trp Ala Glu Met Val Ala Glu Gln Leu Leu Met Ser Ala Ala
                405                 410                 415

Glu Pro Pro Thr Ala Leu Leu Trp Leu Leu Ala Phe Tyr Tyr Gly Pro
            420                 425                 430

Arg Asp Gly Arg Gln Gln Arg Ala Gln Thr Met Val Gln Val Lys Ala
435                 440                 445

Val Leu Gly His Leu Leu Ala Met Ser Arg Ser Ser Ser Leu Ser Ala
450                 455                 460

Gln Asp Leu Gln Thr Val Ala Gly Gln Gly Thr Asp Thr Asp Leu Arg
465                 470                 475                 480

Ala Pro Ala Gln Gln Leu Ile Arg His Leu Leu Leu Asn Phe Leu Leu
                485                 490                 495

Trp Ala Pro Gly Gly His Thr Ile Ala Trp Asp Val Ile Thr Leu Met
                500                 505                 510

Ala His Thr Ala Glu Ile Thr His Glu Ile Ile Gly Phe Leu Asp Gln
            515                 520                 525

Thr Leu Tyr Arg Trp Asn Arg Leu Gly Ile Glu Ser Pro Arg Ser Glu
530                 535                 540

Lys Leu Ala Arg Glu Leu Leu Lys Glu Leu Arg Thr Gln Val
545                 550                 555

<210> SEQ ID NO 124
<211> LENGTH: 536
<212> TYPE: PRT
<213> ORGANISM: Homo sapiens

<400> SEQUENCE: 124

Met Ala Thr Pro Asp Ala Gly Leu Pro Gly Ala Glu Gly Val Glu Pro
1               5                   10                  15

Ala Pro Trp Ala Gln Leu Glu Ala Pro Ala Arg Leu Leu Leu Gln Ala
                20                  25                  30

Leu Gln Ala Gly Pro Glu Gly Ala Arg Arg Gly Leu Gly Val Leu Arg
            35                  40                  45

Ala Leu Gly Ser Arg Gly Trp Glu Pro Phe Asp Trp Gly Arg Leu Leu
        50                  55                  60

Glu Ala Leu Cys Arg Glu Glu Pro Val Val Gln Gly Pro Asp Gly Arg
65                  70                  75                  80

Leu Glu Leu Lys Pro Leu Leu Arg Leu Pro Arg Ile Cys Gln Arg
                85                  90                  95

Asn Leu Met Ser Leu Leu Met Ala Val Arg Pro Ser Leu Pro Glu Ser
                100                 105                 110

Gly Leu Leu Ser Val Leu Gln Ile Ala Gln Gln Asp Leu Ala Pro Asp
            115                 120                 125

Pro Asp Ala Trp Leu Arg Ala Leu Gly Glu Leu Leu Arg Arg Asp Leu
130                 135                 140

Gly Val Gly Thr Ser Met Glu Gly Ala Ser Pro Leu Ser Glu Arg Cys
145                 150                 155                 160

Gln Arg Gln Leu Gln Ser Leu Cys Arg Gly Leu Gly Leu Gly Gly Arg
                165                 170                 175

Arg Leu Lys Ser Pro Gln Ala Pro Asp Pro Glu Glu Glu Glu Asn Arg
            180                 185                 190

Asp Ser Gln Gln Pro Gly Lys Arg Arg Lys Asp Ser Glu Glu Ala
        195                 200                 205

Ala Ser Pro Glu Gly Lys Arg Val Pro Lys Arg Leu Arg Cys Trp Glu
        210                 215                 220

Glu Glu Glu Asp His Glu Lys Glu Arg Pro Glu His Lys Ser Leu Glu
225                 230                 235                 240

Ser Leu Ala Asp Gly Gly Ser Ala Ser Pro Ile Lys Asp Gln Pro Val
                245                 250                 255

Met Ala Val Lys Thr Gly Glu Asp Gly Ser Asn Leu Asp Asp Ala Lys
                260                 265                 270

Gly Leu Ala Glu Ser Leu Glu Leu Pro Lys Ala Ile Gln Asp Gln Leu
                275                 280                 285

Pro Arg Leu Gln Gln Leu Leu Lys Thr Leu Glu Glu Gly Leu Glu Gly
        290                 295                 300

Leu Glu Asp Ala Pro Pro Val Glu Leu Gln Leu Leu His Glu Cys Ser
305                 310                 315                 320

Pro Ser Gln Met Asp Leu Leu Cys Ala Gln Leu Gln Leu Pro Gln Leu
                325                 330                 335

Ser Asp Leu Gly Leu Leu Arg Leu Cys Thr Trp Leu Leu Ala Leu Ser
                340                 345                 350

Pro Asp Leu Ser Leu Ser Asn Ala Thr Val Leu Thr Arg Ser Leu Phe
        355                 360                 365

Leu Gly Arg Ile Leu Ser Leu Thr Ser Ser Ala Ser Arg Leu Leu Thr
        370                 375                 380

Thr Ala Leu Thr Ser Phe Cys Ala Lys Tyr Thr Tyr Pro Val Cys Ser
385                 390                 395                 400

Ala Leu Leu Asp Pro Val Leu Gln Ala Pro Gly Thr Gly Pro Ala Gln
                405                 410                 415

Thr Glu Leu Leu Cys Cys Leu Val Lys Met Glu Ser Leu Glu Pro Asp
                420                 425                 430

Ala Gln Val Leu Met Leu Gly Gln Ile Leu Glu Leu Pro Trp Lys Glu
                435                 440                 445

Glu Thr Phe Leu Val Leu Gln Ser Leu Leu Glu Arg Gln Val Glu Met
        450                 455                 460

Thr Pro Glu Lys Phe Ser Val Leu Met Glu Lys Leu Cys Lys Lys Gly
465                 470                 475                 480

Leu Ala Ala Thr Thr Ser Met Ala Tyr Ala Lys Leu Met Leu Thr Val
                485                 490                 495

Met Thr Lys Tyr Gln Ala Asn Ile Thr Glu Thr Gln Arg Leu Gly Leu
                500                 505                 510

Ala Met Ala Leu Glu Pro Asn Thr Thr Phe Leu Arg Lys Ser Leu Lys
                515                 520                 525

Ala Ala Leu Lys His Leu Gly Pro
        530                 535

<210> SEQ ID NO 125
<211> LENGTH: 374
<212> TYPE: PRT
<213> ORGANISM: Homo sapiens

<400> SEQUENCE: 125

Met Glu Ser Leu Leu Gln His Leu Asp Arg Phe Ser Glu Leu Leu Ala
1               5                   10                  15

Val Ser Ser Thr Thr Tyr Val Ser Thr Trp Asp Pro Ala Thr Val Arg

```
                20                  25                  30
Arg Ala Leu Gln Trp Ala Arg Tyr Leu Arg His Ile His Arg Arg Phe
         35                  40                  45

Gly Arg His Gly Pro Ile Arg Thr Ala Leu Glu Arg Leu His Asn
     50                  55                  60

Gln Trp Arg Gln Glu Gly Phe Gly Arg Gly Pro Val Pro Gly Leu
 65                  70                  75                  80

Ala Asn Phe Gln Ala Leu Gly His Cys Asp Val Leu Ser Leu Arg
                 85                  90                  95

Leu Leu Glu Asn Arg Ala Leu Gly Asp Ala Ala Arg Tyr His Leu Val
             100                 105                 110

Gln Gln Leu Phe Pro Gly Pro Val Arg Asp Ala Asp Glu Glu Thr
             115                 120                 125

Leu Gln Glu Ser Leu Ala Arg Leu Ala Arg Arg Ser Ala Val His
         130                 135                 140

Met Leu Arg Phe Asn Gly Tyr Arg Glu Asn Pro Asn Leu Gln Glu Asp
145                 150                 155                 160

Ser Leu Met Lys Thr Gln Ala Glu Leu Leu Leu Glu Arg Leu Gln Glu
                 165                 170                 175

Val Gly Lys Ala Glu Ala Glu Arg Pro Ala Arg Phe Leu Ser Ser Leu
             180                 185                 190

Trp Glu Arg Leu Pro Gln Asn Asn Phe Leu Lys Val Ile Ala Val Ala
         195                 200                 205

Leu Leu Gln Pro Pro Leu Ser Arg Arg Pro Gln Glu Glu Leu Glu Pro
     210                 215                 220

Gly Ile His Lys Ser Pro Gly Glu Gly Ser Gln Val Leu Val His Trp
225                 230                 235                 240

Leu Leu Gly Asn Ser Glu Val Phe Ala Ala Phe Cys Arg Ala Leu Pro
                 245                 250                 255

Ala Gly Leu Leu Thr Leu Val Thr Ser Arg His Pro Ala Leu Ser Pro
             260                 265                 270

Val Tyr Leu Gly Leu Leu Thr Asp Trp Gly Gln Arg Leu His Tyr Asp
         275                 280                 285

Leu Gln Lys Gly Ile Trp Val Gly Thr Glu Ser Gln Asp Val Pro Trp
     290                 295                 300

Glu Glu Leu His Asn Arg Phe Gln Ser Leu Cys Gln Ala Pro Pro Pro
305                 310                 315                 320

Leu Lys Asp Lys Val Leu Thr Ala Leu Glu Thr Cys Lys Ala Gln Asp
                 325                 330                 335

Gly Asp Phe Glu Val Pro Gly Leu Ser Ile Trp Thr Asp Leu Leu Leu
             340                 345                 350

Ala Leu Arg Ser Gly Ala Phe Arg Lys Arg Gln Val Leu Gly Leu Ser
         355                 360                 365

Ala Gly Leu Ser Ser Val
     370

<210> SEQ ID NO 126
<211> LENGTH: 622
<212> TYPE: PRT
<213> ORGANISM: Homo sapiens

<400> SEQUENCE: 126

Met Ser Arg Gln Thr Thr Ser Val Gly Ser Ser Cys Leu Asp Leu Trp
1               5                   10                  15
```

-continued

```
Arg Glu Lys Asn Asp Arg Leu Val Arg Gln Ala Lys Val Ala Gln Asn
             20                  25                  30
Ser Gly Leu Thr Leu Arg Arg Gln Gln Leu Ala Gln Asp Ala Leu Glu
         35                  40                  45
Gly Leu Arg Gly Leu Leu His Ser Leu Gln Gly Leu Pro Ala Ala Val
     50                  55                  60
Pro Val Leu Pro Leu Glu Leu Thr Val Thr Cys Asn Phe Ile Ile Leu
65                  70                  75                  80
Arg Ala Ser Leu Ala Gln Gly Phe Thr Glu Asp Gln Ala Gln Asp Ile
                 85                  90                  95
Gln Arg Ser Leu Glu Arg Val Leu Glu Thr Gln Glu Gln Gln Gly Pro
            100                 105                 110
Arg Leu Glu Gln Gly Leu Arg Glu Leu Trp Asp Ser Val Leu Arg Ala
        115                 120                 125
Ser Cys Leu Leu Pro Glu Leu Leu Ser Ala Leu His Arg Leu Val Gly
    130                 135                 140
Leu Gln Ala Ala Leu Trp Leu Ser Ala Asp Arg Leu Gly Asp Leu Ala
145                 150                 155                 160
Leu Leu Leu Glu Thr Leu Asn Gly Ser Gln Ser Gly Ala Ser Lys Asp
                165                 170                 175
Leu Leu Leu Leu Leu Lys Thr Trp Ser Pro Ala Glu Glu Leu Asp
            180                 185                 190
Ala Pro Leu Thr Leu Gln Asp Ala Gln Gly Leu Lys Asp Val Leu Leu
        195                 200                 205
Thr Ala Phe Ala Tyr Arg Gln Gly Leu Gln Glu Leu Ile Thr Gly Asn
    210                 215                 220
Pro Asp Lys Ala Leu Ser Ser Leu His Glu Ala Ser Gly Leu Cys
225                 230                 235                 240
Pro Arg Pro Val Leu Val Gln Val Tyr Thr Ala Leu Gly Ser Cys His
                245                 250                 255
Arg Lys Met Gly Asn Pro Gln Arg Ala Leu Leu Tyr Leu Val Ala Ala
            260                 265                 270
Leu Lys Glu Gly Ser Ala Trp Gly Pro Pro Leu Leu Glu Ala Ser Arg
        275                 280                 285
Leu Tyr Gln Gln Leu Gly Asp Thr Thr Ala Glu Leu Glu Ser Leu Glu
    290                 295                 300
Leu Leu Val Glu Ala Leu Asn Val Pro Cys Ser Ser Lys Ala Pro Gln
305                 310                 315                 320
Phe Leu Ile Glu Val Glu Leu Leu Pro Pro Asp Leu Ala Ser
                325                 330                 335
Pro Leu His Cys Gly Thr Gln Ser Gln Thr Lys His Ile Leu Ala Ser
            340                 345                 350
Arg Cys Leu Gln Thr Gly Arg Ala Gly Asp Ala Ala Glu His Tyr Leu
        355                 360                 365
Asp Leu Leu Ala Leu Leu Leu Asp Ser Ser Glu Pro Arg Phe Ser Pro
    370                 375                 380
Pro Pro Ser Pro Pro Gly Pro Cys Met Pro Glu Val Phe Leu Glu Ala
385                 390                 395                 400
Ala Val Ala Leu Ile Gln Ala Gly Arg Ala Gln Asp Ala Leu Thr Leu
                405                 410                 415
Cys Glu Glu Leu Leu Ser Arg Thr Ser Ser Leu Leu Pro Lys Met Ser
            420                 425                 430
Arg Leu Trp Glu Asp Ala Arg Lys Gly Thr Lys Glu Leu Pro Tyr Cys
```

```
                435                 440                 445
Pro Leu Trp Val Ser Ala Thr His Leu Leu Gln Gly Gln Ala Trp Val
    450                 455                 460
Gln Leu Gly Ala Gln Lys Val Ala Ile Ser Glu Phe Ser Arg Cys Leu
465                 470                 475                 480
Glu Leu Leu Phe Arg Ala Thr Pro Glu Glu Lys Glu Gln Gly Ala Ala
                485                 490                 495
Phe Asn Cys Glu Gln Gly Cys Lys Ser Asp Ala Ala Leu Gln Gln Leu
            500                 505                 510
Arg Ala Ala Leu Ile Ser Arg Gly Leu Glu Trp Val Ala Ser Gly
        515                 520                 525
Gln Asp Thr Lys Ala Leu Gln Asp Phe Leu Leu Ser Val Gln Met Cys
    530                 535                 540
Pro Gly Asn Arg Asp Thr Tyr Phe His Leu Leu Gln Thr Leu Lys Arg
545                 550                 555                 560
Leu Asp Arg Arg Asp Glu Ala Thr Ala Leu Trp Trp Arg Leu Glu Ala
                565                 570                 575
Gln Thr Lys Gly Ser His Glu Asp Ala Leu Trp Ser Leu Pro Leu Tyr
            580                 585                 590
Leu Glu Ser Tyr Leu Ser Trp Ile Arg Pro Ser Asp Arg Asp Ala Phe
        595                 600                 605
Leu Glu Glu Phe Arg Thr Ser Leu Pro Lys Ser Cys Asp Leu
    610                 615                 620
```

<210> SEQ ID NO 127
<211> LENGTH: 1110
<212> TYPE: DNA
<213> ORGANISM: Artificial Sequence
<220> FEATURE:
<223> OTHER INFORMATION: codon optimized Human gammaC DNA

<400> SEQUENCE: 127

```
atgctgaaac caagcctgcc ctttacaagc ctgctgttcc tgcagctgcc actgctgggg      60
gtcggactga atactacaat cctgacacca acggaaatg aggacaccac agccgatttc     120
tttctgacta ccatgcccac tgacagtctg tcagtgagca ccctgccact gcccgaggtc     180
cagtgcttcg tgtttaacgt cgaatatatg aactgtacct ggaatagctc ctctgaacct     240
cagccaacaa atctgactct gcactactgg tataagaact ctgacaatga aggtgcag      300
aaatgctcac attatctgtt cagcgaggaa atcacctccg gctgtcagct gcagaagaaa     360
gagattcacc tgtaccagac atttgtggtc cagctgcagg atccccggga acctcggaga     420
caggccactc agatgctgaa gctgcagaac ctggtcatcc catgggctcc gagaatctg     480
accctgcata aactgtccga gtctcagctg aactgaact ggaacaatag gttcctgaat     540
cactgcctgg agcatctggt gcagtaccgc acagactggg atcactcttg gactgaacag     600
agtgtggact atcgacataa gtttagtctg ccttcagtgg atgggcagaa aaggtacaca     660
ttcagggtcc gctctcggtt caacccactg tgcggaagcg cccagcactg gagcgagtgg     720
tcccacccca tccattgggg gtctaacacc agcaaggaga tccttccct gtttgccctg     780
gaagctgtgg tcatttcagt gggaagcatg ggcctgatca ttagcctgct gtgcgtgtac     840
ttctggctgg agcggaccat gcctagaatc caacactga gaacctggaa ggacctggtg     900
acagaatatc acggcaattt tccgcttgg tctggggtca gtaaaggact ggcagagagc     960
ctgcagcccg attactccga gcggctgtgc ctggtgtccg aaattccccc taaaggcggg    1020
```

| | |
|---|---|
| gcactgggag aaggccctgg ggcctccccc tgcaaccagc actcacccta ttgggcacca | 1080 |
| ccctgttaca ccctgaaacc cgaaacttaa | 1110 |

<210> SEQ ID NO 128
<211> LENGTH: 1110
<212> TYPE: DNA
<213> ORGANISM: Homo sapiens

<400> SEQUENCE: 128

| | |
|---|---|
| atgttgaagc catcattacc attcacatcc ctcttattcc tgcagctgcc cctgctggga | 60 |
| gtggggctga acacgacaat tctgacgccc aatgggaatg aagacaccac agctgatttc | 120 |
| ttcctgacca ctatgcccac tgactccctc agcgtttcca ctctgcccct cccagaggtt | 180 |
| cagtgttttg tgttcaatgt cgagtacatg aattgcactt ggaacagcag ctctgagccc | 240 |
| cagcctacca acctcactct gcattattgg tacaagaact cggataatga taaagtccag | 300 |
| aagtgcagcc actatctatt ctctgaagaa atcacttctg ctgtcagtt gcaaaaaaag | 360 |
| gagatccacc tctaccaaac atttgttgtt cagctccagg acccacggga acccaggaga | 420 |
| caggccacac agatgctaaa actgcagaat ctggtgatcc cctgggctcc agagaaccta | 480 |
| acacttcaca aactgagtga atcccagcta gaactgaact ggaacaacag attcttgaac | 540 |
| cactgtttgg agcacttggt gcagtaccgg actgactggg accacagctg gactgaacaa | 600 |
| tcagtggatt atagacataa gttctccttg cctagtgtgg atgggcagaa acgctacacg | 660 |
| tttcgtgttc ggagccgctt taacccactc tgtggaagtg ctcagcattg gagtgaatgg | 720 |
| agccacccaa tccactgggg gagcaatact tcaaaagaga atcctttcct gtttgcattg | 780 |
| gaagccgtgg ttatctctgt tggctccatg ggattgatta tcagccttct ctgtgtgtat | 840 |
| ttctggctgg aacggacgat gccccgaatt cccaccctga gaacctaga ggatcttgtt | 900 |
| actgaatacc acgggaactt ttcggcctgg agtggtgtgt ctaagggact ggctgagagt | 960 |
| ctgcagccag actacagtga acgactctgc ctcgtcagtg agattccccc aaaaggaggg | 1020 |
| gcccttgggg aggggcctgg ggcctcccca tgcaaccagc atagccccta ctgggccccc | 1080 |
| ccatgttaca ccctaaagcc tgaaacctga | 1110 |

<210> SEQ ID NO 129
<211> LENGTH: 1114
<212> TYPE: DNA
<213> ORGANISM: Canis lupus familiaris

<400> SEQUENCE: 129

| | |
|---|---|
| atgttgaagc caccattgcc actcagatcc ctcttattcc tgcagctgtc tctgctgggg | 60 |
| gtggggctga actccacggt ccccatgccc aatgggaatg aagacatcac acctgatttc | 120 |
| ttcctgaccg ctacaccctc cgagaccctc agtgtttcct ccctgcccct cccagaggtc | 180 |
| cagtgttttg tgttcaatgt tgagtacatg aattgcactt ggaacagcag ctctgagccc | 240 |
| cggcccacca acctgaccct gcactactgg tataagaact ccaatgatga taaagtccag | 300 |
| gagtgtggcc actacctatt ctctagagag gtcactgctg ctgttggtt gcagaaggag | 360 |
| gagatccatc tctacgaaac atttgttgtc cagctccggg acccacggga acccaggagg | 420 |
| cagtccacac agaagctaaa actgcaaaat ctggtgatcc cctgggctcc ggagaaccta | 480 |
| acccttcaca aactgagcga atcccagcta gaactgagct ggagcaacag acacttggac | 540 |
| cactgtttgg agcatgttgt gcagtaccgg agtgactggg accgcagctg gactgaacag | 600 |
| tcagtggacc accgaaatag cttctctctg cctagcgtgg atgggcagaa gttctacacg | 660 |

```
ttccgtgtcc gaagccgcta taacccactc tgtggaagcg ctcagcgttg gagtgaatgg      720
agccacccta tccactgggg gagcaatacc tccaaggaga atcctttgtt tgcatcggaa      780
gctgtgctta tccccctttgg ctccatggga ttgattatta gccttatctg tgtgtactac    840
```

```
ttccgtgtcc gaagccgcta taacccactc tgtggaagcg ctcagcgttg gagtgaatgg      720
agccacccta tccactgggg gagcaatacc tccaaggaga atcctttgtt tgcatcggaa      780
gctgtgctta tccccctttgg ctccatggga ttgattatta gccttatctg tgtgtactac    840
tggctggaac ggtcgatccc ccgaattcct accctcaaga acctggagga tctggttact     900
gaatatcacg ggaattttttc ggcctggagt ggagtgtcta agggactggc ggagagtctg    960
cagccagact acagtgaatg gctctgccac gtcagtgaga ttcccccaaa aggaggggct     1020 ccagggagg gtcctggggg ctccccctgc agccagcata gcccctactg ggctccccca     1080
tgttataccc tgaaacctga aactggagcc ctga                                 1114
```

<210> SEQ ID NO 130
<211> LENGTH: 369
<212> TYPE: PRT
<213> ORGANISM: Homo sapiens

<400> SEQUENCE: 130

Met Leu Lys Pro Ser Leu Pro Phe Thr Ser Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285
```

```
Arg Ile Pro Thr Leu Lys Asn Leu Glu Asp Leu Val Thr Glu Tyr His
    290                 295                 300
Gly Asn Phe Ser Ala Trp Ser Gly Val Ser Lys Gly Leu Ala Glu Ser
305                 310                 315                 320
Leu Gln Pro Asp Tyr Ser Glu Arg Leu Cys Leu Val Ser Glu Ile Pro
                325                 330                 335
Pro Lys Gly Gly Ala Leu Gly Glu Gly Pro Gly Ala Ser Pro Cys Asn
                340                 345                 350
Gln His Ser Pro Tyr Trp Ala Pro Pro Cys Tyr Thr Leu Lys Pro Glu
                355                 360                 365
Thr

<210> SEQ ID NO 131
<211> LENGTH: 373
<212> TYPE: PRT
<213> ORGANISM: Canis lupus familiaris

<400> SEQUENCE: 131

Met Leu Lys Pro Pro Leu Pro Leu Arg Ser Leu Leu Phe Leu Gln Leu
1               5                   10                  15
Ser Leu Leu Gly Val Gly Leu Asn Ser Thr Val Pro Met Pro Asn Gly
                20                  25                  30
Asn Glu Asp Ile Thr Pro Asp Phe Phe Leu Thr Ala Thr Pro Ser Glu
            35                  40                  45
Thr Leu Ser Val Ser Ser Leu Pro Leu Pro Glu Val Gln Cys Phe Val
    50                  55                  60
Phe Asn Val Glu Tyr Met Asn Cys Thr Trp Asn Ser Ser Ser Glu Pro
65                  70                  75                  80
Arg Pro Thr Asn Leu Thr Leu His Tyr Trp Tyr Lys Asn Ser Asn Asp
                85                  90                  95
Asp Lys Val Gln Glu Cys Gly His Tyr Leu Phe Ser Arg Glu Val Thr
            100                 105                 110
Ala Gly Cys Trp Leu Gln Lys Glu Glu Ile His Leu Tyr Glu Thr Phe
        115                 120                 125
Val Val Gln Leu Arg Asp Pro Arg Glu Pro Arg Arg Gln Ser Thr Gln
    130                 135                 140
Lys Leu Lys Leu Gln Asn Leu Val Ile Pro Trp Ala Pro Glu Asn Leu
145                 150                 155                 160
Thr Leu His Asn Leu Ser Glu Ser Gln Leu Glu Leu Ser Trp Ser Asn
                165                 170                 175
Arg His Leu Asp His Cys Leu Glu His Val Val Gln Tyr Arg Ser Asp
            180                 185                 190
Trp Asp Arg Ser Trp Thr Glu Gln Ser Val Asp His Arg Asn Ser Phe
        195                 200                 205
Ser Leu Pro Ser Val Asp Gly Gln Lys Phe Tyr Thr Phe Arg Val Arg
    210                 215                 220
Ser Arg Tyr Asn Pro Leu Cys Gly Ser Ala Gln Arg Trp Ser Glu Trp
225                 230                 235                 240
Ser His Pro Ile His Trp Gly Ser Asn Thr Ser Lys Glu Asn Pro Leu
                245                 250                 255
Phe Ala Ser Glu Ala Val Leu Ile Pro Leu Gly Ser Met Gly Leu Ile
            260                 265                 270
Ile Ser Leu Ile Cys Val Tyr Tyr Trp Leu Glu Arg Ser Ile Pro Arg
        275                 280                 285
```

```
Ile Pro Thr Leu Lys Asn Leu Glu Asp Leu Val Thr Glu Tyr His Gly
    290                 295                 300

Asn Phe Ser Ala Trp Ser Gly Val Ser Lys Gly Leu Ala Glu Ser Leu
305                 310                 315                 320

Gln Pro Asp Tyr Ser Glu Trp Leu Cys His Val Ser Glu Ile Pro Pro
                325                 330                 335

Lys Gly Ala Pro Gly Glu Gly Pro Gly Gly Ser Pro Cys Ser Gln
            340                 345                 350

His Ser Pro Tyr Trp Ala Pro Pro Cys Tyr Thr Leu Lys Pro Glu Thr
            355                 360                 365

Gly Ala Leu Ile Pro
    370

<210> SEQ ID NO 132
<211> LENGTH: 3375
<212> TYPE: DNA
<213> ORGANISM: Homo sapiens

<400> SEQUENCE: 132
```

| | | | | | |
|---|---|---|---|---|---|
| atggcacctc | caagtgaaga | gacgcccctg | atccctcagc | gttcatgcag | cctcttgtcc | 60 |
| acggaggctg | gtgccctgca | tgtgctgctg | cccgctcggg | gccccgggcc | ccccagcgc | 120 |
| ctatctttct | cctttgggga | ccacttggct | gaggacctgt | gcgtgcaggc | tgccaaggcc | 180 |
| agcggcatcc | tgcctgtgta | ccactccctc | tttgctctgg | ccacggagga | cctgtcctgc | 240 |
| tggttccccc | cgagccacat | cttctccgtg | gaggatgcca | gcacccaagt | cctgctgtac | 300 |
| aggattcgct | tttacttccc | caattggttt | gggctgagaa | gtgccaccg | cttcgggcta | 360 |
| cgcaaggatt | tggccagtgc | tatccttgac | ctgccagtcc | tggagcacct | ctttgcccag | 420 |
| caccgcagtg | aacctggtgag | tgggcgcctc | ccgtgggcc | tcagtctcaa | ggagcagggt | 480 |
| gagtgtctca | gcctggccgt | gttggacctg | gccggatgg | cgcgagagca | ggcccagcgg | 540 |
| ccggagagc | tgctgaagac | tgtcagctac | aaggcctgcc | tacccccaag | cctgcgcgac | 600 |
| ctgatccagg | gcctgagctt | cgtgacgcgg | aggcgtattc | ggaggacggt | gcgcagagcc | 660 |
| ctgcgccgcg | tggccgcctg | ccaggcagac | cggcactcgc | tcatggccaa | gtacatcatg | 720 |
| gacctggagc | ggctggatcc | agccggggcc | gccgagacct | tccacgtggg | cctccctggg | 780 |
| gcccttggtg | gccacgacgg | gctggggctg | ctccgcgtgg | ctggtgacgg | cggcatcgcc | 840 |
| tggacccagg | gagaacagga | ggtcctccag | cccttctgcg | actttccaga | aatcgtagac | 900 |
| attagcatca | gcaggcccc | gcgcgttggc | ccggccggag | agcaccgcct | ggtcactgtt | 960 |
| accaggacag | acaaccagat | tttagaggcc | gagttcccag | ggctgcccga | ggctctgtcg | 1020 |
| ttcgtggcgc | tcgtggacgg | ctacttccgg | ctgaccacgg | actccagca | cttcttctgc | 1080 |
| aaggaggtgg | caccgccgag | gctgctggag | gaagtggccg | agcagtgcca | cggccccatc | 1140 |
| actctggact | tgccatcaa | caagctcaag | actggggct | cacgtcctgg | ctcctatgtt | 1200 |
| ctccgccgca | gccccagga | cttgacagc | ttcctcctca | ctgtctgtgt | ccagaacccc | 1260 |
| cttggtcctg | attataaggg | ctgcctcatc | cggcgcagcc | ccacaggaac | cttccttctg | 1320 |
| gttgccctca | gccgaccca | cagcagtctt | cgagagctcc | tggcaacctg | ctgggatggg | 1380 |
| gggctgcacg | tagatggggt | ggcagtgacc | ctcacttcct | gctgtatccc | cagacccaaa | 1440 |
| gaaaagtcca | acctgatcgt | ggtccagaga | ggtcacagcc | cacccacatc | atccttggtt | 1500 |
| cagccccaat | cccaatacca | gctgagtcag | atgacatttc | acaagatccc | tgctgacagc | 1560 |
| ctggagtggc | atgagaacct | gggccatggg | tccttcacca | agatttaccg | ggctgtcgc | 1620 |

-continued

```
catgaggtgg tggatgggga ggcccgaaag acagaggtgc tgctgaaggt catggatgcc    1680
aagcacaaga actgcatgga gtcattcctg gaagcagcga gcttgatgag ccaagtgtcg    1740
taccggcatc tcgtgctgct ccacggcgtg tgcatggctg agacagcac catggtgcag     1800 gaatttgtac acctgggggc catagacatg tatctgcgaa aacgtggcca cctggtgcca    1860
gccagctgga agctgcaggt ggtcaaacag ctggcctacg ccctcaacta tctggaggac    1920
aaaggcctgc cccatggcaa tgtctctgcc cggaaggtgc tcctggctcg ggaggggct     1980 gatgggagcc cgcccttcat caagctgagt gaccctgggg tcagccccgc tgtgttaagc    2040
ctggagatgt tcaccgacag gatcccctgg gtggcccccg agtgtctccg ggaggcgcag    2100
acacttagct tggaagctga caagtggggc ttcggcgcca cggtctggga agtgtttagt    2160
ggcgtcacca tgcccatcag tgccctggat cctgctaaga aactccaatt ttatgaggac    2220
cggcagcagc tgccggcccc caagtggaca gagctggccc tgctgattca acagtgcatg    2280
gcctatgagc cggtccagag gccctccttc cgagccgtca ttcgtgacct caatagcctc    2340
atctcttcag actatgagct cctctcagac cccacacctg gtgccctggc acctcgtgat    2400
gggctgtgga atggtgccca gctctatgcc tgccaagacc ccacgatctt cgaggagaga    2460
cacctcaagt acatctcaca gctgggcaag ggcaactttg gcagcgtgga gctgtgccgc    2520
tatgacccgc taggcgacaa tacaggtgcc ctggtggccg tgaaacagct gcagcacagc    2580
gggccagacc agcagaggga cttttcagcgg gagattcaga tcctcaaagc actgcacagt    2640
gatttcattg tcaagtatcg tggtgtcagc tatggcccgg ccgccagag cctgcggctg     2700 gtcatggagt acctgcccag cggctgcttg cgcgacttcc tgcagcggca ccgcgcgcgc    2760
ctcgatgcca gccgcctcct tctctattcc tcgcagatct gcaagggcat ggagtacctg    2820
ggctcccgcc gctgcgtgca ccgcgacctg gccgcccgaa acatcctcgt ggagagcgag    2880
gcacacgtca agatcgctga cttcggccta gctaagctgc tgccgcttga caaagactac    2940
tacgtggtcc gcgagccagg ccagagcccc atttttctggt atgcccccga atccctctcg    3000
gacaacatct tctctcgcca gtcagacgtc tggagcttcg gggtcgtcct gtacgagctc    3060
ttcacctact gcgacaaaag ctgcagcccc tcggccgagt tcctgcggat gatgggatgt    3120
gagcgggatg tccccgcccct ctgccgcctc ttggaactgc tggaggaggg ccagaggctg    3180
ccggcgcctc ctgcctgccc tgctgaggtt cacgagctca tgaagctgtg ctgggcccct    3240
agcccacagg accggccatc attcagcgcc ctgggccccc agctggacat gctgtggagc    3300
ggaagccggg ggtgtgagac tcatgccttc actgctcacc cagagggcaa acaccactcc    3360
ctgtcctttt catag                                                     3375
```

<210> SEQ ID NO 133
<211> LENGTH: 870
<212> TYPE: DNA
<213> ORGANISM: Homo sapiens

<400> SEQUENCE: 133

```
atggagaacg gatacaccta tgaagattat aagaacactg cagaatggct tctgtctcac     60
actaagcacc gacctcaagt tgcaataatc tgtggttctg gattaggagg tctgactgat    120
aaattaactc aggcccagat ctttgactac ggtgaaatcc ccaactttcc ccgaagtaca    180
gtgccaggtc atgctggccg actggtgttt gggttcctga atggcaggc ctgtgtgatg    240 atgcagggca ggttccacat gtatgaaggg tacccactct ggaaggtgac attcccagtg    300
```

| | |
|---|---|
| agggttttcc accttctggg tgtggacacc ctggtagtca ccaatgcagc aggagggctg | 360 |
| aaccccaagt ttgaggttgg agatatcatg ctgatccgtg accatatcaa cctacctggt | 420 |
| ttcagtggtc agaaccctct cagagggccc aatgatgaaa ggtttggaga tcgtttccct | 480 |
| gccatgtctg atgcctacga ccggactatg aggcagaggg ctctcagtac ctggaaacaa | 540 |
| atgggggagc aacgtgagct acaggaaggc acctatgtga tggtggcagg ccccagcttt | 600 |
| gagactgtgg cagaatgtcg tgtgctgcag aagctgggag cagacgctgt tggcatgagt | 660 |
| acagtaccag aagttatcgt tgcacggcac tgtggacttc gagtctttgg cttctcactc | 720 |
| atcactaaca aggtcatcat ggattatgaa agcctggaga aggccaacca tgaagaagtc | 780 |
| ttagcagctg gcaaacaagc tgcacagaaa ttggaacagt ttgtctccat tcttatggcc | 840 |
| agcattccac tccctgacaa agccagttga | 870 |

<210> SEQ ID NO 134
<211> LENGTH: 1092
<212> TYPE: DNA
<213> ORGANISM: Homo sapiens

<400> SEQUENCE: 134

| | |
|---|---|
| atggcccaga cgcccgcctt cgacaagccc aaagtagaac tgcatgtcca cctagacgga | 60 |
| tccatcaagc ctgaaaccat cttatactat ggcaggagga gagggatcgc cctcccagct | 120 |
| aacacagcag aggggctgct gaacgtcatt ggcatggaca agccgctcac ccttccagac | 180 |
| ttcctggcca gtttgactac tacatgcct gctatcgcgg gctgccggga ggctatcaaa | 240 |
| aggatcgcct atgagtttgt agagatgaag gccaaagagg gcgtggtgta tgtggaggtg | 300 |
| cggtacagtc cgcacctgct ggccaactcc aaagtggagc caatcccctg gaaccaggct | 360 |
| gaaggggacc tcaccccaga cgaggtggtg gccctagtgg gccagggcct gcaggagggg | 420 |
| gagcgagact tcggggtcaa ggcccggtcc atcctgtgct gcatgcgcca ccagcccaac | 480 |
| tggtccccca aggtggtgga gctgtgtaag aagtaccagc agcagaccgt ggtagccatt | 540 |
| gacctggctg agatgagac catcccagga agcagcctct tgcctggaca tgtccaggcc | 600 |
| taccaggagc tgtgaagag cggcattcac cgtactgtcc acgccgggga ggtgggctcg | 660 |
| gccgaagtag taaaagaggc tgtggacata ctcaagacag agcggctggg acacggctac | 720 |
| cacaccctgg aagaccaggc cctttataac aggctgcggc aggaaaacat gcacttcgag | 780 |
| atctgcccct ggtccagcta cctcactggt gcctggaagc cggacacgga gcatgcagtc | 840 |
| attcggctca aaaatgacca ggctaactac tcgctcaaca cagatgaccc gctcatcttc | 900 |
| aagtccaccc tggacactga ttaccagatg accaaacggg acatgggctt tactgaagag | 960 |
| gagtttaaaa ggctgaacat caatgcggcc aaatctagtt tcctcccaga agatgaaaag | 1020 |
| agggagcttc tcgacctgct ctataaagcc tatgggatgc accttcagc ctctgcaggg | 1080 |
| cagaaccctct ga | 1092 |

<210> SEQ ID NO 135
<211> LENGTH: 3132
<212> TYPE: DNA
<213> ORGANISM: Homo sapiens

<400> SEQUENCE: 135

| | |
|---|---|
| atggcagcct ctttcccacc caccttggga ctcagttctg ccccagatga aattcagcac | 60 |
| ccacatatta aattttcaga atggaaattt aagctgttcc gggtgagatc ctttgaaaag | 120 |
| acacctgaag aagctcaaaa ggaaaagaag gattccttg aggggaaacc ctctctggag | 180 |

-continued

```
caatctccag cagtcctgga caaggctgat ggtcagaagc cagtcccaac tcagccattg    240
ttaaaagccc accctaagtt ttcaaagaaa tttcacgaca acgagaaagc aagaggcaaa    300
gcgatccatc aagccaacct tcgacatctc tgccgcatct gtgggaattc ttttagagct    360
gatgagcaca acaggagata tccagtccat ggtcctgtgg atggtaaaac cctaggcctt    420
ttacgaaaga aggaaaagag agctacttcc tggccggacc tcattgccaa ggttttccgg    480
atcgatgtga aggcagatgt tgactcgatc caccccactg agttctgcca taactgctgg    540
agcatcatgc acaggaagtt tagcagtgcc ccatgtgagg tttacttccc gaggaacgtg    600
accatggagt ggcaccccca cacaccatcc tgtgacatct gcaacactgc ccgtcgggga    660
ctcaagagga agagtcttca gccaaacttg cagctcagca aaaaactcaa aactgtgctt    720
gaccaagcaa acaagcccg tcagcgcaag agaagagctc aggcaaggat cagcagcaag    780
gatgtcatga agaagatcgc caactgcagt aagatacatc ttagtaccaa gctccttgca    840
gtggacttcc cagagcactt tgtgaaatcc atctcctgcc agatctgtga acacattctg    900
gctgaccctg tggagaccaa ctgtaagcat gtcttttgcc gggtctgcat tctcagatgc    960
ctcaaagtca tgggcagcta ttgtccctct tgccgatatc catgcttccc tactgacctg    1020
gagagtccag tgaagtcctt tctgagcgtc ttgaattccc tgatggtgaa atgtccagca    1080
aaagagtgca atgaggaggt cagtttggaa aaatataatc accacatctc aagtcacaag    1140
gaatcaaaag agatttttgt gcacattaat aaaggggggcc ggccccgcca acatcttctg    1200
tcgctgactc ggagagctca gaagcaccgg ctgagggagc tcaagctgca agtcaaagcc    1260
tttgctgaca agaagaagg tggagatgtg aagtccgtgt gcatgacctt gttcctgctg    1320
gctctgaggg cgaggaatga gcacaggcaa gctgatgagc tggaggccat catgcaggga    1380
aagggctctg gcctgcagcc agctgtttgc ttggccatcc gtgtcaacac cttcctcagc    1440
tgcagtcagt accacaagat gtacaggact gtgaaagcca tcacagggag acagattttt    1500
cagcctttgc atgcccttcg gaatgctgag aaggtacttc tgccaggcta ccaccacttt    1560
gagtggcagc cacctctgaa gaatgtgtct tccagcactg atgttggcat tattgatggg    1620
ctgtctggac tatcatcctc tgtggatgat tacccagtgg acaccattgc aaagaggttc    1680
cgctatgatt cagctttggt gtctgctttg atggacatgg aagaagacat cttggaaggc    1740
atgagatccc aagaccttga tgattacctg aatggcccct tcactgtggt ggtgaaggag    1800
tcttgtgatg aatgggagag cgtgagtgag aagcatggga gtgggcctgt agttccagaa    1860
aaggcagtcc gttttttcatt cacaatcatg aaaattacta ttgcccacag ctctcagaat    1920
gtgaaagtat ttgaagaagc caaacctaac tctgaactgt gttgcaagcc attgtgcctt    1980
atgctggcag atgagtctga ccacgagacg ctgactgcca tcctgagtcc tctcattgct    2040
gagagggagg ccatgaagag cagtgaatta atgcttgagc tgggaggcat tctccggact    2100
ttcaagttca tcttcagggg caccggctat gatgaaaaac ttgtgcggga agtggaaggc    2160
ctcgaggctt ctggctcagt ctacatttgt actctttgtg atgccacccg tctggaagcc    2220
tctcaaaatc ttgtcttcca ctctataacc agaagccatg ctgagaacct ggaacgttat    2280
gaggtctggc gttccaaccc ttaccatgag tctgtggaag aactgcggga tcgggtgaaa    2340
ggggtctcag ctaaaccttt cattgagaca gtcccttcca tagatgcact ccactgtgac    2400
attggcaatg cagctgagtt ctacaagatc ttccagctag atataggga agtgtataag    2460 aatcccaatg cttccaaaga ggaaaggaaa aggtggcagg ccacactgga caagcatctc    2520
```

```
cggaagaaga tgaacctcaa accaatcatg aggatgaatg caactttgc caggaagctc      2580 atgaccaaag agactgtgga tgcagtttgt gagttaattc cttccgagga gaggcacgag      2640
gctctgaggg agctgatgga tctttacctg aagatgaaac cagtatggcg atcatcatgc      2700
cctgctaaag agtgcccaga atccctctgc cagtacagtt tcaattcaca gcgttttgct      2760
gagctccttt ctacgaagtt caagtatagg tatgagggaa aaatcaccaa ttattttcac      2820
aaaaccctgg cccatgttcc tgaaattatt gagagggatg ctccattgg ggcatgggca      2880 agtgagggaa atgagtctgg taacaaactg tttaggcgct tccggaaaat gaatgccagg      2940
cagtccaaat gctatgagat ggaagatgtc ctgaaacacc actggttgta cacctccaaa      3000
tacctccaga gtttatgaa tgctcataat gcattaaaaa cctctgggtt taccatgaac      3060
cctcaggcaa gcttagggga cccattaggc atagaggact ctctggaaag ccaagattca      3120 atggaattt aa                                                         3132

<210> SEQ ID NO 136
<211> LENGTH: 1584
<212> TYPE: DNA
<213> ORGANISM: Homo sapiens

<400> SEQUENCE: 136
atgtctctgc agatggtaac agtcagtaat aacatagcct taattcagcc aggcttctca        60
ctgatgaatt ttgatggaca agttttcttc tttggacaaa aaggctggcc caaaagatcc       120
tgccccactg gagttttcca tctggatgta aagcataacc atgtcaaact gaagcctaca       180
attttctcta aggattcctg ctacctccct cctcttcgct acccagccac ttgcacattc       240
aaaggcagct tggagtctga aaagcatcaa tacatcatcc atggagggaa acaccaaac       300 aatgaggttt cagataagat ttatgtcatg tctattgttt gcaagaacaa caaaaggtt       360 acttttcgct gcacagagaa agacttggta ggagatgttc ctgaagccag atatggtcat       420
tccattaatg tggtgtacag ccgagggaaa agtatggtg ttctctttgg aggacgctca       480
tacatgcctt ctacccacag aaccacagaa aaatggaata gtgtagctga ctgcctgccc       540
tgtgttttcc tggtggattt tgaatttggg tgtgctacat catacattct tccagaactt       600
caggatgggc tatcttttca tgtctctatt gccaaaaatg acaccatcta tattttagga       660
ggacattcac ttgccaataa tatccggcct gccaacctgt acagaataag ggttgatctt       720
cccctgggta gcccagctgt gaattgcaca gtcttgccag gaggaatctc tgtctccagt       780
gcaatcctga ctcaaactaa caatgatgaa tttgttattg ttggtggcta tcagcttgaa       840
aatcaaaaaa gaatgatctg caacatcatc tctttagagg acaacaagat agaaattcgt       900
gagatggaga cccagattg gacccccagac attaagcaca gcaagatatg gtttggaagc       960
aacatgggaa atggaactgt ttttcttggc ataccaggag acaataaaca gttgtttca      1020 gaaggattct atttctatat gttgaaatgt gctgaagatg atactaatga agagcagaca      1080
acattcacaa acagtcaaac atcaacagaa gatccagggg attccactcc ctttgaagac      1140
tctgaagaat tttgttcag tgcagaagca aatagttttg atggtgatga tgaatttgac      1200
acctataatg aagatgatga agaagatgag tctgagacag gctactggat tacatgctgc      1260
cctacttgtg atgtggatat caacacttgg gtaccattct attcaactga gctcaacaaa      1320
cccgccatga tctactgctc tcatggggat gggcactggg tccatgctca gtgcatggat      1380
ctggcagaac gcacactcat ccatctgtca gcaggaagca acaagtatta ctgcaatgag      1440
catgtggaga tagcaagagc tctacacact ccccaaagag tcctacccctt aaaaaagcct      1500
```

```
ccaatgaaat ccctccgtaa aaaggttct ggaaaaatct tgactcctgc caagaaatcc    1560
tttcttagaa ggttgtttga ttag                                         1584
```

<210> SEQ ID NO 137
<211> LENGTH: 1124
<212> TYPE: PRT
<213> ORGANISM: Homo sapiens

<400> SEQUENCE: 137

```
Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350
```

-continued

```
Thr Asp Ser Gln His Phe Phe Cys Lys Glu Val Ala Pro Arg Leu
    355                 360                 365
Leu Glu Glu Val Ala Glu Gln Cys His Gly Pro Ile Thr Leu Asp Phe
370                 375                 380
Ala Ile Asn Lys Leu Lys Thr Gly Gly Ser Arg Pro Gly Ser Tyr Val
385                 390                 395                 400
Leu Arg Arg Ser Pro Gln Asp Phe Asp Ser Phe Leu Leu Thr Val Cys
                405                 410                 415
Val Gln Asn Pro Leu Gly Pro Asp Tyr Lys Gly Cys Leu Ile Arg Arg
            420                 425                 430
Ser Pro Thr Gly Thr Phe Leu Leu Val Gly Leu Ser Arg Pro His Ser
        435                 440                 445
Ser Leu Arg Glu Leu Leu Ala Thr Cys Trp Asp Gly Leu His Val
    450                 455                 460
Asp Gly Val Ala Val Thr Leu Thr Ser Cys Cys Ile Pro Arg Pro Lys
465                 470                 475                 480
Glu Lys Ser Asn Leu Ile Val Val Gln Arg Gly His Ser Pro Pro Thr
                485                 490                 495
Ser Ser Leu Val Gln Pro Gln Ser Gln Tyr Gln Leu Ser Gln Met Thr
            500                 505                 510
Phe His Lys Ile Pro Ala Asp Ser Leu Glu Trp His Glu Asn Leu Gly
        515                 520                 525
His Gly Ser Phe Thr Lys Ile Tyr Arg Gly Cys Arg His Glu Val Val
    530                 535                 540
Asp Gly Glu Ala Arg Lys Thr Glu Val Leu Leu Lys Val Met Asp Ala
545                 550                 555                 560
Lys His Lys Asn Cys Met Glu Ser Phe Leu Glu Ala Ala Ser Leu Met
                565                 570                 575
Ser Gln Val Ser Tyr Arg His Leu Val Leu Leu His Gly Val Cys Met
            580                 585                 590
Ala Gly Asp Ser Thr Met Val Gln Glu Phe Val His Leu Gly Ala Ile
        595                 600                 605
Asp Met Tyr Leu Arg Lys Arg Gly His Leu Val Pro Ala Ser Trp Lys
    610                 615                 620
Leu Gln Val Val Lys Gln Leu Ala Tyr Ala Leu Asn Tyr Leu Glu Asp
625                 630                 635                 640
Lys Gly Leu Pro His Gly Asn Val Ser Ala Arg Lys Val Leu Leu Ala
                645                 650                 655
Arg Glu Gly Ala Asp Gly Ser Pro Pro Phe Ile Lys Leu Ser Asp Pro
            660                 665                 670
Gly Val Ser Pro Ala Val Leu Ser Leu Glu Met Leu Thr Asp Arg Ile
        675                 680                 685
Pro Trp Val Ala Pro Glu Cys Leu Arg Glu Ala Gln Thr Leu Ser Leu
    690                 695                 700
Glu Ala Asp Lys Trp Gly Phe Gly Ala Thr Val Trp Glu Val Phe Ser
705                 710                 715                 720
Gly Val Thr Met Pro Ile Ser Ala Leu Asp Pro Ala Lys Lys Leu Gln
                725                 730                 735
Phe Tyr Glu Asp Arg Gln Gln Leu Pro Ala Pro Lys Trp Thr Glu Leu
            740                 745                 750
Ala Leu Leu Ile Gln Gln Cys Met Ala Tyr Glu Pro Val Gln Arg Pro
        755                 760                 765
Ser Phe Arg Ala Val Ile Arg Asp Leu Asn Ser Leu Ile Ser Ser Asp
```

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
            805                 810                 815

Phe Glu Glu Arg His Leu Lys Tyr Ile Ser Gln Leu Gly Lys Gly Asn
        820                 825                 830

Phe Gly Ser Val Glu Leu Cys Arg Tyr Asp Pro Leu Gly Asp Asn Thr
    835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
            885                 890                 895

Ser Leu Arg Leu Val Met Glu Tyr Leu Pro Ser Gly Cys Leu Arg Asp
        900                 905                 910

Phe Leu Gln Arg His Arg Ala Arg Leu Asp Ala Ser Arg Leu Leu Leu
    915                 920                 925

Tyr Ser Ser Gln Ile Cys Lys Gly Met Glu Tyr Leu Gly Ser Arg Arg
930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
            965                 970                 975

Asp Lys Asp Tyr Tyr Val Val Arg Glu Pro Gly Gln Ser Pro Ile Phe
        980                 985                 990

Trp Tyr Ala Pro Glu Ser Leu Ser Asp Asn Ile Phe Ser Arg Gln Ser
    995                 1000                1005

Asp Val Trp Ser Phe Gly Val Val Leu Tyr Glu Leu Phe Thr Tyr
1010                1015                1020

Cys Asp Lys Ser Cys Ser Pro Ser Ala Glu Phe Leu Arg Met Met
1025                1030                1035

Gly Cys Glu Arg Asp Val Pro Ala Leu Cys Arg Leu Leu Glu Leu
1040                1045                1050

Leu Glu Glu Gly Gln Arg Leu Pro Ala Pro Pro Ala Cys Pro Ala
1055                1060                1065

Glu Val His Glu Leu Met Lys Leu Cys Trp Ala Pro Ser Pro Gln
1070                1075                1080

Asp Arg Pro Ser Phe Ser Ala Leu Gly Pro Gln Leu Asp Met Leu
1085                1090                1095

Trp Ser Gly Ser Arg Gly Cys Glu Thr His Ala Phe Thr Ala His
1100                1105                1110

Pro Glu Gly Lys His His Ser Leu Ser Phe Ser
1115                1120

<210> SEQ ID NO 138
<211> LENGTH: 289
<212> TYPE: PRT
<213> ORGANISM: Homo sapiens

<400> SEQUENCE: 138

Met Glu Asn Gly Tyr Thr Tyr Glu Asp Tyr Lys Asn Thr Ala Glu Trp
1               5                   10                  15

-continued

Leu Leu Ser His Thr Lys His Arg Pro Gln Val Ala Ile Ile Cys Gly
            20                  25                  30

Ser Gly Leu Gly Gly Leu Thr Asp Lys Leu Thr Gln Ala Gln Ile Phe
        35                  40                  45

Asp Tyr Gly Glu Ile Pro Asn Phe Pro Arg Ser Thr Val Pro Gly His
    50                  55                  60

Ala Gly Arg Leu Val Phe Gly Phe Leu Asn Gly Arg Ala Cys Val Met
65                  70                  75                  80

Met Gln Gly Arg Phe His Met Tyr Glu Gly Tyr Pro Leu Trp Lys Val
                85                  90                  95

Thr Phe Pro Val Arg Val Phe His Leu Leu Gly Val Asp Thr Leu Val
            100                 105                 110

Val Thr Asn Ala Ala Gly Gly Leu Asn Pro Lys Phe Glu Val Gly Asp
        115                 120                 125

Ile Met Leu Ile Arg Asp His Ile Asn Leu Pro Gly Phe Ser Gly Gln
    130                 135                 140

Asn Pro Leu Arg Gly Pro Asn Asp Glu Arg Phe Gly Asp Arg Phe Pro
145                 150                 155                 160

Ala Met Ser Asp Ala Tyr Asp Arg Thr Met Arg Gln Arg Ala Leu Ser
                165                 170                 175

Thr Trp Lys Gln Met Gly Glu Gln Arg Glu Leu Gln Glu Gly Thr Tyr
            180                 185                 190

Val Met Val Ala Gly Pro Ser Phe Glu Thr Val Ala Glu Cys Arg Val
        195                 200                 205

Leu Gln Lys Leu Gly Ala Asp Ala Val Gly Met Ser Thr Val Pro Glu
    210                 215                 220

Val Ile Val Ala Arg His Cys Gly Leu Arg Val Phe Gly Phe Ser Leu
225                 230                 235                 240

Ile Thr Asn Lys Val Ile Met Asp Tyr Glu Ser Leu Glu Lys Ala Asn
                245                 250                 255

His Glu Glu Val Leu Ala Ala Gly Lys Gln Ala Ala Gln Lys Leu Glu
            260                 265                 270

Gln Phe Val Ser Ile Leu Met Ala Ser Ile Pro Leu Pro Asp Lys Ala
        275                 280                 285

Ser

<210> SEQ ID NO 139
<211> LENGTH: 363
<212> TYPE: PRT
<213> ORGANISM: Homo sapiens

<400> SEQUENCE: 139

Met Ala Gln Thr Pro Ala Phe Asp Lys Pro Lys Val Glu Leu His Val
1               5                   10                  15

His Leu Asp Gly Ser Ile Lys Pro Glu Thr Ile Leu Tyr Tyr Gly Arg
            20                  25                  30

Arg Arg Gly Ile Ala Leu Pro Ala Asn Thr Ala Glu Gly Leu Leu Asn
        35                  40                  45

Val Ile Gly Met Asp Lys Pro Leu Thr Leu Pro Asp Phe Leu Ala Lys
    50                  55                  60

Phe Asp Tyr Tyr Met Pro Ala Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

```
Tyr Val Glu Val Arg Tyr Ser Pro His Leu Leu Ala Asn Ser Lys Val
                100                 105                 110

Glu Pro Ile Pro Trp Asn Gln Ala Gly Asp Leu Thr Pro Asp Glu
    115                 120                 125

Val Val Ala Leu Val Gly Gln Gly Leu Gln Glu Gly Glu Arg Asp Phe
130                 135                 140

Gly Val Lys Ala Arg Ser Ile Leu Cys Cys Met Arg His Gln Pro Asn
145                 150                 155                 160

Trp Ser Pro Lys Val Glu Leu Cys Lys Tyr Gln Gln Gln Thr
                165                 170                 175

Val Val Ala Ile Asp Leu Ala Gly Asp Glu Thr Ile Pro Gly Ser Ser
                180                 185                 190

Leu Leu Pro Gly His Val Gln Ala Tyr Gln Glu Ala Val Lys Ser Gly
                195                 200                 205

Ile His Arg Thr Val His Ala Gly Glu Val Gly Ser Ala Glu Val Val
                210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
                260                 265                 270

Lys Pro Asp Thr Glu His Ala Val Ile Arg Leu Lys Asn Asp Gln Ala
                275                 280                 285

Asn Tyr Ser Leu Asn Thr Asp Asp Pro Leu Ile Phe Lys Ser Thr Leu
                290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Arg Glu Leu Leu Asp Leu Leu Tyr Lys Ala Tyr Gly
                340                 345                 350

Met Pro Pro Ser Ala Ser Ala Gly Gln Asn Leu
                355                 360

<210> SEQ ID NO 140
<211> LENGTH: 1043
<212> TYPE: PRT
<213> ORGANISM: Homo sapiens

<400> SEQUENCE: 140

Met Ala Ala Ser Phe Pro Pro Thr Leu Gly Leu Ser Ser Ala Pro Asp
1               5                   10                  15

Glu Ile Gln His Pro His Ile Lys Phe Ser Glu Trp Lys Phe Lys Leu
                20                  25                  30

Phe Arg Val Arg Ser Phe Glu Lys Thr Pro Glu Glu Ala Gln Lys Glu
            35                  40                  45

Lys Lys Asp Ser Phe Glu Gly Lys Pro Ser Leu Glu Gln Ser Pro Ala
        50                  55                  60

Val Leu Asp Lys Ala Asp Gly Gln Lys Pro Val Pro Thr Gln Pro Leu
65                  70                  75                  80

Leu Lys Ala His Pro Lys Phe Ser Lys Phe His Asp Asn Glu Lys
                85                  90                  95

Ala Arg Gly Lys Ala Ile His Gln Ala Asn Leu Arg His Leu Cys Arg
                100                 105                 110
```

```
Ile Cys Gly Asn Ser Phe Arg Ala Asp Glu His Asn Arg Arg Tyr Pro
            115                 120                 125

Val His Gly Pro Val Asp Gly Lys Thr Leu Gly Leu Leu Arg Lys Lys
130                 135                 140

Glu Lys Arg Ala Thr Ser Trp Pro Asp Leu Ile Ala Lys Val Phe Arg
145                 150                 155                 160

Ile Asp Val Lys Ala Asp Val Asp Ser Ile His Pro Thr Glu Phe Cys
                165                 170                 175

His Asn Cys Trp Ser Ile Met His Arg Lys Phe Ser Ser Ala Pro Cys
            180                 185                 190

Glu Val Tyr Phe Pro Arg Asn Val Thr Met Glu Trp His Pro His Thr
            195                 200                 205

Pro Ser Cys Asp Ile Cys Asn Thr Ala Arg Arg Gly Leu Lys Arg Lys
    210                 215                 220

Ser Leu Gln Pro Asn Leu Gln Leu Ser Lys Lys Leu Lys Thr Val Leu
225                 230                 235                 240

Asp Gln Ala Arg Gln Ala Arg Gln His Lys Arg Arg Ala Gln Ala Arg
                245                 250                 255

Ile Ser Ser Lys Asp Val Met Lys Lys Ile Ala Asn Cys Ser Lys Ile
                260                 265                 270

His Leu Ser Thr Lys Leu Leu Ala Val Asp Phe Pro Glu His Phe Val
            275                 280                 285

Lys Ser Ile Ser Cys Gln Ile Cys Glu His Ile Leu Ala Asp Pro Val
            290                 295                 300

Glu Thr Asn Cys Lys His Val Phe Cys Arg Val Cys Ile Leu Arg Cys
305                 310                 315                 320

Leu Lys Val Met Gly Ser Tyr Cys Pro Ser Cys Arg Tyr Pro Cys Phe
                325                 330                 335

Pro Thr Asp Leu Glu Ser Pro Val Lys Ser Phe Leu Ser Val Leu Asn
            340                 345                 350

Ser Leu Met Val Lys Cys Pro Ala Lys Glu Cys Asn Glu Glu Val Ser
            355                 360                 365

Leu Glu Lys Tyr Asn His Ile Ser Ser His Lys Glu Ser Lys Glu
            370                 375                 380

Ile Phe Val His Ile Asn Lys Gly Gly Arg Pro Arg Gln His Leu Leu
385                 390                 395                 400

Ser Leu Thr Arg Arg Ala Gln Lys His Arg Leu Arg Glu Leu Lys Leu
                405                 410                 415

Gln Val Lys Ala Phe Ala Asp Lys Glu Gly Gly Asp Val Lys Ser
                420                 425                 430

Val Cys Met Thr Leu Phe Leu Leu Ala Leu Arg Ala Arg Asn Glu His
            435                 440                 445

Arg Gln Ala Asp Glu Leu Glu Ala Ile Met Gln Gly Lys Gly Ser Gly
    450                 455                 460

Leu Gln Pro Ala Val Cys Leu Ala Ile Arg Val Asn Thr Phe Leu Ser
465                 470                 475                 480

Cys Ser Gln Tyr His Lys Met Tyr Arg Thr Val Lys Ala Ile Thr Gly
                485                 490                 495

Arg Gln Ile Phe Gln Pro Leu His Ala Leu Arg Asn Ala Glu Lys Val
                500                 505                 510

Leu Leu Pro Gly Tyr His His Phe Glu Trp Gln Pro Pro Leu Lys Asn
            515                 520                 525
```

-continued

Val Ser Ser Ser Thr Asp Val Gly Ile Ile Asp Gly Leu Ser Gly Leu
    530                 535                 540

Ser Ser Ser Val Asp Asp Tyr Pro Val Asp Thr Ile Ala Lys Arg Phe
545                 550                 555                 560

Arg Tyr Asp Ser Ala Leu Val Ser Ala Leu Met Asp Met Glu Glu Asp
                565                 570                 575

Ile Leu Glu Gly Met Arg Ser Gln Asp Leu Asp Asp Tyr Leu Asn Gly
            580                 585                 590

Pro Phe Thr Val Val Lys Glu Ser Cys Asp Gly Met Gly Asp Val
        595                 600                 605

Ser Glu Lys His Gly Ser Gly Pro Val Val Pro Glu Lys Ala Val Arg
    610                 615                 620

Phe Ser Phe Thr Ile Met Lys Ile Thr Ile Ala His Ser Ser Gln Asn
625                 630                 635                 640

Val Lys Val Phe Glu Glu Ala Lys Pro Asn Ser Glu Leu Cys Cys Lys
                645                 650                 655

Pro Leu Cys Leu Met Leu Ala Asp Glu Ser Asp His Glu Thr Leu Thr
            660                 665                 670

Ala Ile Leu Ser Pro Leu Ile Ala Glu Arg Glu Ala Met Lys Ser Ser
        675                 680                 685

Glu Leu Met Leu Glu Leu Gly Gly Ile Leu Arg Thr Phe Lys Phe Ile
690                 695                 700

Phe Arg Gly Thr Gly Tyr Asp Glu Lys Leu Val Arg Glu Val Glu Gly
705                 710                 715                 720

Leu Glu Ala Ser Gly Ser Val Tyr Ile Cys Thr Leu Cys Asp Ala Thr
                725                 730                 735

Arg Leu Glu Ala Ser Gln Asn Leu Val Phe His Ser Ile Thr Arg Ser
            740                 745                 750

His Ala Glu Asn Leu Glu Arg Tyr Glu Val Trp Arg Ser Asn Pro Tyr
        755                 760                 765

His Glu Ser Val Glu Glu Leu Arg Asp Arg Val Lys Gly Val Ser Ala
    770                 775                 780

Lys Pro Phe Ile Glu Thr Val Pro Ser Ile Asp Ala Leu His Cys Asp
785                 790                 795                 800

Ile Gly Asn Ala Ala Glu Phe Tyr Lys Ile Phe Gln Leu Glu Ile Gly
                805                 810                 815

Glu Val Tyr Lys Asn Pro Asn Ala Ser Lys Glu Arg Lys Arg Trp
            820                 825                 830

Gln Ala Thr Leu Asp Lys His Leu Arg Lys Met Asn Leu Lys Pro
        835                 840                 845

Ile Met Arg Met Asn Gly Asn Phe Ala Arg Lys Leu Met Thr Lys Glu
850                 855                 860

Thr Val Asp Ala Val Cys Glu Leu Ile Pro Ser Glu Arg His Glu
865                 870                 875                 880

Ala Leu Arg Glu Leu Met Asp Leu Tyr Leu Lys Met Lys Pro Val Trp
                885                 890                 895

Arg Ser Ser Cys Pro Ala Lys Glu Cys Pro Glu Ser Leu Cys Gln Tyr
            900                 905                 910

Ser Phe Asn Ser Gln Arg Phe Ala Glu Leu Leu Ser Thr Lys Phe Lys
        915                 920                 925

Tyr Arg Tyr Glu Gly Lys Ile Thr Asn Tyr Phe His Lys Thr Leu Ala
    930                 935                 940

His Val Pro Glu Ile Ile Glu Arg Asp Gly Ser Ile Gly Ala Trp Ala

```
                945                 950                 955                 960
Ser Glu Gly Asn Glu Ser Gly Asn Lys Leu Phe Arg Arg Phe Arg Lys
                    965                 970                 975
Met Asn Ala Arg Gln Ser Lys Cys Tyr Glu Met Glu Asp Val Leu Lys
                    980                 985                 990
His His Trp Leu Tyr Thr Ser Lys Tyr Leu Gln Lys Phe Met Asn Ala
                    995                 1000                1005
His Asn Ala Leu Lys Thr Ser Gly Phe Thr Met Asn Pro Gln Ala
        1010                1015                1020
Ser Leu Gly Asp Pro Leu Gly Ile Glu Asp Ser Leu Glu Ser Gln
        1025                1030                1035
Asp Ser Met Glu Phe
        1040

<210> SEQ ID NO 141
<211> LENGTH: 527
<212> TYPE: PRT
<213> ORGANISM: Homo sapiens

<400> SEQUENCE: 141

Met Ser Leu Gln Met Val Thr Val Ser Asn Asn Ile Ala Leu Ile Gln
1               5                   10                  15
Pro Gly Phe Ser Leu Met Asn Phe Asp Gly Gln Val Phe Phe Phe Gly
                20                  25                  30
Gln Lys Gly Trp Pro Lys Arg Ser Cys Pro Thr Gly Val Phe His Leu
            35                  40                  45
Asp Val Lys His Asn His Val Lys Leu Lys Pro Thr Ile Phe Ser Lys
        50                  55                  60
Asp Ser Cys Tyr Leu Pro Pro Leu Arg Tyr Pro Ala Thr Cys Thr Phe
65                  70                  75                  80
Lys Gly Ser Leu Glu Ser Glu Lys His Gln Tyr Ile Ile His Gly Gly
                85                  90                  95
Lys Thr Pro Asn Asn Glu Val Ser Asp Lys Ile Tyr Val Met Ser Ile
                100                 105                 110
Val Cys Lys Asn Asn Lys Val Thr Phe Arg Cys Thr Glu Lys Asp
            115                 120                 125
Leu Val Gly Asp Val Pro Glu Ala Arg Tyr Gly His Ser Ile Asn Val
        130                 135                 140
Val Tyr Ser Arg Gly Lys Ser Met Gly Val Leu Phe Gly Gly Arg Ser
145                 150                 155                 160
Tyr Met Pro Ser Thr His Arg Thr Thr Glu Lys Trp Asn Ser Val Ala
                165                 170                 175
Asp Cys Leu Pro Cys Val Phe Leu Val Asp Phe Glu Phe Gly Cys Ala
            180                 185                 190
Thr Ser Tyr Ile Leu Pro Glu Leu Gln Asp Gly Leu Ser Phe His Val
        195                 200                 205
Ser Ile Ala Lys Asn Asp Thr Ile Tyr Ile Leu Gly Gly His Ser Leu
        210                 215                 220
Ala Asn Asn Ile Arg Pro Ala Asn Leu Tyr Arg Ile Arg Val Asp Leu
225                 230                 235                 240
Pro Leu Gly Ser Pro Ala Val Asn Cys Thr Val Leu Pro Gly Gly Ile
                245                 250                 255
Ser Val Ser Ser Ala Ile Leu Thr Gln Thr Asn Asn Asp Glu Phe Val
                260                 265                 270
```

Ile Val Gly Gly Tyr Gln Leu Glu Asn Gln Lys Arg Met Ile Cys Asn
               275                 280                 285

Ile Ile Ser Leu Glu Asp Asn Lys Ile Glu Ile Arg Glu Met Glu Thr
       290                 295                 300

Pro Asp Trp Thr Pro Asp Ile Lys His Ser Lys Ile Trp Phe Gly Ser
305                 310                 315                 320

Asn Met Gly Asn Gly Thr Val Phe Leu Gly Ile Pro Gly Asp Asn Lys
                325                 330                 335

Gln Val Val Ser Glu Gly Phe Tyr Phe Tyr Met Leu Lys Cys Ala Glu
            340                 345                 350

Asp Asp Thr Asn Glu Glu Gln Thr Thr Phe Thr Asn Ser Gln Thr Ser
        355                 360                 365

Thr Glu Asp Pro Gly Asp Ser Thr Pro Phe Glu Asp Ser Glu Glu Phe
    370                 375                 380

Cys Phe Ser Ala Glu Ala Asn Ser Phe Asp Gly Asp Asp Glu Phe Asp
385                 390                 395                 400

Thr Tyr Asn Glu Asp Asp Glu Glu Asp Glu Ser Glu Thr Gly Tyr Trp
                405                 410                 415

Ile Thr Cys Cys Pro Thr Cys Asp Val Asp Ile Asn Thr Trp Val Pro
            420                 425                 430

Phe Tyr Ser Thr Glu Leu Asn Lys Pro Ala Met Ile Tyr Cys Ser His
        435                 440                 445

Gly Asp Gly His Trp Val His Ala Gln Cys Met Asp Leu Ala Glu Arg
    450                 455                 460

Thr Leu Ile His Leu Ser Ala Gly Ser Asn Lys Tyr Tyr Cys Asn Glu
465                 470                 475                 480

His Val Glu Ile Ala Arg Ala Leu His Thr Pro Gln Arg Val Leu Pro
                485                 490                 495

Leu Lys Lys Pro Pro Met Lys Ser Leu Arg Lys Lys Gly Ser Gly Lys
            500                 505                 510

Ile Leu Thr Pro Ala Lys Lys Ser Phe Leu Arg Arg Leu Phe Asp
        515                 520                 525

<210> SEQ ID NO 142
<211> LENGTH: 4904
<212> TYPE: DNA
<213> ORGANISM: Artificial Sequence
<220> FEATURE:
<223> OTHER INFORMATION: PGK promoter associated with FANCA gene

<400> SEQUENCE: 142
ggggttgggg ttgcgccttt tccaaggcag ccctgggttt gcgcagggac gcggctgctc    60
tgggcgtggt tccgggaaac gcagcggcgc cgaccctggg tctcgcacat tcttcacgtc   120
cgttcgcagc gtcacccgga tcttcgccgc taccctgtg ggccccccgg cgacgcttcc   180
tgctccgccc ctaagtcggg aaggttcctt gcggttcgcg gcgtgccgga cgtgacaaac   240
ggaagccgca cgtctcacta gtaccctcgc agacggacag cgccagggag caatggcagc   300
gcgccgaccg cgatgggctg tggccaatag cggctgctca gcggggcgcg ccgagagcag   360
cggccgggaa gggcggtgc gggaggcggg gtgtggggcg gtagtgtggg ccctgttcct   420
gcccgcgcgg tgttccgcat tctgcaagcc tccggagcgc acgtcggcag tcggctccct   480
cgttgaccga atcaccgacc tctctcccca gggggatcca ccgtccgcc aaggccatgt   540 ccgactcgtg gtcccgaac tccgcctcgg gccaggaccc aggggccgc cggagggcct   600 gggccgagct gctggcggga agggtcaaga gggaaaaata taatcctgaa agggcacaga   660

```
aattaaagga atcagctgtg cgcctcctgc gaagccatca ggacctgaat gcccttttgc    720
ttgaggtaga aggtccactg tgtaaaaaat tgtctctcag caaagtgatt gactgtgaca    780
gttctgaggc ctatgctaat cattctagtt catttatagg ctctgctttg caggatcaag    840
cctcaaggct gggggttccc gtgggtattc tctcagccgg gatggttgcc tctagcgtgg    900
gacagatctg cacggctcca gcggagacca gtcaccctgt gctgctgact gtggagcaga    960
gaaagaagct gtcttccctg ttagagtttg ctcagtattt attggcacac agtatgttct   1020
cccgtctttc cttctgtcaa gaattatgga aaatacagag ttctttgttg cttgaagcgg   1080
tgtggcatct tcacgtacaa ggcattgtga gcctgcaaga gctgctggaa agccatcccg   1140
acatgcatgc tgtgggatcg tggctcttca ggaatctgtg ctgcctttgt gaacagatgg   1200
aagcatcctg ccagcatgct gacgtcgcca gggccatgct ttctgatttt gttcaaatgt   1260
ttgttttgag gggatttcag aaaaactcag atctgagaag aactgtggag cctgaaaaaa   1320
tgccgcaggt cacggttgat gtactgcaga gaatgctgat ttttgcactt gacgctttgg   1380
ctgctggagt acaggaggag tcctccactc acaagatcgt gaggtgctgg ttcggagtgt   1440
tcagtggaca cacgcttggc agtgtaattt ccacagatcc tctgaagagg ttcttcagtc   1500
ataccctgac tcagatactc actcacagcc ctgtgctgaa agcatctgat gctgttcaga   1560
tgcagagaga gtggagcttt gcgcggacac accctctgct cacctcactg taccgcaggc   1620
tctttgtgat gctgagtgca gaggagttgg ttggccattt gcaagaagtt ctggaaacgc   1680
aggaggttca ctgcagagga gtgctctcct ttgtgtctgc cctggttgtc tgctttccag   1740
aagcgcagca gctgcttgaa gactgggtgg cgcgtttgat ggcccaggca ttcgagagct   1800
gccagctgga cagcatggtc actgcgttcc tggttgtgcg ccaggcagca ctggagggcc   1860
cctctgcgtt cctgtcatat gcagactggt tcaaggcctc ctttgggagc acacgaggct   1920
accatggctg cagcaagaag gccctggtct tcctgtttac gttcttgtca gaactcgtgc   1980
cttttgagtc tccccggtac ctgcaggtgc acattctcca cccacccctg gttcccagca   2040
agtaccgctc cctcctcaca gactacatct cattggccaa gacacggctg gccgacctca   2100
aggtttctat agaaaacatg ggactctacg aggatttgtc atcagctggg gacattactg   2160
agccccacag ccaagctctt caggatgttg aaaaggccat catggtgttt gagcatacgg   2220
ggaacatccc agtcaccgtc atggaggcca gcatattcag gaggcttac tacgtgtccc   2280
acttcctccc cgccctgctc acacctcgag tgctccccaa agtccctgac tcccgtgtgg   2340
cgtttataga gtctctgaag agagcagata aaatcccccc atctctgtac tccacctact   2400
gccaggcctg ctctgctgct gaagagaagc agaagatgc agccctggga gtgagggcag   2460
aacccaactc tgctgaggag ccctgggac agctcacagc tgcactggga gagctgagag   2520
cctccatgac agacccagc cagcgtgatg ttatatcggc acaggtggca gtgatttctg   2580
aaagactgag ggctgtcctg gccacaatg aggatgacag cagcgttgag atatcaaaga   2640
ttcagctcag catcaacacg ccgagactgg agccacggga acacattgct gtggacctcc   2700
tgctgacgtc tttctgtcag aacctgatgg ctgcctccag tgtcgctccc ccggagaggc   2760
agggtccctg ggctgccctc ttcgtgagga ccatgtgtgg acgtgtgctc cctgcagtgc   2820
tcacccggct ctgccagctg ctccgtcacc agggcccgag cctgagtgcc ccacatgtgc   2880
tggggttggc tgcccggcc gtgcacctgg gtgagtccag gtctgcgctc ccagaggtgg   2940
atgtgggtcc tcctgcacct ggtgctggcc ttcctgtccc tgcgctcttt gacagcctcc   3000
```

| | |
|---|---|
| tgacctgtag gacgagggat tccttgttct tctgcctgaa attttgtaca gcagcaattt | 3060 |
| cttactctct ctgcaagttt tcttcccagt cacgagatac tttgtgcagc tgcttatctc | 3120 |
| caggccttat taaaaagttt cagttcctca tgttcagatt gttctcagag gcccgacagc | 3180 |
| ctctttctga ggaggacgta gccagccttt cctggagacc cttgcacctt ccttctgcag | 3240 |
| actggcagag agctgccctc tctctctgga cacacagaac cttccgagag gtgttgaaag | 3300 |
| aggaagatgt tcacttaact taccaagact ggttacacct ggagctggaa attcaacctg | 3360 |
| aagctgatgc tctttcagat actgaacggc aggacttcca ccagtgggcg atccatgagc | 3420 |
| actttctccc tgagtcctcg gcttcagggg gctgtgacgg agacctgcag gctgcgtgta | 3480 |
| ccattcttgt caacgcactg atggatttcc accaaagctc aaggagttat gaccactcag | 3540 |
| aaaattctga tttggtcttt ggtggccgca caggaaatga ggatattatt tccagattgc | 3600 |
| aggagatggt agctgacctg gagctgcagc aagacctcat agtgcctctc ggccacaccc | 3660 |
| cttcccagga gcacttcctc tttgagattt ccgcagacg gctccaggct ctgacaagcg | 3720 |
| ggtggagcgt ggctgccagc cttcagagac agagggagc gctaatgtac aaacggatcc | 3780 |
| tcctccgcct gccttcgtct gtcctctgcg gcagcagctt ccaggcagaa cagcccatca | 3840 |
| ctgccagatg cgagcagttc ttccacttgg tcaactctga gatgagaaac ttctgctccc | 3900 |
| acggaggtgc cctgacacag gacatcactg cccacttctt caggggcctc ctgaacgcct | 3960 |
| gtctgcggag cagagacccc tccctgatgg tcgacttcat actggccaag tgccagacga | 4020 |
| aatgccccett aattttgacc tctgctctgg tgtggtggcc gagcctggag cctgtgctgc | 4080 |
| tctgccggtg gaggagacac tgccagagcc cgctgccccg ggaactgcag aagctacaag | 4140 |
| aaggccggca gtttgccagc gatttcctct cccctgaggc tgcctcccca gcacccaacc | 4200 |
| cggactggct ctcagctgct gcactgcact ttgcgattca acaagtcagg gaagaaaaca | 4260 |
| tcaggaagca gctaaagaag ctggactgcg agagagagga gctattggtt ttccttttct | 4320 |
| tcttctcctt gatgggcctg ctgtcgtcac atctgacctc aaatagcacc acagacctgc | 4380 |
| caaaggcttt ccacgtttgt gcagcaatcc tcgagtgttt agagaagagg aagatatcct | 4440 |
| ggctggcact ctttcagttg acagagagtg acctcaggct ggggcggctc ctcctccgtg | 4500 |
| tggccccgga tcagcacacc aggctgctgc ctttcgcttt ttacagtctt ctctcctact | 4560 |
| tccatgaaga cgcggccatc agggaagagg ccttcctgca tgttgctgtg gacatgtact | 4620 |
| tgaagctggt ccagctcttc gtggctgggg ataaagcac agtttcacct ccagctggca | 4680 |
| ggagcctgga gctcaagggt cagggcaacc ccgtggaact gataacaaaa gctcgtcttt | 4740 |
| ttctgctgca gttaatacct cggtgcccga aaaagagctt ctcacacgtg gcagagctgc | 4800 |
| tggctgatcg tggggactgc gacccagagg tgagcgccgc cctccagagc agacagcagg | 4860 |
| ctgccctga cgctgacctg tcccaggagc ctcatctctt ctga | 4904 |

<210> SEQ ID NO 143
<211> LENGTH: 12265
<212> TYPE: DNA
<213> ORGANISM: Artificial Sequence
<220> FEATURE:
<223> OTHER INFORMATION: 506 PGK.FancA

<400> SEQUENCE: 143

| | |
|---|---|
| tcgcgcgttc tcgaggagct tggcccattg catacgttgt atccatatca taatatgtac | 60 |
| atttatattg gctcatgtcc aacattaccg ccatgttgac attgattatt gactagttat | 120 |
| taatagtaat caattacggg gtcattagtt catagcccat atatggagtt ccgcgttaca | 180 |

```
taacttacgg taaatggccc gcctggctga ccgcccaacg accccgccc attgacgtca      240 ataatgacgt atgttcccat agtaacgcca atagggactt tccattgacg tcaatgggtg     300
gagtatttac gctaaactgc ccacttggca gtacatcaag tgtatcatat gccaagtacg     360 cccctattg acgtcaatga cggtaaatgg cccgcctggc attatgccca gtacatgacc      420
ttatgggact ttcctacttg gcagtacatc tacgtattag tcatcgctat taccatggtg     480
atgcggtttt ggcagtacat caatgggcgt ggatagcggt ttgactcacg ggatttcca     540 agtctccacc ccattgacgc aaatgggcgg taggcgtgta cggtgggagg tctatataag     600
cagagcttct agattgtacg ggagctctct cttcactact cgctgcgtcg agagtgtacg     660
agactctcca ggtttggtaa gaaatatttt atattgttat aatgttacta tgatccatta    720
acactctgct tatagattgt aagggtgatt gcaatgcttt ctgcataaaa ctttggtttt     780
cttgttaatc aataaaccga cttgattcga gaacctactc atatattatt gtctctttta    840
tactttatta gtaaaagga tttgtatatt agccttgcta agggagacat ctagtgtatat    900 aagtgtgaac tacacttatc ttaaatgatg taactcctta ggataatcaa tatacaaaat     960
tccatgacaa ttggcgccca acgtggggct cgaatataag tcgggtttat ttgtaaatta    1020
tccctaggga cctccgagca tagcgggagg catataaaag ccaatagaca atggctagca    1080
ggaagtaatg ttgaagaata tgaacttgat gttgaagctc tggttgtaat tttaagagat    1140
agaaatatac caagaaatcc tttacatgga gaagttatag gtcttcgcct tactgaagga    1200
tggtggggac aaattgagag atttcagatg gtacgttgat tcgaattaag gctatggatt    1260
tggccatggg acaagaaata ttagtttata gtcccattgt atctatgact aaaatacaaa    1320
aaactccact accagaaaga aaagctttac ccattgagtg gataacatgg atgacttatt    1380
tagaagatcc aagaatccaa tttcattatg ataaaacctt accagaactt aagcatattc    1440
cagatgtata tacatctagt cagtctcctg ttaaacatcc ttctcaatat gaaggagtgt    1500
tttatactga tggctcggcc atcaaaagtc ctgatcctac aaaaagcaat aatgctggca    1560
tgggaatagt acatgccaca tacaaacctg aatatcaagt tttgaatcaa tggtcaatac    1620
cactaggtaa tcatactgct cagatggctg aaatagctgc agttgaattt gcctgtaaaa    1680
aagctttaaa aatacctggt cctgtattag ttataactga tagtttctat gtagcagaaa    1740
gtgctaataa agaattacca tactggaaat ctaatgggtt tgttaataat aagaaaaagc    1800
ctcttaaaca tatctccaaa tggaaatcta ttgctgagtg tttatctatg aaaccagaca    1860
ttactattca acatgaaaaa ggcatcagcc tacaaatacc agtattcata ctgaaaggca    1920
atgccctagc agataagctt gccacccaag gaagttatgt ggttaattgt ataccaaaa    1980 aaccaaacct ggatgcagag ttggatcaat tattacaggg tcattatata aaaggatatc    2040
ccaaacaata tacatatttt ttagaagatg gcaaagtaaa agtttccaga cctgaagggg    2100
ttaaaattat tcccccctcag tcagacagac aaaaaattgt gcttcaagcc cacaatttgg    2160
ctcacaccgg acgtgaagcc actctttaa aaattgccaa cctttattgg tggccaaata    2220
tgagaaagga tgtggttaaa caactaggac gctgtcaaca gtgtttaatc acaaatgctt    2280
ccaacaaagc ctctggtcct attctaagac cagataggcc tcaaaaacct tttgataaat    2340
tctttattga ctatattgga cctttgccac cttcacaggg ataacctatat gtattagtag    2400 ttgttgatgg aatgacagga ttcacttggt tatacccccac taaggctcct tctactagcg    2460
caactgttaa atctctcaat gtactcacta gtattgcaat tccaaaggtg attcactctg    2520
```

```
atcaaggtgc agcattcact tcttcaacct ttgctgaatg ggcaaaggaa agaggtatac    2580
atttggaatt cagtactcct tatcaccccc aaagtggtag taaggtggaa aggaaaaata    2640
gtgatataaa acgactttta actaaactgc tagtaggaag acccacaaag tggtatgacc    2700
tattgcctgt tgtacaactt gctttaaaca acacctatag ccctgtatta aaatatactc    2760
cacatcaact cttatttggt atagattcaa atactccatt tgcaaatcaa gatacacttg    2820
acttgaccag agaagaagaa cttcctctttt acaggaaat tcgtacttct ttataccatc    2880
catccacccc tccagcctcc tctcgttcct ggtctcctgt tgttggccaa ttggtccagg    2940
agagggtggc taggcctgct tctttgagac ctcgttggca taaccgtct actgtactta    3000
aggtgttgaa tccaaggact gttgttattt tggaccatct tggcaacaac agaactgtaa    3060
gtatagataa tttaaaacct acttctcatc agaatggcac caccaatgac actgcaacaa    3120
tggatcattt ggaaaaaaat gaataaagcg catgaggcac ttcaaaatac aacaactgtg    3180
actgaacagc agaaggaaca aattatactg gacattcaaa atgaagaagt acaaccaact    3240
aggagagata atttagata tctgctttat acttgttgtg ctactagctc aagagtattg    3300
gcctggatgt ttttagtttg tatattgtta atcattgttt tggtttcatg ctttgtgact    3360
atatccagaa tacaatggaa taaggatatt caggtattag gacctgtaat agactggaat    3420
gttactcaaa gagctgttta tcaaccctta cagactagaa ggattgcacg ttcccttaga    3480
atgcagcatc ctgttccaaa atatgtggag gtaaatatga ctagtattcc acaaggtgta    3540
tactatgaac cccatccggc gcgccagatc tgcatgccac ggggttgggg ttgcgccttt    3600
tccaaggcag ccctgggttt gcgcaggac gcggctgctc tgggcgtggt tccgggaaac    3660
gcagcggcgc cgaccctggg tctcgcacat tcttcacgtc cgttcgcagc gtcacccgga    3720
tcttcgccgc taccccttgtg gcccccccgg cgacgcttcc tgctccgccc ctaagtcggg    3780
aaggttcctt gcggttcgcg gcgtgccgga cgtgacaaac ggaagccgca cgtctcacta    3840
gtaccctcgc agacggacag cgccaggag caatggcagc gcgccgaccg cgatgggctg    3900
tggccaatag cggctgctca gcggggcgcg ccgagagcag cggccgggaa ggggcggtgc    3960
gggaggcggg gtgtggggcg gtagtgtggg ccctgttcct gcccgcgcgg tgttccgcat    4020
tctgcaagcc tccggagcgc acgtcggcag tcggctccct cgttgaccga atcaccgacc    4080
tctctcccca gggggatcca ccggtccgcc aaggccatgt ccgactcgtg ggtcccgaac    4140
tccgcctcgg gccaggaccc aggggggccgc cggagggcct gggccgagct gctggcggga    4200
agggtcaaga gggaaaaata taatcctgaa agggcacaga aattaaagga atcagctgtg    4260
cgcctcctgc gaagccatca ggacctgaat gccctttgc ttgaggtaga aggtccactg    4320
tgtaaaaaat tgtctctcag caaagtgatt gactgtgaca gttctgaggc ctatgctaat    4380
cattctagtt catttatagg ctctgctttg caggatcaag cctcaaggct ggggggttccc    4440
gtgggtattc tctcagccgg gatggttgcc tctagcgtgg gacagatctg cacggctcca    4500
gcggagacca gtcaccctgt gctgctgact gtggagcaga gaaagaagct gtcttccctg    4560
ttagagtttg ctcagtattt attggcacac agtatgttct cccgtctttc cttctgtcaa    4620
gaattatgga aaatacagag ttcttttgttg cttgaagcgg tgtggcatct tcacgtacaa    4680
ggcattgtga gcctgcaaga gctgctggaa agccatcccg acatgcatgc tgtgggatcg    4740
tggctcttca ggaatctgtg ctgcctttgt gaacagatgg aagcatcctg ccagcatgct    4800
gacgtcgcca gggccatgct ttctgatttt tgttcaaatgt ttgttttgag gggatttcag    4860
aaaaactcag atctgagaag aactgtggag cctgaaaaaa tgccgcaggt cacggttgat    4920
```

```
gtactgcaga gaatgctgat tttttgcactt gacgctttgg ctgctggagt acaggaggag    4980
tcctccactc acaagatcgt gaggtgctgg ttcggagtgt tcagtggaca cacgcttggc    5040
agtgtaattt ccacagatcc tctgaagagg ttcttcagtc atacccctgac tcagatactc   5100 actcacagcc ctgtgctgaa agcatctgat gctgttcaga tgcagagaga gtggagcttt    5160
gcgcggacac accctctgct cacctcactg taccgcaggc tctttgtgat gctgagtgca    5220
gaggagttgg ttggccattt gcaagaagtt ctggaaacgc aggaggttca ctggcagaga    5280
gtgctctcct ttgtgtctgc cctggttgtc tgctttccag aagcgcagca gctgcttgaa    5340
gactgggtgg cgcgtttgat ggcccaggca ttcgagagct gccagctgga cagcatggtc    5400
actgcgttcc tggttgtgcg ccaggcagca ctggagggcc cctctgcgtt cctgtcatat    5460
gcagactggt tcaaggcctc ctttgggagc acacgaggct accatggctg cagcaagaag    5520
gccctggtct tcctgtttac gttcttgtca gaactcgtgc cttttgagtc tccccggtac    5580
ctgcaggtgc acattctcca cccacccctg gttcccagca agtaccgctc cctcctcaca    5640
gactacatct cattggccaa gacacggctg gccgacctca aggtttctat agaaaacatg    5700
ggactctacg aggatttgtc atcagctggg gacattactg agccccacag ccaagctctt    5760
caggatgttg aaaaggccat catggtgttt gagcatacgg ggaacatccc agtcaccgtc    5820
atggaggcca gcatattcag gaggccttac tacgtgtccc acttcctccc cgccctgctc    5880
acacctcgag tgctccccaa agtccctgac tcccgtgtgg cgtttataga gtctctgaag    5940
agagcagata aaatcccccc atctctgtac tccacctact gccaggcctg ctctgctgct    6000
gaagagaagc cagaagatgc agccctggga gtgagggcag aacccaactc tgctgaggag    6060
cccctgggac agctcacagc tgcactggga gagctgagag cctccatgac agaccccagc    6120
cagcgtgatg ttatatcggc acaggtggca gtgatttctg aaagactgag ggctgtcctg    6180
ggccacaatg aggatgacag cagcgttgag atatcaaaga ttcagctcag catcaacacg    6240
ccgagactgg agccacggga acacattgct gtggacctcc tgctgacgtc tttctgtcag    6300
aacctgatgg ctgcctccag tgtcgctccc ccggagaggc agggtccctg gctgccctc    6360 ttcgtgagga ccatgtgtgg acgtgtgctc cctgcagtgc tcacccggct ctgccagctg    6420
ctccgtcacc agggcccgag cctgagtgcc ccacatgtgc tggggttggc tgccctggcc    6480
gtgcacctgg gtgagtccag gtctgcgctc ccagaggtga tgtgggtcc tcctgcacct    6540 ggtgctggcc ttcctgtccc tgcgctcttt gacagcctcc tgacctgtag gacgagggat    6600
tccttgttct tctgcctgaa attttgtaca gcagcaattt cttactctct ctgcaagttt    6660
tcttcccagt cacgagatac tttgtgcagc tgcttatctc caggccttat taaaaagttt    6720
cagttcctca tgttcagatt gttctcagag gcccgacagc ctctttctga ggaggacgta    6780
gccagccttt cctggagacc cttgcacctt ccttctgcag actggcagag agctgccctc    6840
tctctctgga cacacagaac cttccgagag gtgttgaaag aggaagatgt tcacttaact    6900
taccaagact ggttacacct ggagctggaa attcaacctg aagctgatgc tctttcagat    6960
actgaacggc aggacttcca ccagtgggcg atccatgagc actttctccc tgagtcctcg    7020
gcttcagggg gctgtgacgg agacctgcag gctgcgtgta ccattcttgt caacgcactg    7080
atggatttcc accaaagctc aaggagttat gaccactcag aaaattctga tttggtctttt   7140 ggtggccgca caggaaatga ggatattatt tccagattgc aggagatggt agctgacctg    7200
gagctgcagc aagacctcat agtgcctctc ggccacaccc cttcccagga gcacttcctc    7260
```

```
tttgagattt tccgcagacg gctccaggct ctgacaagcg ggtggagcgt ggctgccagc    7320
cttcagagac agagggagct gctaatgtac aaacggatcc tcctccgcct gccttcgtct    7380
gtcctctgcg gcagcagctt ccaggcagaa cagcccatca ctgccagatg cgagcagttc    7440
ttccacttgg tcaactctga gatgagaaac ttctgctccc acggaggtgc cctgacacag    7500
gacatcactg cccacttctt caggggcctc ctgaacgcct gtctgcggag cagagacccc    7560
tccctgatgg tcgacttcat actgccaagt gccagacga atgccccctt aattttgacc    7620
tctgctctgg tgtggtggcc gagcctggag cctgtgctgc tctgccggtg gaggagacac    7680
tgccagagcc cgctgccccg ggaactgcag aagctacaag aaggccggca gtttgccagc    7740
gatttcctct cccctgaggc tgcctcccca gcacccaacc cggactggct ctcagctgct    7800
gcactgcact ttgcgattca acaagtcagg gaagaaaaca tcaggaagca gctaaagaag    7860
ctggactgcg agagagagga gctattggtt ttccttttct tcttctcctt gatgggcctg    7920
ctgtcgtcac atctgacctc aaatagcacc acagacctgc caaaggcttt ccacgttttgt   7980
gcagcaatcc tcgagtgttt agagaagagg aagatatcct ggctggcact cttttcagttg    8040
acagagagtg acctcaggct ggggcggctc ctcctccgtg tggccccgga tcagcacacc    8100
aggctgctgc ctttcgcttt ttacagtctt ctctcctact tccatgaaga cgcggccatc    8160
agggaagagg ccttcctgca tgttgctgtg gacatgtact tgaagctggt ccagctcttc    8220
gtggctgggg atacaagcac agtttcacct ccagctggca ggagcctgga gctcaagggt    8280
cagggcaacc ccgtggaact gataacaaaa gctcgtcttt ttctgctgca gttaatacct    8340
cggtgcccga aaaagagctt ctcacacgtg gcagagctgc tggctgatcg tggggactgc    8400
gacccagagg tgagcgccgc cctccagagc agacagcagg ctgcccctga cgctgacctg    8460
tcccaggagc ctcatctctt ctgacgggac ctgccactgc acaccagccc agctcccgtg    8520
taaataattt attacaagca taacatggag ctcttgttgc actaaaaagt ggattacaaa    8580
tctcctcgac tgctttagtg gggaaaggaa tcaattattt atgaactgtc cggccccgag    8640
tcactcagcg tttgcgggaa aataaaccac tggtcccaga gcagaggaag gctacttgag    8700
ccggacacca agcccgcctc cagcaccaag ggcgggcagc accctccgac cctcccatgc    8760
gggtgcacac gaagggtgag gctgacacag ccactgcgga gtccaggctg ctagaggtgc    8820
tcatcctcac tgccgtcctc aggtgggttc gggcttcacc gcctggccct ctgtggtcac    8880
agaggggctc ggtggcccag gtggtggttc cgcctccagg ggcagggcct tgtcctgggt    8940
ctgtgtcagc gggtgcacca tggacatgtg tacaagtaaa gcggccgcgt cgagggctgc    9000
aggaattcga gcatcttacc gccatttatt cccatatttg ttctgttttt cttgatttgg    9060
gtatacattt aaatgttaat aaacaaaat ggtggggcaa tcatttacat ttttagggat    9120
atgtaattac tagttcaggt gtattgccac aagacaaaca tgttaagaaa ctttcccgtt    9180
atttacgctc tgttcctgtt aatcaacctc tggattacaa aatttgtgaa agattgactg    9240
atattcttaa ctatgttgct cctttttacgc tgtgtggata tgctgcttta tagcctctgt    9300
atctagctat tgcttcccgt acggctttcg ttttctcctc cttgtataaa tcctggttgc    9360
tgtctctttt agaggagttg tggcccgttg tccgtcaacg tggcgtggtg tgctctgtgt    9420
ttgctgacgc aaccccccact ggctggggca ttgccaccac ctgtcaactc ctttctggga    9480
cttttcgcttt cccctcccg atcgccacgg cagaactcat cgccgcctgc cttgcccgct    9540
gctgacaggg gctaggttg ctgggcactg ataattccgt ggtgttgtcg gggaagctga    9600
cgtcctttcg aattcgatat caagcttatc gataccgtcg acggttacca agcagctatg    9660
```

```
gaagcttatg gacctcagag aggaagtaac gaggagaggg tgtggtggaa tgccactaga   9720
aaccagggaa aacaaggagg agagtattac agggaaggag gtgaagaacc tcattaccca   9780
aatactcctg ctcctcatag acgtacctgg gatgagagac acaaggttct taaattgtcc   9840
tcattcgcta ctccctctga catccaacgc tgggctacta actctagatt gtacgggagc   9900
tctcttcact actcgctgcg tcgagagtgt acgagactct ccaggtttgg taagaaatat   9960
tttatattgt tataatgtta ctatgatcca ttaacactct gcttatagat tgtaagggtg  10020
attgcaatgc tttctgcata aaactttggt tttcttgtta atcaataaac cgacttgatt  10080
cgagaaccta ctcatatatt attgtctctt ttatacttta ttaagtaaaa ggatttgtat  10140
attagccttg ctaagggaga catctagtga tataagtgtg aactacactt atcttaaatg  10200
atgtaactcc ttaggataat caatatacaa aattccatga caattggcga tacccagctg  10260
cgctcttccg cttcctcgct cactgactcg ctgcgctcgg tcgttcggct gcggcgagcg  10320
gtatcagctc actcaaaggc ggtaatacgg ttatccacag aatcagggga taacgcagga  10380
aagaacatgt gagcaaaagg ccagcaaaag gccaggaacc gtaaaaaggc cgcgttgctg  10440
gcgttttttcc ataggctccg ccccctgac gagcatcaca aaaatcgacg ctcaagtcag  10500
aggtggcgaa acccgacagg actataaaga taccaggcgt ttccccctgg aagctccctc  10560
gtgcgctctc ctgttccgac cctgccgctt accggatacc tgtccgcctt tctcccttcg  10620
ggaagcgtgg cgctttctca tagctcacgc tgtaggtatc tcagttcggt gtaggtcgtt  10680
cgctccaagc tgggctgtgt gcacgaaccc cccgttcagc ccgaccgctg cgccttatcc  10740
ggtaactatc gtcttgagtc aacccggta agacacgact tatcgccact ggcagcagcc  10800
actggtaaca ggattagcag agcgaggtat gtaggcggtg ctacagagtt cttgaagtgg  10860
tggcctaact acggctacac tagaagaaca gtatttggta tctgcgctct gctgaagcca  10920
gttaccttcg gaaaaagagt tggtagctct tgatccggca acaaaccac cgctggtagc  10980
ggtggttttt ttgtttgcaa gcagcagatt acgcgcagaa aaaaggatc tcaagaagat  11040
cctttgatct tttctacggg gtctgacgct cagtggaacg aaaactcacg ttaagggatt  11100
ttggtcatga gattatcaaa aaggatcttc acctagatcc ttttaaatta aaaatgaagt  11160
tttaaatcaa tctaaagtat atatgagtaa acttggtctg acagttacca atgcttaatc  11220
agtgaggcac ctatctcagc gatctgtcta tttcgttcat ccatagttgc ctgactcccc  11280
gtcgtgtaga taactacgat acgggagggc ttaccatctg gccccagtgc tgcaatgata  11340
ccgcgagacc cacgctcacc ggctccagat ttatcagcaa taaaccagcc agccggaagg  11400
gccgagcgca gaagtggtcc tgcaacttta tccgcctcca tccagtctat taattgttgc  11460
cgggaagcta gagtaagtag ttcgccagtt aatagtttgc gcaacgttgt tgccattgct  11520
acaggcatcg tggtgtcacg ctcgtcgttt ggtatggctt cattcagctc cggttcccaa  11580
cgatcaaggc gagttacatg atccccccatg ttgtgcaaaa aagcggttag ctccttcggt  11640
cctccgatcg ttgtcagaag taagttggcc gcagtgttat cactcatggt tatggcagca  11700
ctgcataatt ctcttactgt catgccatcc gtaagatgct tttctgtgac tggtgagtac  11760
tcaaccaagt cattctgaga atagtgtatg cggcgaccga gttgctcttg cccggcgtca  11820
atacgggata taccgcgcc acatagcaga actttaaaag tgctcatcat tggaaaacgt  11880
tcttcggggc gaaaactctc aaggatctta ccgctgttga tccagttc gatgtaaccc  11940
actcgtgcac ccaactgatc ttcagcatct tttactttca ccagcgtttc tgggtgagca  12000
```

```
aaaacaggaa ggcaaaatgc cgcaaaaaag ggaataaggg cgacacggaa atgttgaata    12060
ctcatactct tccttttca atattattga agcatttatc agggttattg tctcatgagc    12120
ggatacatat ttgaatgtat ttagaaaaat aaacaaatag gggttccgcg cacatttccc    12180
cgaaaagtgc cacctgacgt ctaagaaacc attattatca tgacattaac ctataaaaat    12240
aggcgtatca cgaggcccctt tcgtc                                         12265
```

<210> SEQ ID NO 144
<211> LENGTH: 361
<212> TYPE: PRT
<213> ORGANISM: Artificial Sequence
<220> FEATURE:
<223> OTHER INFORMATION: chimeric antigen receptor

<400> SEQUENCE: 144

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320
```

```
Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
                340                 345                 350

Leu His Met Gln Ala Leu Pro Pro Arg
            355                 360

<210> SEQ ID NO 145
<211> LENGTH: 367
<212> TYPE: PRT
<213> ORGANISM: Artificial Sequence
<220> FEATURE:
<223> OTHER INFORMATION: chimeric antigen receptor

<400> SEQUENCE: 145

Met Leu Leu Leu Val Thr Ser Leu Leu Cys Glu Leu Pro His Pro
 1               5                  10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Gly Met Ser Trp Val Arg Gln Ala Pro Arg
        50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Thr Tyr Tyr Cys Ala Arg Pro Leu Asn Tyr Tyr Tyr Tyr Met
        115                 120                 125

Asp Val Trp Gly Lys Gly Thr Thr Val Thr Val Ser Ser Ala Ala Ala
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320
```

```
Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 146
<211> LENGTH: 6
<212> TYPE: PRT
<213> ORGANISM: Artificial Sequence
<220> FEATURE:
<223> OTHER INFORMATION: His tag

<400> SEQUENCE: 146

His His His His His His
1               5

<210> SEQ ID NO 147
<211> LENGTH: 8
<212> TYPE: PRT
<213> ORGANISM: Artificial Sequence
<220> FEATURE:
<223> OTHER INFORMATION: Flag tag

<400> SEQUENCE: 147

Asp Tyr Lys Asp Asp Asp Asp Lys
1               5

<210> SEQ ID NO 148
<211> LENGTH: 8
<212> TYPE: PRT
<213> ORGANISM: Artificial Sequence
<220> FEATURE:
<223> OTHER INFORMATION: Xpress tag

<400> SEQUENCE: 148

Asp Leu Tyr Asp Asp Asp Asp Lys
1               5

<210> SEQ ID NO 149
<211> LENGTH: 15
<212> TYPE: PRT
<213> ORGANISM: Artificial Sequence
<220> FEATURE:
<223> OTHER INFORMATION: Avi tag

<400> SEQUENCE: 149

Gly Leu Asn Asp Ile Phe Glu Ala Gln Lys Ile Glu Trp His Glu
1               5                   10                  15

<210> SEQ ID NO 150
<211> LENGTH: 26
<212> TYPE: PRT
<213> ORGANISM: Artificial Sequence
<220> FEATURE:
<223> OTHER INFORMATION: Calmodulin tag

<400> SEQUENCE: 150

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

```
<210> SEQ ID NO 151
<211> LENGTH: 9
<212> TYPE: PRT
<213> ORGANISM: Artificial Sequence
<220> FEATURE:
<223> OTHER INFORMATION: HA tag

<400> SEQUENCE: 151

Tyr Pro Tyr Asp Val Pro Asp Tyr Ala
1               5

<210> SEQ ID NO 152
<211> LENGTH: 10
<212> TYPE: PRT
<213> ORGANISM: Artificial Sequence
<220> FEATURE:
<223> OTHER INFORMATION: Myc tag

<400> SEQUENCE: 152

Glu Gln Lys Leu Ile Ser Glu Glu Asp Leu
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Softag 1

<400> SEQUENCE: 153

Ser Leu Ala Glu Leu Leu Asn Ala Gly Leu Gly Gly Ser
1               5                   10

<210> SEQ ID NO 154
<211> LENGTH: 8
<212> TYPE: PRT
<213> ORGANISM: Artificial Sequence
<220> FEATURE:
<223> OTHER INFORMATION: Softag 3

<400> SEQUENCE: 154

Thr Gln Asp Pro Ser Arg Val Gly
1               5

<210> SEQ ID NO 155
<211> LENGTH: 14
<212> TYPE: PRT
<213> ORGANISM: Artificial Sequence
<220> FEATURE:
<223> OTHER INFORMATION: V5 tag

<400> SEQUENCE: 155

Gly Lys Pro Ile Pro Asn Pro Leu Leu Gly Leu Asp Ser Thr
1               5                   10
```